United States Patent
Dunn et al.

(10) Patent No.: US 9,771,366 B2
(45) Date of Patent: Sep. 26, 2017

(54) SUBSTITUTED TETRAHYDROPYRIDO [3',2':4,5]PYRROLO[1,2-A]PYRAZINE-2-CARBOXAMIDES AS RSK INHIBITORS

(71) Applicant: Phoenix Molecular Designs, Richmond (CA)

(72) Inventors: Sandra E. Dunn, Vancouver (CA); Aarthi Jayanthan, Vancouver (CA); Jaipal Reddy Nagireddy, Brantford (CA); Subhash Annedi, Mississauga (CA); John H. Van Drie, North Andover, MA (US); Timothy S. Daynard, Vancouver (CA); My-my Huynh, Vancouver (CA)

(73) Assignee: PHOENIX MOLECULAR DESIGN, British Columbia (CA)

( * ) Notice: Subject to any disclaimer, the term of this patent is extended or adjusted under 35 U.S.C. 154(b) by 0 days.

(21) Appl. No.: 15/436,587

(22) Filed: Feb. 17, 2017

(65) Prior Publication Data
US 2017/0240549 A1 Aug. 24, 2017

Related U.S. Application Data

(60) Provisional application No. 62/297,522, filed on Feb. 19, 2016.

(51) Int. Cl.
| | | |
|---|---|---|
| *A61K 31/4985* | (2006.01) | |
| *C07D 487/04* | (2006.01) | |
| *C07D 471/14* | (2006.01) | |
| *A61K 45/06* | (2006.01) | |

(52) U.S. Cl.
CPC ........ *C07D 471/14* (2013.01); *A61K 31/4985* (2013.01); *A61K 45/06* (2013.01)

(58) Field of Classification Search
CPC ......................... A61K 31/4985; C07D 487/04
USPC .................... 514/250; 544/346; 548/373.1
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 9,073,926 B2 | 7/2015 | Boyer et al. | |
| 9,150,577 B2 | 10/2015 | Boyer et al. | |
| 2006/0276453 A1 | 12/2006 | Goldberg et al. | |

FOREIGN PATENT DOCUMENTS

| | | |
|---|---|---|
| CN | 103724251 A | 4/2014 |
| WO | WO-9815545 A1 | 4/1998 |
| WO | WO-9850016 A2 | 11/1998 |
| WO | WO-9900357 A1 | 1/1999 |
| WO | WO-03087087 A2 | 10/2003 |
| WO | WO-2005005414 A2 | 1/2005 |
| WO | WO-2006002421 A2 | 1/2006 |
| WO | WO-2006108965 A2 | 10/2006 |
| WO | WO-2009036175 A2 | 3/2009 |
| WO | WO-2009040512 A2 | 4/2009 |
| WO | WO-2011071716 A1 | 6/2011 |
| WO | WO-2011071725 A1 | 6/2011 |
| WO | WO-2013181742 A1 | 12/2013 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Hackam, et al. JAMA, 296(14), 2006, 1731-1732.*
Castellana et al., Interplay between YB-1 and IL-6 promotes the metastatic phenotype in breast cancer cells. Oncotarget 6(35):38239-38256, 2015.
Clark et al., The serine/threonine protein kinase, p90 ribosomal S6 kinase, is an important regulator of prostate cancer cell proliferation. Cancer Res 65(8):3108-3116, 2005.
Davies et al., Inhibition of RSK with the novel small-molecule inhibitor LJI308 overcomes chemoresistance by eliminating cancer stem cells. Oncotarget 6(24):20570-20577, 2015.
Davies et al., YB-1 transforms human mammary epithelial cells through chromatin remodeling leading to the development of basal-like breast cancer. Stem Cells 32(6):1437-1450, 2014.
Dhillon et al., The expression of activated Y-box binding protein-1 serine 102 mediates trastuzumab resistance in breast cancer cells by increasing CD44+ cells. Oncogene 29:6294-6300, 2010.

(Continued)

*Primary Examiner* — Douglas M Willis
(74) *Attorney, Agent, or Firm* — Wilson Sonsini Goodrich & Rosati

(57) ABSTRACT

Described herein are carboxamide derivatives of Formula (II) that are useful as inhibitors of p90 ribosomal S6 kinase (RSK), pharmaceutical compositions comprising the derivatives, and methods of using the derivatives in treating diseases or conditions associated with RSK activity:

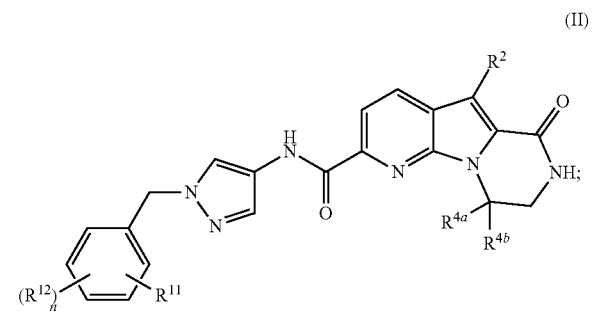

(II)

wherein $R^2$, $R^{4a}$, $R^{4b}$, $R^{11}$, $R^{12}$, and n are defined in the specification.

20 Claims, 13 Drawing Sheets

(56) References Cited

OTHER PUBLICATIONS

Fryer et al., Mitigation of off-target adrenergic binding and effects on cardiovascular function in the discovery of novel ribosomal S6 kinase 2 inhibitors. Journal of Pharmacology and Experimental Therapeutics, 340(2):492-500, 2012.
Gluz et al., Triple-negative breast cancer—current status and future directions. Annals of Oncology, 20(12)1913-1927, 2009.
Imada et al., Mutual regulation between Raf/MEK/ERK signaling and Y-box-binding protein-1 promotes prostate cancer progression. Clin Cancer Res 19(17):4638-4650, 2013.
Kang, S., and J. Chen. Targeting RSK2 in human malignancies. Expert Opin Ther Targets 15(1):11-20, 2011.
Kuzma et al., Regional Anesthesia 22(6):543-551, 1997 (Abstract only).
Larrea et al., RSK1 drives p27Kip1 phosphorylation at T198 to promote RhoA inhibition and increase cell motility. Proc Natl Acad Sci USA 106(23):9268-9273, 2009.
Li et al., The prometastatic ribosomal S6 kinase 2-cAMP response element-binding protein (RSK2-CREB) signaling pathway up-regulates the actin-binding protein fascin-1 to promote tumor metastasis. J Biol Chem 288:32528-32538, 2013.
Ma et al., Ribosomal protein S6 kinase (RSK)-2 as a central effector molecule in RON receptor tyrosine kinase mediated epithelial to mesenchymal transition induced by macrophage-stimulating protein. Mol Cancer 28(10):1-15, 2011.
Pambid et al., Overcoming resistance to Sonic Hedgehog inhibition by targeting p90 ribosomal S6 kinase in pediatric medulloblastoma. Pediatr Blood Cancer 61(1):107-115, 2014.
Panupinthu et al., Self-reinforcing loop of amphiregulin and Y-box binding protein-1 contributes to poor outcomes in ovarian cancer. Oncogene 33(22):2846-2856, 2014.
Peng et al., Tumor necrosis factor receptor-associated factor family protein 2 is a key mediator of the epidermal growth factor-induced ribosomal S6 kinase 2/cAMP-responsive element—binding protein/Fos protein signaling pathway. J Biol Chem 287(31):25881-25892, 2012.
Poomakkoth et al., p90 ribosomal S6 kinase: a potential therapeutic target in lung cancer. J Transl Med 14:1-6, 2016.
Reipas et al., Luteolin is a novel p90 ribosomal S6 kinase (RSK) inhibitor that suppresses Notch4 signaling by blocking the activation of Y-box binding protein-1 (YB-1), Oncotarget 4(2):329-345, 2013.
Romeo et al., Regulation and function of the RSK family of protein kinases. Biochem J 441(2):553-569, 2012.
Salhi et al., RSK1 activation promotes invasion in nodular melanoma. Am J Pathol 185(3): 704-716, 2015.
Shahbazian et al., The mTOR/PI3K and MAPK pathways converge on eIF4B to control its phosphorylation and activity. EMBO Journal, 25(12): 2781-2791, 2006.
Shiota et al., Interaction between docetaxel resistance and castration resistance in prostate cancer: implications of Twist1 , YB-1, and androgen receptor. Prostate 73(12):1336-1344, 2013.
Shiota et al., Potential Role for YB-1 in Castration-Resistant Prostate Cancer and Resistance to Enzalutamide Through the Androgen Receptor V7. J Natl Cancer Inst 108(7):10 pages. (ahead of print), 2016.
Smith et al., Identification of the first specific inhibitor of p90 ribosomal S6 kinase (RSK) reveals an unexpected role for RSK in cancer cell proliferation. Cancer Res 65(3):1027-1034, 2015.
Stratford et al., Epidermal growth factor receptor (EGFR) is transcriptionally induced by the Y-box binding protein-1 (YB-1) and can be inhibited with Iressa in basal-like breast cancer, providing a potential target for therapy. Breast Cancer Res 9:R61, 2007.
Stratford et al., Targeting p90 ribosomal S6 kinase eliminates tumor-initiating cells by inactivating Y-box binding protein-1 in triple-negative breast cancers. Stem Cells 30(7):1338-1348, 2012.
Stratford et al., The promise and challenges of targeting RSK for the treatment of cancer. Expert Opin Ther Targets 15(1):1-4, 2011.
Stratford et al., Y-box binding protein-1 (Yb-1) serine 102 is a downstream target of p90 ribosomal S6 kinase (RSK) in basal-like breast cancer cells. Breast Cancer Res 10(6):R99:Epub ahead of print, 2008.
Vogel et al., Efficacy and safety of trastuzumab as a single agent in first-line treatment of Her-2 over-expressing metastatic breast cancer. J Clin Onc 20:719-726, 2002.
Ward, Chiral separations. Analytical Chemistry, 74(12)2863-2872, 2002.
Xiong et al., Synthesis and SAR studies of indole-based MK2 inhibitors. Bioorganic and Medicinal Chemistry Letters, 18:1994-1998, 2008.
Yoo et al., The conformation and activity relationship of benzofuran derivatives as angiotensin II receptors antagonists. Bioorg. & Med. Chem., 5(2):445-459, 1997.
Zhang et al., Myricetin exerts anti-proliferative, anti-invasive, and pro-apoptotic effects on esophageal carcinoma EC9706 and KYSE30 cells via RSK2. Tumour Biol 35(12):12583-12592, 2014.
Zhu et al., RNA interference screening identifies lenalidomide sensitizers in multiple myeloma, including RSK2. Blood 125:483-491, 2015.
PCT/IB2017/000237 International Search Report and Written Opinion dated Jul. 7, 2017.

* cited by examiner

SUBSTITUTED TETRAHYDROPYRIDO[3',2':4,5]PYRROLO[1,2-A]PYRAZINE-2-CARBOXAMIDES AS RSK INHIBITORS

CROSS-REFERENCE

This application claims benefit of U.S. Provisional Application No. 62/297,522, filed on Feb. 19, 2016, which is herein incorporated by reference in its entirety.

FIELD OF THE INVENTION

Described herein are carboxamide derivatives and pharmaceutical compositions comprising the compounds and methods of using the compounds and the pharmaceutical compositions in treating diseases or conditions, such as cancer, as well as other diseases and conditions associated with the p90 ribosomal S6 kinase (RSK).

BACKGROUND OF THE INVENTION

The p90 ribosomal S6 kinase (RSK) family is comprised of four isoforms, RSK1, RSK2, RSK3 and RSK4. These isoforms are pivotal for transmitting cell signalling from cell surface receptors such as growth factors, hormones, and cytokines. RSK1 and RSK2 are the isoforms most common to cancer where they control cell growth, invasion and the suppression of apoptosis. RSK3 is not commonly expressed in cancer, however, it has been associated with drug resistance as have RSK1 and RSK2. RSK4 is not commonly expressed in cancer. The RSK family is also fundamental to inflammation, diabetes and heart disease.

In the field of oncology, RSK inhibitors provide an opportunity for targeted therapy to improve the treatment of cancer. Inhibiting RSK also affords an opportunity to overcome drug resistance through multiple mechanisms including the elimination of cancer stem cells (CSC) or tumor-initiating cells (TIC). RSK inhibitors can reportedly overcome resistance to targeted therapies such as Herceptin, Gefitinib, and Enzalutamide. RSK inhibitors can also be used to augment resistance to microtubule cytotoxics such as paclitaxel.

There are many types of cancers associated with RSK activity, including, but not limited to, breast, prostate, lung, brain, blood, skin, bone, and ovarian cancers. In the field of breast and prostate cancer research, RSK inhibitors have been shown to block hormone signalling. As with many types of cancer, those that arise in the breast are genetically diverse and as such have been categorized into three main types: Type 1, which is hormone positive expressing the estrogen and progesterone receptors (ER and PR respectively); Type 2, which is Her-2 positive; and Type 3, which is triple-negative as the cancer cells lack ER, PR and Her-2 receptors. The triple-negative breast cancer (TNBC) is currently considered the most aggressive and is associated with the worst outcomes for patients. It constitutes 15-25% of all breast cancers and is more common in younger women. Women with mutations in the breast cancer susceptibility genes 1 and 2 (BRCA1 and BRCA2) are more likely to develop TNBC then the other types of breast cancer.

Accordingly, there is a need for small molecule inhibitors of RSK which are useful in treating diseases and conditions associated with the activity of RSK, such as cancer.

SUMMARY OF THE INVENTION

In one aspect described herein, are compounds which are useful in inhibiting RSK activity. In some embodiments described herein, are compounds of formula (I):

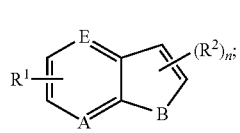

wherein:
n is 1 or 2;
A is $-N=$ or $-C(R^3)=$;
B is $-O-$, $-N(R^4)-$, or $-S(O)_t$ (where t is 0, 1 or 2)-;
E is $-N=$ or $-C(R^3)=$;
$R^1$ is $R^5-C(O)N(R^6)-$, $R^7-N(R^6)C(O)-$, $R^5-N(R^6)C(O)N(R^6)-$, or $R^5-N(R^6)C(=NR^6)N(R^6)-$;
each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;
or two $R^2$, together with the adjacent carbons to which they are attached, form a fused optionally substituted 6-membered N-heterocyclyl;
each $R^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;
$R^4$ is hydrogen, alkyl, haloalkyl, optionally substituted aryl or optionally substituted aralkyl;
or $R^4$, together with the nitrogen to which it is attached, and a $R^2$, together with the adjacent carbon to which it is attached, together form a fused 6-membered N-heterocyclyl of the following structure:

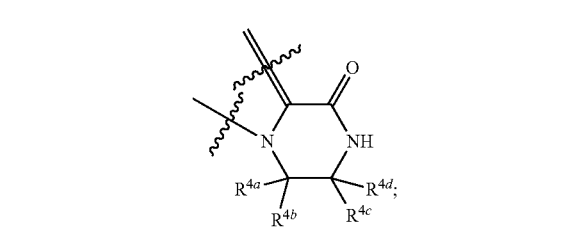

where ⌇ indicates the point of fusion and $R^{4a}$, $R^{4b}$, $R^{4c}$, and $R^{4d}$ are each independently hydrogen, alkyl, halo or haloalkyl or $R^{4a}$ and $R^{4b}$, together with the carbon to which they are both attached, form a cycloalkyl or $R^{4c}$ and $R^{4d}$, together with the carbon to which they are both attached, form a cycloalkyl, and the remaining $R^2$, if present, is selected from hydrogen, alkyl, halo or haloalkyl;
$R^5$ is optionally substituted aryl or optionally substituted N-heteroaryl;
each $R^6$ is independently hydrogen, alkyl, haloalkyl, optionally substituted aryl or optionally substituted aralkyl;
$R^7$ is optionally substituted aryl or optionally substituted N-heteroaryl when E is $-N=$;
or $R^7$ is a monocyclic N-heteroaryl substituted with an optionally substituted aralkyl when E is $-C(R^3)=$ and one $R^2$ is halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or $R^7$ is a monocyclic N-heteroaryl substituted with an optionally substituted aralkyl when E is —C($R^3$)═ and one of $R^{4a}$ and $R^{4b}$ is not methyl and the other is not hydrogen;

or $R^7$ is a monocyclic N-heteroaryl substituted with an optionally substituted aralkyl when E is —C($R^3$)═ and two of $R^{4a}$, $R^{4b}$, $R^{4c}$, and $R^{4d}$ on adjacent carbons are not both methyl and the other two are not both hydrogen;

or $R^7$ is a monocyclic N-heteroaryl substituted with an optionally substituted aralkyl when E is —C($R^3$)═ and $R^{4a}$ and $R^{4b}$, together with the carbon to which they are both attached, form a cycloalkyl or $R^{4c}$ and $R^{4d}$, together with the carbon to which they are both attached, form a cycloalkyl;

or $R^7$ is a monocyclic N-heteroaryl substituted by an aralkyl substituted with halo, haloalkyl, —CN, —NO$_2$, —N($R^6$)$_2$, —N($R^6$)C(O)O$R^6$, —C(O)$R^6$, —C(O)O$R^6$ or —C(O)N($R^6$)$_2$ when E is —C($R^3$)═ and $R^{4a}$ is methyl and $R^{4b}$, $R^{4c}$, and $R^{4d}$ are each hydrogen or when E is —C($R^3$)═ and $R^{4a}$ and $R^{4c}$ are each methyl and $R^{4b}$ and $R^{4d}$ are each hydrogen;

or $R^7$ is a monocyclic N-heteroaryl substituted with optionally substituted N-heterocyclylalkyl when E is —C($R^3$)═;

as an individual stereoisomer, enantiomer or tautomer thereof or a mixture thereof;

or a pharmaceutically acceptable salt, solvate, or prodrug thereof.

In another aspect is a compound of formula (II) having the structure:

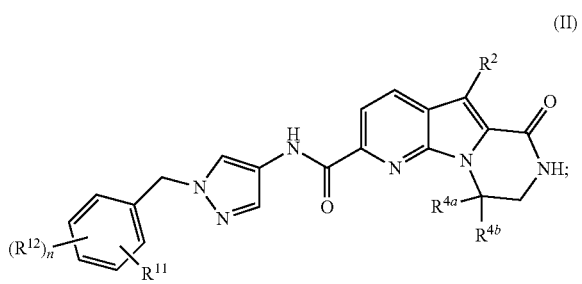

(II)

wherein:

$R^2$ is independently hydrogen, halo, $C_{1-6}$alkyl, or $C_{1-6}$haloalkyl;

$R^{4a}$ and $R^{4b}$ are each independently hydrogen, halo, $C_{1-6}$alkyl, or $C_{1-6}$haloalkyl; or $R^{4a}$ and $R^{4b}$, together with the carbon to which they are both attached, form a cycloalkyl;

each $R^6$ is independently hydrogen or $C_{1-6}$alkyl;

$R^{11}$ is halo, $C_{1-6}$haloalkyl, —N($R^6$)$_2$, —$C_{1-6}$alkyl-N($R^6$)$_2$, or —C(O)N($R^6$)$_2$;

each $R^{12}$ is independently —OH, —CN, halo, $C_{1-6}$alkyl, $C_{1-6}$haloalkyl, $C_{1-6}$alkoxy, $C_{1-6}$haloalkoxy, —N($R^6$)$_2$, —$C_{1-6}$alkyl-N($R^6$)$_2$, —C(O)$R^6$, —C(O)O$R^6$, —C(O)N($R^6$)$_2$, aryl, aralkyl, cycloalkyl, heterocyclyl, or heteroaryl; and n is 0, 1, 2, 3, or 4;

as an individual stereoisomer, enantiomer or tautomer thereof or a mixture thereof;

or a pharmaceutically acceptable salt, solvate, or prodrug thereof.

In some embodiments is a compound of formula (II) wherein $R^2$ is hydrogen. In some embodiments is a compound of formula (II) wherein $R^2$ is halo. In some embodiments is a compound of formula (II) wherein $R^2$ is —F. In some embodiments is a compound of formula (II) wherein $R^2$ is —Cl. In some embodiments is a compound of formula (II) wherein $R^2$ is $C_{1-6}$alkyl. In some embodiments is a compound of formula (II) wherein $R^2$ is —CH$_3$. In some embodiments is a compound of formula (II) wherein $R^{4a}$ is $C_{1-6}$alkyl. In some embodiments is a compound of formula (II) wherein $R^{4a}$ is —CH$_3$. In some embodiments is a compound of formula (II) wherein $R^{4b}$ is hydrogen. In some embodiments is a compound of formula (II) wherein each $R^{12}$ is independently —OH, —CN, halo, $C_{1-6}$alkyl, $C_{1-6}$haloalkyl, $C_{1-6}$alkoxy, $C_{1-6}$haloalkoxy, —N($R^6$)$_2$, —$C_{1-6}$alkyl-N($R^6$)$_2$, —C(O)$R^6$, —C(O)O$R^6$, or —C(O)N($R^6$)$_2$. In some embodiments is a compound of formula (II) wherein each $R^{12}$ is independently halo, $C_{1-6}$alkyl, —N($R^6$)$_2$, —$C_{1-6}$alkyl-N($R^6$)$_2$, or $C_{1-6}$haloalkyl. In some embodiments is a compound of formula (II) wherein n is 1. In some embodiments is a compound of formula (II) wherein n is 0. In some embodiments is a compound of formula (II) wherein $R^{11}$ is halo. In some embodiments is a compound of formula (II) wherein $R^{11}$ is —F. In some embodiments is a compound of formula (II) wherein $R^{11}$ is $C_{1-6}$haloalkyl. In some embodiments is a compound of formula (II) wherein $R^{11}$ is —CF$_3$. In some embodiments is a compound of formula (II) wherein $R^{11}$ is —N($R^6$)$_2$ or —$C_{1-6}$alkyl-N($R^6$)$_2$. In some embodiments is a compound of formula (II) wherein $R^{11}$ is —N($R^6$)$_2$. In some embodiments is a compound of formula (II) wherein $R^{11}$ is —NH$_2$. In some embodiments is a compound of formula (II) wherein $R^{11}$ is —$C_{1-6}$alkyl-N($R^6$)$_2$. In some embodiments is a compound of formula (II) wherein $R^{11}$ is —CH$_2$NH$_2$.

In another aspect is a compound of formula (III) having the structure:

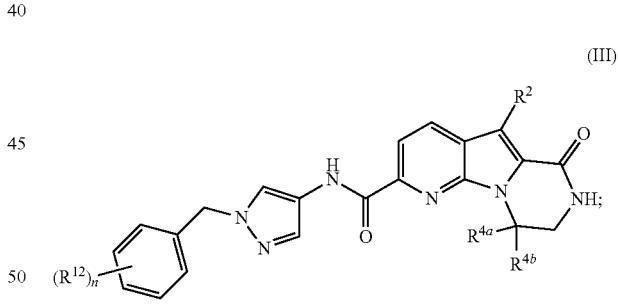

(III)

wherein:

$R^2$ is independently halo, $C_{1-6}$alkyl, or $C_{1-6}$haloalkyl;

$R^{4a}$ and $R^{4b}$ are each independently hydrogen, halo, $C_{1-6}$alkyl, or $C_{1-6}$haloalkyl; or $R^{4a}$ and $R^{4b}$, together with the carbon to which they are both attached, form a cycloalkyl;

each $R^6$ is independently hydrogen or $C_{1-6}$alkyl;

each $R^{12}$ is independently —OH, —CN, halo, $C_{1-6}$alkyl, $C_{1-6}$haloalkyl, $C_{1-6}$alkoxy, $C_{1-6}$haloalkoxy, —N($R^6$)$_2$, —$C_{1-6}$alkyl-N($R^6$)$_2$, —C(O)$R^6$, —C(O)O$R^6$, —C(O)N($R^6$)$_2$, aryl, aralkyl, cycloalkyl, heterocyclyl, or heteroaryl; and n is 0, 1, 2, 3, or 4;

as an individual stereoisomer, enantiomer or tautomer thereof or a mixture thereof;

or a pharmaceutically acceptable salt, solvate, or prodrug thereof.

In some embodiments is a compound of formula (III) wherein $R^2$ is halo. In some embodiments is a compound of formula (III) wherein $R^2$ is —F. In some embodiments is a compound of formula (III) wherein $R^2$ is —Cl. In some embodiments is a compound of formula (III) wherein $R^2$ is $C_{1-6}$alkyl. In some embodiments is a compound of formula (III) wherein $R^2$ is —CH$_3$. In some embodiments is a compound of formula (III) wherein $R^{4a}$ is $C_{1-6}$alkyl. In some embodiments is a compound of formula (III) wherein $R^{4a}$ is —CH$_3$. In some embodiments is a compound of formula (III) wherein $R^{4b}$ is hydrogen. In some embodiments is a compound of formula (III) wherein each $R^{12}$ is independently —OH, —CN, halo, $C_{1-6}$alkyl, $C_{1-6}$haloalkyl, $C_{1-6}$alkoxy, $C_{1-6}$haloalkoxy, —N(R$^6$)$_2$, —C$_{1-6}$alkyl-N(R$^6$)$_2$, —C(O)R$^6$, —C(O)OR$^6$, or —C(O)N(R$^6$)$_2$. In some embodiments is a compound of formula (III) wherein each $R^{12}$ is independently halo, $C_{1-6}$alkyl, $C_{1-6}$haloalkyl, —N(R$^6$)$_2$, —C$_{1-6}$alkyl-N(R$^6$)$_2$, or —C(O)N(R$^6$)$_2$. In some embodiments is a compound of formula (III) wherein $R^{12}$ is halo. In some embodiments is a compound of formula (III) wherein $R^{12}$ is —F. In some embodiments is a compound of formula (III) wherein $R^{12}$ is —Cl. In some embodiments is a compound of formula (III) wherein $R^{12}$ is $C_{1-6}$haloalkyl. In some embodiments is a compound of formula (III) wherein $R^{12}$ is —CF$_3$. In some embodiments is a compound of formula (III) wherein $R^{12}$ is —N(R$^6$)$_2$ or —C$_{1-6}$alkyl-N(R$^6$)$_2$. In some embodiments is a compound of formula (III) wherein $R^{12}$ is —N(R$^6$)$_2$. In some embodiments is a compound of formula (III) wherein $R^{12}$ is —NH$_2$. In some embodiments is a compound of formula (III) wherein $R^{12}$ is —C$_{1-6}$alkyl-N(R$^6$)$_2$. In some embodiments is a compound of formula (III) wherein $R^{12}$ is —CH$_2$NH$_2$. In some embodiments is a compound of formula (III) wherein n is 1. In some embodiments is a compound of formula (III) wherein n is 0.

In another aspect is a compound of formula (IV) having the structure:

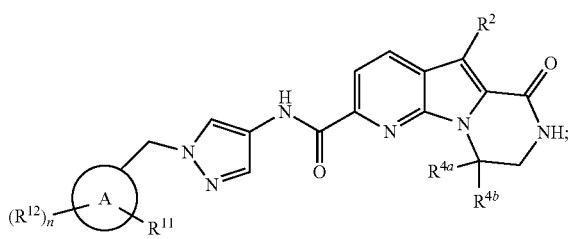

(IV)

wherein:

is heterocyclyl;
$R^2$ is independently hydrogen, halo, $C_{1-6}$alkyl, or $C_{1-6}$haloalkyl;
$R^{4a}$ and $R^{4b}$ are each independently hydrogen, halo, $C_{1-6}$alkyl, or $C_{1-6}$haloalkyl; or $R^{4a}$ and $R^{4b}$, together with the carbon to which they are both attached, form a cycloalkyl;
each $R^6$ is independently hydrogen or $C_{1-6}$alkyl;

$R^{11}$ is halo, $C_{1-6}$alkyl, $C_{1-6}$haloalkyl, —N(R$^6$)$_2$, —C$_{1-6}$alkyl-N(R$^6$)$_2$, or —C(O)N(R$^6$)$_2$; each $R^{12}$ is independently —OH, —CN, halo, $C_{1-6}$alkyl, $C_{1-6}$haloalkyl, $C_{1-6}$alkoxy, $C_{1-6}$haloalkoxy, —N(R$^6$)$_2$, —C$_{1-6}$alkyl-N(R$^6$)$_2$, —C(O)R$^6$, —C(O)OR$^6$, —C(O)N(R$^6$)$_2$, aryl, aralkyl, cycloalkyl, heterocyclyl, or heteroaryl; and
n is 0, 1, 2, 3, or 4;
as an individual stereoisomer, enantiomer or tautomer thereof or a mixture thereof;
or a pharmaceutically acceptable salt, solvate, or prodrug thereof.

In some embodiments is a compound of formula (IV) wherein $R^2$ is hydrogen. In some embodiments is a compound of formula (IV) wherein $R^2$ is halo. In some embodiments is a compound of formula (IV) wherein $R^2$ is —F. In some embodiments is a compound of formula (IV) wherein $R^2$ is —Cl. In some embodiments is a compound of formula (IV) wherein $R^2$ is $C_{1-6}$alkyl. In some embodiments is a compound of formula (IV) wherein $R^2$ is —CH$_3$. In some embodiments is a compound of formula (IV) wherein $R^{4a}$ is $C_{1-6}$alkyl. In some embodiments is a compound of formula (IV) wherein $R^{4a}$ is —CH$_3$. In some embodiments is a compound of formula (IV) wherein $R^{4b}$ is hydrogen. In some embodiments is a compound of formula (IV) wherein each $R^{12}$ is independently —OH, —CN, halo, $C_{1-6}$alkyl, $C_{1-6}$haloalkyl, $C_{1-6}$alkoxy, $C_{1-6}$haloalkoxy, —N(R$^6$)$_2$, —C$_{1-6}$alkyl-N(R$^6$)$_2$, —C(O)R$^6$, —C(O)OR$^6$, or —C(O)N(R$^6$)$_2$. In some embodiments is a compound of formula (IV) wherein each $R^{12}$ is independently halo, $C_{1-6}$alkyl, —N(R$^6$)$_2$, —C$_{1-6}$alkyl-N(R$^6$)$_2$, or $C_{1-6}$haloalkyl. In some embodiments is a compound of formula (IV) wherein n is 1. In some embodiments is a compound of formula (IV) wherein n is 0. In some embodiments is a compound of formula (IV) wherein $R^{11}$ is halo. In some embodiments is a compound of formula (IV) wherein $R^{11}$ is —F. In some embodiments is a compound of formula (IV) wherein $R^{11}$ is $C_{1-6}$alkyl. In some embodiments is a compound of formula (IV) wherein $R^{11}$ is —CH$_3$. In some embodiments is a compound of formula (IV) wherein $R^{11}$ is —N(R$^6$)$_2$ or —C$_{1-6}$alkyl-N(R$^6$)$_2$. In some embodiments is a compound of formula (IV) wherein $R^{11}$ is —N(R$^6$)$_2$. In some embodiments is a compound of formula (IV) wherein $R^{11}$ is —NH$_2$. In some embodiments is a compound of formula (IV) wherein $R^{11}$ is —C$_{1-6}$alkyl-N(R$^6$)$_2$. In some embodiments is a compound of formula (IV) wherein $R^{11}$ is —CH$_2$NH$_2$. In some embodiments is a compound of formula (IV) wherein

is piperidine. In some embodiments is a compound of formula (IV) wherein

is piperazine.

In some embodiments is a compound selected from:
(R)-1-benzyl-N-(9-methyl-6-oxo-6,7,8,9-tetrahydropyrido [3',2':4,5]pyrrolo[1,2-a]pyrazin-2-yl)-1H-pyrazole-4-carboxamide; (R)—N-(1-(3-aminobenzyl)-1H-pyrazol-4-yl)-9-methyl-6-oxo-6,7, 8,9-tetrahydropyrido[3',2':4,5]

pyrrolo[1,2-a]pyrazine-2-carboxamide; (R)—N-(1-(2-aminobenzyl)-1H-pyrazol-4-yl)-9-methyl-6-oxo-6,7,8,9-tetrahydropyrido[3',2':4,5]pyrrolo[1,2-a]pyrazine-2-carboxamide; and (R)-1-(3-aminobenzyl)-N-(9-methyl-6-oxo-6,7,8,9-tetrahydropyrido[3',2':4,5]pyrrolo[1,2-a]pyrazin-2-yl)-1H-pyrazole-4-carboxamide;
or a pharmaceutically acceptable salt, solvate, or prodrug thereof.

In some embodiments is a compound having the structure:
(R)-9-methyl-N-(1-((1-methylpiperidin-4-yl)methyl)-1H-pyrazol-4-yl)-6-oxo-6,7,8,9-tetrahydropyrido[3',2':4,5]pyrrolo[1,2-a]pyrazine-2-carboxamide;
or a pharmaceutically acceptable salt, solvate, or prodrug thereof.

In some embodiments is a compound selected from:
(R)-9-methyl-6-oxo-N-(1-(4-(trifluoromethyl)benzyl)-1H-pyrazol-4-yl)-6,7,8,9-tetrahydropyrido[3',2':4,5]pyrrolo[1,2-a]pyrazine-2-carboxamide; (R)—N-(1-(2,4-difluorobenzyl)-1H-pyrazol-4-yl)-9-methyl-6-oxo-6,7,8,9-tetrahydropyrido[3',2':4,5]pyrrolo[1,2-a]pyrazine-2-carboxamide; and (R)—N-(1-benzyl-1H-pyrazol-4-yl)-5-chloro-9-methyl-6-oxo-6,7,8,9-tetrahydropyrido[3',2':4,5]pyrrolo[1,2-a]pyrazine-2-carboxamide; or a pharmaceutically acceptable salt, solvate, or prodrug thereof.

In some embodiments is a compound having the structure:
(R)—N-(1-(4-(aminomethyl)benzyl)-1H-pyrazol-4-yl)-9-methyl-6-oxo-6,7,8,9-tetrahydropyrido[3',2':4,5]pyrrolo[1,2-a]pyrazine-2-carboxamide;
or a pharmaceutically acceptable salt, solvate, or prodrug thereof.

In some embodiments is a compound having the structure:
(R)—N-(1-(4-(aminomethyl)benzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride salt;
or a pharmaceutically acceptable solvate or prodrug thereof.

In some embodiments is a compound having the structure:
(R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide;
or a pharmaceutically acceptable salt, solvate, or prodrug thereof.

In some embodiments is a compound having the structure:
(R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride salt; or a pharmaceutically acceptable solvate or prodrug thereof.

In some embodiments is a compound having the structure:
(R)—N-(2-carbamoylphenyl)-9-methyl-6-oxo-6,7,8,9-tetrahydropyrido[3',2':4,5]pyrrolo[1,2-a]pyrazine-2-carboxamide; or a pharmaceutically acceptable salt, solvate, or prodrug thereof.

In another aspect described herein, are pharmaceutical compositions comprising a pharmaceutically acceptable excipient and a compound described herein as described above, as an individual stereoisomer, enantiomer or tautomer thereof or a mixture thereof; or a pharmaceutically acceptable salt, solvate, or prodrug thereof.

In another aspect is a method of treating a disease or condition associated with RSK activity in a mammal, wherein the method comprises administering to the mammal a therapeutically effective amount of a compound as described herein, as an individual stereoisomer, enantiomer or tautomer thereof or a mixture thereof; or a pharmaceutically acceptable salt, solvate, or prodrug thereof. In some embodiments, the disease or condition associated with RSK activity in a mammal is cancer. In some embodiments, the cancer is breast cancer, prostate cancer, lung cancer, brain cancer, skin cancer, bone cancer, ovarian cancer, multiple myeloma or leukemia. In some embodiments is a method of treating a disease or condition associated with RSK activity in a mammal, wherein the method comprises administering to the mammal a therapeutically effective amount of a compound as described herein, as an individual stereoisomer, enantiomer or tautomer thereof or a mixture thereof; or a pharmaceutically acceptable salt, solvate, or prodrug thereof; further comprising the administration of a second therapeutic agent. In some embodiments, the second therapeutic agent is a chemotherapeutic agent, hormonal therapeutic agent, or an immunotherapeutic agent. In some embodiments, the second therapeutic agent is a poly ADP-ribose polymerase (PARP) inhibitor, STAT 3 inhibitor, Janus Kinase inhibitor, or EGFR inhibitor. In some embodiments, the second therapeutic agent is a chemotherapeutic agent (small molecule or antibody). In some embodiments, the second therapeutic agent is paclitaxel. In some embodiments, the second therapeutic agent is methotrexate. In some embodiments, the second therapeutic agent is 5-fluorouracil. In some embodiments, the second therapeutic agent is adriamycin.

In some embodiments, the method further comprises the administration of radiation therapy.

In another aspect described herein are assays to determine the effectiveness of a compound described herein in inhibiting RSK activity in a cell-based assay.

In another aspect described herein is a method of inhibiting an activity of RSK, comprising contacting in vitro RSK with an amount of a compound effective to inhibit the activity of RSK wherein the compound is selected from the compounds described herein, or a pharmaceutically acceptable salt thereof, as described herein.

In another aspect described herein is a method of inhibiting an activity of RSK comprising contacting in a cell RSK with an amount of a compound effective to inhibit the activity of RSK wherein the compound is selected from the compounds described herein, or a pharmaceutically acceptable salt thereof, as described herein.

BRIEF DESCRIPTION OF THE DRAWINGS

FIG. 14A also depicts a lack of effect compound 16 and 18 have on the master regulator CIITA.

FIG. 14B also depicts a lack of effect compound 18 had on the master regulator CIITA.

DETAILED DESCRIPTION OF THE INVENTION

Definitions

Figure 1:
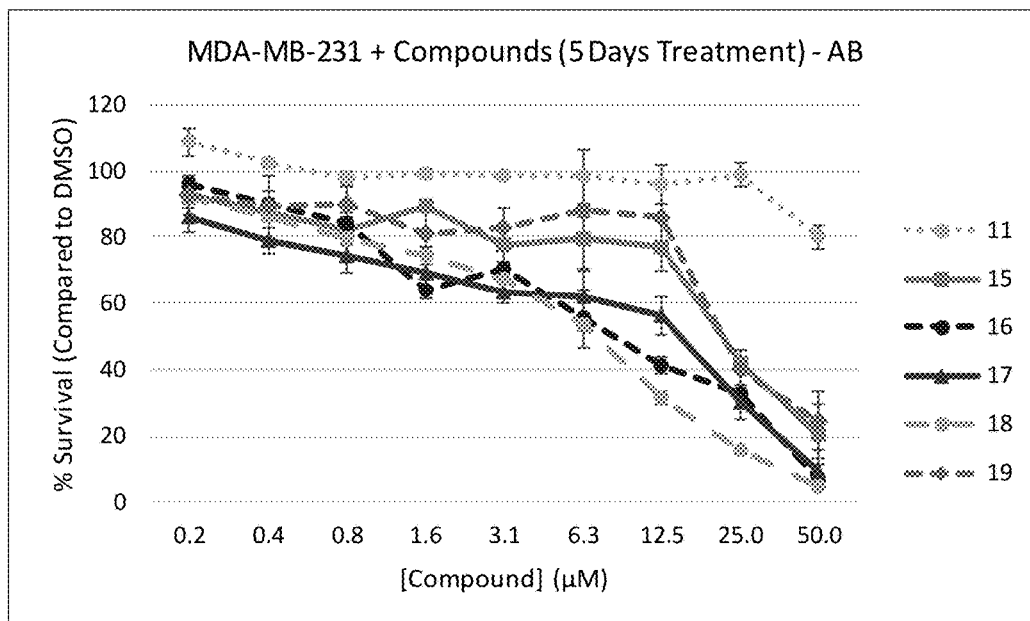
FIG. 1 depicts the percent survival of MDA-MB-231 breast cancer cells in the Alamar blue assay when treated with varying concentrations of compounds described herein.
Figure 2:
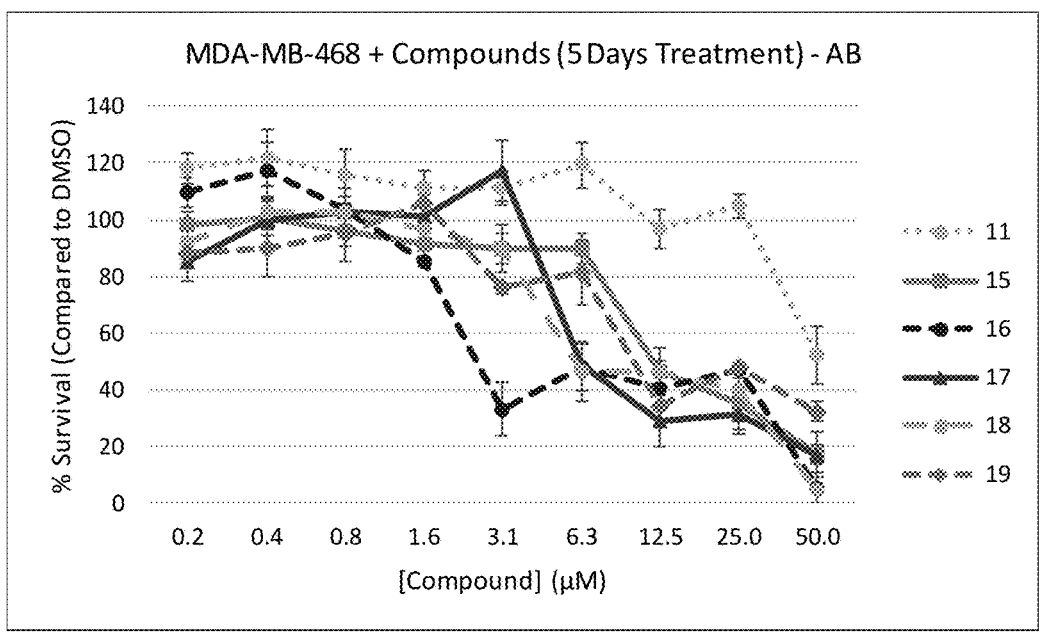
FIG. 2 depicts the percent survival of MDA-MB-468 breast cancer cells in the Alamar blue assay when treated with varying concentrations of compounds described herein.
Figure 3:
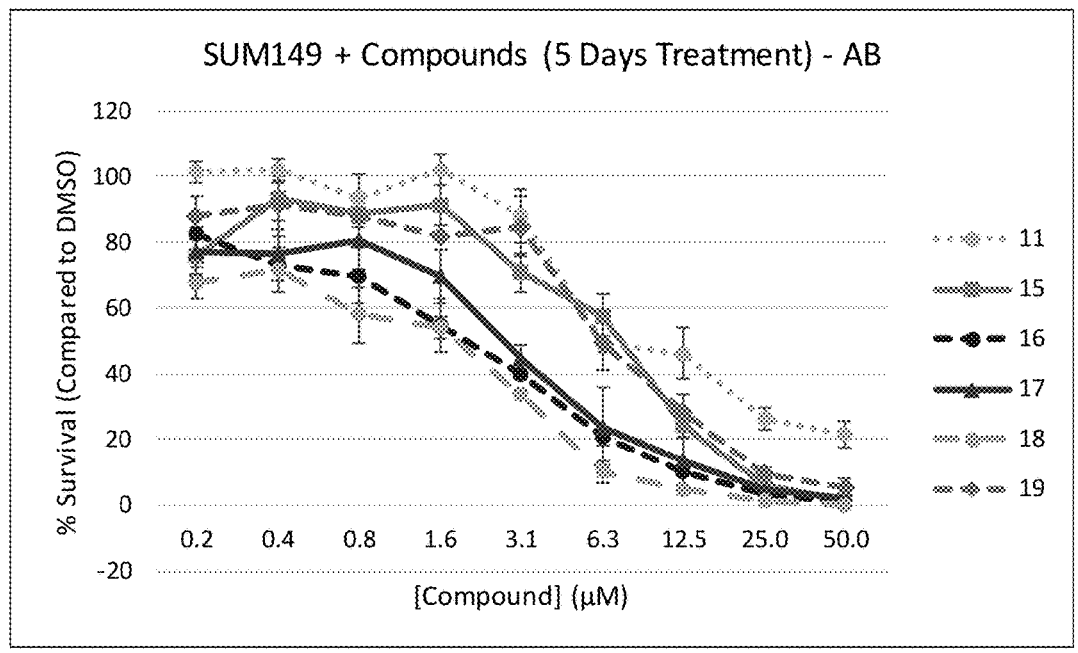
FIG. 3 depicts the percent survival of SUM149 breast cancer cells in the Alamar blue assay when treated with varying concentrations of compounds described herein.
Figure 4:
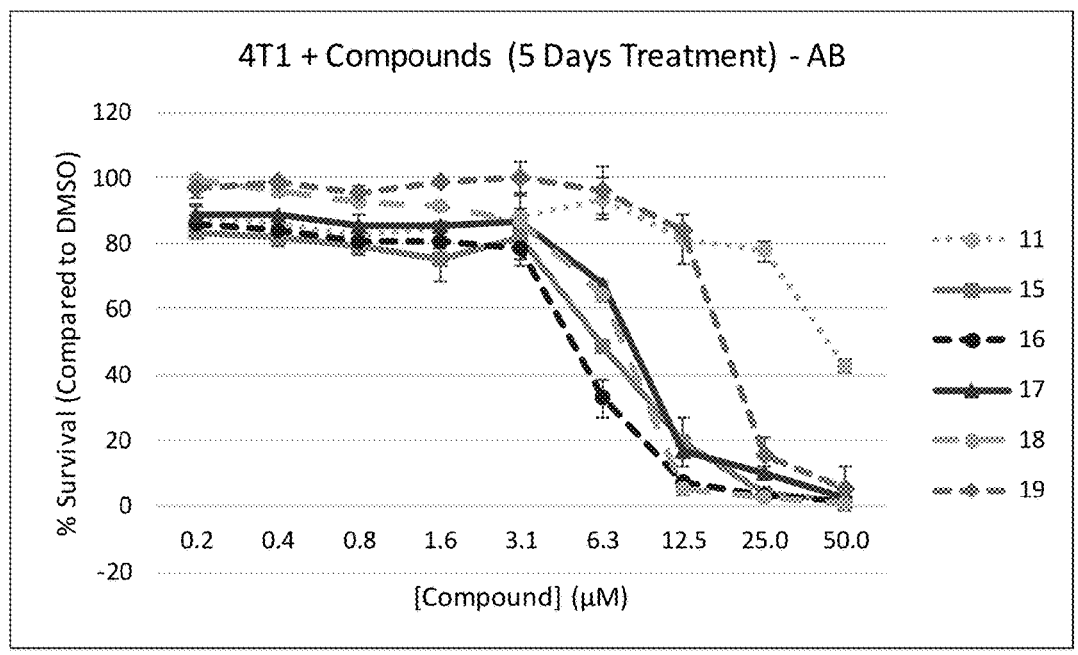
FIG. 4 depicts the percent survival of 4T1 breast cancer cells in the Alamar blue assay when treated with varying concentrations of compounds described herein.
Figure 5:
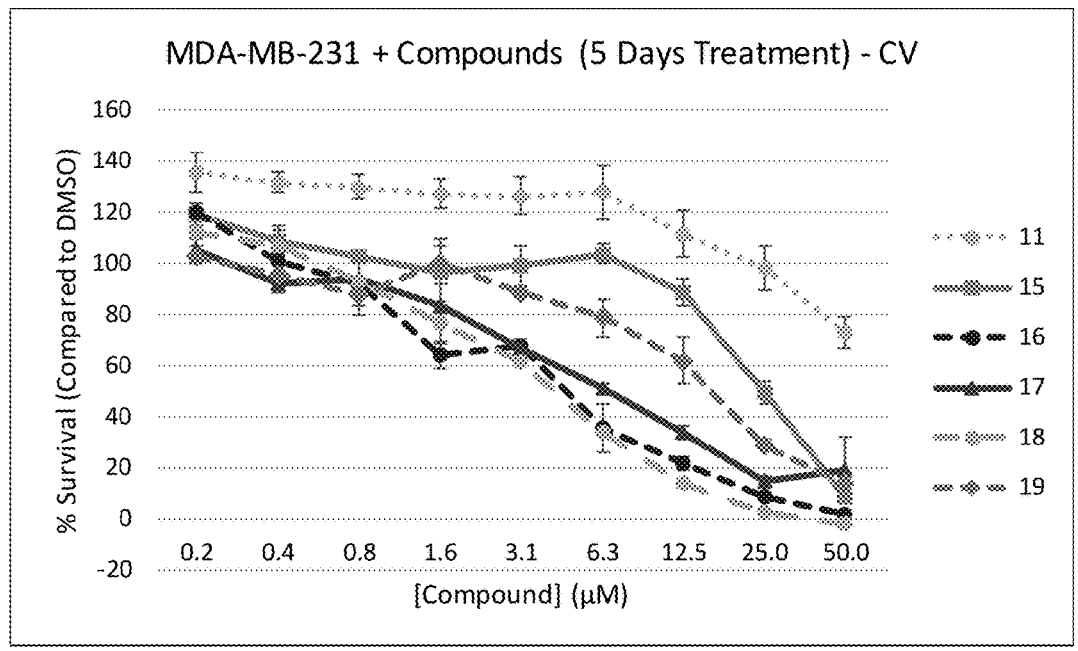
FIG. 5 depicts the percent survival of MDA-MB-231 breast cancer cells in the crystal violet assay when treated with varying concentrations of compounds described herein.
Figure 6:
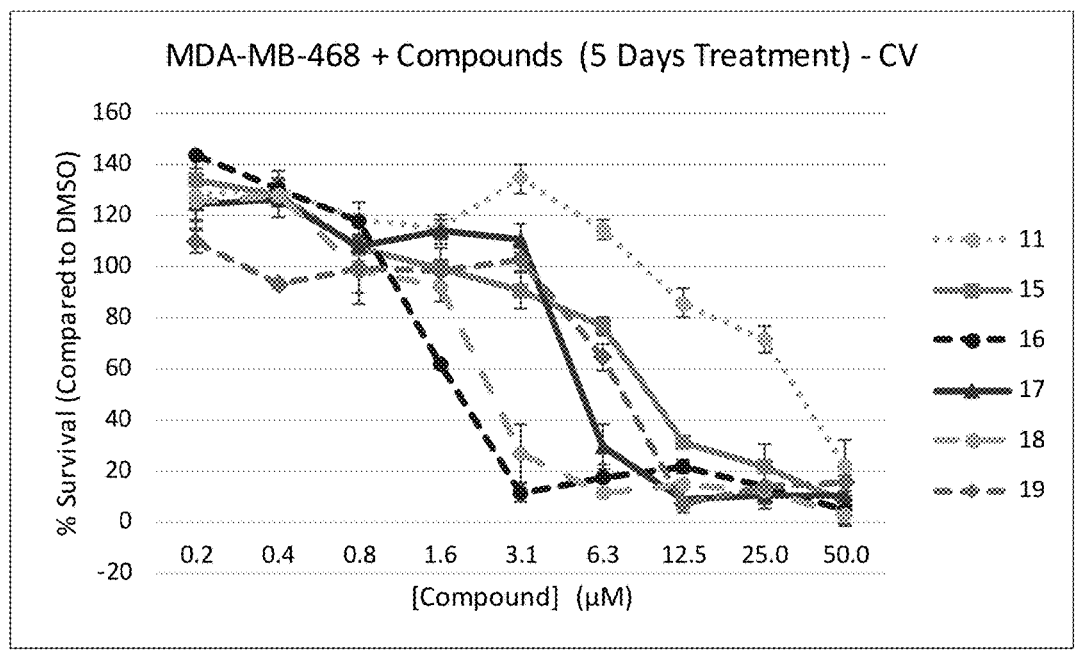
FIG. 6 depicts the percent survival of MDA-MB-468 breast cancer cells in the crystal violet assay when treated with varying concentrations of compounds described herein.
Figure 7:
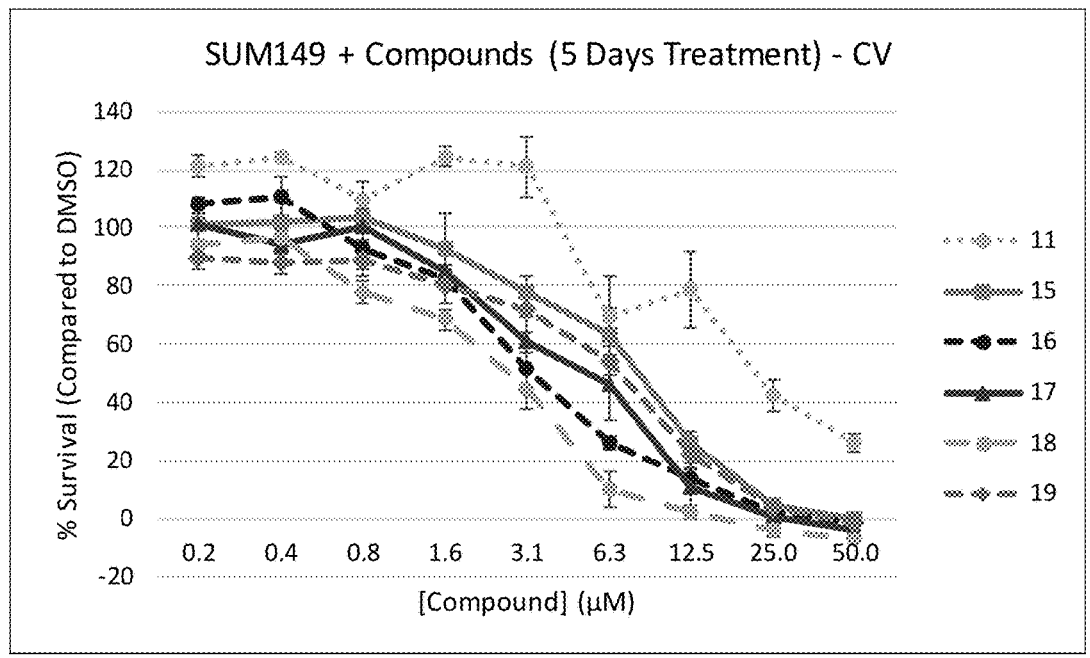
FIG. 7 depicts the percent survival of SUM149 breast cancer cells in the crystal violet assay when treated with varying concentrations of compounds described herein.
Figure 8:
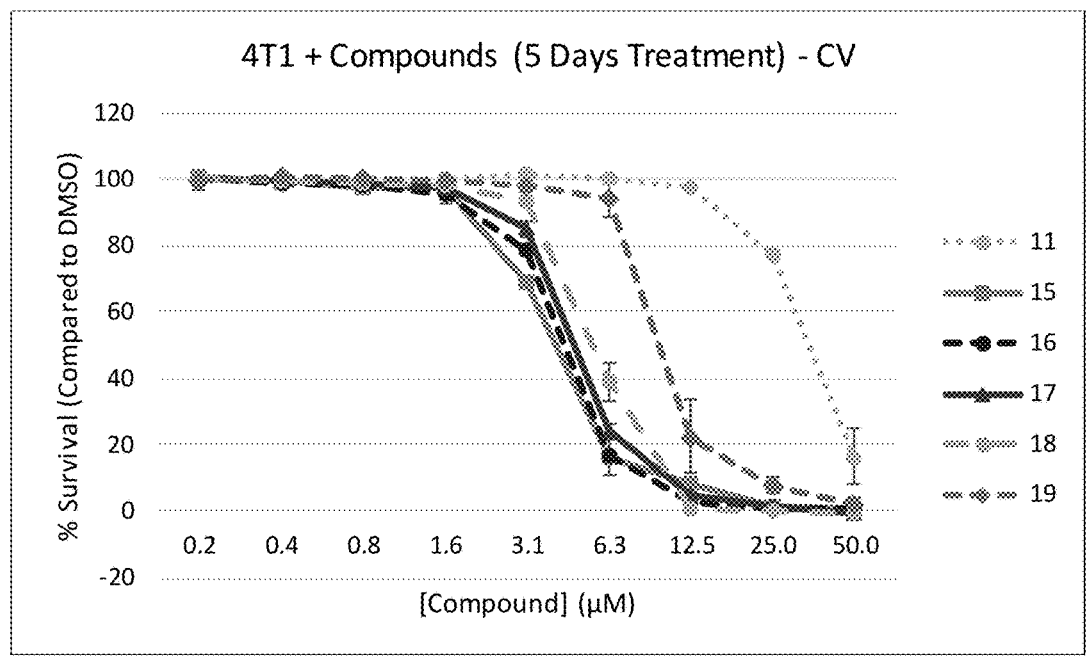
FIG. 8 depicts the percent survival of 4T1 breast cancer cells in the crystal violet assay when treated with varying concentrations of compounds described herein.

As used in the specification and appended claims, unless specified to the contrary, the following terms have the meaning indicated:

"Amino" refers to the —$NH_2$ radical.
"Cyano" refers to the —CN radical.
"Formyl" refers to the —C(O)H radical.
"Hydroxy" refers to the —OH radical.
"Nitro" refers to the —$NO_2$ radical.
"Oxo" refers to the =O substituent.
"Thioxo" refers to the =S substituent.
"Trifluoromethyl" refers to the —$CF_3$ radical.
"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. When specifically stated in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)$OR^{20}$, —C(O)$N(R^{20})_2$, —$N(R^{20})C(O)OR^{22}$, —$N(R^{20})C(O)R^{22}$, —$N(R^{20})S(O)_pR^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., methylene, ethylene, propylene, n-butylene, and the like. The alkylene chain may optionally contain one or more heteroatoms wherein a carbon in the alkylene chain is replaced with a heteroatom selected from oxygen, nitrogen or sulfur. The alkylene chain is attached to the rest of the molecule through a single bond and to the radical group through a single bond or is attached to two parts of the molecule through a single bond at each point of attachment. When specifically stated in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)$OR^{20}$, —C(O)$N(R^{20})_2$, —$N(R^{20})C(O)OR^{22}$, —$N(R^{20})C(O)R^{22}$, —$N(R^{20})S(O)_pR^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{21}$—$OR^{20}$, $R^{21}$—OC(O)—$R^{20}$, $R^{21}$—$N(R^{20})_2$, —$R^{21}$—C(O)$R^{20}$, —$R^{21}$C(O)$OR^{20}$, —$R^{21}$—C(O)$N(R^{20})_2$, —$R^{21}$—$N(R^{20})C(O)OR^{22}$, —$R^{21}$—$N(R^{20})C(O)R^{22}$, —$R^{21}$—N($R^{20}$)S(O)$_pR^{22}$ (where p is 1 to 2), —$R^{21}$—N=C($OR^{20}$)$R^{20}$, —$R^{21}$—S(O)$_pOR^{22}$ (where p is 1 to 2), —$R^{21}$—S(O)$_tR^{22}$ (where t is 0 to 2), and —$R^{21}$—S(O)$_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. When specifically stated in the specification, the alkylene chain part of the aralkyl radical may be optionally substituted as described above for an optionally substituted alkylene chain. When specifically stated in the specification, the aryl part of the aralkyl radical may be optionally substituted as described above for an optionally substituted aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{21}$—$OR^{20}$, $R^{21}$—OC(O)—$R^{20}$, $R^{21}$—N($R^{20}$)$_2$, —$R^{21}$—C(O)$R^{20}$, —$R^{21}$C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p R^{22}$ (where p is 1 to 2), —$R^{21}$—N=C($OR^{20}$)$R^{20}$, —$R^{21}$—S(O)$_p OR^{22}$ (where p is 1 to 2), —$R^{21}$—S(O)$_t R^{22}$ (where t is 0 to 2), and —$R^{21}$—S(O)$_p$N($R^{20}$)$_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_b R_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. When specifically stated in the specification, a heterocyclyl group may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{21}$—$OR^{20}$, $R^{21}$—OC(O)—$R^{20}$, $R^{21}$—N($R^{20}$)$_2$, —$R^{21}$—C(O)$R^{20}$, —$R^{21}$C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p R^{22}$ (where p is 1 to 2), —$R^{21}$—N=C($OR^{20}$)$R^{20}$, —$R^{21}$—S(O)$_p OR^{22}$ (where p is 1 to 2), —$R^{21}$—S(O)$_t R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heterocyclyl" refers to a heterocyclyl radical as defined above containing at least one nitrogen. The point of attachment of the N-heterocyclyl to the rest of the molecule can be through a nitrogen atom or a carbon atom in the N-heterocyclyl. When specifically stated in the specification, an N-heterocyclyl radical may be optionally substituted as described above for an optionally substituted heterocyclyl radical.

"Heterocyclylalkyl" refers to a radical of the formula —$R_b R_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkyene chain. When specifically stated in the specification, the heterocyclyl part of the heterocyclylalkyl radical may be optionally substituted as defined above for an optionally substituted heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). When specifically stated in the specification, a heteroaryl group may be optionally substituted by one or more substituents selected from the group consisting of alkyl, alkenyl, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —$R^{21}$—$OR^{20}$, $R^{21}$—OC(O)—$R^{20}$, $R^{21}$—N($R^{20}$)$_2$, —$R^{21}$—C(O)$R^{20}$, —$R^{21}$C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p$$R^{22}$ (where p is 1 to 2), —$R^{21}$—N=C($OR^{20}$)$R^{20}$, —$R^{21}$—S(O)$_p$$OR^{22}$ (where p is 1 to 2), —$R^{21}$—S(O)$_t$$R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical.

"Heteroarylalkyl" refers to a radical of the formula —$R_b$$R_i$ where $R_b$ is an alkylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Prodrugs" is meant to indicate a compound that may be converted under physiological conditions or by solvolysis to a biologically active compound of the invention. Thus, the term "prodrug" refers to a metabolic precursor of a compound described herein that is pharmaceutically acceptable. A prodrug may be inactive when administered to a subject in need thereof, but is converted in vivo to an active compound of the invention. Prodrugs are typically rapidly transformed in vivo to yield the parent compound described herein, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. In some embodiemnts, prodrugs of a compound described herein are prepared by modifying functional groups present in the compound in such a way that the modifications are cleaved, either in routine manipulation or in vivo, to the parent compound described herein. Prodrugs include compounds described herein wherein a hydroxy, amino or mercapto group is bonded to any group that, when the prodrug of the compound described herein is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds described herein and the like.

The invention disclosed herein is also meant to encompass all pharmaceutically acceptable compounds of formula (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F $^{36}$Cl, $^{123}$I, and $^{125}$I, respectively. These radiolabelled compounds could be useful to help determine or measure the effectiveness of the compounds, by characterizing, for example, the site or mode of action on the RSK, or binding affinity to pharmacologically important site of action on the RSK. Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples and Preparations as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound described herein in a detectable dose to an animal, such as rat, mouse, guinea pig, monkey, or to human, allowing sufficient time for metabolism to occur, and isolating its coversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildelife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound described herein. As used herein, the term "solvate" refers to an aggregate that comprises one or more molecules of a compound described herein with one or more molecules of solvent. In some embodiments, the solvent is water, in which case the solvate is a hydrate. Alternatively, in some embodiments, the solvent is an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some embodiments, the compound described herein is a true solvate, while in other cases, the compound described herein may merely retain adventitious water or be a mixture of water plus some adventitious solvent.

A "pharmaceutical composition" refers to a formulation of a compound described herein and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound described herein which, when administered to a mammal, preferably a human, is sufficient to effect treatment, as defined below, of RSK-mediated disease or condition in the mammal, preferably a human. The amount of a compound described herein which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving (or ameliorating) the disease or condition, i.e., causing regression of the disease or condition; or (d) relieving (or ameliorating) the symptoms resulting from the disease or condition, e.g., relieving cancer symptoms without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds described herein, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)-for amino acids. The present invention is meant to include all such possible isomers, as well as their racemic and optically pure forms. In some embodiments, optically active (+) and (−), (R)- and (S)-, or (D)- and (L)-isomers are prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposeable mirror images of one another. See, for example, Smith, M. B. and J. March, *March's Advanced Organic Chemistry: Reactions, Mechanisms, and Structure*, current edition (Wiley), for a detailed description of the structure and properties of enantiomers and stereoisomers.

A "tautomer" refers to a proton shift from one atom of a molecule to another atom of the same molecule. The present invention includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. The use of brackets in a substituent group indicates that the group enclosed within the brackets is also attached directly to the atom preceding the parenthesis.

The chemical naming protocol and structure diagrams used herein are a modified form of the I.U.P.A.C. nomenclature system, using ChemBioDraw Ultra Version 12.0 software program, wherein the compounds described herein are named herein as derivatives of a central core structure, e.g., the carboxamide structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

"Enantiomers" refer to asymmetric molecules that can exist in two different isomeric forms which have different configurations in space. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions).

The designations, "R" and "S", for the absolute configuration of an enantiomer of a compound described herein may appear as a prefix or as a suffix in the name of the compound; they may or may not be separated from the enantiomer name by a hyphen; they may or may not be hyphenated; and they may or may not be surrounded by parentheses.

"Resolution" or "resolving" when used in reference to a racemic compound or a racemic mixture of a compound described herein refers to the separation of the racemic compound or a racemic mixture into its two enantiomeric forms (i.e., (+) and (−); (R) and (S) forms).

"Enantiomeric excess" or "ee" as used herein refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purposes of this invention, the (S)-enantiomer of a compound prepared by the methods disclosed herein is considered to be "substantially free" of the corresponding (R)-enantiomer when the (S)-enantiomer is present in enantiomeric excess of greater than 80%, preferably greater than 90%, more preferably greater than 95% and most preferably greater than 99%.

EMBODIMENTS OF THE INVENTION

Of the various aspects of the invention set forth above in the Summary of the Invention, certain embodiments are preferred.

Compounds

Of the compounds of formula (I) as described above in the Summary of the Invention, one embodiment is the compounds of formula (I) wherein $R^1$ is $R^5$—C(O)N($R^6$)—, i.e., a compound having the formula (Ia):

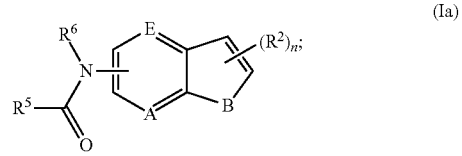

(Ia)

wherein:
n is 1 or 2;
A is —N= or —C($R^3$)=;
B is —O—, —N($R^4$)—, or —S(O)$_t$ (where t is 0, 1 or 2)-;
E is —N= or —C($R^3$)=;
each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two $R^2$, together with the adjacent carbons to which they are attached, form a fused optionally substituted 6-membered N-heterocyclyl;

each $R^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

$R^4$ is hydrogen, alkyl, haloalkyl, optionally substituted aryl or optionally substituted aralkyl;

or $R^4$, together with the nitrogen to which it is attached, and a $R^2$, together with the adjacent carbon to which it is attached, together form a fused 6-membered N-heterocyclyl of the following structure:

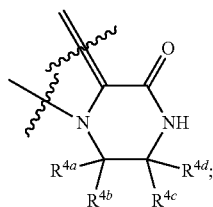

where ⁓ indicates the point of fusion and $R^{4a}$, $R^{4b}$, $R^{4c}$, and $R^{4d}$ are each independently hydrogen, alkyl, halo or haloalkyl or $R^{4a}$ and $R^{4b}$, together with the carbon to which they are both attached, form a cycloalkyl or $R^{4c}$ and $R^{4d}$, together with the carbon to which they are both attached, form a cycloalkyl, and the remaining $R^2$, if present, is selected from hydrogen, alkyl, halo or haloalkyl;

$R^5$ is optionally substituted aryl or optionally substituted N-heteroaryl; and $R^6$ is hydrogen, alkyl, haloalkyl, optionally substituted aryl or optionally substituted aralkyl.

Of this embodiment, an embodiment is a compound of formula (Ia) wherein A is —C($R^3$)═, i.e., a compound having the formula (Ia1):

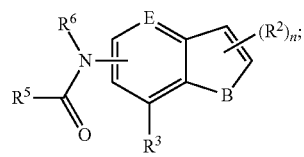

wherein:
n is 1 or 2;
B is —O—, —N($R^4$)—, or —S(O)$_t$ (where t is 0, 1 or 2)-;
E is —N═ or —C($R^3$)═;
each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two $R^2$, together with the adjacent carbons to which they are attached, form a fused optionally substituted 6-membered N-heterocyclyl;

each $R^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

$R^4$ is hydrogen, alkyl, haloalkyl, optionally substituted aryl or optionally substituted aralkyl;

or $R^4$, together with the nitrogen to which it is attached, and a $R^2$, together with the adjacent carbon to which it is attached, together form a fused 6-membered N-heterocyclyl of the following structure:

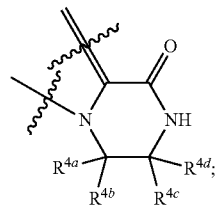

where ⁓ indicates the point of fusion and $R^{4a}$, $R^{4b}$, $R^{4c}$, and $R^{4d}$ are each independently hydrogen, alkyl, halo or haloalkyl or $R^{4a}$ and $R^{4b}$, together with the carbon to which they are both attached, form a cycloalkyl or $R^{4c}$ and $R^{4d}$, together with the carbon to which they are both attached, form a cycloalkyl, and the remaining $R^2$, if present, is selected from hydrogen, alkyl, halo or haloalkyl;

$R^5$ is optionally substituted aryl or optionally substituted N-heteroaryl; and $R^6$ is hydrogen, alkyl, haloalkyl, optionally substituted aryl or optionally substituted aralkyl.

Of this embodiment, an embodiment is a compound of formula (Ia1) wherein:
n is 1 or 2;
B is —N($R^4$)—;
E is —N═ or —C($R^3$)═;
each $R^2$ is independently hydrogen, halo, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two $R^2$, together with the adjacent carbons to which they are attached, form a fused optionally substituted 6-membered N-heterocyclyl;

each $R^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

$R^4$ is hydrogen, alkyl, haloalkyl, optionally substituted aryl or optionally substituted aralkyl;

or $R^4$, together with the nitrogen to which it is attached, and a $R^2$, together with the adjacent carbon to which it is attached, together form a fused 6-membered N-heterocyclyl of the following structure:

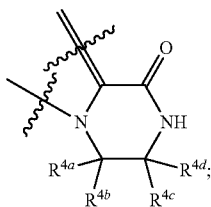

where ⁓ indicates the point of fusion and $R^{4a}$, $R^{4b}$, $R^{4c}$, and $R^{4d}$ are each independently hydrogen, alkyl, halo or haloalkyl or $R^{4a}$ and $R^{4b}$, together with the carbon to which they are both attached, form a cycloalkyl or $R^{4c}$ and $R^{4d}$, together with the carbon to which they are both attached, form a cycloalkyl, and the remaining $R^2$, if present, is selected from hydrogen, alkyl, halo or haloalkyl;

$R^5$ is optionally substituted aryl or optionally substituted N-heteroaryl; and $R^6$ is hydrogen, alkyl, haloalkyl, optionally substituted aryl or optionally substituted aralkyl.

Of this embodiment, one embodiment is a compound selected from:
1-benzyl-N-(3-(morpholinomethyl)-1H-indol-5-yl)-1H-pyrazole-4-carboxamide hydrochloride;
1-benzyl-N-(3-(morpholinomethyl)-1H-indol-6-yl)-1H-pyrazole-4-carboxamide hydrochloride;
1-benzyl-N-(3-((4-methylpiperazin-1-yl)methyl)-1H-indol-5-yl)-1H-pyrazole-4-carboxamide dihydrochloride;
1-benzyl-N-(3-((4-methylpiperazin-1-yl)methyl)-1H-indol-6-yl)-1H-pyrazole-4-carboxamide dihydrochloride;
1-benzyl-N-(2-methyl-2,3,4,5-tetrahydro-1H-pyrido[4,3-b]indol-8-yl)-1H-pyrazole-4-carboxamide hydrochloride;
(S)-1-benzyl-N-(6-methyl-9-oxo-6,7,8,9-tetrahydropyrido[2′,3′:4,5]pyrrolo[1,2-a]pyrazin-3-yl)-1H-pyrazole-4-carboxamide; and
(S)-1-benzyl-N-(6-methyl-9-oxo-6,7,8,9-tetrahydropyrido[2′,3′:4,5]pyrrolo[1,2-a]pyrazin-2-yl)-1H-pyrazole-4-carboxamide.

Another embodiment of a compound of formula (Ia1) is a compound of formula (Ia1) wherein:
n is 1 or 2;
B is —O—;
E is —N= or —C($R^3$)=;
each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;
or two $R^2$, together with the adjacent carbons to which they are attached, form a fused optionally substituted 6-membered N-heterocyclyl;
each $R^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

$R^5$ is optionally substituted aryl or optionally substituted N-heteroaryl; and $R^6$ is hydrogen, alkyl, haloalkyl, optionally substituted aryl or optionally substituted aralkyl.

Of this embodiment, an embodiment is a compound selected from:
1-benzyl-N-(3-(morpholinomethyl)benzofuran-6-yl)-1H-pyrazole-4-carboxamide hydrochloride;
1-benzyl-N-(3-(morpholinomethyl)benzofuran-5-yl)-1H-pyrazole-4-carboxamide hydrochloride;
1-benzyl-N-(3-(piperazin-1-ylmethyl)benzofuran-5-yl)-1H-pyrazole-4-carboxamide dihydrochloride;
1-benzyl-N-(3-(piperazin-1-ylmethyl)benzofuran-6-yl)-1H-pyrazole-4-carboxamide dihydrochloride; and
1-benzyl-N-(2-methyl-1,2,3,4-tetrahydrobenzofuro[3,2-c]pyridin-8-yl)-1H-pyrazole-4-carboxamide hydrochloride.

Another embodiment of a compound of formula (Ia1) is a compound of formula (Ia1) wherein:
n is 1 or 2;
B is —S(O)$_t$ (where t is 0, 1 or 2)-;
E is —N= or —C($R^3$)=;
each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;
or two $R^2$, together with the adjacent carbons to which they are attached, form a fused optionally substituted 6-membered N-heterocyclyl;
each $R^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

$R^5$ is optionally substituted aryl or optionally substituted N-heteroaryl; and $R^6$ is hydrogen, alkyl, haloalkyl, optionally substituted aryl or optionally substituted aralkyl.

Of this embodiment, an embodiment is a compound selected from:
1-benzyl-N-(3-(morpholinomethyl)benzo[b]thiophen-5-yl)-1H-pyrazole-4-carboxamide hydrochloride; and
1-benzyl-N-(3-(piperazin-1-ylmethyl)benzo[b]thiophen-5-yl)-1H-pyrazole-4-carboxamide dihydrochloride.

Of this embodiment, another embodiment is a compound of formula (Ia) wherein A is —N=, i.e., a compound having the formula (Ia2):

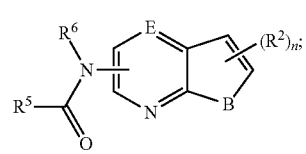

wherein:
n is 1 or 2;
B is —O—, —N($R^4$)—, or —S(O)$_t$ (where t is 0, 1 or 2)-;
E is —N= or —C($R^3$)=;
each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two $R^2$, together with the adjacent carbons to which they are attached, form a fused optionally substituted 6-membered N-heterocyclyl;

$R^3$ is hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

$R^4$ is hydrogen, alkyl, haloalkyl, optionally substituted aryl or optionally substituted aralkyl;

or $R^4$, together with the nitrogen to which it is attached, and a $R^2$, together with the adjacent carbon to which it is attached, together form a fused 6-membered N-heterocyclyl of the following structure:

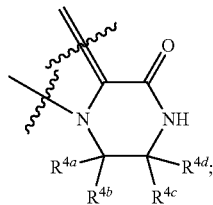

where ⁓ indicates the point of fusion and $R^{4a}$, $R^{4b}$, $R^{4c}$, and $R^{4d}$ are each independently hydrogen, alkyl, halo or haloalkyl or $R^{4a}$ and $R^{4b}$, together with the carbon to which they are both attached, form a cycloalkyl or $R^{4c}$ and $R^{4d}$, together with the carbon to which they are both attached, form a cycloalkyl, and the remaining $R^2$, if present, is selected from hydrogen, alkyl, halo or haloalkyl;

$R^5$ is optionally substituted aryl or optionally substituted N-heteroaryl; and $R^6$ is hydrogen, alkyl, haloalkyl, optionally substituted aryl or optionally substituted aralkyl.

Of this embodiment, an embodiment is a compound of formula (Ia2) wherein:

n is 1 or 2;
B is —N($R^4$)—;
E is —N= or —C($R^3$)=;

each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two $R^2$, together with the adjacent carbons to which they are attached, form a fused optionally substituted 6-membered N-heterocyclyl;

$R^3$ is hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

$R^4$ is hydrogen, alkyl, haloalkyl, optionally substituted aryl or optionally substituted aralkyl;

or $R^4$, together with the nitrogen to which it is attached, and a $R^2$, together with the adjacent carbon to which it is attached, together form a fused 6-membered N-heterocyclyl of the following structure:

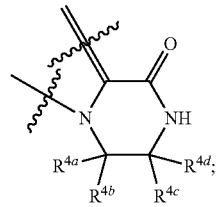

where ⁓ indicates the point of fusion and $R^{4a}$, $R^{4b}$, $R^{4c}$, and $R^{4d}$ are each independently hydrogen, alkyl, halo or haloalkyl or $R^{4a}$ and $R^{4b}$, together with the carbon to which they are both attached, form a cycloalkyl or $R^{4c}$ and $R^{4d}$, together with the carbon to which they are both attached, form a cycloalkyl, and the remaining $R^2$, if present, is selected from hydrogen, alkyl, halo or haloalkyl;

$R^5$ is optionally substituted aryl or optionally substituted N-heteroaryl; and $R^6$ is hydrogen, alkyl, haloalkyl, optionally substituted aryl or optionally substituted aralkyl.

Of this embodiment, one embodiment is a compound selected from:

(R)-1-benzyl-N-(4-methyl-1-oxo-1,2,3,4-tetrahydropyrazino[1,2-a]indol-7-yl)-1H-pyrazole-4-carboxamide;

1-benzyl-N-(1-oxo-1,2,3,4-tetrahydropyrazino[1,2-a]indol-7-yl)-1H-pyrazole-4-carboxamide;

1-benzyl-N-((9R)-9-methyl-6-oxo-5,5a,6,7,8,9-hexahydropyrido[3',2':4,5]pyrrolo[1,2-a]pyrazin-2-yl)-1H-pyrazole-4-carboxamide; and (R)-1-(3-aminobenzyl)-N-(9-methyl-6-oxo-6,7,8,9-tetrahydropyrido[3',2':4,5]pyrrolo[1,2-a]pyrazin-2-yl)-1H-pyrazole-4-carboxamide.

Another embodiment of a compound of formula (Ia2) is a compound of formula (Ia2) wherein:

n is 1 or 2;
B is —O—;
E is —N= or —C($R^3$)=;

each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two $R^2$, together with the adjacent carbons to which they are attached, form a fused optionally substituted 6-membered N-heterocyclyl;

$R^3$ is hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

$R^5$ is optionally substituted aryl or optionally substituted N-heteroaryl; and $R^6$ is hydrogen, alkyl, haloalkyl, optionally substituted aryl or optionally substituted aralkyl.

Another embodiment of a compound of formula (Ia2) is a compound of formula (Ia2) wherein:

n is 1 or 2;

B is —S(O)$_t$ (where t is 0, 1 or 2)-;

E is —N= or —C(R$^3$)=;

each R$^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two R$^2$, together with the adjacent carbons to which they are attached, form a fused optionally substituted 6-membered N-heterocyclyl;

R$^3$ is hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

R$^5$ is optionally substituted aryl or optionally substituted N-heteroaryl; and R$^6$ is hydrogen, alkyl, haloalkyl, optionally substituted aryl or optionally substituted aralkyl.

Of the compounds of formula (I) as described above in the Summary of the Invention, one embodiment is the compounds of formula (I) wherein R$^1$ is R$^7$—N(R$^6$)C(O)—, i.e., a compound having the formula (Ib):

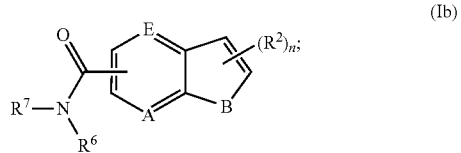
(Ib)

wherein:

n is 1 or 2;

A is —N= or —C(R$^3$)=;

B is —O—, —N(R$^4$)—, or —S(O)$_t$ (where t is 0, 1 or 2)-;

E is —N= or —C(R$^3$)=;

each R$^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two R$^2$, together with the adjacent carbons to which they are attached, form a fused optionally substituted 6-membered N-heterocyclyl;

each R$^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

R$^4$ is hydrogen, alkyl, haloalkyl, optionally substituted aryl or optionally substituted aralkyl;

or R$^4$, together with the nitrogen to which it is attached, and a R$^2$, together with the adjacent carbon to which it is attached, together form a fused 6-membered N-heterocyclyl of the following structure:

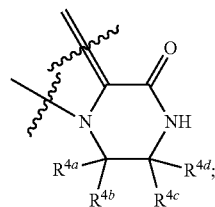

where ⌇ indicates the point of fusion and R$^{4a}$, R$^{4b}$, R$^{4c}$, and R$^{4d}$ are each independently hydrogen, alkyl, halo or haloalkyl or R$^{4a}$ and R$^{4b}$, together with the carbon to which they are both attached, form a cycloalkyl or R$^{4c}$ and R$^{4d}$, together with the carbon to which they are both attached, form a cycloalkyl, and the remaining R$^2$, if present, is selected from hydrogen, alkyl, halo or haloalkyl;

each R$^6$ is independently hydrogen, alkyl, haloalkyl, optionally substituted aryl or optionally substituted aralkyl; and R$^7$ is optionally substituted aryl or optionally substituted N-heteroaryl when E is —N=;

or R$^7$ is a monocyclic N-heteroaryl substituted with an optionally substituted aralkyl when E is —C(R$^3$)= and one R$^2$ is halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or R$^7$ is a monocyclic N-heteroaryl substituted with an optionally substituted aralkyl when E is —C(R$^3$)= and one of R$^{4a}$ and R$^{4b}$ is not methyl and the other is not hydrogen;

or R$^7$ is a monocyclic N-heteroaryl substituted with an optionally substituted aralkyl when E is —C(R$^3$)= and two of R$^{4a}$, R$^{4b}$, R$^{4c}$, and R$^{4d}$ on adjacent carbons are not both methyl and the other two are not both hydrogen;

or R$^7$ is a monocyclic N-heteroaryl substituted with an optionally substituted aralkyl when E is —C(R$^3$)= and R$^{4a}$ and R$^{4b}$, together with the carbon to which they are both attached, form a cycloalkyl or R$^{4c}$ and R$^{4d}$, together with the carbon to which they are both attached, form a cycloalkyl;

or R$^7$ is a monocyclic N-heteroaryl substituted by an aralkyl substituted with halo, haloalkyl, —CN, —NO$_2$, —N(R$^6$)$_2$, —N(R$^6$)C(O)OR$^6$, —C(O)R$^6$, —C(O)OR$^6$ or —C(O)N(R$^6$)$_2$ when E is —C(R$^3$)= and R$^{4a}$ is methyl and R$^{4b}$, R$^{4c}$, and R$^{4d}$ are each hydrogen or when E is —C(R$^3$)= and R$^{4a}$ and R$^{4c}$ are each methyl and R$^{4b}$ and R$^{4d}$ are each hydrogen;

or R$^7$ is a monocyclic N-heteroaryl substituted with optionally substituted N-heterocyclylalkyl when E is —C(R$^3$)=.

Of this embodiment, an embodiment is a compound of formula (Ib) wherein A is —C(R$^3$)=,i.e., a compound having the formula (Ib1):

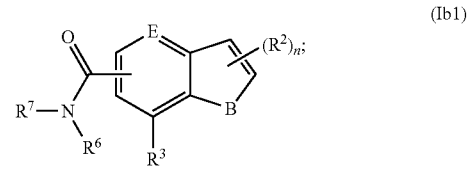
(Ib1)

wherein:

n is 1 or 2;

B is —O—, —N(R$^4$)—, or —S(O)$_t$ (where t is 0, 1 or 2)-;

E is —N═ or —C(R$^3$)═;

each R$^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two R$^2$, together with the adjacent carbons to which they are attached, form a fused optionally substituted 6-membered N-heterocyclyl;

each R$^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

R$^4$ is hydrogen, alkyl, haloalkyl, optionally substituted aryl or optionally substituted aralkyl;

or R$^4$, together with the nitrogen to which it is attached, and a R$^2$, together with the adjacent carbon to which it is attached, together form a fused 6-membered N-heterocyclyl of the following structure:

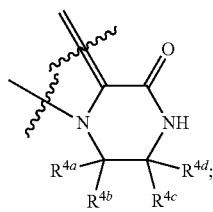

where ⌇ indicates the point of fusion and R$^{4a}$, R$^{4b}$, R$^{4c}$, and R$^{4d}$ are each independently hydrogen, alkyl, halo or haloalkyl or R$^{4a}$ and R$^{4b}$, together with the carbon to which they are both attached, form a cycloalkyl or R$^{4c}$ and R$^{4d}$, together with the carbon to which they are both attached, form a cycloalkyl, and the remaining R$^2$, if present, is selected from hydrogen, alkyl, halo or haloalkyl;

each R$^6$ is independently hydrogen, alkyl, haloalkyl, optionally substituted aryl or optionally substituted aralkyl; and R$^7$ is optionally substituted aryl or optionally substituted N-heteroaryl when E is —N═;

or R$^7$ is a monocyclic N-heteroaryl substituted with an optionally substituted aralkyl when E is —C(R$^3$)═ and one R$^2$ is halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or R$^7$ is a monocyclic N-heteroaryl substituted with an optionally substituted aralkyl when E is —C(R$^3$)═ and one of R$^{4a}$ and R$^{4b}$ is not methyl and the other is not hydrogen;

or R$^7$ is a monocyclic N-heteroaryl substituted with an optionally substituted aralkyl when E is —C(R$^3$)═ and two of R$^{4a}$, R$^{4b}$, R$^{4c}$, and R$^{4d}$ on adjacent carbons are not both methyl and the other two are not both hydrogen;

or R$^7$ is a monocyclic N-heteroaryl substituted with an optionally substituted aralkyl when E is —C(R$^3$)═ and R$^{4a}$ and R$^{4b}$, together with the carbon to which they are both attached, form a cycloalkyl or R$^{4c}$ and R$^{4d}$, together with the carbon to which they are both attached, form a cycloalkyl;

or R$^7$ is a monocyclic N-heteroaryl substituted by an aralkyl substituted with halo, haloalkyl, —CN, —NO$_2$, —N(R$^6$)$_2$, —N(R$^6$)C(O)OR$^6$, —C(O)R$^6$, —C(O)OR$^6$ or —C(O)N(R$^6$)$_2$ when E is —C(R$^3$)═ and R$^{4a}$ is methyl and R$^{4b}$, R$^{4c}$, and R$^{4d}$ are each hydrogen or when E is —C(R$^3$)═ and R$^{4a}$ and R$^{4c}$ are each methyl and R$^{4b}$ and R$^{4d}$ are each hydrogen;

or R$^7$ is a monocyclic N-heteroaryl substituted with optionally substituted N-heterocyclylalkyl when E is —C(R$^3$)═.

Of this embodiment, an embodiment is a compound of formula (Ib1) wherein:

n is 1 or 2;

B is —N(R$^4$)—;

E is —N═ or —C(R$^3$)═;

each R$^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two R$^2$, together with the adjacent carbons to which they are attached, form a fused optionally substituted 6-membered N-heterocyclyl;

each R$^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

R$^4$ is hydrogen, alkyl, haloalkyl, optionally substituted aryl or optionally substituted aralkyl;

R$^4$ is hydrogen, alkyl, haloalkyl, optionally substituted aryl or optionally substituted aralkyl;

or R$^4$, together with the nitrogen to which it is attached, and a R$^2$, together with the adjacent carbon to which it is attached, together form a fused 6-membered N-heterocyclyl of the following structure:

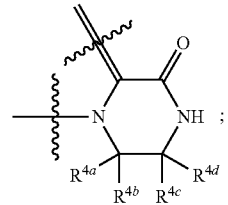

where ⌇ indicates the point of fusion and R$^{4a}$, R$^{4b}$, R$^{4c}$, and R$^{4d}$ are each independently hydrogen, alkyl, halo or haloalkyl or R$^{4a}$ and R$^{4b}$, together with the carbon to which they are both attached, form a cycloalkyl or R$^{4c}$ and R$^{4d}$, together with the carbon to which they are both attached, form a cycloalkyl, and the remaining R$^2$, if present, is selected from hydrogen, alkyl, halo or haloalkyl;

$R^7$ is optionally substituted aryl or optionally substituted N-heteroaryl when E is —N═;

or $R^7$ is a monocyclic N-heteroaryl substituted with an optionally substituted aralkyl when E is —C($R^3$)═ and one $R^2$ is halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or $R^7$ is a monocyclic N-heteroaryl substituted with an optionally substituted aralkyl when E is —C($R^3$)═ and one of $R^{4a}$ and $R^{4b}$ is not methyl and the other is not hydrogen;

or $R^7$ is a monocyclic N-heteroaryl substituted with an optionally substituted aralkyl when E is —C($R^3$)═ and two of $R^{4a}$, $R^{4b}$, $R^{4c}$, and $R^{4d}$ on adjacent carbons are not both methyl and the other two are not both hydrogen;

or $R^7$ is a monocyclic N-heteroaryl substituted with an optionally substituted aralkyl when E is —C($R^3$)═ and $R^{4a}$ and $R^{4b}$, together with the carbon to which they are both attached, form a cycloalkyl or $R^{4c}$ and $R^{4d}$, together with the carbon to which they are both attached, form a cycloalkyl;

or $R^7$ is a monocyclic N-heteroaryl substituted by an aralkyl substituted with halo, haloalkyl, —CN, —$NO_2$, —N($R^6$)$_2$, —N($R^6$)C(O)O$R^6$, —C(O)$R^6$, —C(O)O$R^6$ or —C(O)N($R^6$)$_2$ when E is —C($R^3$)═ and $R^{4a}$ is methyl and $R^{4b}$, $R^{4c}$, and $R^{4d}$ are each hydrogen or when E is —C($R^3$)═ and $R^{4a}$ and $R^{4c}$ are each methyl and $R^{4b}$ and $R^{4d}$ are each hydrogen;

or $R^7$ is a monocyclic N-heteroaryl substituted with optionally substituted N-heterocyclylalkyl when E is —C($R^3$)═.

Of this embodiment, one embodiment is a compound selected from:

(S)—N-(1-benzyl-1H-pyrazol-4-yl)-6-methyl-9-oxo-6,7,8,9-tetrahydropyrido[2',3':4,5]pyrrolo[1,2-a]pyrazine-3-carboxamide; and (S)—N-(1-benzyl-1H-pyrazol-4-yl)-6-methyl-9-oxo-6,7,8,9-tetrahydropyrido[2',3':4,5]pyrrolo[1,2-a]pyrazine-2-carboxamide.

Another embodiment of a compound of formula (Ib1) is a compound of formula (Ib1) wherein:

n is 1 or 2;
B is —O—;
E is —N═ or —C($R^3$)═;
each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;
or two $R^2$, together with the adjacent carbons to which they are attached, form a fused optionally substituted 6-membered N-heterocyclyl;
each $R^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;
each $R^6$ is independently hydrogen, alkyl, haloalkyl, optionally substituted aryl or optionally substituted aralkyl; and $R^7$ is optionally substituted aryl or optionally substituted N-heteroaryl when E is —N═;

or $R^7$ is a monocyclic N-heteroaryl substituted with an optionally substituted aralkyl when E is —C($R^3$)═ and one $R^2$ is halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or $R^7$ is a monocyclic N-heteroaryl substituted with an optionally substituted aralkyl when E is —C($R^3$)═ and one of $R^{4a}$ and $R^{4b}$ is not methyl and the other is not hydrogen;

or $R^7$ is a monocyclic N-heteroaryl substituted with an optionally substituted aralkyl when E is —C($R^3$)═ and two of $R^{4a}$, $R^{4b}$, $R^{4c}$, and $R^{4d}$ on adjacent carbons are not both methyl and the other two are not both hydrogen;

or $R^7$ is a monocyclic N-heteroaryl substituted with an optionally substituted aralkyl when E is —C($R^3$)═ and $R^{4a}$ and $R^{4b}$, together with the carbon to which they are both attached, form a cycloalkyl or $R^{4c}$ and $R^{4d}$, together with the carbon to which they are both attached, form a cycloalkyl;

or $R^7$ is a monocyclic N-heteroaryl substituted by an aralkyl substituted with halo, haloalkyl, —CN, —$NO_2$, —N($R^6$)$_2$, —N($R^6$)C(O)O$R^6$, —C(O)$R^6$, —C(O)O$R^6$ or —C(O)N($R^6$)$_2$ when E is —C($R^3$)═ and $R^{4a}$ is methyl and $R^{4b}$, $R^{4c}$, and $R^{4d}$ are each hydrogen or when E is —C($R^3$)═ and $R^{4a}$ and $R^{4c}$ are each methyl and $R^{4b}$ and $R^{4d}$ are each hydrogen;

or $R^7$ is a monocyclic N-heteroaryl substituted with optionally substituted N-heterocyclylalkyl when E is —C($R^3$)═.

Another embodiment of a compound of formula (Ib1) is a compound of formula (Ib1) wherein:

n is 1 or 2;
B is —S(O)$_t$— (where t is 0, 1 or 2)-;
E is —N═ or —C($R^3$)═;
each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;
or two $R^2$, together with the adjacent carbons to which they are attached, form a fused optionally substituted 6-membered N-heterocyclyl;
each $R^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;
each $R^6$ is independently hydrogen, alkyl, haloalkyl, optionally substituted aryl or optionally substituted aralkyl; and
$R^7$ is optionally substituted aryl or optionally substituted N-heteroaryl when E is —N═;

or $R^7$ is a monocyclic N-heteroaryl substituted with an optionally substituted aralkyl when E is —C($R^3$)═ and one $R^2$ is halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or R⁷ is a monocyclic N-heteroaryl substituted with an optionally substituted aralkyl when E is —C(R³)═ and one of R⁴ᵃ and R⁴ᵇ is not methyl and the other is not hydrogen;

or R⁷ is a monocyclic N-heteroaryl substituted with an optionally substituted aralkyl when E is —C(R³)═ and two of R⁴ᵃ, R⁴ᵇ, R⁴ᶜ, and R⁴ᵈ on adjacent carbons are not both methyl and the other two are not both hydrogen;

or R⁷ is a monocyclic N-heteroaryl substituted with an optionally substituted aralkyl when E is —C(R³)═ and R⁴ᵃ and R⁴ᵇ, together with the carbon to which they are both attached, form a cycloalkyl or R⁴ᶜ and R⁴ᵈ, together with the carbon to which they are both attached, form a cycloalkyl;

or R⁷ is a monocyclic N-heteroaryl substituted by an aralkyl substituted with halo, haloalkyl, —CN, —NO₂, —N(R⁶)₂, —N(R⁶)C(O)OR⁶, —C(O)R⁶, —C(O)OR⁶ or —C(O)N(R⁶)₂ when E is —C(R³)═ and R⁴ᵃ is methyl and R⁴ᵇ, R⁴ᶜ, and R⁴ᵈ are each hydrogen or when E is —C(R³)═ and R⁴ᵃ and R⁴ᶜ are each methyl and R⁴ᵇ and R⁴ᵈ are each hydrogen;

or R⁷ is a monocyclic N-heteroaryl substituted with optionally substituted N-heterocyclylalkyl when E is —C(R³)═.

Of this embodiment, another embodiment is a compound of formula (Ib) wherein A is —N═, i.e., a compound having the formula (Ib2):

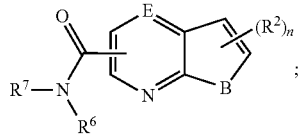

wherein:
n is 1 or 2;
B is —O—, —N(R⁴)—, or —S(O)ₜ (where t is 0, 1 or 2)-;
E is —N═ or —C(R³)═;
each R² is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two R², together with the adjacent carbons to which they are attached, form a fused optionally substituted 6-membered N-heterocyclyl;

R³ is hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

R⁴ is hydrogen, alkyl, haloalkyl, optionally substituted aryl or optionally substituted aralkyl;

or R⁴, together with the nitrogen to which it is attached, and a R², together with the adjacent carbon to which it is attached, together form a fused 6-membered N-heterocyclyl of the following structure:

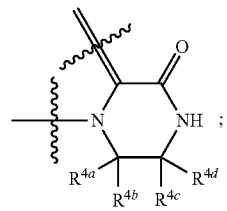

where ⁓ indicates the point of fusion and R⁴ᵃ, R⁴ᵇ, R⁴ᶜ, and R⁴ᵈ are each independently hydrogen, alkyl, halo or haloalkyl or R⁴ᵃ and R⁴ᵇ, together with the carbon to which they are both attached, form a cycloalkyl or R⁴ᶜ and R⁴ᵈ, together with the carbon to which they are both attached, form a cycloalkyl, and the remaining R², if present, is selected from hydrogen, alkyl, halo or haloalkyl;

each R⁶ is independently hydrogen, alkyl, haloalkyl, optionally substituted aryl or optionally substituted aralkyl;

R⁷ is optionally substituted aryl or optionally substituted N-heteroaryl when E is —N═;

or R⁷ is a monocyclic N-heteroaryl substituted with an optionally substituted aralkyl when E is —C(R³)═ and one R² is halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or R⁷ is a monocyclic N-heteroaryl substituted with an optionally substituted aralkyl when E is —C(R³)═ and one of R⁴ᵃ and R⁴ᵇ is not methyl and the other is not hydrogen;

or R⁷ is a monocyclic N-heteroaryl substituted with an optionally substituted aralkyl when E is —C(R³)═ and two of R⁴ᵃ, R⁴ᵇ, R⁴ᶜ, and R⁴ᵈ on adjacent carbons are not both methyl and the other two are not both hydrogen;

or R⁷ is a monocyclic N-heteroaryl substituted with an optionally substituted aralkyl when E is —C(R³)═ and R⁴ᵃ and R⁴ᵇ, together with the carbon to which they are both attached, form a cycloalkyl or R⁴ᶜ and R⁴ᵈ, together with the carbon to which they are both attached, form a cycloalkyl;

or R⁷ is a monocyclic N-heteroaryl substituted by an aralkyl substituted with halo, haloalkyl, —CN, —NO₂, —N(R⁶)₂, —N(R⁶)C(O)OR⁶, —C(O)R⁶, —C(O)OR⁶ or —C(O)N(R⁶)₂ when E is —C(R³)═ and R⁴ᵃ is methyl and R⁴ᵇ, R⁴ᶜ, and R⁴ᵈ are each hydrogen or when E is —C(R³)═ and R⁴ᵃ and R⁴ᶜ are each methyl and R⁴ᵇ and R⁴ᵈ are each hydrogen;

or R⁷ is a monocyclic N-heteroaryl substituted with optionally substituted N-heterocyclylalkyl when E is —C(R³)═.

Of this embodiment, an embodiment is a compound of formula (Ib2) wherein:
n is 1 or 2;
B is —N(R⁴)—;
E is —N═ or —C(R³)═;
each R² is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two R² together with the adjacent carbons to which they are attached, form a fused optionally substituted 6-membered N-heterocyclyl;

R³ is hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

R⁴ is hydrogen, alkyl, haloalkyl, optionally substituted aryl or optionally substituted aralkyl;

or R⁴, together with the nitrogen to which it is attached, and a R², together with the adjacent carbon to which it is attached, together form a fused 6-membered N-heterocyclyl of the following structure:

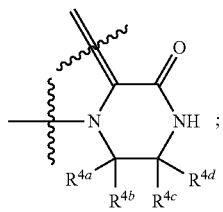

where ⁓ indicates the point of fusion and R⁴ᵃ, R⁴ᵇ, R⁴ᶜ, and R⁴ᵈ are each independently hydrogen, alkyl, halo or haloalkyl or R⁴ᵃ and R⁴ᵇ, together with the carbon to which they are both attached, form a cycloalkyl or R⁴ᶜ and R⁴ᵈ, together with the carbon to which they are both attached, form a cycloalkyl, and the remaining R², if present, is selected from hydrogen, alkyl, halo or haloalkyl;

each R⁶ is independently hydrogen, alkyl, haloalkyl, optionally substituted aryl or optionally substituted aralkyl; and R⁷ is optionally substituted aryl or optionally substituted N-heteroaryl when E is —N=;

or R⁷ is a monocyclic N-heteroaryl substituted with an optionally substituted aralkyl when E is —C(R³)= and one R² is halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or R⁷ is a monocyclic N-heteroaryl substituted with an optionally substituted aralkyl when E is —C(R³)= and one of R⁴ᵃ and R⁴ᵇ is not methyl and the other is not hydrogen;

or R⁷ is a monocyclic N-heteroaryl substituted with an optionally substituted aralkyl when E is —C(R³)= and two of R⁴ᵃ, R⁴ᵇ, R⁴ᶜ, and R⁴ᵈ on adjacent carbons are not both methyl and the other two are not both hydrogen;

or R⁷ is a monocyclic N-heteroaryl substituted with an optionally substituted aralkyl when E is —C(R³)= and R⁴ᵃ and R⁴ᵇ, together with the carbon to which they are both attached, form a cycloalkyl or R⁴ᶜ and R⁴ᵈ, together with the carbon to which they are both attached, form a cycloalkyl;

or R⁷ is a monocyclic N-heteroaryl substituted by an aralkyl substituted with halo, haloalkyl, —CN, —NO₂, —N(R⁶)₂, —N(R⁶)C(O)OR⁶, —C(O)R⁶, —C(O)OR⁶ or —C(O)N(R⁶)₂ when E is —C(R³)= and R⁴ᵃ is methyl and R⁴ᵇ, R⁴ᶜ, and R⁴ᵈ are each hydrogen or when E is —C(R³)= and R⁴ᵃ and R⁴ᶜ are each methyl and R⁴ᵇ and R⁴ᵈ are each hydrogen;

or R⁷ is a monocyclic N-heteroaryl substituted with optionally substituted N-heterocyclylalkyl when E is —C(R³)=.

Of this embodiment, one embodiment is a compound selected from:

(R)—N-(1-(3-aminobenzyl)-1H-pyrazol-4-yl)-9-methyl-6-oxo-6,7,8,9-tetrahydropyrido[3',2':4,5]pyrrolo[1,2-a]pyrazine-2-carboxamide;

(R)—N-(1-(2-aminobenzyl)-1H-pyrazol-4-yl)-9-methyl-6-oxo-6,7,8,9-tetrahydropyrido[3',2':4,5]pyrrolo[1,2-a]pyrazine-2-carboxamide;

(R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide;

(R)—N-(1-benzyl-1H-pyrazol-4-yl)-5-fluoro-9-methyl-6-oxo-6,7,8,9-tetrahydropyrido[3',2':4,5]pyrrolo[1,2-a]pyrazine-2-carboxamide;

(R)—N-(1-benzyl-1H-pyrazol-4-yl)-9-isopropyl-6-oxo-6,7,8,9-tetrahydropyrido[3',2':4,5]pyrrolo[1,2-a]pyrazine-2-carboxamide;

(S)—N-(1-benzyl-1H-pyrazol-4-yl)-9-trifluoromethyl-6-oxo-6,7,8,9-tetrahydropyrido[3',2':4,5]pyrrolo[1,2-a]pyrazine-2-carboxamide;

N-(1-benzyl-1H-pyrazol-4-yl)-6'-oxo-7',8'-dihydro-6'H-spiro[cyclopropane-1,9'-pyrido[3',2':4,5]pyrrolo[1,2-a]pyrazine]-2'-carboxamide;

(R)—N-(1-(4-methylpiperazinyl)-1H-pyrazol-4-yl)-9-methyl-6-oxo-6,7,8,9-tetrahydropyrido[3',2':4,5]pyrrolo[1,2-a]pyrazine-2-carboxamide;

(R)—N-(1-benzyl-1H-pyrazol-4-yl)-5-chloro-9-methyl-6-oxo-6,7,8,9-tetrahydropyrido[3',2':4,5]pyrrolo[1,2-a]pyrazine-2-carboxamide;

(S)—N-(1-benzyl-1H-pyrazol-4-yl)-9-isopropyl-6-oxo-6,7,8,9-tetrahydropyrido[3',2':4,5]pyrrolo[1,2-a]pyrazine-2-carboxamide;

(R)—N-(1-benzyl-1H-pyrazol-4-yl)-9-trifluoromethyl-6-oxo-6,7,8,9-tetrahydropyrido[3',2':4,5]pyrrolo[1,2-a]pyrazine-2-carboxamide;

N-(1-benzyl-1H-pyrazol-4-yl)-9,9-dimethyl-6-oxo-6,7,8,9-tetrahydropyrido[3',2':4,5]pyrrolo[1,2-a]pyrazine-2-carboxamide;

(R)-5-fluoro-9-methyl-N-(1-((4-methylpiperazin-1-yl)methyl)-1H-pyrazol-4-yl)-6-oxo-6,7,8,9-tetrahydropyrido[3',2':4,5]pyrrolo[1,2-a]pyrazine-2-carboxamide;

(R)-5-fluoro-9-methyl-N-(1-((1-methylpiperidin-4-yl)methyl)-1H-pyrazol-4-yl)-6-oxo-6,7,8,9-tetrahydropyrido[3',2':4,5]pyrrolo[1,2-a]pyrazine-2-carboxamide; and (R)—N-(1-benzyl-1H-pyrazol-4-yl)-6-methyl-9-oxo-6,7,8,9-tetrahydropyrrolo[1,5-a:2,3-b']dipyrazine-3-carboxamide.

Another embodiment of a compound of formula (Ib2) is a compound of formula (Ib2) wherein:

n is 1 or 2;

B is —O—;

E is —N= or —C(R³)=;

each R² is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two R², together with the adjacent carbons to which they are attached, form a fused optionally substituted 6-membered N-heterocyclyl;

$R^3$ is hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

each $R^6$ is independently hydrogen, alkyl, haloalkyl, optionally substituted aryl or optionally substituted aralkyl; and $R^7$ is optionally substituted aryl or optionally substituted N-heteroaryl when E is —N=;

or $R^7$ is a monocyclic N-heteroaryl substituted with an optionally substituted aralkyl when E is —C($R^3$)= and one $R^2$ is halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or $R^7$ is a monocyclic N-heteroaryl substituted with an optionally substituted aralkyl when E is —C($R^3$)= and one of $R^{4a}$ and $R^{4b}$ is not methyl and the other is not hydrogen;

or $R^7$ is a monocyclic N-heteroaryl substituted with an optionally substituted aralkyl when E is —C($R^3$)= and two of $R^{4a}$, $R^{4b}$, $R^{4c}$, and $R^{4d}$ on adjacent carbons are not both methyl and the other two are not both hydrogen;

or $R^7$ is a monocyclic N-heteroaryl substituted with an optionally substituted aralkyl when E is —C($R^3$)= and $R^{4a}$ and $R^{4b}$, together with the carbon to which they are both attached, form a cycloalkyl or $R^{4c}$ and $R^{4d}$, together with the carbon to which they are both attached, form a cycloalkyl;

or $R^7$ is a monocyclic N-heteroaryl substituted by an aralkyl substituted with halo, haloalkyl, —CN, —NO$_2$, —N($R^6$)$_2$, —N($R^6$)C(O)O$R^6$, —C(O)$R^6$, —C(O)O$R^6$ or —C(O)N($R^6$)$_2$ when E is —C($R^3$)= and $R^{4a}$ is methyl and $R^{4b}$, $R^{4c}$, and $R^{4d}$ are each hydrogen or when E is —C($R^3$)= and $R^{4a}$ and $R^{4c}$ are each methyl and $R^{4b}$ and $R^{4d}$ are each hydrogen;

or $R^7$ is a monocyclic N-heteroaryl substituted with optionally substituted N-heterocyclylalkyl when E is —C($R^3$)=.

Another embodiment of a compound of formula (Ib2) is a compound of formula (Ib2) wherein:

n is 1 or 2;

B is —S(O)$_t$ (where t is 0, 1 or 2)-;

E is —N= or —C($R^3$)=;

each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two $R^2$, together with the adjacent carbons to which they are attached, form a fused optionally substituted 6-membered N-heterocyclyl;

$R^3$ is hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

each $R^6$ is independently hydrogen, alkyl, haloalkyl, optionally substituted aryl or optionally substituted aralkyl; and $R^7$ is optionally substituted aryl or optionally substituted N-heteroaryl when E is —N=;

or $R^7$ is a monocyclic N-heteroaryl substituted with an optionally substituted aralkyl when E is —C($R^3$)= and one $R^2$ is halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or $R^7$ is a monocyclic N-heteroaryl substituted with an optionally substituted aralkyl when E is —C($R^3$)= and one of $R^{4a}$ and $R^{4b}$ is not methyl and the other is not hydrogen;

or $R^7$ is a monocyclic N-heteroaryl substituted with an optionally substituted aralkyl when E is —C($R^3$)= and two of $R^{4a}$, $R^{4b}$, $R^{4c}$, and $R^{4d}$ on adjacent carbons are not both methyl and the other two are not both hydrogen;

or $R^7$ is a monocyclic N-heteroaryl substituted with an optionally substituted aralkyl when E is —C($R^3$)= and $R^{4a}$ and $R^{4b}$, together with the carbon to which they are both attached, form a cycloalkyl or $R^{4c}$ and $R^{4d}$, together with the carbon to which they are both attached, form a cycloalkyl;

or $R^7$ is a monocyclic N-heteroaryl substituted by an aralkyl substituted with halo, haloalkyl, —CN, —NO$_2$, —N($R^6$)$_2$, —N($R^6$)C(O)O$R^6$, —C(O)$R^6$, —C(O)O$R^6$ or —C(O)N($R^6$)$_2$ when E is —C($R^3$)= and $R^{4a}$ is methyl and $R^{4b}$, $R^{4c}$, and $R^{4d}$ are each hydrogen or when E is —C($R^3$)= and $R^{4a}$ and $R^{4c}$ are each methyl and $R^{4b}$ and $R^{4d}$ are each hydrogen;

or $R^7$ is a monocyclic N-heteroaryl substituted with optionally substituted N-heterocyclylalkyl when E is —C($R^3$)=.

Of the compounds of formula (I) as described above in the Summary of the Invention, one embodiment is the compounds of formula (I) wherein $R^1$ is $R^5$—N($R^6$)C(O)N($R^6$)—, i.e., a compound having the formula (Ic):

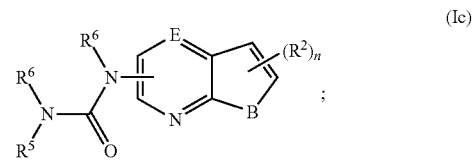

wherein:

n is 1 or 2;

A is —N= or —C($R^3$)=;

B is —O—, —N($R^4$)—, or —S(O)$_t$ (where t is 0, 1 or 2)-;

E is —N= or —C($R^3$)=;

each $R^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two $R^2$, together with the adjacent carbons to which they are attached, form a fused optionally substituted 6-membered N-heterocyclyl;

each $R^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

R$^4$ is hydrogen, alkyl, haloalkyl, optionally substituted aryl or optionally substituted aralkyl;

or R$^4$, together with the nitrogen to which it is attached, and a R$^2$, together with the adjacent carbon to which it is attached, together form a fused 6-membered N-heterocyclyl of the following structure:

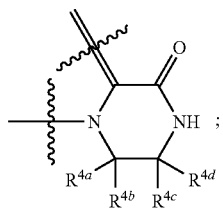

where ∼∼∼ indicates the point of fusion and R$^{4a}$, R$^{4b}$, R$^{4c}$, and R$^{4d}$ are each independently hydrogen, alkyl, halo or haloalkyl or R$^{4a}$ and R$^{4b}$, together with the carbon to which they are both attached, form a cycloalkyl or R$^{4c}$ and R$^{4d}$, together with the carbon to which they are both attached, form a cycloalkyl, and the remaining R$^2$, if present, is selected from hydrogen, alkyl, halo or haloalkyl;

R$^5$ is optionally substituted aryl or optionally substituted N-heteroaryl; and each R$^6$ is independently hydrogen, alkyl, haloalkyl, optionally substituted aryl or optionally substituted aralkyl.

Of this embodiment, one embodiment is a compound which is (R)-1-(1-benzyl-1H-pyrazol-4-yl)-3-(9-methyl-6-oxo-6,7,8,9-tetrahydropyrido[3',2':4,5]pyrrolo[1,2-a]pyrazin-2-yl)urea.

Of the compounds of formula (I) as described above in the Summary of the Invention, one embodiment is the compounds of formula (I) wherein R$^1$ is R$^1$ is R$^5$—N(R$^6$)C(=NR$^6$)N(R$^6$)—, i.e., a compound having the formula (Id):

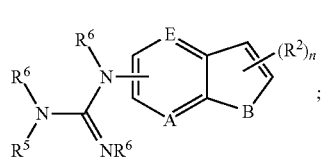

wherein:
n is 1 or 2;
A is —N= or —C(R$^3$)=;
B is —O—, —N(R$^4$)—, or —S(O)$_t$ (where t is 0, 1 or 2)-;
E is —N= or —C(R$^3$)=;
each R$^2$ is independently hydrogen, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two R$^2$, together with the adjacent carbons to which they are attached, form a fused optionally substituted 6-membered N-heterocyclyl;

each R$^3$ is independently hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

R$^4$ is hydrogen, alkyl, haloalkyl, optionally substituted aryl or optionally substituted aralkyl;

or R$^4$, together with the nitrogen to which it is attached, and a R$^2$, together with the adjacent carbon to which it is attached, together form a fused 6-membered N-heterocyclyl of the following structure:

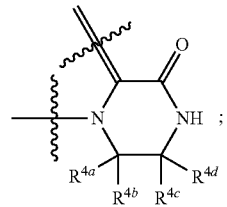

where ∼∼∼ indicates the point of fusion and R$^{4a}$, R$^{4b}$, R$^{4c}$, and R$^{4d}$ are each independently hydrogen, alkyl, halo or haloalkyl or R$^{4a}$ and R$^{4b}$, together with the carbon to which they are both attached, form a cycloalkyl or R$^{4c}$ and R$^{4d}$, together with the carbon to which they are both attached, form a cycloalkyl, and the remaining R$^2$, if present, is selected from hydrogen, alkyl, halo or haloalkyl;

R$^5$ is optionally substituted aryl or optionally substituted N-heteroaryl; and each R$^6$ is independently hydrogen, alkyl, haloalkyl, optionally substituted aryl or optionally substituted aralkyl.

Of this embodiment, one embodiment is a compound which is (R)-1-(1-benzyl-1H-pyrazol-4-yl)-3-(9-methyl-6-oxo-6,7,8,9-tetrahydropyrido[3',2':4,5]pyrrolo[1,2-a]pyrazin-2-yl)guanidine.

In another aspect is a compound of formula (II) having the structure:

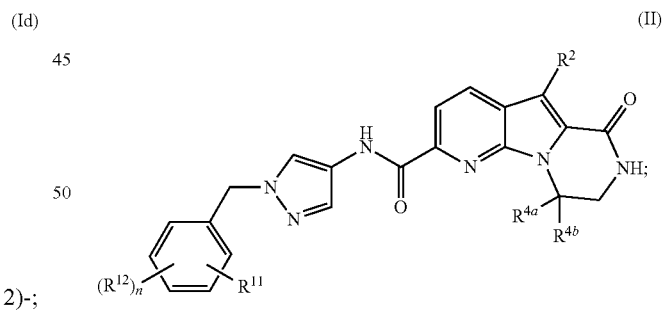

wherein:
R$^2$ is independently hydrogen, halo, C$_{1-6}$alkyl, or C$_{1-6}$haloalkyl;

R$^{4a}$ and R$^{4b}$ are each independently hydrogen, halo, C$_{1-6}$alkyl, or C$_{1-6}$haloalkyl; or R$^{4a}$ and R$^{4b}$, together with the carbon to which they are both attached, form a cycloalkyl;

each R$^6$ is independently hydrogen or C$_{1-6}$alkyl;

R$^{11}$ is halo, C$_{1-6}$haloalkyl, —N(R$^6$)$_2$, —C$_{1-6}$alkyl-N(R$^6$)$_2$, or —C(O)N(R$^6$)$_2$;

each R$^{12}$ is independently —OH, —CN, halo, C$_{1-6}$alkyl, C$_{1-6}$haloalkyl, C$_{1-6}$alkoxy, C$_{1-6}$haloalkoxy, —N(R$^6$)$_2$, —$C_{1-6}$alkyl-$N(R^6)_2$, —$C(O)R^6$, —$C(O)OR^6$, —$C(O)N(R^6)_2$, aryl, aralkyl, cycloalkyl, heterocyclyl, or heteroaryl; and n is 0, 1, 2, 3, or 4;

as an individual stereoisomer, enantiomer or tautomer thereof or a mixture thereof;

or a pharmaceutically acceptable salt, solvate, or prodrug thereof.

In some embodiments is a compound of formula (II) wherein $R^2$ is hydrogen. In some embodiments is a compound of formula (II) wherein $R^2$ is halo. In some embodiments is a compound of formula (II) wherein $R^2$ is —F. In some embodiments is a compound of formula (II) wherein $R^2$ is —Cl. In some embodiments is a compound of formula (II) wherein $R^2$ is $C_{1-6}$alkyl. In some embodiments is a compound of formula (II) wherein $R^2$ is —$CH_3$. In some embodiments is a compound of formula (II) wherein $R^2$ is —$CH_2CH_3$. In some embodiments is a compound of formula (II) wherein $R^2$ is —$CH(CH_3)_2$. In some embodiments is a compound of formula (II) wherein $R^2$ is $C_{1-6}$haloalkyl. In some embodiments is a compound of formula (II) wherein $R^2$ is —$CF_3$.

In some embodiments is a compound of formula (II) wherein $R^{4a}$ is hydrogen. In some embodiments is a compound of formula (II) wherein $R^{4a}$ is halo. In some embodiments is a compound of formula (II) wherein $R^{4a}$ is —F. In some embodiments is a compound of formula (II) wherein $R^{4a}$ is —Cl. In some embodiments is a compound of formula (II) wherein $R^{4a}$ is $C_{1-6}$alkyl. In some embodiments is a compound of formula (II) wherein $R^{4a}$ is —$CH_3$. In some embodiments is a compound of formula (II) wherein $R^{4a}$ is —$CH_2CH_3$. In some embodiments is a compound of formula (II) wherein $R^{4a}$ is —$CH(CH_3)_2$. In some embodiments is a compound of formula (II) wherein $R^{4b}$ is hydrogen. In some embodiments is a compound of formula (II) wherein $R^{4b}$ is halo. In some embodiments is a compound of formula (II) wherein $R^{4b}$ is —F. In some embodiments is a compound of formula (II) wherein $R^{4b}$ is —Cl. In some embodiments is a compound of formula (II) wherein $R^{4b}$ is $C_{1-6}$alkyl. In some embodiments is a compound of formula (II) wherein $R^{4b}$ is —$CH_3$. In some embodiments is a compound of formula (II) wherein $R^{4b}$ is —$CH_2CH_3$. In some embodiments is a compound of formula (II) wherein $R^{4b}$ is —$CH(CH_3)_2$. In some embodiments is a compound of formula (II) wherein $R^{4b}$ is $C_{1-6}$haloalkyl. In some embodiments is a compound of formula (II) wherein $R^{4b}$ is —$CF_3$. In some embodiments is a compound of formula (II) wherein $R^{4a}$ is $C_{1-6}$alkyl and $R^{4b}$ is hydrogen. In some embodiments is a compound of formula (II) wherein $R^{4a}$ is —$CH_3$ and $R^{4b}$ is hydrogen. In some embodiments is a compound of formula (II) wherein $R^{4a}$ and $R^{4b}$, together with the carbon to which they are both attached, form a cycloalkyl. In some embodiments is a compound of formula (II) wherein $R^{4a}$ and $R^{4b}$, together with the carbon to which they are both attached, form a cyclopropyl. In some embodiments is a compound of formula (II) wherein $R^{4a}$ and $R^{4b}$, together with the carbon to which they are both attached, form a cyclobutyl. In some embodiments is a compound of formula (II) wherein $R^{4a}$ and $R^{4b}$, together with the carbon to which they are both attached, form a cyclopentyl. In some embodiments is a compound of formula (II) wherein $R^{4a}$ and $R^{4b}$, together with the carbon to which they are both attached, form a cyclohexyl.

In some embodiments is a compound of formula (II) wherein each $R^{12}$ is independently —OH, —CN, halo, $C_{1-6}$alkyl, $C_{1-6}$haloalkyl, $C_{1-6}$alkoxy, $C_{1-6}$haloalkoxy, —$N(R^6)_2$, —$C_{1-6}$alkyl-$N(R^6)_2$, —$C(O)R^6$, —$C(O)OR^6$, or —$C(O)N(R^6)_2$. In some embodiments is a compound of formula (II) wherein each $R^{12}$ is independently halo, $C_{1-6}$alkyl, —$N(R^6)_2$, —$C_{1-6}$alkyl-$N(R^6)_2$, or $C_{1-6}$haloalkyl. In some embodiments is a compound of formula (II) wherein $R^{12}$ is halo. In some embodiments is a compound of formula (II) wherein $R^{12}$ is —F. In some embodiments is a compound of formula (II) wherein $R^{12}$ is —Cl. In some embodiments is a compound of formula (II) wherein $R^{12}$ is $C_{1-6}$haloalkyl. In some embodiments is a compound of formula (II) wherein $R^{12}$ is —$CF_3$. In some embodiments is a compound of formula (II) wherein $R^{12}$ is —$N(R^6)_2$. In some embodiments is a compound of formula (II) wherein $R^{12}$ is —$NH_2$. In some embodiments is a compound of formula (II) wherein $R^{12}$ is —$C_{1-6}$alkyl-$N(R^6)_2$. In some embodiments is a compound of formula (II) wherein $R^{12}$ is —$CH_2N(R^6)_2$. In some embodiments is a compound of formula (II) wherein $R^{12}$ is —$CH_2NH_2$. In some embodiments is a compound of formula (II) wherein $R^{12}$ is —$C(O)N(R^6)_2$. In some embodiments is a compound of formula (II) wherein $R^{12}$ is —$C(O)NH_2$. In some embodiments is a compound of formula (II) wherein n is 3. In some embodiments is a compound of formula (II) wherein n is 2. In some embodiments is a compound of formula (II) wherein n is 1. In some embodiments is a compound of formula (II) wherein n is 0. In some embodiments is a compound of formula (II) wherein n is 1 and $R^{12}$ is halo. In some embodiments is a compound of formula (II) wherein n is 1 and $R^{12}$ is —F. In some embodiments is a compound of formula (II) wherein n is 1 and $R^{12}$ is —Cl. In some embodiments is a compound of formula (II) wherein n is 1 and $R^{12}$ is $C_{1-6}$haloalkyl. In some embodiments is a compound of formula (II) wherein n is 1 and $R^{12}$ is —$CF_3$. In some embodiments is a compound of formula (II) wherein n is 1 and $R^{12}$ is —$N(R^6)_2$. In some embodiments is a compound of formula (II) wherein n is 1 and $R^{12}$ is —$NH_2$. In some embodiments is a compound of formula (II) wherein n is 1 and $R^{12}$ is —$C_{1-6}$alkyl-$N(R^6)_2$. In some embodiments is a compound of formula (II) wherein n is 1 and $R^{12}$ is —$CH_2N(R^6)_2$. In some embodiments is a compound of formula (II) wherein n is 1 and $R^{12}$ is —$CH_2NH_2$. In some embodiments is a compound of formula (II) wherein n is 1 and $R^{12}$ is —$C(O)N(R^6)_2$. In some embodiments is a compound of formula (II) wherein n is 1 and $R^{12}$ is —$C(O)NH_2$.

In some embodiments is a compound of formula (II) wherein $R^{11}$ is halo. In some embodiments is a compound of formula (II) wherein $R^{11}$ is —F. In some embodiments is a compound of formula (II) wherein $R^{11}$ is —Cl. In some embodiments is a compound of formula (II) wherein $R^{11}$ is $C_{1-6}$haloalkyl. In some embodiments is a compound of formula (II) wherein $R^{11}$ is —$CF_3$. In some embodiments is a compound of formula (II) wherein $R^{11}$ is —$N(R^6)_2$. In some embodiments is a compound of formula (II) wherein $R^{11}$ is —$NH_2$. In some embodiments is a compound of formula (II) wherein $R^{11}$ is —$N(H)CH_3$. In some embodiments is a compound of formula (II) wherein $R^{11}$ is —$N(CH_3)_2$. In some embodiments is a compound of formula (II) wherein $R^{11}$ is —$C_{1-6}$alkyl-$N(R^6)_2$. In some embodiments is a compound of formula (II) wherein $R^{11}$ is —$CH_2N(R^6)_2$. In some embodiments is a compound of formula (II) wherein $R^{11}$ is —$CH_2NH_2$. In some embodiments is a compound of formula (II) wherein $R^{11}$ is —$CH_2N(H)CH_3$. In some embodiments is a compound of formula (II) wherein $R^{11}$ is —$CH_2N(CH_3)_2$. In some embodiments is a compound of formula (II) wherein $R^{11}$ is —$CH_2CH_2N(R^6)_2$. In some embodiments is a compound of formula (II) wherein $R^{11}$ is —$CH_2CH_2NH_2$. In some embodiments is a compound of formula (II) wherein $R^{11}$ is —CH$_2$CH$_2$N(H) CH$_3$. In some embodiments is a compound of formula (II) wherein $R^{11}$ is —CH$_2$CH$_2$N(CH$_3$)$_2$. In some embodiments is a compound of formula (II) wherein $R^{11}$ is —CH$_2$CH$_2$CH$_2$N(R$^6$)$_2$. In some embodiments is a compound of formula (II) wherein $R^{11}$ is —CH$_2$CH$_2$CH$_2$NH$_2$. In some embodiments is a compound of formula (II) wherein $R^{11}$ is —CH$_2$CH$_2$CH$_2$N(H)CH$_3$. In some embodiments is a compound of formula (II) wherein $R^{11}$ is —CH$_2$CH$_2$CH$_2$N(CH$_3$)$_2$. In some embodiments is a compound of formula (II) wherein $R^{11}$ is —N(R$^6$)$_2$ or —C$_{1-6}$alkyl-N(R$^6$)$_2$. In some embodiments is a compound of formula (II) wherein $R^{11}$ is —C(O)N(R$^6$)$_2$. In some embodiments is a compound of formula (II) wherein $R^{11}$ is —C(O)NH$_2$. In some embodiments is a compound of formula (II) wherein $R^{11}$ is —C(O)N(H)CH$_3$. In some embodiments is a compound of formula (II) wherein $R^{11}$ is —C(O)N(CH$_3$)$_2$.

In another aspect is a compound of formula (III) having the structure:

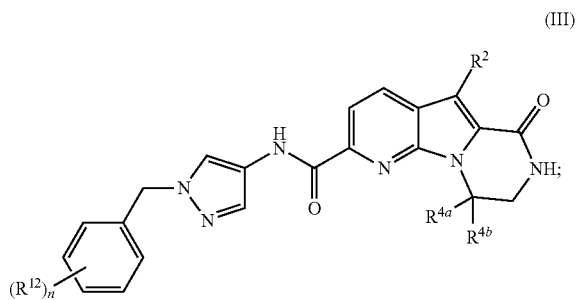

(III)

wherein:
$R^2$ is independently halo, C$_{1-6}$alkyl, or C$_{1-6}$haloalkyl;
$R^{4a}$ and $R^{4b}$ are each independently hydrogen, halo, C$_{1-6}$alkyl, or C$_{1-6}$haloalkyl; or $R^{4a}$ and $R^{4b}$, together with the carbon to which they are both attached, form a cycloalkyl;
each $R^6$ is independently hydrogen or C$_{1-6}$alkyl;
each $R^{12}$ is independently —OH, —CN, halo, C$_{1-6}$alkyl, C$_{1-6}$haloalkyl, C$_{1-6}$alkoxy, C$_{1-6}$haloalkoxy, —N(R$^6$)$_2$, —C$_{1-6}$alkyl-N(R$^6$)$_2$, —C(O)R$^6$, —C(O)OR$^6$, —C(O)N(R$^6$)$_2$, aryl, aralkyl, cycloalkyl, heterocyclyl, or heteroaryl; and
n is 0, 1, 2, 3, or 4;
as an individual stereoisomer, enantiomer or tautomer thereof or a mixture thereof;
or a pharmaceutically acceptable salt, solvate, or prodrug thereof.

In some embodiments is a compound of formula (III) wherein $R^2$ is halo. In some embodiments is a compound of formula (III) wherein $R^2$ is —F. In some embodiments is a compound of formula (III) wherein $R^2$ is —Cl. In some embodiments is a compound of formula (III) wherein $R^2$ is C$_{1-6}$alkyl. In some embodiments is a compound of formula (III) wherein $R^2$ is —CH$_3$. In some embodiments is a compound of formula (III) wherein $R^2$ is —CH$_2$CH$_3$. In some embodiments is a compound of formula (III) wherein $R^2$ is —CH(CH$_3$)$_2$. In some embodiments is a compound of formula (III) wherein $R^2$ is C$_{1-6}$haloalkyl. In some embodiments is a compound of formula (III) wherein $R^2$ is —CF$_3$.

In some embodiments is a compound of formula (III) wherein $R^{4a}$ is hydrogen. In some embodiments is a compound of formula (III) wherein $R^{4a}$ is halo. In some embodiments is a compound of formula (III) wherein $R^{4a}$ is —F. In some embodiments is a compound of formula (III) wherein $R^{4a}$ is —Cl. In some embodiments is a compound of formula (III) wherein $R^{4a}$ is C$_{1-6}$alkyl. In some embodiments is a compound of formula (III) wherein $R^{4a}$ is —CH$_3$. In some embodiments is a compound of formula (III) wherein $R^{4a}$ is —CH$_2$CH$_3$. In some embodiments is a compound of formula (III) wherein $R^{4a}$ is —CH(CH$_3$)$_2$. In some embodiments is a compound of formula (III) wherein $R^{4b}$ is hydrogen. In some embodiments is a compound of formula (III) wherein $R^{4b}$ is halo. In some embodiments is a compound of formula (III) wherein $R^{4b}$ is —F. In some embodiments is a compound of formula (III) wherein $R^{4b}$ is —Cl. In some embodiments is a compound of formula (III) wherein $R^{4b}$ is C$_{1-6}$alkyl. In some embodiments is a compound of formula (III) wherein $R^{4b}$ is —CH$_3$. In some embodiments is a compound of formula (III) wherein $R^{4b}$ is —CH$_2$CH$_3$. In some embodiments is a compound of formula (III) wherein $R^{4b}$ is —CH(CH$_3$)$_2$. In some embodiments is a compound of formula (III) wherein $R^{4b}$ is C$_{1-6}$haloalkyl. In some embodiments is a compound of formula (III) wherein $R^{4b}$ is —CF$_3$. In some embodiments is a compound of formula (III) wherein $R^{4a}$ is C$_{1-6}$alkyl and $R^{4b}$ is hydrogen. In some embodiments is a compound of formula (III) wherein $R^{4a}$ is —CH$_3$ and $R^{4b}$ is hydrogen. In some embodiments is a compound of formula (III) wherein $R^{4a}$ and $R^{4b}$, together with the carbon to which they are both attached, form a cycloalkyl. In some embodiments is a compound of formula (III) wherein $R^{4a}$ and $R^{4b}$, together with the carbon to which they are both attached, form a cyclopropyl. In some embodiments is a compound of formula (III) wherein $R^{4a}$ and $R^{4b}$, together with the carbon to which they are both attached, form a cyclobutyl. In some embodiments is a compound of formula (III) wherein $R^{4a}$ and $R^{4b}$, together with the carbon to which they are both attached, form a cyclopentyl. In some embodiments is a compound of formula (III) wherein $R^{4a}$ and $R^{4b}$, together with the carbon to which they are both attached, form a cyclohexyl.

In some embodiments is a compound of formula (III) wherein each $R^{12}$ is independently —OH, —CN, halo, C$_{1-6}$alkyl, C$_{1-6}$haloalkyl, C$_{1-6}$alkoxy, C$_{1-6}$haloalkoxy, —N(R$^6$)$_2$, —C$_{1-6}$alkyl-N(R$^6$)$_2$, —C(O)R$^6$, —C(O)OR$^6$, or —C(O)N(R$^6$)$_2$. In some embodiments is a compound of formula (III) wherein each $R^{12}$ is independently halo, C$_{1-6}$alkyl, C$_{1-6}$haloalkyl, —N(R$^6$)$_2$, —C$_{1-6}$alkyl-N(R$^6$)$_2$, or —C(O)N(R$^6$)$_2$. In some embodiments is a compound of formula (III) wherein each $R^{12}$ is independently halo, C$_{1-6}$alkyl, —N(R$^6$)$_2$, —C$_{1-6}$alkyl-N(R$^6$)$_2$, or C$_{1-6}$haloalkyl. In some embodiments is a compound of formula (III) wherein $R^{12}$ is halo. In some embodiments is a compound of formula (III) wherein $R^{12}$ is —F. In some embodiments is a compound of formula (III) wherein $R^{12}$ is —Cl. In some embodiments is a compound of formula (III) wherein $R^{12}$ is C$_{1-6}$haloalkyl. In some embodiments is a compound of formula (III) wherein $R^{12}$ is —CF$_3$. In some embodiments is a compound of formula (III) wherein $R^{12}$ is —N(R$^6$)$_2$. In some embodiments is a compound of formula (III) wherein $R^{12}$ is —NH$_2$. In some embodiments is a compound of formula (III) wherein $R^{11}$ is —N(H)CH$_3$. In some embodiments is a compound of formula (III) wherein $R^{12}$ is —N(CH$_3$)$_2$. In some embodiments is a compound of formula (III) wherein $R^{12}$ is —C$_{1-6}$alkyl-N(R$^6$)$_2$. In some embodiments is a compound of formula (III) wherein $R^{12}$ is —CH$_2$N(R$^6$)$_2$. In some embodiments is a compound of formula (III) wherein $R^{12}$ is —CH$_2$NH$_2$. In some embodiments is a compound of formula (III) wherein $R^{12}$ is —CH$_2$N(H)CH$_3$. In some embodiments is a compound of formula (III) wherein $R^{12}$ is —CH$_2$N(CH$_3$)$_2$. In some embodiments is a compound of formula (III) wherein R$^{12}$ is —CH$_2$CH$_2$N(R$^6$)$_2$. In some embodiments is a compound of formula (III) wherein R$^{12}$ is —CH$_2$CH$_2$NH$_2$. In some embodiments is a compound of formula (III) wherein R$^{12}$ is —CH$_2$CH$_2$N(H)CH$_3$. In some embodiments is a compound of formula (III) wherein R$^{12}$ is —CH$_2$CH$_2$N(CH$_3$)$_2$. In some embodiments is a compound of formula (III) wherein R$^{12}$ is —CH$_2$CH$_2$CH$_2$N(R$^6$)$_2$. In some embodiments is a compound of formula (III) wherein R$^{12}$ is —CH$_2$CH$_2$CH$_2$NH$_2$. In some embodiments is a compound of formula (III) wherein R$^{12}$ is —CH$_2$CH$_2$CH$_2$N(H)CH$_3$. In some embodiments is a compound of formula (III) wherein R$^{12}$ is —CH$_2$CH$_2$CH$_2$N(CH$_3$)$_2$. In some embodiments is a compound of formula (III) wherein R$^{12}$ is —N(R$^6$)$_2$ or —C$_{1-6}$alkyl-N(R$^6$)$_2$. In some embodiments is a compound of formula (III) wherein R$^{12}$ is —C(O)N(R$^6$)$_2$. In some embodiments is a compound of formula (III) wherein R$^{12}$ is —C(O)NH$_2$. In some embodiments is a compound of formula (III) wherein n is 3. In some embodiments is a compound of formula (III) wherein n is 2. In some embodiments is a compound of formula (III) wherein n is 1. In some embodiments is a compound of formula (III) wherein n is 0. In some embodiments is a compound of formula (III) wherein n is 1 and R$^{12}$ is halo. In some embodiments is a compound of formula (III) wherein n is 1 and R$^{12}$ is —F. In some embodiments is a compound of formula (III) wherein n is 1 and R$^{12}$ is —Cl. In some embodiments is a compound of formula (III) wherein n is 1 and R$^{12}$ is C$_{1-6}$haloalkyl. In some embodiments is a compound of formula (III) wherein n is 1 and R$^{12}$ is —CF$_3$. In some embodiments is a compound of formula (III) wherein n is 1 and R$^{12}$ is —N(R$^6$)$_2$. In some embodiments is a compound of formula (III) wherein n is 1 and R$^{12}$ is —NH$_2$. In some embodiments is a compound of formula (III) wherein n is 1 and R$^{12}$ is —C(O)N(R$^6$)$_2$. In some embodiments is a compound of formula (III) wherein n is 1 and R$^{12}$ is —C(O)NH$_2$.

In some embodiments is a compound selected from:
(R)-1-benzyl-N-(9-methyl-6-oxo-6,7,8,9-tetrahydropyrido[3',2':4,5]pyrrolo[1,2-a]pyrazin-2-yl)-1H-pyrazole-4-carboxamide; (R)—N-(1-(3-aminobenzyl)-1H-pyrazol-4-yl)-9-methyl-6-oxo-6,7,8,9-tetrahydropyrido[3',2':4,5]pyrrolo[1,2-a]pyrazine-2-carboxamide; (R)—N-(1-(2-aminobenzyl)-1H-pyrazol-4-yl)-9-methyl-6-oxo-6,7,8,9-tetrahydropyrido[3',2':4,5]pyrrolo[1,2-a]pyrazine-2-carboxamide; and (R)-1-(3-aminobenzyl)-N-(9-methyl-6-oxo-6,7,8,9-tetrahydropyrido[3',2':4,5]pyrrolo[1,2-a]pyrazin-2-yl)-1H-pyrazole-4-carboxamide;
or a pharmaceutically acceptable salt, solvate, or prodrug thereof.

In another aspect is a compound of formula (IV) having the structure:

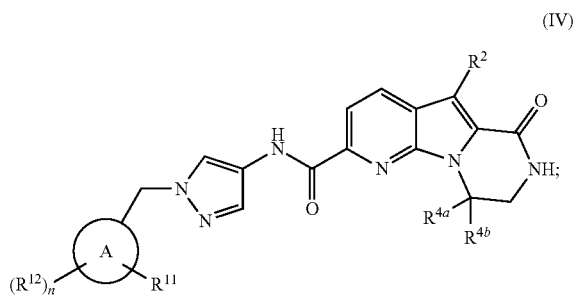

(IV)

wherein:

is heterocyclyl;
R$^2$ is independently hydrogen, halo, C$_{1-6}$alkyl, or C$_{1-6}$haloalkyl;
R$^{4a}$ and R$^{4b}$ are each independently hydrogen, halo, C$_{1-6}$alkyl, or C$_{1-6}$haloalkyl; or R$^{4a}$ and R$^{4b}$, together with the carbon to which they are both attached, form a cycloalkyl; each R$^6$ is independently hydrogen or C$_{1-6}$alkyl;
R$^{11}$ is halo, C$_{1-6}$alkyl, C$_{1-6}$haloalkyl, —N(R$^6$)$_2$, —C$_{1-6}$alkyl-N(R$^6$)$_2$, or —C(O)N(R$^6$)$_2$;
each R$^{12}$ is independently —OH, —CN, halo, C$_{1-6}$alkyl, C$_{1-6}$haloalkyl, C$_{1-6}$alkoxy, C$_{1-6}$haloalkoxy, —N(R$^6$)$_2$, —C$_{1-6}$alkyl-N(R$^6$)$_2$, —C(O)R$^6$, —C(O)OR$^6$, —C(O)N(R$^6$)$_2$, aryl, aralkyl, cycloalkyl, heterocyclyl, or heteroaryl; and
n is 0, 1, 2, 3, or 4;
as an individual stereoisomer, enantiomer or tautomer thereof or a mixture thereof;
or a pharmaceutically acceptable salt, solvate, or prodrug thereof.

In some embodiments is a compound of formula (IV) wherein R$^2$ is hydrogen. In some embodiments is a compound of formula (IV) wherein R$^2$ is halo. In some embodiments is a compound of formula (IV) wherein R$^2$ is —F. In some embodiments is a compound of formula (IV) wherein R$^2$ is —Cl. In some embodiments is a compound of formula (IV) wherein R$^2$ is C$_{1-6}$alkyl. In some embodiments is a compound of formula (IV) wherein R$^2$ is —CH$_3$. In some embodiments is a compound of formula (IV) wherein R$^2$ is —CH$_2$CH$_3$. In some embodiments is a compound of formula (IV) wherein R$^2$ is —CH(CH$_3$)$_2$. In some embodiments is a compound of formula (IV) wherein R$^2$ is C$_{1-6}$haloalkyl. In some embodiments is a compound of formula (IV) wherein R$^2$ is —CF$_3$.

In some embodiments is a compound of formula (IV) wherein R$^{4a}$ is hydrogen. In some embodiments is a compound of formula (IV) wherein R$^{4a}$ is halo. In some embodiments is a compound of formula (IV) wherein R$^{4a}$ is —F. In some embodiments is a compound of formula (IV) wherein R$^{4a}$ is —Cl. In some embodiments is a compound of formula (IV) wherein R$^{4a}$ is C$_{1-6}$alkyl. In some embodiments is a compound of formula (IV) wherein R$^{4a}$ is —CH$_3$. In some embodiments is a compound of formula (IV) wherein R$^{4a}$ is —CH$_2$CH$_3$. In some embodiments is a compound of formula (IV) wherein R$^{4a}$ is —CH(CH$_3$)$_2$. In some embodiments is a compound of formula (IV) wherein R$^{4b}$ is hydrogen. In some embodiments is a compound of formula (IV) wherein R$^{4b}$ is halo. In some embodiments is a compound of formula (IV) wherein R$^{4b}$ is —F. In some embodiments is a compound of formula (IV) wherein R$^{4b}$ is —Cl. In some embodiments is a compound of formula (IV) wherein R$^{4b}$ is C$_{1-6}$alkyl. In some embodiments is a compound of formula (IV) wherein R$^{4b}$ is —CH$_3$. In some embodiments is a compound of formula (IV) wherein R$^{4b}$ is —CH$_2$CH$_3$. In some embodiments is a compound of formula (IV) wherein R$^{4b}$ is —CH(CH$_3$)$_2$. In some embodiments is a compound of formula (IV) wherein R$^{4b}$ is C$_{1-6}$haloalkyl. In some embodiments is a compound of formula (IV) wherein R$^{4b}$ is —CF$_3$. In some embodiments is a compound of formula (IV) wherein R$^{4a}$ is C$_{1-6}$alkyl and R$^{4b}$ is hydrogen. In some embodiments is a compound of formula (IV) wherein $R^{4a}$ is —$CH_3$ and $R^{4b}$ is hydrogen. In some embodiments is a compound of formula (IV) wherein $R^{4a}$ and $R^{4b}$, together with the carbon to which they are both attached, form a cycloalkyl. In some embodiments is a compound of formula (IV) wherein $R^{4a}$ and $R^{4b}$, together with the carbon to which they are both attached, form a cyclopropyl. In some embodiments is a compound of formula (IV) wherein $R^{4a}$ and $R^{4b}$, together with the carbon to which they are both attached, form a cyclobutyl. In some embodiments is a compound of formula (IV) wherein $R^{4a}$ and $R^{4b}$, together with the carbon to which they are both attached, form a cyclopentyl. In some embodiments is a compound of formula (IV) wherein $R^{4a}$ and $R^{4b}$, together with the carbon to which they are both attached, form a cyclohexyl.

In some embodiments is a compound of formula (IV) wherein each $R^{12}$ is independently —OH, —CN, halo, $C_{1-6}$alkyl, $C_{1-6}$haloalkyl, $C_{1-6}$alkoxy, $C_{1-6}$haloalkoxy, —$N(R^6)_2$, —$C_{1-6}$alkyl-$N(R^6)_2$, —$C(O)R^6$, —$C(O)OR^6$, or —$C(O)N(R^6)_2$. In some embodiments is a compound of formula (IV) wherein each $R^{12}$ is independently halo, $C_{1-6}$alkyl, —$N(R^6)_2$, —$C_{1-6}$alkyl-$N(R^6)_2$, or $C_{1-6}$haloalkyl. In some embodiments is a compound of formula (IV) wherein $R^{12}$ is halo. In some embodiments is a compound of formula (IV) wherein $R^{12}$ is —F. In some embodiments is a compound of formula (IV) wherein $R^{12}$ is —Cl. In some embodiments is a compound of formula (IV) wherein $R^{12}$ is $C_{1-6}$haloalkyl. In some embodiments is a compound of formula (IV) wherein $R^{12}$ is —$CF_3$. In some embodiments is a compound of formula (IV) wherein $R^{12}$ is —$N(R^6)_2$. In some embodiments is a compound of formula (IV) wherein $R^{12}$ is —$NH_2$. In some embodiments is a compound of formula (IV) wherein $R^{12}$ is —$C_{1-6}$alkyl-$N(R^6)_2$. In some embodiments is a compound of formula (IV) wherein $R^{12}$ is —$CH_2N(R^6)_2$. In some embodiments is a compound of formula (IV) wherein $R^{12}$ is —$CH_2NH_2$. In some embodiments is a compound of formula (IV) wherein $R^{12}$ is —$C(O)N(R^6)_2$. In some embodiments is a compound of formula (IV) wherein $R^{12}$ is —$C(O)NH_2$. In some embodiments is a compound of formula (IV) wherein n is 3. In some embodiments is a compound of formula (IV) wherein n is 2. In some embodiments is a compound of formula (IV) wherein n is 1. In some embodiments is a compound of formula (IV) wherein n is 0. In some embodiments is a compound of formula (IV) wherein n is 1 and $R^{12}$ is halo. In some embodiments is a compound of formula (IV) wherein n is 1 and $R^{12}$ is —F. In some embodiments is a compound of formula (IV) wherein n is 1 and $R^{12}$ is —Cl. In some embodiments is a compound of formula (IV) wherein n is 1 and $R^{12}$ is $C_{1-6}$haloalkyl. In some embodiments is a compound of formula (IV) wherein n is 1 and $R^{12}$ is —$CF_3$. In some embodiments is a compound of formula (IV) wherein n is 1 and $R^{12}$ is —$N(R^6)_2$. In some embodiments is a compound of formula (IV) wherein n is 1 and $R^{12}$ is —$NH_2$. In some embodiments is a compound of formula (IV) wherein n is 1 and $R^{12}$ is —$C_{1-6}$alkyl-$N(R^6)_2$. In some embodiments is a compound of formula (IV) wherein n is 1 and $R^{12}$ is —$CH_2N(R^6)_2$. In some embodiments is a compound of formula (IV) wherein n is 1 and $R^{12}$ is —$CH_2NH_2$. In some embodiments is a compound of formula (IV) wherein n is 1 and $R^{12}$ is —$C(O)N(R^6)_2$. In some embodiments is a compound of formula (IV) wherein n is 1 and $R^{12}$ is —$C(O)NH_2$.

In some embodiments is a compound of formula (IV) wherein $R^{11}$ is halo. In some embodiments is a compound of formula (IV) wherein $R^{11}$ is —F. In some embodiments is a compound of formula (IV) wherein $R^{11}$ is —Cl. In some embodiments is a compound of formula (IV) wherein $R^{11}$ is $C_{1-6}$haloalkyl. In some embodiments is a compound of formula (IV) wherein $R^{11}$ is —$CF_3$. In some embodiments is a compound of formula (IV) wherein $R^{11}$ is —$N(R^6)_2$. In some embodiments is a compound of formula (IV) wherein $R^{11}$ is —$NH_2$. In some embodiments is a compound of formula (IV) wherein $R^{11}$ is —$N(H)CH_3$. In some embodiments is a compound of formula (IV) wherein $R^{11}$ is —$N(CH_3)_2$. In some embodiments is a compound of formula (IV) wherein $R^{11}$ is —$C_{1-6}$alkyl-$N(R^6)_2$. In some embodiments is a compound of formula (IV) wherein $R^{11}$ is —$CH_2N(R^6)_2$. In some embodiments is a compound of formula (IV) wherein $R^{11}$ is —$CH_2NH_2$. In some embodiments is a compound of formula (IV) wherein $R^{11}$ is —$CH_2N(H)CH_3$. In some embodiments is a compound of formula (IV) wherein $R^{11}$ is —$CH_2N(CH_3)_2$. In some embodiments is a compound of formula (IV) wherein $R^{11}$ is —$CH_2CH_2N(R^6)_2$. In some embodiments is a compound of formula (IV) wherein $R^{11}$ is —$CH_2CH_2NH_2$. In some embodiments is a compound of formula (IV) wherein $R^{11}$ is —$CH_2CH_2N(H)CH_3$. In some embodiments is a compound of formula (IV) wherein $R^{11}$ is —$CH_2CH_2N(CH_3)_2$. In some embodiments is a compound of formula (IV) wherein $R^{11}$ is —$CH_2CH_2CH_2N(R^6)_2$. In some embodiments is a compound of formula (IV) wherein $R^{11}$ is —$CH_2CH_2CH_2NH_2$. In some embodiments is a compound of formula (IV) wherein $R^{11}$ is —$CH_2CH_2CH_2N(H)CH_3$. In some embodiments is a compound of formula (IV) wherein $R^{11}$ is —$CH_2CH_2CH_2N(CH_3)_2$. In some embodiments is a compound of formula (IV) wherein $R^{11}$ is —$N(R^6)_2$ or —$C_{1-6}$alkyl-$N(R^6)_2$. In some embodiments is a compound of formula (IV) wherein $R^{11}$ is —$C(O)N(R^6)_2$. In some embodiments is a compound of formula (IV) wherein $R^{11}$ is —$C(O)NH_2$. In some embodiments is a compound of formula (IV) wherein $R^{11}$ is —$C(O)N(H)CH_3$. In some embodiments is a compound of formula (IV) wherein $R^{11}$ is —$C(O)N(CH_3)_2$.

In some embodiments is a compound of formula (IV) wherein

is piperidine.

In some embodiments is a compound of formula (IV) wherein

is piperazine. In some embodiments is a compound of formula (IV) wherein

is morpholine. In some embodiments is a compound of formula (IV) wherein

is thiomorpholine. In some embodiments is a compound of formula (IV) wherein

is tetrahydropyran. In some embodiments is a compound of formula (IV) wherein

is pyrrolidine. In some embodiments is a compound of formula (IV) wherein

is tetrahydrofuran.

In some embodiments is a compound having the structure:
(R)-9-methyl-N-(1-((1-methylpiperidin-4-yl)methyl)-1H-pyrazol-4-yl)-6-oxo-6,7,8,9-tetrahydropyrido[3',2':4,5]pyrrolo[1,2-a]pyrazine-2-carboxamide;
or a pharmaceutically acceptable salt, solvate, or prodrug thereof.

In some embodiments is a compound selected from:
(R)-9-methyl-6-oxo-N-(1-(4-(trifluoromethyl)benzyl)-1H-pyrazol-4-yl)-6,7,8,9-tetrahydropyrido[3',2':4,5]pyrrolo[1,2-a]pyrazine-2-carboxamide; (R)—N-(1-(2,4-difluorobenzyl)-1H-pyrazol-4-yl)-9-methyl-6-oxo-6,7,8,9-tetrahydropyrido[3',2':4,5]pyrrolo[1,2-a]pyrazine-2-carboxamide; and (R)—N-(1-benzyl-1H-pyrazol-4-yl)-5-chloro-9-methyl-6-oxo-6,7,8,9-tetrahydropyrido[3',2':4,5]pyrrolo[1,2-a]pyrazine-2-carboxamide; or a pharmaceutically acceptable salt, solvate, or prodrug thereof.

In some embodiments is a compound having the structure:
(R)—N-(1-(4-(aminomethyl)benzyl)-1H-pyrazol-4-yl)-9-methyl-6-oxo-6,7,8,9-tetrahydropyrido[3',2':4,5]pyrrolo[1,2-a]pyrazine-2-carboxamide;
or a pharmaceutically acceptable salt, solvate, or prodrug thereof.

In some embodiments is a compound having the structure:
(R)—N-(1-(4-(aminomethyl)benzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride salt;
or a pharmaceutically acceptable solvate or prodrug thereof.

In some embodiments is a compound having the structure:
(R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide;
or a pharmaceutically acceptable salt, solvate, or prodrug thereof.

In some embodiments is a compound having the structure:
(R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride salt; or a pharmaceutically acceptable solvate or prodrug thereof.

In some embodiments is a compound having the structure:
(R)—N-(2-carbamoylphenyl)-9-methyl-6-oxo-6,7,8,9-tetrahydropyrido[3',2':4,5]pyrrolo[1,2-a]pyrazine-2-carboxamide; or a pharmaceutically acceptable salt, solvate, or prodrug thereof.

Utility and Testing of the Compounds of the Invention

This invention is directed to compounds which inhibit RSK proteins by competing for ATP in the N-terminal kinase domain. As referred to herein, RSK refers to all known isoforms of RSK, including RSK1, RSK2, RSK3 and RSK4. In particular, the compounds described herein were designed to block RSK activity. The compounds are therefore useful in treating diseases and conditions which are associated with RSK activity, including the activity of the individual isoforms or any combination thereof.

The compounds described herein were also designed for direct cellular uptake and adaptability for the development of antibody drug conjugates. In addition, the compounds described herein were synthesized to inform the structure activity relationship of these RSK inhibitors. There was a good correlation between kinase inhibition in vitro and growth suppression in vivo based on crystal violet staining, Alamar Blue and soft agar assays.

The models used were cancer cell lines derived from human and murine sources, as set forth below in Table 1A and Table 1B:

TABLE 1A

| Cell Line | Subtype | Species | Age | Site of Origin | Tumour Type | Molecular Classification | Additional Details |
| --- | --- | --- | --- | --- | --- | --- | --- |
| MDA-MB-231 | TN | Human | 51 | Pleural Effusion | Adenocarcinoma | Basal B | P53 Mutation; BRCA1 WT; KRAS Mutation; Gefitinib Insensitive |
| MDA-MB-468 | TN | Human | 51 | Pleural Effusion | Adenocarcinoma | Basal A | P53 Mutation; BRCA1 WT; Amplified EGFR |
| SUM149 | TN | Human | N/A | Pleural Effusion | Inflammatory Ductal Carcinoma | Basal B | P53 Mutation; BRCA1 Mutant; Gefitinib Sensitive |
| SUM149-PTXR | TN | Human | N/A | Pleural Effusion | Inflammatory Ductal Carcinoma | Basal B | P53 Mutation; BRCA1 Mutant; Paclitaxel Resistant |
| MDA-MB-435 | TN | Human | 31 | Pleural Effusion | Invasive Ductal Carcinoma | Basal B | P53 Mutation; BRCA1WT |
| HCC1143 | TN | Human | 52 | Primary Tumour | Ductal Carcinoma | Basal A | P53 Mutation; BRCA1WT |
| 4T1 | TN | Mouse | N/A | Primary Tumour | Carcinoma | Basal-Like | Metastatic TNBC Model; Paclitaxel Resistant |

TABLE 1A-continued

| Cell Line | Subtype | Species | Age | Site of Origin | Tumour Type | Molecular Classification | Additional Details |
|---|---|---|---|---|---|---|---|
| 147D | ER/PR | Human | 54 | Pleural Effusion | Invasive Ductal Carcinoma | Luminal A | Hormone Responsive |

TABLE 1B

| Cell Line | Subtype | Species | Age | Site of Origin | Tumour Type | Molecular Classification | Additional Details |
|---|---|---|---|---|---|---|---|
| HCC1937 | TN | Human | 23 | Primary Tumour | Ductal Carcinoma | Basal A | P53 Mutation; BRCA1 Mutant; PTEN Deletion |
| JIMT-1 | HER2 | Human | 62 | Pleural Effusion | Invasive Ductal Carcinoma | ERBB2 | Herceptin Resistant |
| PC3 | Prostate | Human | 62 | Bone Metastasis | Adenocarcinoma | SCNC | No Androgen Receptor (AR) or Prostaste Specific Antigen (PSA) Expression |

Compounds described herein demonstrated activity in these TNBC cell lines which harboured mutations, p53 mutation, amplification of epidermal growth factor receptors as well as those that were drug resistant. Despite the diverse genetic composition of TNBC, the compounds described herein were uniformly active in suppressing cancer cell growth.

The compounds are therefore useful for suppressing RSK activity, cancer cell growth, metabolism, cell signalling, and for promoting cell death. The potency of the compounds in inhibiting the activity of RSK can be assessed directly using a cell-free kinase assay with human recombinant RSK. The specificity of the inhibitors for RSK can be addressed by evaluating the small molecules in assays containing other kinases that are structurally related, such as MK2 (Mitogen-activated protein kinase-activated protein kinase 2). Cell growth can be measured using DNA stains such as crystal violet. Metabolism is altered by RSK inhibitors and can be assessed using Alamar Blue. The mammosphere assay is a convenient means to measure the way in which RSK inhibitors block self-renewal. There are several RSK substrates in cancer, however the most reliable marker for RSK inactivation is through the loss of phosphorylated Y-box binding protein-1 (P—YB-1S102). RSK inhibitors will trigger cell death in cancer cells that can be assessed by a number of methods including PARP cleavage. The safety of RSK inhibitors can be assessed using a colony formation assay with CD34+ cells. CD34+ cells are primary bone marrow progenitor cells. They can be induced to differentiate into mature eurythocytes and monocytes using defined media.

In some embodiments of the methods of using the compounds of formula (I), (II), (III), or (IV) as described herein, is a method of treating a disease or condition associated with RSK activity in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof. In some embodiments is a method of treating a disease or condition associated with p90 ribosomal S6 kinase (RSK) activity in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof. In some embodiments is a method of treating a disease or condition associated with p90 ribosomal S6 kinase (RSK) activity in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof; wherein the disease or condition is cancer. In some embodiments is a method of treating cancer in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof; wherein the cancer is breast cancer, prostate cancer, lung cancer, brain cancer, skin cancer, bone cancer, ovarian cancer, or a blood cancer. In some embodiments is a method of treating prostate cancer in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof. In some embodiments is a method of treating lung cancer in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof. In some embodiments is a method of treating brain cancer in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof. In some embodiments is a method of treating skin cancer in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof. In some embodiments is a method of treating bone cancer in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof. In some embodiments is a method of treating ovarian cancer in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof. In some embodiments is a method of treating a blood cancer in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof. In some embodiments is a method of treating breast cancer in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof. In some embodiments is a method of treating breast cancer in a mammal, wherein the method comprises administering to the mammal a therapeutically effective amount of a compound of formula (I), (II), (III), or (IV) as an individual stereoisomer, enantiomer or tautomer thereof or a mixture thereof; or a pharmaceutically acceptable salt, solvate, or prodrug thereof; wherein the breast cancer is selected from Luminal A, Luminal B, Her-2 positive, triple-negative breast cancer, basal-like breast cancer, inflammatory breast cancer, BRCA1/2 mutated breast cancer, drug resistant breast cancer, murine breast cancer, gefitinib insensitive: MDA-MB-231, and metastatic breast cancer.

Specific embodiments of the methods described herein, including the suitable conditions for each of the above described embodiments, are described in more detail below in the following sections.

Combination Treatments

In some embodiments, the compounds of formula (I), (II), (III), or (IV) described herein, and compositions thereof, are used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In some embodiments, it is appropriate to administer at least one compound described herein in combination with another therapeutic agent. By way of example only, if one of the side effects experienced by a patient upon receiving one of the compounds herein, such as a compound of formula (I), (II), (III), or (IV), is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

For therapeutic applications, in some embodiments the compounds or drugs of the present invention are administered alone or co-administered in combination with conventional chemotherapy, radiotherapy, hormonal therapy, and/or immunotherapy.

As a non-limiting example, in some embodiments the compounds of formula (I), (II), (III), or (IV) described herein are co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), and the like.

In some embodiments, the compounds of formula (I), (II), (III), or (IV) described herein are co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

In some embodiments, the compounds of formula (I), (II), (III), or (IV) described herein are co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In further embodiments, the compounds of formula (I), (II), (III), or (IV) described herein are co-administered with a poly ADP-ribose polymerase (PARP) inhibitor, STAT 3 inhibitor, Janus Kinase inhibitor, or EGFR inhibitor.

The particular choice of compounds used will depend upon the diagnosis of the attending physicians and their judgment of the condition of the patient and the appropriate treatment protocol. In some embodiments, the compounds are administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of formula (I), (II), (III), or (IV) described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In some embodiments, the compounds described herein are used in combination with procedures that may provide additional or synergistic benefit to the patient. In some embodiments, the compounds of formula (I), (II), (III), or (IV) described herein are administered with radiation therapy. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies are administered before, during or after the occurrence of a disease or condition, and the timing of administering the composition containing a compound can vary. Thus, for example, in some embodiments the compounds are used as a prophylactic and are administered continuously to subjects with a propensity to develop conditions or diseases in order to prevent the occurrence of the disease or condition. In some embodiments, the compounds and compositions can be administered to a subject during or as soon as possible after the onset of the symptoms. In some embodiments, the administration of the compounds is initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Pharmaceutical Compositions of the Invention and Administration

The present invention also relates to pharmaceutical composition containing the compounds disclosed herein. In one embodiment, the present invention relates to a composition comprising compounds described herein in a pharmaceutically acceptable carrier, excipient or diluent and in an amount effective to inhibit the activity of RSK when administered to an animal, preferably a mammal, most preferably a human patient.

In some embodiments is a pharmaceutical composition comprising a compound of formula (I), (II), (III), or (IV) as an individual stereoisomer, enantiomer or tautomer thereof or a mixture thereof; or a pharmaceutically acceptable salt, solvate, or prodrug thereof, and at least one pharmaceutically acceptable excipient. In some embodiments is a pharmaceutical composition comprising a compound of formula (I) as an individual stereoisomer, enantiomer or tautomer thereof or a mixture thereof; or a pharmaceutically acceptable salt, solvate, or prodrug thereof, and at least one pharmaceutically acceptable excipient. In some embodiments is a pharmaceutical composition comprising a compound of formula (II) as an individual stereoisomer, enantiomer or tautomer thereof or a mixture thereof; or a pharmaceutically acceptable salt, solvate, or prodrug thereof, and at least one pharmaceutically acceptable excipient. In some embodiments is a pharmaceutical composition comprising a compound of formula (III) as an individual stereoisomer, enantiomer or tautomer thereof or a mixture thereof; or a pharmaceutically acceptable salt, solvate, or prodrug thereof, and at least one pharmaceutically acceptable excipient.

A pharmaceutical composition, as used herein, refers to a mixture of a compound of formula (I), (II), (III), or (IV) described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds of formula (I), (II), (III), or (IV) can be used singly or in combination with one or more therapeutic agents as components of mixtures (as in combination therapy).

Administration of the compounds described herein, or their pharmaceutically acceptable salts, in pure form or in an appropriate pharmaceutical composition, can be carried out via any of the accepted modes of administration of agents for serving similar utilities. The pharmaceutical compositions described herein can be prepared by combining a compound described herein with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term "parenteral" as used herein includes subcutaneous injections, intravenous, intramuscular, intrasternal injection or infusion techniques. Pharmaceutical compositions described herein are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound described herein in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound described herein, or a pharmaceutically acceptable salt thereof, for treatment of a disease or condition of interest in accordance with the teachings of this invention.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

In some embodiments, a pharmaceutical composition described herein is in the form of a solid or liquid. In one aspect, the carrier(s) are particulate, so that the compositions are, for example, in tablet or powder form. In some embodiments, the carrier(s) is liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

In some embodiments, as a solid composition for oral administration, the pharmaceutical composition is formulated into a powder, granule, compressed tablet, pill, capsule, chewing gum, wafer or the like form. Such a solid composition will typically contain one or more inert diluents or edible carriers. In some embodiments, one or more of the following is present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

In some embodiments, the pharmaceutical composition is in the form of a liquid, for example, an elixir, syrup, solution, emulsion or suspension. In some embodiments, the liquid is for oral administration or for delivery by injection, as two examples. When intended for oral administration, preferred composition contain, in addition to the present compounds, one or more of a sweetening agent, preservatives, dye/colorant and flavor enhancer. In some embodiments, in a composition intended to be administered by injection, one or more of a surfactant, preservative, wetting agent, dispersing agent, suspending agent, buffer, stabilizer and isotonic agent is included.

The liquid pharmaceutical compositions described herein, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition described herein intended for either parenteral or oral administration should contain an amount of a compound described herein such that a suitable dosage will be obtained. Typically, this amount is at least 0.01% of a compound described herein in the composition. When intended for oral administration, this amount may be varied to be between 0.1 and about 70% of the weight of the composition. Preferred oral pharmaceutical compositions contain between about 4% and about 50% of the compound described herein. Preferred pharmaceutical compositions and preparations according to the present invention are prepared so that a parenteral dosage unit contains between 0.01 to 10% by weight of the compound prior to dilution described herein.

In some embodiments, the pharmaceutical composition described herein is intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. In some embodiments, thickening agents are present in a pharmaceutical composition for topical administration. In some embodiments intended for transdermal administration, the composition includes a transdermal patch or iontophoresis device. In some embodiments, topical formulations contain a concentration of the compound described herein from about 0.1 to about 10% w/v (weight per unit volume).

In some embodiments, the pharmaceutical composition described herein is intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition described herein may include various materials, which modify the physical form of a solid or liquid dosage unit. For example, the composition may include materials that form a coating shell around the active ingredients. In some embodiments, the materials that form the coating shell are typically inert, and are selected from, for example, sugar, shellac, and other enteric coating agents. Alternatively, in some embodiments, the active ingredients is encased in a gelatin capsule.

The pharmaceutical composition described herein in solid or liquid form may include an agent that binds to the compound described herein and thereby assists in the delivery of the compound. Suitable agents that may act in this capacity include a monoclonal or polyclonal antibody, a protein or a liposome.

The pharmaceutical composition described herein may consist of dosage units that can be administered as an aerosol. The term aerosol is used to denote a variety of systems ranging from those of colloidal nature to systems consisting of pressurized packages. In some embodiments, delivery is by a liquefied or compressed gas or by a suitable pump system that dispenses the active ingredients. In some embodiments, aerosols of compounds described herein are delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

In some embodiments, the pharmaceutical compositions described herein are prepared by methodology well known in the pharmaceutical art. For example, in some embodiments, a pharmaceutical composition intended to be administered by injection is prepared by combining a compound described herein with sterile, distilled water so as to form a solution. In some embodiments, a surfactant is added to facilitate the formation of a homogeneous solution or suspension. Surfactants are compounds that non-covalently interact with the compound described herein so as to facilitate dissolution or homogeneous suspension of the compound in the aqueous delivery system.

In some embodiments, the pharmaceutical compositions described herein are formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

In some embodiments, the pharmaceutical compositions described herein are delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

In some embodiments, the pharmaceutical compositions described herein also relate to an intravaginal shell or core drug delivery device suitable for administration to the human or animal female. In some embodiments, the device is comprised of the active pharmaceutical ingredient in a polymer matrix, surrounded by a sheath, and capable of releasing the compound in a substantially zero order pattern on a daily basis similar to devises used to apply testosterone as desscribed in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transport ionized drugs into and through body tissues). Those skilled in the art would combine the best suited excipients with the compound for safe and effective intra-occular administration.

The most suitable route will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the compounds to a subject in need thereof.

Methods of Dosing and Treatment Regimens

The compounds described herein can be used in the preparation of medicaments for the treatment of cancer, or for the treatment of diseases or conditions that would benefit, at least in part, from RSK inhibition. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compounds described herein, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.7 mg) to about 50 mg/Kg (i.e., 3.5 g); more preferably a therapeutically effective dose is (for a 70 Kg mammal) from about 1 mg/kg (i.e., 70 mg) to about 25 mg/Kg (i.e., 1.75 g). In some embodiments, the daily dosages appropriate for the compounds described herein described herein are from about 0.01 mg/kg to about 20 mg/kg. In some embodiments, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. In some embodiments, suitable unit dosage forms for oral administration include from about 1 to about 500 mg active ingredient. In some embodiments, the unit dosage is about 1 mg, about 5 mg, about, 10 mg, about 20 mg, about 50 mg, about 100 mg, about 200 mg, about 250 mg, about 400 mg, or about 500 mg.

The ranges of effective doses provided herein are not intended to be limiting and represent preferred dose ranges. Such dosages may be altered depending on a number of variables, not limited to the activity of the compound used, the disease or condition to be treated, the mode of administration, the requirements of the individual subject, the severity of the disease or condition being treated, and the judgment of the practitioner. However, the most preferred dosage will be tailored to the individual subject, as is understood and determinable by one skilled in the relevant arts. (see, e.g., Berkow et al., eds., *The Merck Manual*, 16$^{th}$ edition, Merck and Co., Rahway, N.J., 1992; Goodmanetna., eds., *Goodman and Cilman's The Pharmacological Basis of Therapeutics*, 10$^{th}$ edition, Pergamon Press, Inc., Elmsford, N.Y., (2001); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985); Osolci al., eds., *Remington's Pharmaceutical Sciences*, 18$^{th}$ edition, Mack Publishing Co., Easton, Pa. (1990); Katzung, *Basic and Clinical Pharmacology*, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions described herein can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds, in some embodiments, is administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds, in some embodiments, is given continuously; alternatively, in some embodiments, the dose of drug being administered is temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. In some embodiments, the dose reduction during a drug holiday is from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

In some embodiments, the pharmaceutical composition described herein is in unit dosage forms suitable for single administration of precise dosages. In unit dosage form, the formulation is divided into unit doses containing appropriate quantities of one or more compound. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, in some embodiments, multiple-dose reclosable containers are used, in which case it is typical to include a preservative in the composition. By way of example only, in some embodiments, formulations for parenteral injection are presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Preparation of the Compounds of the Invention

The following Reaction Schemes illustrate methods to make compounds of this invention, i.e., compounds of formula (I):

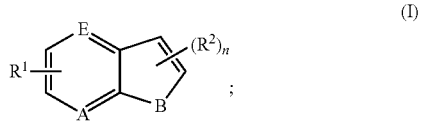

where n, A, B, E, $R^1$ and $R^2$ are as defined above in the Summary of the Invention, as an individual stereoisomer, enantiomer or tautomer thereof or a mixture thereof; or a pharmaceutically acceptable salt, solvate, or prodrug thereof.

It is understood that one skilled in the art would be able to make the compounds described herein by similar methods or by methods known to one skilled in the art. It is also understood that one skilled in the art would be able to make in a similar manner as described below other compounds described herein not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure*, 6th edition (Wiley, 2007)) or prepared as described herein.

It is also understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or aralkyl), p-methoxybenzyl, trityl and the like. Suitable protecting groups for carboxylic acid include alkyl, aryl or arylalkyl esters.

In some embodiments, protecting groups are added or removed in accordance with standard techniques, which are known to one skilled in the art and as described herein.

The use of protecting groups is described in detail in Greene, T. W. and P. G. M. Wuts, *Greene's Protective Groups in Organic Synthesis* (2006), 4$^{th}$ Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds described herein which are pharmacologically active. Such derivatives may therefore be described as "prodrugs". All prodrugs of compounds of this invention are included within the scope of the compounds described herein.

The compounds of formula (I), (II), (III), or (IV) may contain at least one asymmetric carbon atom and thus can exist as racemates, enantiomers and/or diastereoisomers. In some embodiments, specific enantiomers or diastereoisomers are prepared by utilizing the appropriate chiral starting material. Alternatively, in some embodiments, diastereoisomeric mixtures or racemic mixtures of compounds of formula (I), (II), (III), or (IV) are resolved into their respective enantiomers or diastereoisomers. Methods for resolution of diastereoisomeric mixtures or racemic mixtures of the compounds of formula (I), (II), (III), or (IV), as described herein, or intermediates prepared herein, are well known in the art (e.g., E. L. Eliel and S. H. Wilen, in *Stereochemistry of Organic Compounds*; John Wiley & Sons: New York, 1994; Chapter 7, and references cited therein). Suitable processes such as crystallization (e.g., preferential crystallization, preferential crystallization in the presence of additives), asymmetric transformation of racemates, chemical separation (e.g., formation and separation of diastereomers such as diastereomeric salt mixtures or the use of other resolving agents; separation via complexes and inclusion compounds), kinetic resolution (e.g., with titanium tartrate catalyst), enzymatic resolution (e.g., lipase mediated) and chromatographic separation (e.g., HPLC with chiral stationary phase and/or with simulated moving bed technology, or supercritical fluid chromatography and related techniques) are some of the examples that may be applied (see e.g., T. J. Ward, *Analytical Chemistry*, 2002, 2863-2872).

Preparation of Compounds of Formula (I-1)

Compounds of formula (I-1) are compounds of formula (I) and are prepared as set forth below in Reaction Scheme 1 wherein n, E, A, B, $R^2$ and $R^5$ are as described above in the Summary of the Invention:

REACTION SCHEME 1

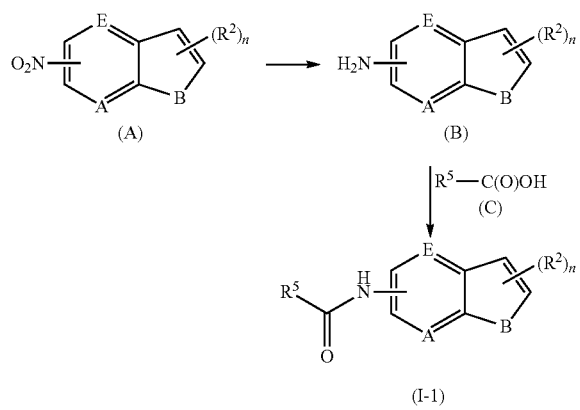

(I-1)

Compounds of formula (A) and formula (C) are commercially available or may be prepared by methods known to one skilled in the art.

In general, compounds of formula (I-1) are prepared by first reducing a compound of formula (A) in a protic solvent, such as methanol, under standard reduction conditions, such as treatment with Raney-Nickel at room temperature. The compound of formula (B) is then isolated from the reaction mixture by standard techniques, such as evaporation and purification by flash column chromatography. The compound of formula (B) is then treated with a compound of formula (C) at room temperature under standard amide formation conditions to yield a compound of formula (I-1), which is isolated from the reaction conditions by standard isolation techniques, such as organic solvent extraction, evaporation and column chromatography.

Preparation of Compounds of Formula (I-2)

Compounds of formula (I-2) are compounds of formula (I) and are prepared as set forth below in Reaction Scheme 2 wherein E, A, B and $R^5$ are as described above in the Summary of the Invention and each X is independently bromo or chloro and $R^9$ is alkylene:

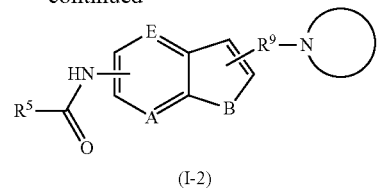

(I-2)

Compounds of formula (C), formula (D) and formula (E) are commercially available or may be prepared by methods known to one skilled in the art. In particular, compounds of formula (E) are optionally substituted N-heterocyclics as defined herein.

In general, compounds of formula (I-2) are prepared by first treating a compound of formula (D) under standard alkylation conditions to yield a compounds of formula (F), which is isolated from the reaction mixture by standard isolation techniques, such as evaporation and column chromatography. The compound of formula (F) is then treated under standard Buchwald-Hartwig amination reaction via the palladium-catalyzed cross-coupling of amines with aryl halides conditions to yield a compound of formula (G), which is isolated by standard isolation techniques, such as evaporation and column chromatography. The compound of formula (G) is then treated with a compound of formula (C) under standard amide formation conditions to yield a compound of formula (I-2), which is isolated from the reaction conditions by standard isolation techniques, such as organic extraction, evaporation and column chromatography.

Preparation of Compounds of Formula (I-3)

Compounds of formula (I-3) are compounds of formula (I) and are prepared as set forth below in Reaction Scheme 3 wherein E, A, $R^{4a}$, $R^{4b}$, $R^{4c}$, $R^{4d}$ and $R^5$ are as described above in the Summary of the Invention and each X is independently bromo or chloro, $R^{10}$ is alkyl and PG is a nitrogen protecting group, such as t-butoxycarbonyl:

REACTION SCHEME 2

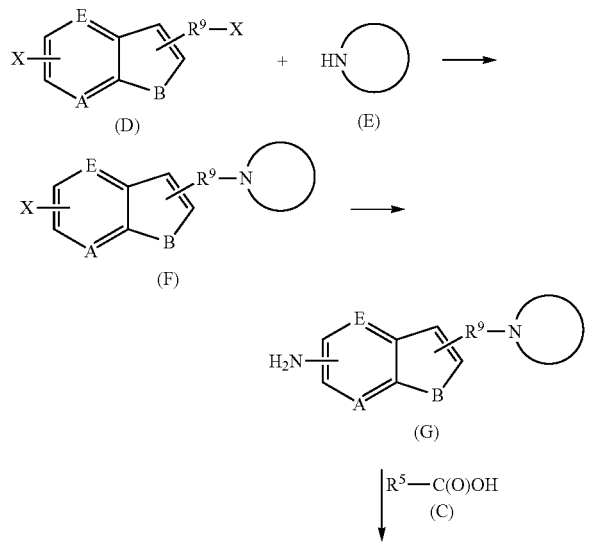

REACTION SCHEME 3

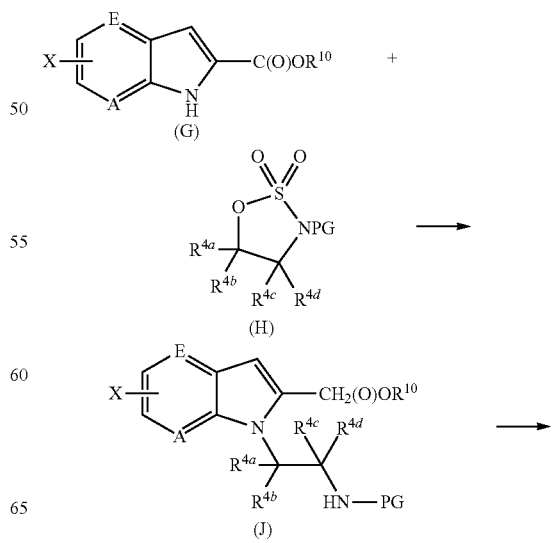

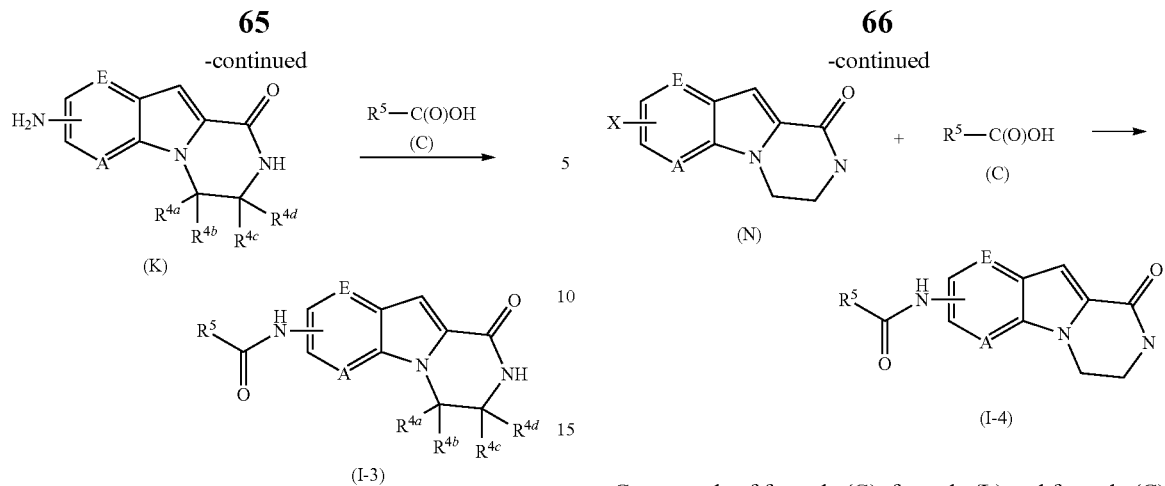

Compounds of formula (G), formula (H) and formula (C) are commercially available or may be prepared by methods known to one skilled in the art.

In general, compounds of formula (I-3) are prepared by first treating a compound of formula (G) with a compound of formula (H) under standard standard nucleophilic substitution under basic conditions to yield a compound of formula (J), which is isolated from the reaction mixture by standard isolation techniques, such as organic solvent extraction, evaporation and column chromatography. The compound of formula (J) is then treated with under standard lactam cyclization conditions to yield a compound of formula (K), which is isolated from the reaction mixture by standard isolation techniques, such as solvent extraction, evaporation and column chromatography. The compound of formula (K) is then treated with a compound of formula (C) under standard amide formation conditions to yield a compound of formula (I-2), which is isolated from the reaction conditions by standard isolation techniques, such as organic extraction, evaporation and column chromatography.

Preparation of Compounds of Formula (I-4)

Compounds of formula (I-4) are compounds of formula (I) and are prepared as set forth below in Reaction Scheme 4 wherein E, A and $R^5$ are as described above in the Summary of the Invention and X is independently bromo or chloro and $R^{10}$ is alkyl:

Compounds of formula (G), formula (L) and formula (C) are commercially available or may be prepared by methods known to one skilled in the art.

In general, compounds of formula (I-4) are prepared by first treating a compound of formula (G) with a compound of formula (L) under standard alkylation conditions to yield a compound of formula (M), which is isolated from the reaction mixture by standard isolation techniques, such as filtration. The compound of formula (M) is then treated with under standard lactam cyclization conditions to yield a compound of formula (N), which is isolated from the reaction mixture by standard isolation techniques, such as evaporation and column chromatography. The compound of formula (N) is then treated with a compound of formula (C) under standard amide formation conditions to yield a compound of formula (I-4), which is isolated from the reaction conditions by standard isolation techniques, such as organic extraction, evaporation and column chromatography.

Preparation of Compounds of Formula (I-5)

Compounds of formula (I-5) are compounds of formula (I) and are prepared as set forth below in Reaction Scheme 5 wherein E, A and $R^5$ are as described above in the Summary of the Invention and X is independently bromo or chloro and $R^{10}$ is alkyl:

REACTION SCHEME 4

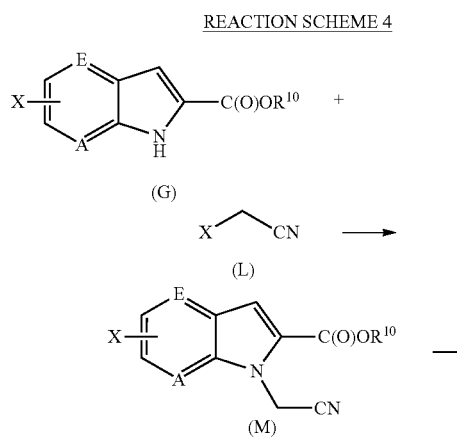

REACTION SCHEME 5

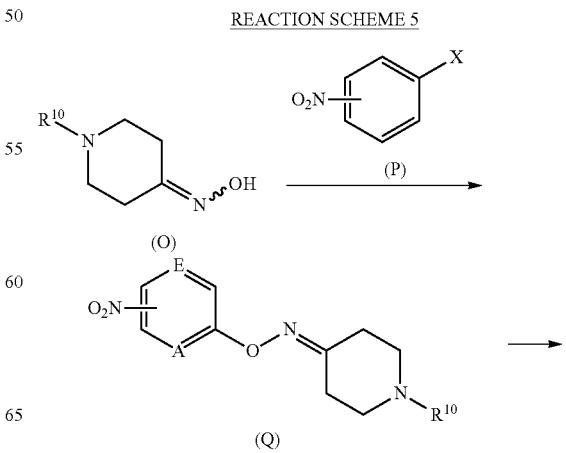

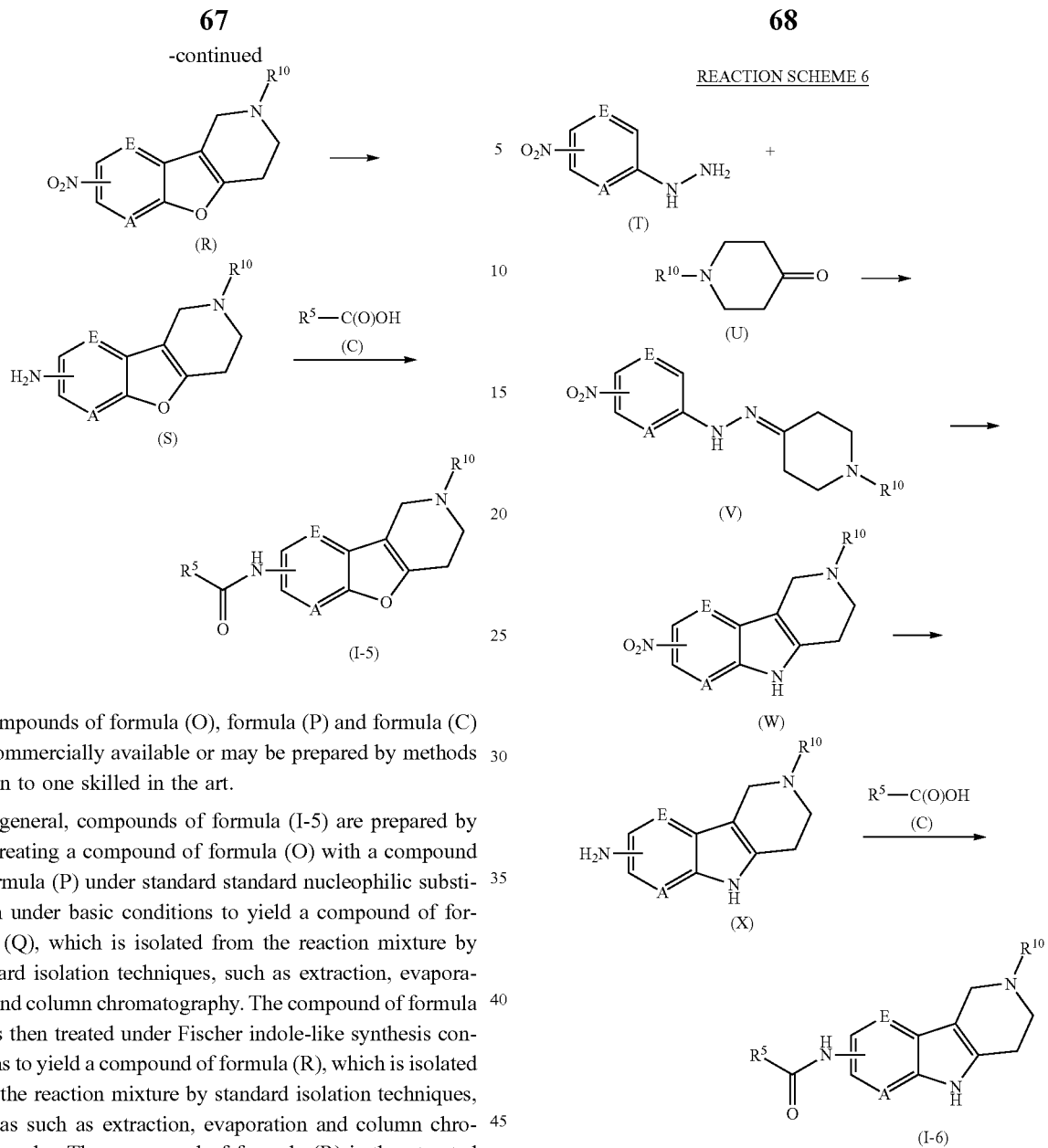

Compounds of formula (O), formula (P) and formula (C) are commercially available or may be prepared by methods known to one skilled in the art.

In general, compounds of formula (I-5) are prepared by first treating a compound of formula (O) with a compound of formula (P) under standard standard nucleophilic substitution under basic conditions to yield a compound of formula (Q), which is isolated from the reaction mixture by standard isolation techniques, such as extraction, evaporation and column chromatography. The compound of formula (Q) is then treated under Fischer indole-like synthesis conditions to yield a compound of formula (R), which is isolated from the reaction mixture by standard isolation techniques, such as such as extraction, evaporation and column chromatography. The compound of formula (R) is then treated under standard reduction conditions, such as treatment with Raney-Nickel and hydrazine hydrate, to yield a compound of formula (S), which is isolated from the reaction mixture by standard isolation techniques, such as such as evaporation and column chromatography. The compound of formula (S) is then treated with a compound of formula (C) under standard amide formation conditions to yield a compound of formula (I-5), which is isolated from the reaction conditions by standard isolation techniques, such as organic extraction, evaporation and column chromatography.

Preparation of Compounds of Formula (I-6)

Compounds of formula (I-6) are compounds of formula (I) and are prepared as set forth below in Reaction Scheme 6 wherein E, A and $R^5$ are as described above in the Summary of the Invention and $R^{10}$ is alkyl:

Compounds of formula (T), formula (U) and formula (C) are commercially available or may be prepared by methods known to one skilled in the art.

In general, compounds of formula (I-6) are prepared by first treating a compound of formula (T) with a compound of formula (U) under standard reductive amination reaction conditions to form a compound of formula (V), which is isolated from the reaction conditions by standard isolation techniques, such as organic solvent extraction and evaporation. The compound of formula (V) is then treated under standard Fischer indole synthesis conditions to form a compound of formula (W), which is isolated from the reaction conditions by standard isolation techniques, such as organic solvent extraction, evaporation and column chromatography. The compound of formula (W) is then treated under standard reduction conditions, such as treatment with Raney-Nickel and hydrazine hydrate at room temperature, to form a compound of formula (X), which is isolated from the reaction conditions by standard isolation techniques, such as filtration, evaporation and flash column chromatography. The compound of formula (X) is then treated with a compound of formula (C) under standard amide formation conditions to yield a compound of formula (I-6), which is isolated from the reaction conditions by standard isolation techniques, such as organic solvent extraction, evaporation and column chromatography.

Preparation of Compounds of Formula (I-7)

Compounds of formula (I-7) are compounds of formula (I) and are prepared as set forth below in Reaction Scheme 7 wherein n, E, A, B and $R^2$ are as described above in the Summary of the Invention and X is bromo or choro, $R^9$ is alkylene, $R^{7b}$ is halo, haloalkyl, —CN, —NO$_2$, —N(R$^6$)$_2$, —N(R$^6$)C(O)OR$^6$, —C(O)R$^6$, —C(O)OR$^6$ or —C(O)N(R$^6$)$_2$ where $R^6$ is as described above in the Summary of the Invention and

is a monocyclic N-heteroaryl:

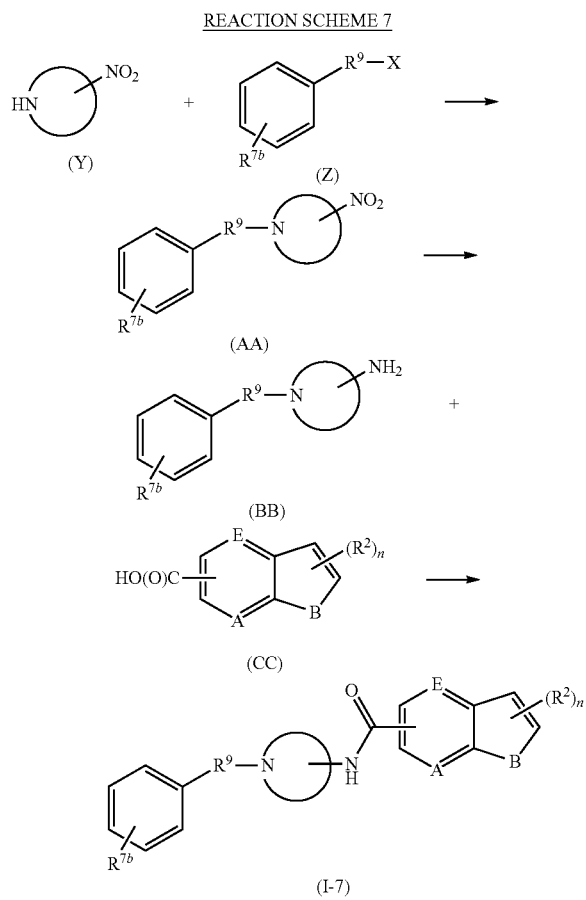

Compounds of formula (Y), formula (Z) and formula (CC) are commercially available or may be prepared by methods known to one skilled in the art.

In general, compounds of formula (I-7) are prepared by first treating a compound of formula (Y) with a compound of formula (Z) under standard nitrogen alkylation conditions to form a compound of formula (AA), which is isolated from the reaction conditions by standard isolation techniques, such as organic solvent extraction and column chromatography. The compound of formula (AA) is then treated under standard reduction conditions, such as treatment with iron in acetic acid, to form a compound of formula (BB), which is isolated from the reaction conditions by standard isolation techniques, such as organic solvent extraction and evaporation. The compound of formula (BB) is then treated with a compound of formula (CC) under standard amide formation conditions to yield a compound of formula (I-7), which is isolated from the reaction conditions by standard isolation techniques, such as organic solvent extraction, evaporation and column chromatography.

Preparation of Compounds of Formula (I-87)

Compounds of formula (I-8) are compounds of formula (I) and are prepared as set forth below in Reaction Scheme 8 wherein n, E, A, B and $R^2$ are as described above in the Summary of the Invention and X is bromo or chloro, $R^9$ is alkylene, $R^{19}$ is alkyl, $R^{5a}$ is halo, haloalkyl, —CN, —NO$_2$, —N(R$^6$)$_2$, —N(R$^6$)C(O)OR$^6$, —C(O)R$^6$, —C(O)OR$^6$ or —C(O)N(R$^6$)$_2$ where $R^6$ is as described above in the Summary of the Invention and

is an optionally substituted N-heteroaryl:

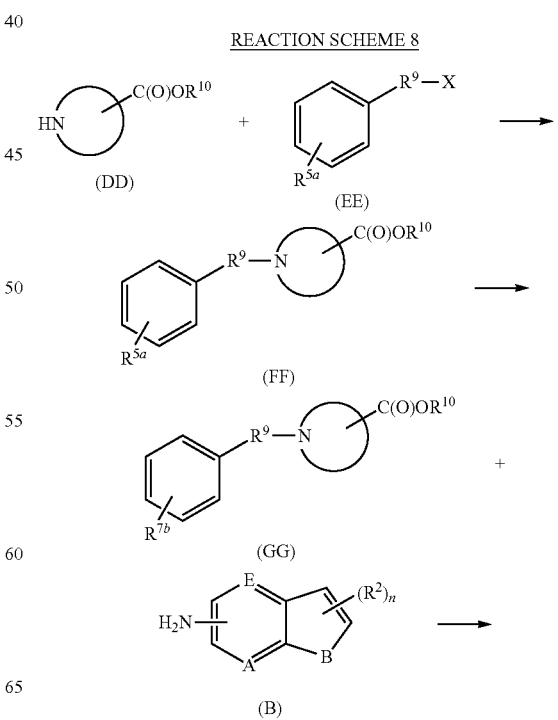

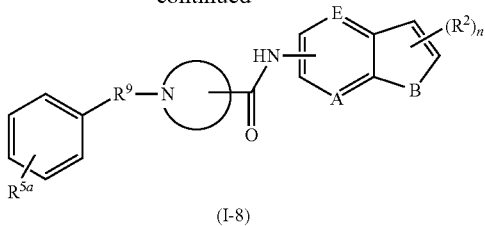

(I-8)

Compounds of formula (DD), formula (EE) and formula (B) are commercially available or may be prepared by methods known to one skilled in the art.

In general, compounds of formula (I-8) are prepared by first treating a compound of formula (DD) with a compound of formula (EE) under standard nitrogen alkylation conditions to form a compound of formula (FF), which is isolated from the reaction conditions by standard isolation techniques, such as organic solvent extraction, evaporation and column chromatography. The compound of formula (FF) is then treated under standard basic hydrolysis conditions to form a compound of formula (GG), which is isolated from the reaction conditions by standard isolation techniques, such as organic solvent extraction and evaporation of solvents. The compound of formula (GG) is then treated with a compound of formula (B) under standard amide formation conditions to yield a compound of formula (I-8), which is isolated from the reaction conditions by standard isolation techniques, such as organic solvent extraction, evaporation and column chromatography.

SYNTHETIC EXAMPLES

The following Synthetic Examples, which are directed to the preparation of the intermediates and/or compounds described herein, are provided as a guide to assist in the practice of the invention, and are not intended as a limitation on the scope of the invention.

Abbreviations

The following abbreviations may be used herein in the following Synthetic Examples:
AcOH for acetic acid;
ACN for acetonitrile;
Boc for t-butoxycarbonyl;
$BH_3$·THF for borane tetrahydrofuran complex;
BOP for benzotriazol-1-yloxy)tris(dimethylamino)phosphonium hexafluorophosphate;
18-crown-6 for 1,4,7,10,13,16-hexaoxacyclooctadecane;
DCM for dichoromethane;
DMF for N,N-dimethylformamide;
$Et_3N$ for triethylamine;
EtOAc for ethyl acetate;
EtOH for ethanol;
h for hours;
HATU for 1-[bis(dimethylamino)methylene]-1H-1,2,3-triazolo[4,5-b]pyridinium 3-oxidhexafluorophosphate;
HBTU for O-(benzotriazol-1-yl)-N,N,N',N'-tetramethyluronium hexafluorophosphate;
LiHMDS for lithium bis(trimethylsilyl)amide;
min for minutes;
MeOH for methanol;
NaOH for sodium hydroxide;
NMR for nuclear magnetic resonance;
Pd/C for palladium metal on charcoal;
$Pd_2(dba)_3$ for Tris(dibenzylideneacetone)dipalladium(0);
Ph for phenyl;
$P^tBu_3$ for tri-tert-butylphosphine;
PPA for polyphosphoric acid
$^iPr_2NEt$ for diisopropylethylamine;
Ra—Ni for Raney-Nickel;
rt for room temperature;
TBAF for tetrabutylammonium fluoride;
TFA for trifluoroacetic acid;
THF for tetrahydrofuran;
TLC for thin layer chromatography.

Synthetic Example 1

Synthesis of 1-Benzyl-N-(3-(morpholinomethyl)-1H-indol-5-yl)-1H-pyrazole-4-carboxamide, Compound #1

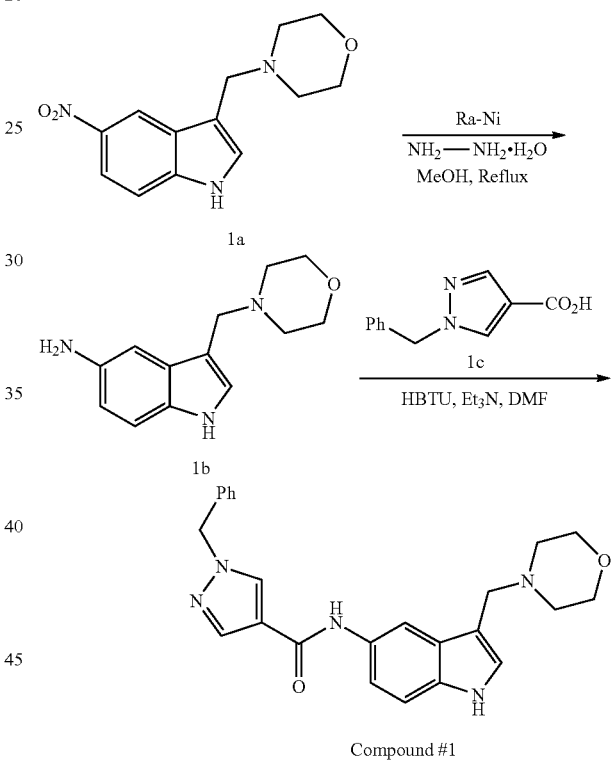

Compound #1

A. A solution of 4-((5-nitro-1H-indol-3-yl)methyl)morpholine (compound (1A) (0.42 g, 1.607 mmol) in MeOH (20 mL) was treated with Raney-Nickel (~100 mg) followed by hydrazine hydrate (0.78 mL, 16.074 mmol) at room temperature. The reaction was refluxed for 10-15 minutes in a pre-heated oil bath and then brought back to room temperature. The solution was filtered through a pad of celite and washed with methanol (2×15 mL). The combined methanol layer was evaporated and crude was purified by flash column chromatography (2M $NH_3$ in MeOH:$CH_2Cl_2$, 5:95) on silica gel to obtain 3-(morpholinomethyl)-1H-indol-5-amine, compound 1b, (0.3 g, 81%) as a brown solid.

B. A solution of 3-(morpholinomethyl)-1H-indol-5-amine (compound 1b, 0.215 g, 0.929 mmol), 1-benzyl-1H-pyrazole-4-carboxylic acid (compound 1c, 0.21 g, 1.022 mmol) and $Et_3N$ (0.26 mL, 1.859 mmol) in dry DMF (10 mL) was treated with HBTU (0.35 g, 0.929 mmol) at room temperature and stirred for 4 hours. The reaction was diluted with 1N NaOH solution (50 mL), water (50 mL) and product was extracted into ethyl acetate (2×50 mL). The combined ethyl acetate layer was washed with brine (50 mL) and dried ($Na_2SO_4$). Solvent was evaporated and crude was purified by column chromatography (2M $NH_3$ in MeOH:$CH_2Cl_2$, 2:98 to 5:95) on silica gel to obtain 1-benzyl-N-(3-(morpholinomethyl)-1H-indol-5-yl)-1H-pyrazole-4-carboxamide, compound #1, (0.3 g, 78%) as an off-white solid. $^1$H NMR (DMSO-$d_6$) δ 2.36 (brs, 4H), 3.50-3.60 (m, 6H), 5.39 (s, 2H), 7.21 (s, 1H), 7.27-7.39 (m, 7H), 7.87 (s, 1H), 8.06 (s, 1H), 8.41 (s, 1H), 9.70 (s, 1H), 10.88 (s, 1H); ESI-MS (m/z, %): 416 ($MH^+$, 100%).

Synthetic Example 2

Synthesis of 1-Benzyl-N-(3-(morpholinomethyl)-1H-indol-6-yl)-1H-pyrazole-4-carboxamide, Compound #2

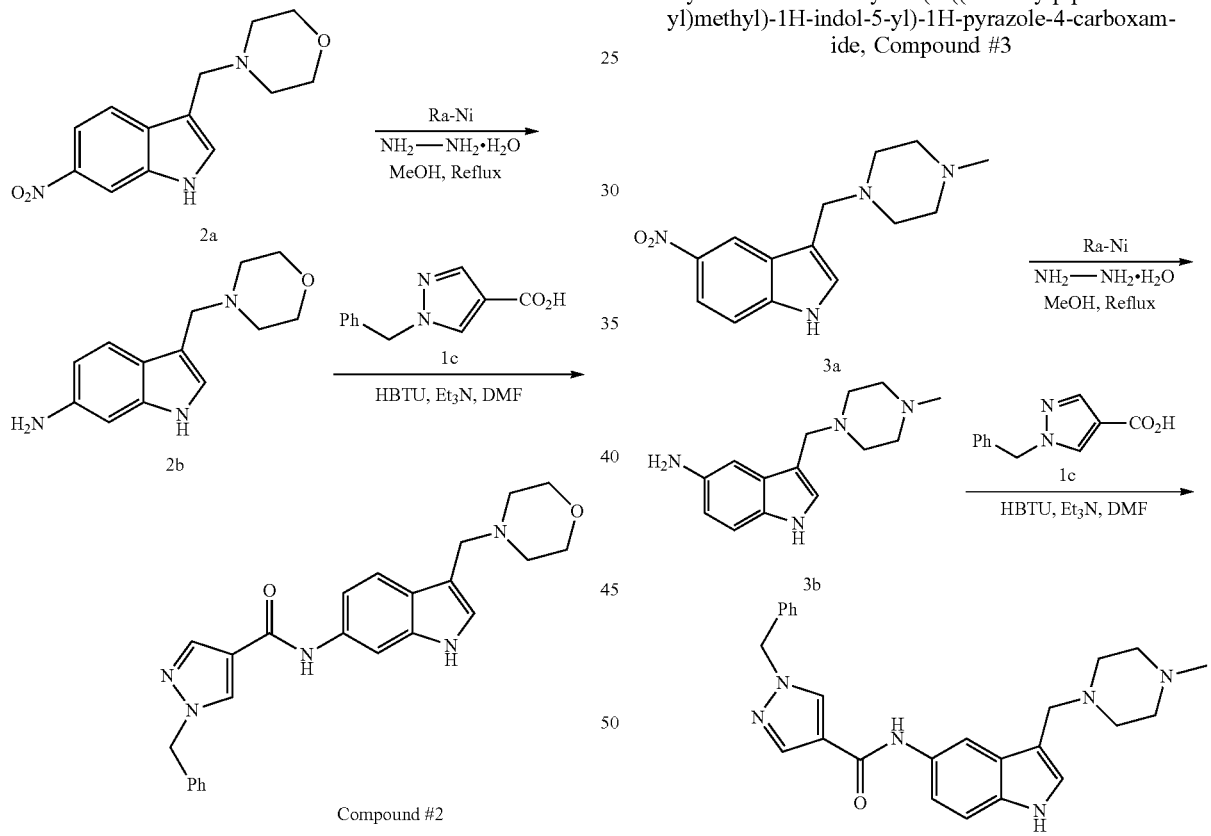

Compound #2

A. A solution of 4-((6-nitro-1H-indol-3-yl)methyl)morpholine (compound 2a, 0.325 g, 1.243 mmol) in MeOH (20 mL) was treated with Raney-Nickel (~50 mg) followed by hydrazine hydrate (0.6 mL, 12.438 mmol) at room temperature. The reaction was refluxed for 10-15 minutes in a pre-heated oil bath and then brought back to room temperature. The solution was filtered through a pad of celite and washed with methanol (2×15 mL). The combined methanol layer was evaporated and crude was purified by flash column chromatography (2M $NH_3$ in MeOH:$CH_2Cl_2$, 5:95) on silica gel to obtain 3-(morpholinomethyl)-1H-indol-6-amine, compound 2b (0.27 g, 94%) as a tan solid.

B. A solution of 3-(morpholinomethyl)-1H-indol-6-amine (compound 2b, 0.26 g, 1.124 mmol), 1-benzyl-1H-pyrazole-4-carboxylic acid (compound 1c, 0.25 g, 1.236 mmol) and $Et_3N$ (0.31 mL, 2.248 mmol) in dry DMF (10 mL) was treated with HBTU (0.42 g, 1.124 mmol) at room temperature and stirred for 4 h. The reaction was diluted with 1N NaOH solution (50 mL), water (50 mL) and product was extracted into ethyl acetate (2×50 mL). The combined ethyl acetate layer was washed with brine (50 mL) and dried ($Na_2SO_4$). Solvent was evaporated and crude was purified by column chromatography (2M $NH_3$ in MeOH:$CH_2Cl_2$, 2:98 to 5:95) on silica gel to obtain 1-benzyl-N-(3-(morpholinomethyl)-1H-indol-6-yl)-1H-pyrazole-4-carboxamide, compound #2, (0.43 g, 92%) as an off-white solid. $^1$H NMR (DMSO-$d_6$) δ 2.36 (brs, 4H), 3.54-3.57 (m, 6H), 5.39 (s, 2H), 7.16-7.18 (m, 2H), 7.28-7.38 (m, 5H), 7.54 (d, 1H, J=4.2 Hz), 7.94 (s, 1H), 8.06 (s, 1H), 8.43 (s, 1H), 9.72 (s, 1H), 10.87 (s, 1H); ESI-MS (m/z, %): 416 ($MH^+$, 100%).

Synthetic Example 3

Synthesis of 1-Benzyl-N-(3-((4-methylpiperazin-1-yl)methyl)-1H-indol-5-yl)-1H-pyrazole-4-carboxamide, Compound #3

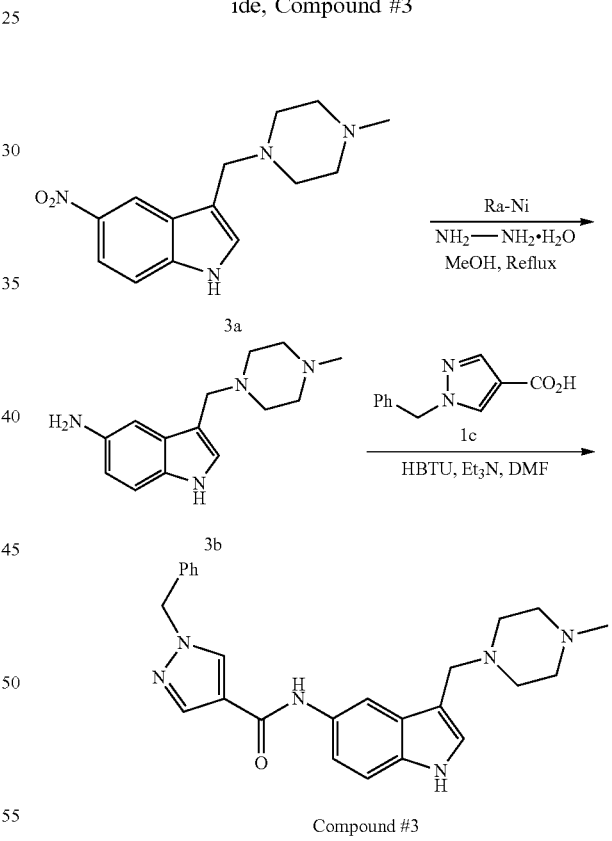

Compound #3

A. A solution of 3-((4-methylpiperazin-1-yl)methyl)-5-nitro-1H-indole (compound 3a, 0.25 g, 0.911 mmol) in MeOH (10 mL) was treated with Raney-Nickel (~50 mg) followed by hydrazine hydrate (0.44 mL, 9.113 mmol) at room temperature. The reaction was refluxed for 10-15 minutes in a pre-heated oil bath and then brought back to room temperature. The solution was filtered through a pad of celite and washed with methanol (2×15 mL). The combined methanol layer was evaporated and crude was purified by flash column chromatography (2M $NH_3$ in MeOH:$CH_2Cl_2$, 5:95) on silica gel to obtain 3-((4-methylpiperazin-1-yl) methyl)-1H-indol-5-amine, compound 3b, (0.19 g, 86%) as a tan solid.

B. A solution of 3-((4-methylpiperazin-1-yl)methyl)-1H-indol-5-amine (compound 3b, 0.175 g, 0.716 mmol), 1-benzyl-1H-pyrazole-4-carboxylic acid (compound 1c, 0.16 g, 0.787 mmol) and Et$_3$N (0.2 mL, 1.432 mmol) in dry DMF (5 mL) was treated with HBTU (0.27 g, 0.716 mmol) at room temperature and stirred for 4 h. The reaction was diluted with 1N NaOH solution (50 mL), water (50 mL) and product was extracted into ethyl acetate (2×50 mL). The combined ethyl acetate layer was washed with brine (50 mL) and dried (Na$_2$SO$_4$). Solvent was evaporated and crude was purified by column chromatography (2M NH$_3$ in MeOH:CH$_2$Cl$_2$, 2:98 to 5:95) on silica gel to obtain 1-benzyl-N-(3-((4-methylpiperazin-1-yl)methyl)-1H-indol-5-yl)-1H-pyrazole-4-carboxamide, compound #3, (0.26 g, 85%) as a pale yellow solid. $^1$H NMR (DMSO-d$_6$) δ 2.21 (s, 3H), 2.25-2.40 (m, 8H), 3.55 (s, 2H), 5.39 (s, 2H), 7.19 (d, 1H, J=1.2 Hz), 7.27-7.39 (m, 7H), 7.83 (s, 1H), 8.06 (s, 1H), 8.41 (s, 1H), 9.69 (s, 1H), 10.85 (s, 1H); ESI-MS (m/z, %): 429 (MH$^+$, 100%).

Synthetic Example 4

Synthesis of 1-Benzyl-N-(3-((4-methylpiperazin-1-yl)methyl)-1H-indol-6-yl)-1H-pyrazole-4-carboxamide, Compound #4 room temperature. The reaction was refluxed for 10-15 minutes in a pre-heated oil bath and then brought back to room temperature. The solution was filtered through a pad of celite and washed with methanol (2×15 mL). The combined methanol layer was evaporated and crude was purified by flash column chromatography (2M NH$_3$ in MeOH:CH$_2$Cl$_2$, 5:95) on silica gel to obtain 3-((4-methylpiperazin-1-yl) methyl)-1H-indol-6-amine, compound 4b, (0.26 g, 91%) as a tan solid.

B. A solution of 3-((4-methylpiperazin-1-yl)methyl)-1H-indol-6-amine (compound 4b, 0.245 g, 1.002 mmol), 1-benzyl-1H-pyrazole-4-carboxylic acid (compound 1c, 0.22 g, 1.102 mmol) and Et$_3$N (0.28 mL, 2.005 mmol) in dry DMF (5 mL) was treated with HBTU (0.38 g, 1.002 mmol) at room temperature and stirred for 4 hours. The reaction was diluted with 1N NaOH solution (50 mL), water (50 mL) and product was extracted into ethyl acetate (2×50 mL). The combined ethyl acetate layer was washed with brine (50 mL) and dried (Na$_2$SO$_4$). Solvent was evaporated and crude was purified by column chromatography (2M NH$_3$ in MeOH:CH$_2$Cl$_2$, 2:98 to 5:95) on silica gel to obtain 1-benzyl-N-(3-((4-methylpiperazin-1-yl)methyl)-1H-indol-6-yl)-1H-pyrazole-4-carboxamide, compound #4, (0.335 g, 80%) as a pale yellow solid. $^1$H NMR (DMSO-d$_6$) δ 2.12 (s, 3H), 2.20-2.40 (m, 8H), 3.56 (s, 2H), 5.39 (s, 2H), 7.14 (d, 1H, J=1.2 Hz), 7.16 (dd, 1H, J=0.9, 4.2 Hz), 7.28-7.33 (m, 3H), 7.36-7.38 (m, 2H), 7.52 (d, 1H, H=4.2 Hz), 7.93 (s, 1H), 8.06 (s, 1H), 8.43 (s, 1H), 9.72 (s, 1H), 10.85 (s, 1H); ESI-MS (m/z, %): 429 (MH$^+$, 100%).

Synthetic Example 5

Synthesis of 1-Benzyl-N-(3-(morpholinomethyl) benzo[b]thiophen-5-yl)-1H-pyrazole-4-carboxamide, Compound #5

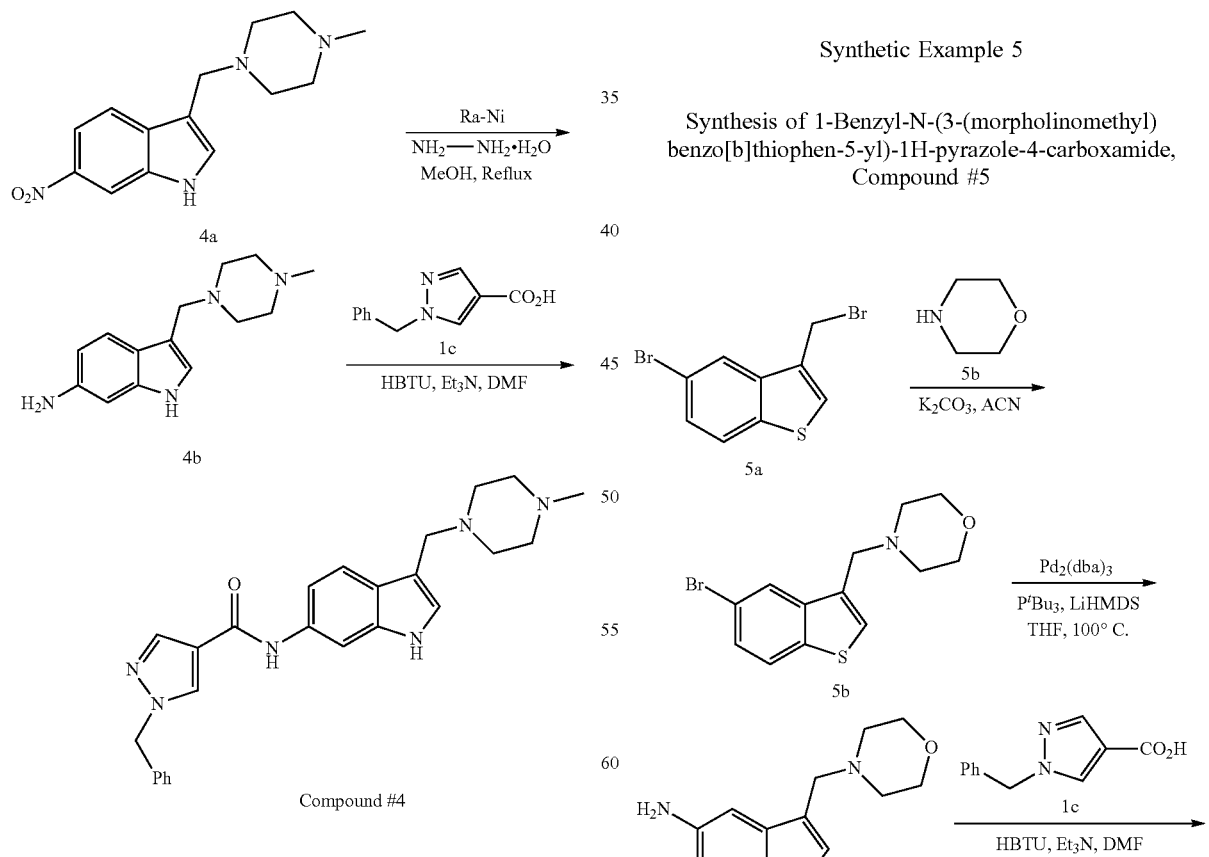

A. A solution of 3-((4-methylpiperazin-1-yl)methyl)-6-nitro-1H-indole (compound 4a, 0.32 g, 1.166 mmol) in MeOH (10 mL) was treated with Raney-Nickel (~50 mg) followed by hydrazine hydrate (0.56 mL, 11.665 mmol) at

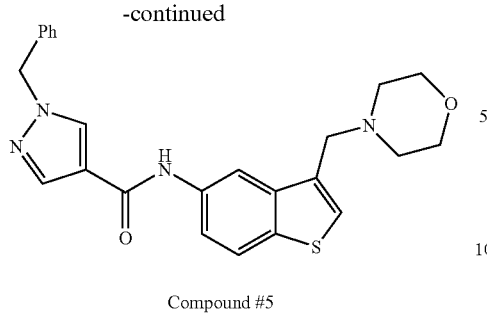

Compound #5

A. A solution of 5-bromo-3-(bromomethyl)benzo[b]thiophene (compound 5a, prepared according to the procedure disclosed in PCT Published Patent Application No. WO 1998/15545, 0.5 g, 1.63 mmol) in acetonitrile (20 mL) was treated with $K_2CO_3$ (0.67 g, 4.90 mmol), followed by morpholine (compound 5b, 0.28 mL, 3.26 mmol) at room temperature and the resulting suspension was refluxed for 1 hour. The reaction was brought to room temperature, the solid was filtered off and washed with $CH_2Cl_2$ (15 mL), followed by a 20% methanol in $CH_2Cl_2$ (2×25 mL). The combined solvent was evaporated and crude was purified by column chromatography (2M $NH_3$ in MeOH:$CH_2Cl_2$, 2:98 to 5:95) on silica gel to obtain 4-((5-bromobenzo[b]thiophen-3-yl)methyl)morpholine, compound 5c, (0.48 g, 94%) as a yellow oil. $^1$H NMR (CDCl$_3$) δ 2.35-2.60 (m, 4H), 3.60-3.80 (m, 6H), 7.31 (brs, 1H), 7.42 (d, 1H, J=4.5 Hz), 7.68 (d, 1H, J=4.2 Hz), 8.12 (s, 1H).

B. A solution of 4-((5-bromobenzo[b]thiophen-3-yl)methyl)morpholine (compound 5c, 0.46 g, 1.473 mmol) in dry THF (10 mL) was treated with Pd$_2$(dba)$_3$ (0.042 g, 0.073 mmol), LiHMDS (2.95 mL, 2.946 mmol, 1M solution in THF), followed by P$^t$Bu$_3$ (0.87 mL, 0.294 mmol, 10% in hexanes) at room temperature. The resulting solution was heated at 100° C. in a sealed tube for 2 hours. The reaction was brought to room temperature, quenched with 2N HCl solution (10 mL) and stirred for 10 minutes. The reaction was basified with 4N NaOH solution and product was extracted into ethyl acetate (2×50 mL). The combined ethyl acetate layer was washed with brine (25 mL) and dried (Na$_2$SO$_4$). Solvent was evaporated and crude was purified by column chromatography (2M $NH_3$ in MeOH:$CH_2Cl_2$, 2.5:97.5 to 5:95) on silica gel to obtain 3-(morpholinomethyl)benzo[b]thiophen-5-amine, compound 5d, (0.35 g, 96%) as a light brown solid.

C. A solution of 3-(morpholinomethyl)benzo[b]thiophen-5-amine (compound 5d, 0.34 g, 1.369 mmol), 1-benzyl-1H-pyrazole-4-carboxylic acid (compound 1c, 0.3 g, 1.505 mmol) and Et$_3$N (0.38 mL, 2.738 mmol) in dry DMF (5 mL) was treated with HBTU (0.52 g, 1.369 mmol) at room temperature and stirred for 4 hours. The reaction was diluted with 1N NaOH solution (50 mL), water (50 mL) and product was extracted into ethyl acetate (2×50 mL). The combined ethyl acetate layer was washed with brine (50 mL) and dried (Na$_2$SO$_4$). Solvent was evaporated and crude was purified by column chromatography (2M $NH_3$ in MeOH:$CH_2Cl_2$, 2:98 to 5:95) on silica gel to obtain 1-benzyl-N-(3-(morpholinomethyl)benzo[b]thiophen-5-yl)-1H-pyrazole-4-carboxamide, compound #5, (0.45 g, 76%) as a cream-coloured solid. $^1$H NMR (DMSO-d$_6$) δ 2.35-2.45 (m, 4H), 3.52-3.60 (m, 4H), 3.66 (s, 2H), 5.40 (s, 2H), 7.29-7.33 (m, 3H), 7.36-7.39 (m, 2H), 7.58 (s, 1H), 7.68 (dd, 1H, J=1.2, 4.3 Hz), 7.89 (d, 1H, J=4.5 Hz), 8.09 (s, 1H), 8.31 (d, 1H, J=0.9 Hz), 8.47 (s, 1H), 9.97 (s, 1H).

Synthetic Example 6

Synthesis of 1-Benzyl-N-(3-(piperazin-1-ylmethyl)benzo[b]thiophen-5-yl)-1H-pyrazole-4-carboxamide, Compound #6

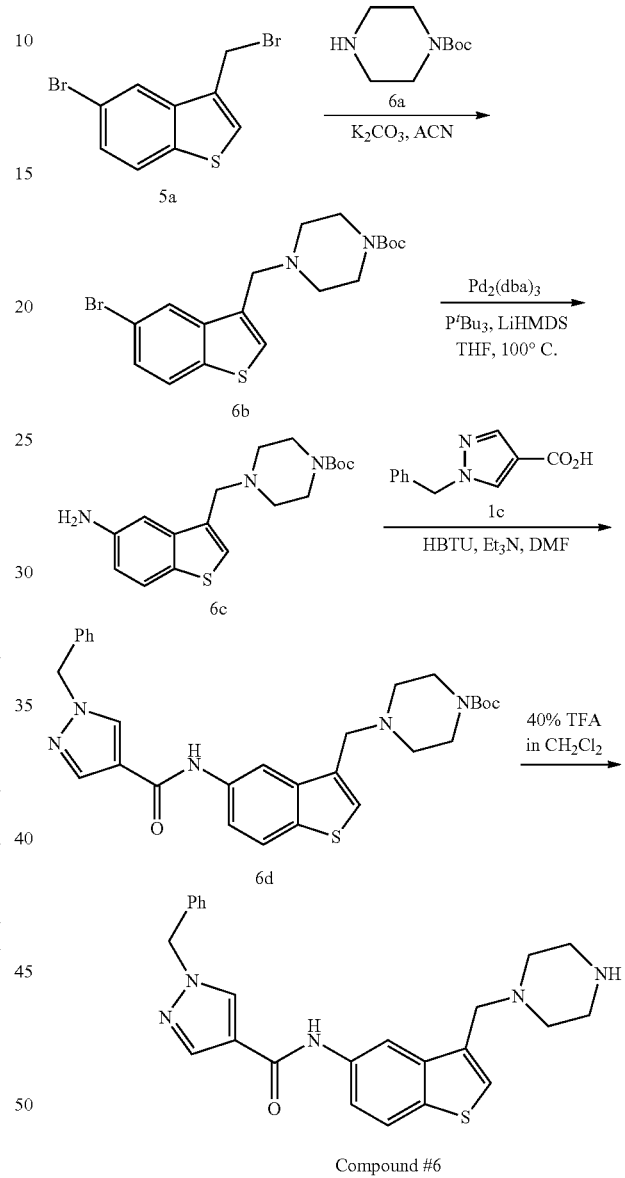

Compound #6

A. A solution of 5-bromo-3-(bromomethyl)benzo[b]thiophene (compound 5a, prepared according to the procedure disclosed in PCT Published Patent Application No. WO 1998/15545, 0.5 g, 1.63 mmol) in acetonitrile (20 mL) was treated with $K_2CO_3$ (0.67 g, 4.90 mmol), followed by tert-butyl piperazine-1-carboxylate (compound 6a, 0.34 g, 1.79 mmol) at room temperature and the resulting suspension was refluxed for 1 hour. The reaction was brought to room temperature, solid was filtered off and washed with $CH_2Cl_2$ (15 mL), followed by a 20% methanol in $CH_2Cl_2$ (2×25 mL). The combined solvent was evaporated and crude was purified by column chromatography (2M $NH_3$ in MeOH:$CH_2Cl_2$, 2:98 to 5:95) on silica gel to obtain tert-butyl 4-((5-bromobenzo[b]thiophen-3-yl)methyl)piperazine-1-carboxylate, compound 6b, (0.78 g, 89%) as a pale yellow solid. ¹H NMR (CDCl₃) δ 1.43 (s, 9H), 2.35-2.48 (m, 4H), 3.40-3.50 (m, 4H), 3.69 (brs, 2H), 7.28-7.36 (m, 1H), 7.42 (d, 1H, J=4.2 Hz), 7.68 (d, 1H, J=4.2 Hz), 8.10 (s, 1H).

B. A solution of Pd₂(dba)₃ (0.053 g, 0.093 mmol) in dry THF (5 mL) was treated with P$^t$Bu₃ (1.11 mL, 0.374 mmol, 10% in hexanes) at room temperature. After stirring for 5 minutes, the reaction was treated with a solution of tert-butyl 4-((5-bromobenzo[b]thiophen-3-yl)methyl)piperazine-1-carboxylate (compound 6b, 0.77 g, 1.871 mmol) in dry THF (10 mL) followed by LiHMDS (3.74 mL, 3.74 mmol, 1M solution in THF). The resulting solution was heated at 100° C. in a sealed tube for 2 hours. The reaction was brought to room temperature, quenched with TBAF (10 mL, 1M in THF) and stirred for 10 minutes. The reaction was basified with 4N NaOH solution and product was extracted into ethyl acetate (2×50 mL). The combined ethyl acetate layer was washed with brine (25 mL) and dried (Na₂SO₄). Solvent was evaporated and crude was purified by column chromatography (2M NH₃ in MeOH:CH₂Cl₂, 2.5:97.5 to 5:95) on silica gel to obtain tert-butyl 4-((5-aminobenzo[b]thiophen-3-yl)methyl)piperazine-1-carboxylate, compound 6c, (0.655 g, quantitative) as a light brown foam.

C. A solution of tert-butyl 4-((5-aminobenzo[b]thiophen-3-yl)methyl)piperazine-1-carboxylate (compound 6c, 0.65 g, 2.057 mmol), 1-benzyl-1H-pyrazole-4-carboxylic acid (compound 1c, 0.42 g, 1.87 mmol) and Et₃N (0.52 mL, 3.741 mmol) in dry DMF (10 mL) was treated with HBTU (0.71 g, 1.87 mmol) at room temperature and stirred for 4 h. The reaction was diluted with 1N NaOH solution (50 mL), water (50 mL) and product was extracted into ethyl acetate (2×50 mL). The combined ethyl acetate layer was washed with brine (50 mL) and dried (Na₂SO₄). Solvent was evaporated and crude was purified by column chromatography (2M NH₃ in MeOH:CH₂Cl₂, 2:98 to 5:95) on silica gel to obtain tert-butyl 4-((5-(1-benzyl-1H-pyrazole-4-carboxamido)benzo[b]thiophen-3-yl)methyl)piperazine-1-carboxylate, compound 6d (0.85 g, 86%) as a yellow solid. ¹H NMR (DMSO-d₆) δ 1.38 (s, 9H), 2.35-2.45 (m, 4H), 3.32-3.40 (m, 4H), 3.68 (s, 2H), 5.40 (s, 2H), 7.29-7.33 (m, 3H), 7.36-7.39 (m, 2H), 7.57 (s, 1H), 7.68 (dd, 1H, J=1.2, 4.3 Hz), 7.89 (d, 1H, J=4.2 Hz), 8.09 (s, 1H), 8.32 (d, 1H, J=0.9 Hz), 8.46 (s, 1H), 9.99 (s, 1H).

D. A suspension of tert-butyl 4-((5-(1-benzyl-1H-pyrazole-4-carboxamido)benzo[b]thiophen-3-yl)methyl)piperazine-1-carboxylate (compound 6d, 0.82 g, 1.542 mmol) in dry CH₂Cl₂ (12 mL) was treated with TFA (8 mL) at 0° C. The reaction was brought to room temperature and stirred for additional 2 hours. Solvent was evaporated and crude was basified with 2N NaOH solution and product was extracted into ethyl acetate (2×25 mL). The combined ethyl acetate layer was washed with brine (25 mL) and dried (Na₂SO₄). Solvent was evaporated and crude was purified by column chromatography (2M NH₃ in MeOH:CH₂Cl₂, 1:9) on silica gel to obtain 1-benzyl-N-(3-(piperazin-1-ylmethyl)benzo[b]thiophen-5-yl)-1H-pyrazole-4-carboxamide, compound #6, (0.5 g, 76%) as a cream colour solid. ¹H NMR (DMSO-d₆) δ 2.30-2.40 (m, 4H), 2.66-2.68 (m, 4H), 3.61 (s, 2H), 5.40 (s, 2H), 7.29-7.33 (m, 3H), 7.36-7.39 (m, 2H), 7.54 (s, 1H), 7.69 (dd, 1H, J=1.2, 4.3 Hz), 7.89 (d, 1H, J=4.2 Hz), 8.09 (s, 1H), 8.30 (d, 1H, J=0.9 Hz), 8.47 (s, 1H), 9.96 (s, 1H).

Synthetic Example 7

Synthesis of 1-benzyl-N-(3-(morpholinomethyl)benzofuran-6-yl)-1H-pyrazole-4-carboxamide, Compound #7

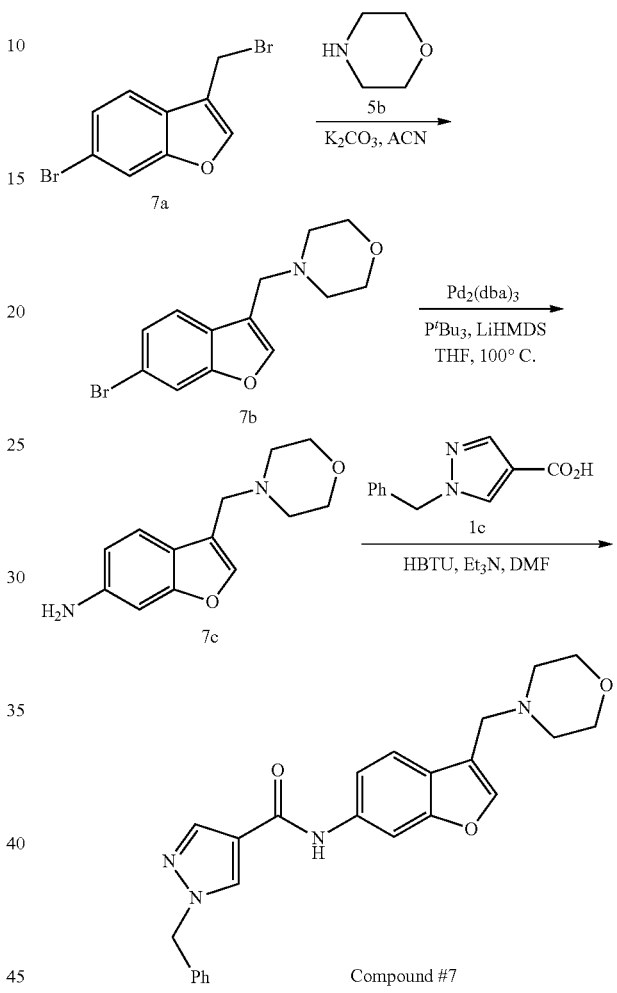

A. A solution of 6-bromo-3-(bromomethyl)benzofuran (compound 7a, prepared according to the methods disclosed in *Bioorg. & Med. Chem.*, 1997, 5, 445-459, 0.66 g, 2.276 mmol) in acetonitrile (20 mL) was treated with K₂CO₃ (0.94 g, 6.828 mmol), followed by morpholine (compound 5b, 0.24 mL, 2.731 mmol) at room temperature and the resulting suspension was refluxed for 1 hour. The reaction was brought to room temperature, solid was filtered off and washed with CH₂Cl₂ (15 mL), followed by a 20% methanol in CH₂Cl₂ (2×25 mL). The combined solvent was evaporated and crude was purified by column chromatography (2M NH₃ in MeOH:CH₂Cl₂, 2:98 to 5:95) on silica gel to obtain 4-((6-bromobenzofuran-3-yl)methyl)morpholine, compound 7b, (0.66 g, 98%) as a yellow oil.

B. A solution of Pd₂(dba)₃ (0.045 g, 0.077 mmol) in dry THF (3 mL) was treated with P$^t$Bu₃ (0.92 mL, 0.310 mmol, 10% in hexanes) at room temperature. After stirring for 5 minutes, the reaction was treated with a solution of 4-((6-bromobenzofuran-3-yl)methyl)morpholine (compound 7b, 0.46 g, 1.553 mmol) in dry THF (7 mL) followed by LiHMDS (3.1 mL, 3.106 mmol, 1M solution in THF). The resulting solution was heated at 100° C. in a sealed tube for 3 hours. The reaction was brought to room temperature, quenched with 2N HCl (10 mL) and stirred for 10 minutes. The reaction was basified with 4N NaOH solution and product was extracted into ethyl acetate (2×50 mL). The combined ethyl acetate layer was washed with brine (25 mL) and dried (Na$_2$SO$_4$). Solvent was evaporated and crude was purified by column chromatography (2M NH$_3$ in MeOH:CH$_2$Cl$_2$, 2.5:97.5 to 5:95) on silica gel to obtain 3-(morpholinomethyl)benzofuran-6-amine, compound 7c, (0.35 g, 97%) as a brown oil.

C. A solution of 3-(morpholinomethyl)benzofuran-6-amine (compound 7c. 0.34 g, 1.463 mmol), 1-benzyl-1H-pyrazole-4-carboxylic acid (compound 1c, 0.33 g, 1.610 mmol) and Et$_3$N (0.4 mL, 2.927 mmol) in dry DMF (10 mL) was treated with HBTU (0.56 g, 1.463 mmol) at room temperature and stirred for 4 hours. The reaction was diluted with 1N NaOH solution (50 mL), water (50 mL) and product was extracted into ethyl acetate (2×50 mL). The combined ethyl acetate layer was washed with brine (50 mL) and dried (Na$_2$SO$_4$). Solvent was evaporated and crude was purified by column chromatography (2M NH$_3$ in MeOH:CH$_2$Cl$_2$, 2:98 to 5:95) on silica gel to obtain 1-benzyl-N-(3-(morpholinomethyl)benzofuran-6-yl)-1H-pyrazole-4-carboxamide, compound #7, (0.24 g, 40%) as a yellow solid. $^1$H NMR (DMSO-d$_6$) δ 2.35-2.45 (m, 4H), 3.52-3.65 (m, 6H), 5.40 (s, 2H), 7.28-7.33 (m, 3H), 7.36-7.38 (m, 2H), 7.45 (dd, 1H, 0.9, 4.3 Hz), 7.65 (d, 1H, J=4.2 Hz), 7.82 (s, 1H), 8.07 (s, 1H), 8.09 (d, 1H, J=0.9 Hz), 8.45 (s, 1H), 9.96 (s, 1H).

Synthetic Example 8

Synthesis of 1-benzyl-N-(3-(morpholinomethyl)benzofuran-5-yl)-1H-pyrazole-4-carboxamide, Compound #8

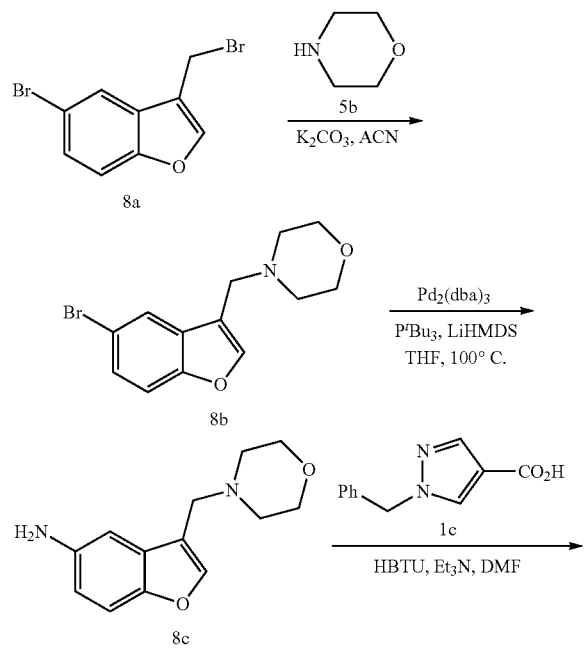

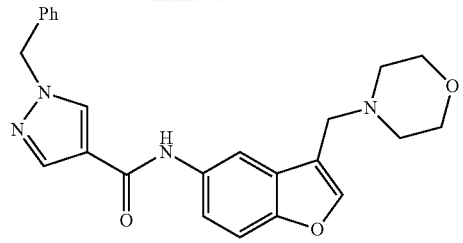

Compound #8

A. A solution of 5-bromo-3-(bromomethyl)benzofuran (compound 8a, prepared according to the methods disclosed in *Bioorg. & Med. Chem.*, 1997, 5, 445-459, 1.0 g, 3.44 mmol) in acetonitrile (20 mL) was treated with K$_2$CO$_3$ (1.43 g, 10.34 mmol), followed by morpholine (compound 5b, 0.36 mL, 4.13 mmol) at room temperature and the resulting suspension was refluxed for 1 h. The reaction was brought to room temperature, solid was filtered off and washed with CH$_2$Cl$_2$ (15 mL), followed by a 20% methanol in CH$_2$Cl$_2$ (2×25 mL). The combined solvent was evaporated and crude was purified by column chromatography (2M NH$_3$ in MeOH:CH$_2$Cl$_2$, 2:98 to 5:95) on silica gel to obtain 4-((5-bromobenzofuran-3-yl)methyl)morpholine, compound 8b, (1.01 g, quantitative) as a pale yellow solid.

B. A solution of Pd$_2$(dba)$_3$ (0.097 g, 0.168 mmol) in dry THF (5 mL) was treated with P$^t$Bu$_3$ (2.0 mL, 0.675 mmol, 10% in hexanes) at room temperature. After stirring for 5 minutes, the reaction was treated with a solution of 4-((5-bromobenzofuran-3-yl)methyl)morpholine (compound 8b,1.0 g, 3.376 mmol) in dry THF (10 mL) followed by LiHMDS (6.75 mL, 6.753 mmol, 1M solution in THF). The resulting solution was heated at 100° C. in a sealed tube for 3 h. The reaction was brought to room temperature, quenched with 2N HCl (10 mL) and stirred for 10 min. The reaction was basified with 4N NaOH solution and product was extracted into ethyl acetate (2×50 mL). The combined ethyl acetate layer was washed with brine (25 mL) and dried (Na$_2$SO$_4$). Solvent was evaporated and crude was purified by column chromatography (2M NH$_3$ in MeOH:CH$_2$Cl$_2$, 2.5:97.5 to 5:95) on silica gel to obtain 3-(morpholinomethyl)benzofuran-5-amine, compound 8c, (0.72 g, 92%) as a brown oil.

C. A solution of 3-(morpholinomethyl)benzofuran-5-amine (0.7 g, 3.013 mmol), 1-benzyl-1H-pyrazole-4-carboxylic acid (0.67 g, 3.314 mmol) and Et$_3$N (0.84 mL, 6.027 mmol) in dry DMF (10 mL) was treated with HBTU (1.14 g, 3.013 mmol) at room temperature and stirred for 4 h. The reaction was diluted with 1N NaOH solution (50 mL), water (50 mL) and product was extracted into ethyl acetate (2×50 mL). The combined ethyl acetate layer was washed with brine (50 mL) and dried (Na$_2$SO$_4$). Solvent was evaporated and crude was purified by column chromatography (2M NH$_3$ in MeOH:CH$_2$Cl$_2$, 2:98 to 5:95) on silica gel to obtain 1-benzyl-N-(3-(morpholinomethyl)benzofuran-5-yl)-1H-pyrazole-4-carboxamide, compound #8, (0.54 g, 44%) as an off-white solid. $^1$H NMR (DMSO-d$_6$) δ 2.35-2.45 (m, 4H), 3.52-3.65 (m, 6H), 5.40 (s, 2H), 7.28-7.33 (m, 3H), 7.36-7.39 (m, 2H), 7.50 (d, 1H, J=4.5 Hz), 7.59 (dd, 1H, 0.9, 4.5 Hz), 7.87 (s, 1H), 8.04 (d, 1H, J=1.2 Hz), 8.07 (s, 1H), 8.44 (s, 1H), 9.89 (s, 1H).

Synthetic Example 9

Synthesis of 1-benzyl-N-(3-(piperazin-1-ylmethyl)benzofuran-5-yl)-1H-pyrazole-4-carboxamide, Compound #9

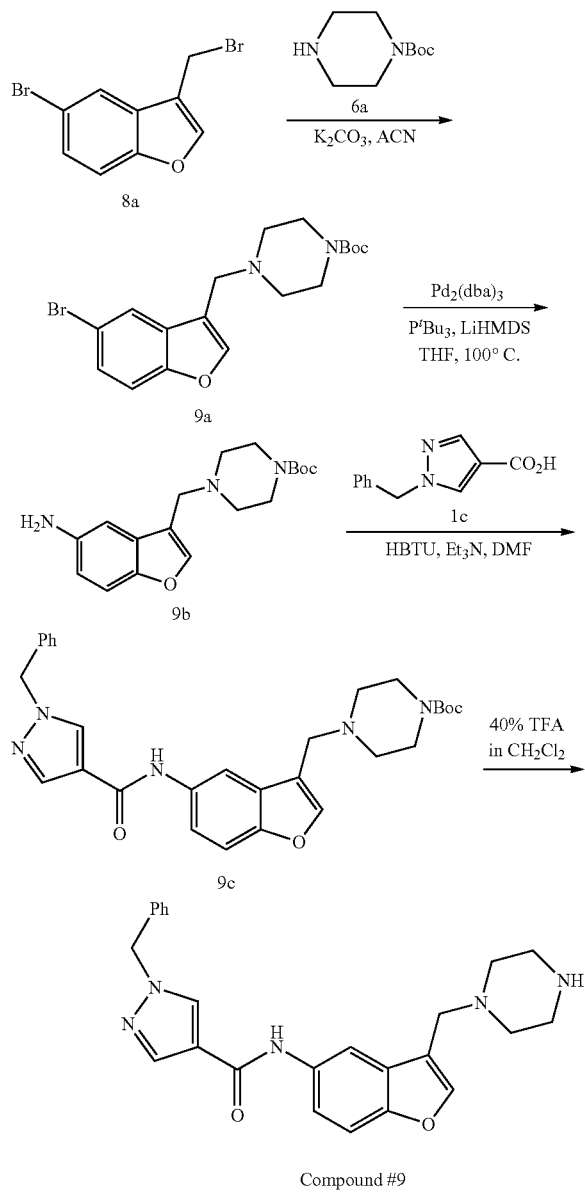

A. A solution of 5-bromo-3-(bromomethyl)benzofuran (compound 8a, prepared according to the methods disclosed in Bioorg. & Med. Chem., 1997, 5, 445-459, 1.0 g, 3.44 mmol) in acetonitrile (20 mL) was treated with $K_2CO_3$ (1.43 g, 10.34 mmol), followed by tert-butyl piperazine-1-carboxylate (compound 6a, 0.7 g, 3.79 mmol) at room temperature and the resulting suspension was refluxed for 1 hour. The reaction was brought to room temperature, solid was filtered off and washed with $CH_2Cl_2$ (15 mL), followed by a 20% methanol in $CH_2Cl_2$ (2×25 mL). The combined solvent was evaporated and crude was purified by column chromatography (2M $NH_3$ in MeOH:$CH_2Cl_2$, 2:98 to 5:95) on silica gel to obtain tert-butyl 4-((5-bromobenzofuran-3-yl)methyl)piperazine-1-carboxylate, compound 9a, (1.35 g, quantitative) as a pale yellow solid.

B. A solution of $Pd_2(dba)_3$ (0.073 g, 0.126 mmol) in dry THF (5 mL) was treated with $P^tBu_3$ (1.5 mL, 0.505 mmol, 10% in hexanes) at room temperature. After stirring for 5 minutes, the reaction was treated with a solution of tert-butyl 4-((5-bromobenzofuran-3-yl)methyl)piperazine-1-carboxylate (compound 9a, 1.0 g, 2.529 mmol) in dry THF (10 mL) followed by LiHMDS (5.05 mL, 5.059 mmol, 1M solution in THF). The resulting solution was heated at 100° C. in a sealed tube for 3 hours. The reaction was brought to room temperature, quenched with TBAF (10 mL, 1M in THF) and stirred for 10 minutes. The reaction was basified with 4N NaOH solution and product was extracted into ethyl acetate (2×50 mL). The combined ethyl acetate layer was washed with brine (25 mL) and dried ($Na_2SO_4$). Solvent was evaporated and crude was purified by column chromatography (2M $NH_3$ in MeOH:$CH_2Cl_2$, 2.5:97.5 to 5:95) on silica gel to obtain tert-butyl 4-((5-aminobenzofuran-3-yl)methyl)piperazine-1-carboxylate, compound 9b, (0.8 g, 95%) as a brown solid.

C. A solution of tert-butyl 4-((5-aminobenzofuran-3-yl)methyl)piperazine-1-carboxylate (compound 9b, 0.75 g, 2.262 mmol), 1-benzyl-1H-pyrazole-4-carboxylic acid (compound 1c, 0.5 g, 2.489 mmol) and $Et_3N$ (0.63 mL, 4.525 mmol) in dry DMF (10 mL) was treated with HBTU (0.86 g, 2.262 mmol) at room temperature and stirred for 4 hours. The reaction was diluted with 1N NaOH solution (50 mL), water (50 mL) and product was extracted into ethyl acetate (2×50 mL). The combined ethyl acetate layer was washed with brine (50 mL) and dried ($Na_2SO_4$). Solvent was evaporated and crude was purified by column chromatography (2M $NH_3$ in MeOH:$CH_2Cl_2$, 2:98 to 5:95) on silica gel to obtain tert-butyl 4-((5-(1-benzyl-1H-pyrazole-4-carboxamido)benzofuran-3-yl)methyl)piperazine-1-carboxylate, compound 9c, (1.13 g, 97%) as a pale yellow solid.

D. A suspension of tert-butyl 4-((5-(1-benzyl-1H-pyrazole-4-carboxamido)benzofuran-3-yl)methyl)piperazine-1-carboxylate (compound 9c, 1.0 g, 1.939 mmol) in dry $CH_2Cl_2$ (12 mL) was treated with TFA (8 mL) at 0° C. The reaction was brought to room temperature and stirred for additional 2 hours. Solvent was evaporated and crude was basified with 2N NaOH solution and product was extracted into ethyl acetate (2×25 mL). The combined ethyl acetate layer was washed with brine (25 mL) and dried ($Na_2SO_4$). Solvent was evaporated and crude was purified by column chromatography (2M $NH_3$ in MeOH:$CH_2Cl_2$, 1:9) on silica gel to obtain 1-benzyl-N-(3-(piperazin-1-ylmethyl)benzofuran-5-yl)-1H-pyrazole-4-carboxamide, compound #9, (0.65 g, 81%) as a pale yellow solid. $^1$H NMR (DMSO-$d_6$) δ 2.30-2.40 (m, 4H), 2.66-2.68 (m, 4H), 3.52 (s, 2H), 5.40 (s, 2H), 7.28-7.33 (m, 3H), 7.36-7.38 (m, 2H), 7.49 (d, 1H, J=4.5 Hz), 7.59 (dd, 1H, J=0.9, 4.5 Hz), 7.85 (s, 1H), 8.03 (s, 1H), 8.07 (s, 1H), 8.45 (s, 1H), 9.89 (s, 1H).

Synthetic Example 10

Synthesis of 1-benzyl-N-(3-(piperazin-1-ylmethyl)benzofuran-6-yl)-1H-pyrazole-4-carboxamide, Compound #10

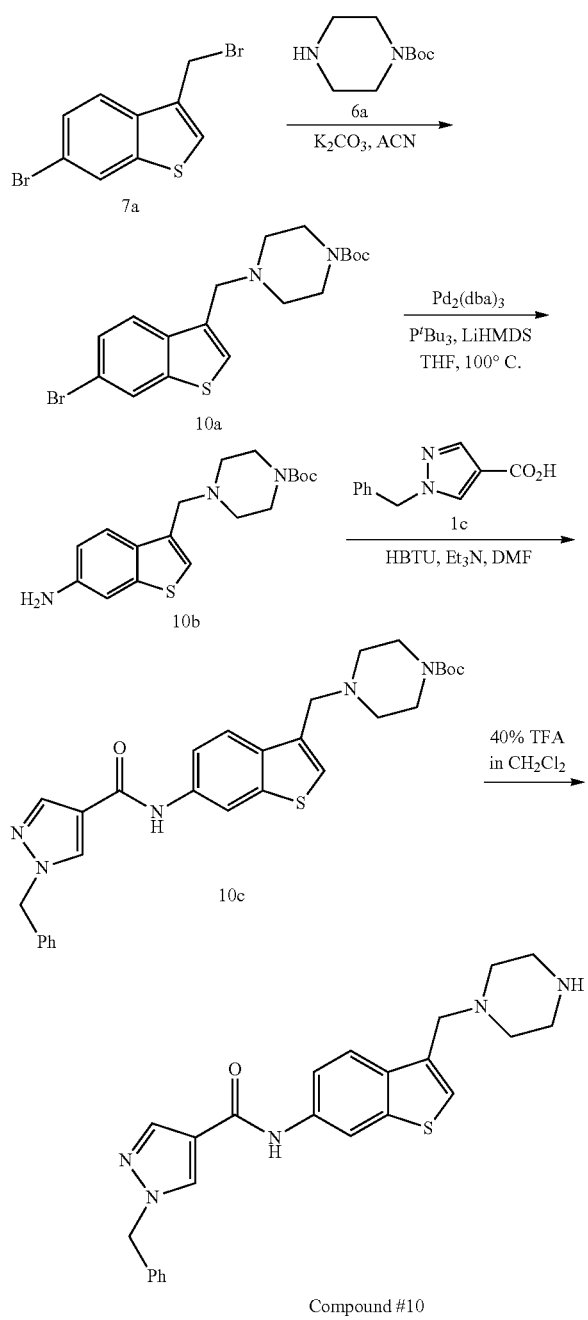

Compound #10

A. A solution of 6-bromo-3-(bromomethyl)benzofuran (compound 7a, 0.745 g, 2.569 mmol) in acetonitrile (25 mL) was treated with $K_2CO_3$ (1.06 g, 7.708 mmol), followed by tert-butyl piperazine-1-carboxylate (compound 6a, 0.53 g, 2.826 mmol) at room temperature and the resulting suspension was refluxed for 1 hour. The reaction was brought to room temperature, solid was filtered off and washed with $CH_2Cl_2$ (15 mL), followed by a 20% methanol in $CH_2Cl_2$ (2×25 mL). The combined solvent was evaporated and crude was purified by column chromatography (2M $NH_3$ in MeOH:$CH_2Cl_2$, 2:98 to 5:95) on silica gel to obtain tert-butyl 4-((6-bromobenzofuran-3-yl)methyl)piperazine-1-carboxylate, compound 10a, (1.0 g, quantitative) as a pale yellow solid.

B. A solution of $Pd_2(dba)_3$ (0.070 g, 0.122 mmol) in dry THF (5 mL) was treated with $P^tBu_3$ (1.46 mL, 0.49 mmol, 10% in hexanes) at room temperature. After stirring for 5 minutes, the reaction was treated with a solution of tert-butyl 4-((6-bromobenzofuran-3-yl)methyl)piperazine-1-carboxylate (compound 10a, 0.97 g, 2.453 mmol) in dry THF (10 mL) followed by LiHMDS (4.9 mL, 4.907 mmol, 1M solution in THF). The resulting solution was heated at 100° C. in a sealed tube for 3 hours. The reaction was brought to room temperature, quenched with TBAF (10 mL, 1M in THF) and stirred for 10 minutes. The reaction was basified with 4N NaOH solution and product was extracted into ethyl acetate (2×50 mL). The combined ethyl acetate layer was washed with brine (25 mL) and dried ($Na_2SO_4$). Solvent was evaporated and crude was purified by column chromatography (2M $NH_3$ in MeOH:$CH_2Cl_2$, 2.5:97.5 to 5:95) on silica gel to obtain tert-butyl 4-((6-aminobenzofuran-3-yl)methyl)piperazine-1-carboxylate, compound 10b, (0.65 g, 80%) as a brown solid.

C. A solution of tert-butyl 4-((6-aminobenzofuran-3-yl)methyl)piperazine-1-carboxylate (compound 10b, 0.62 g, 1.87 mmol), 1-benzyl-1H-pyrazole-4-carboxylic acid (compound 1c, 0.42 g, 2.05 mmol) and $Et_3N$ (0.52 mL, 3.74 mmol) in dry DMF (10 mL) was treated with HBTU (0.71 g, 1.87 mmol) at room temperature and stirred for 4 hours. The reaction was diluted with 1N NaOH solution (50 mL), water (50 mL) and product was extracted into ethyl acetate (2×50 mL). The combined ethyl acetate layer was washed with brine (50 mL) and dried ($Na_2SO_4$). Solvent was evaporated and crude was purified by column chromatography (2M $NH_3$ in MeOH:$CH_2Cl_2$, 2:98 to 5:95) on silica gel to obtain tert-butyl 4-((6-(1-benzyl-1H-pyrazole-4-carboxamido)benzofuran-3-yl)methyl)piperazine-1-carboxylate, compound 10c, (0.44 g, 97%) as a brown solid.

D. A suspension of tert-butyl 4-((6-(1-benzyl-1H-pyrazole-4-carboxamido)benzofuran-3-yl)methyl)piperazine-1-carboxylate (compound 10c, 0.35 g, 0.678 mmol) in dry $CH_2Cl_2$ (12 mL) was treated with TFA (8 mL) at 0° C. The reaction was brought to room temperature and stirred for additional 2 hours. Solvent was evaporated and crude was basified with 2N NaOH solution and product was extracted into ethyl acetate (2×25 mL). The combined ethyl acetate layer was washed with brine (25 mL) and dried ($Na_2SO_4$). Solvent was evaporated and crude was purified by column chromatography (2M $NH_3$ in MeOH:$CH_2Cl_2$, 1:9) on silica gel to obtain 1-benzyl-N-(3-(piperazin-1-ylmethyl)benzofuran-6-yl)-1H-pyrazole-4-carboxamide, compound #10, (0.23 g, 82%) as a pale yellow solid. $^1H$ NMR (DMSO-$d_6$) δ 2.30-2.40 (m, 4H), 2.66-2.70 (m, 4H), 3.53 (s, 2H), 5.40 (s, 2H), 7.28-7.33 (m, 3H), 7.36-7.39 (m, 2H), 7.44 (dd, 1H, J=0.9, 4.2 Hz), 7.64 (d, 1H, J=4.5 Hz), 7.80 (s, 1H), 8.07 (2s, 2H), 8.46 (s, 1H), 9.96 (s, 1H).

Synthetic Example 11

Synthesis of (R)-1-benzyl-N-(4-methyl-1-oxo-1,2,3,4-tetrahydropyrazino[1,2-a]indol-7-yl)-1H-pyrazole-4-carboxamide, Compound #11

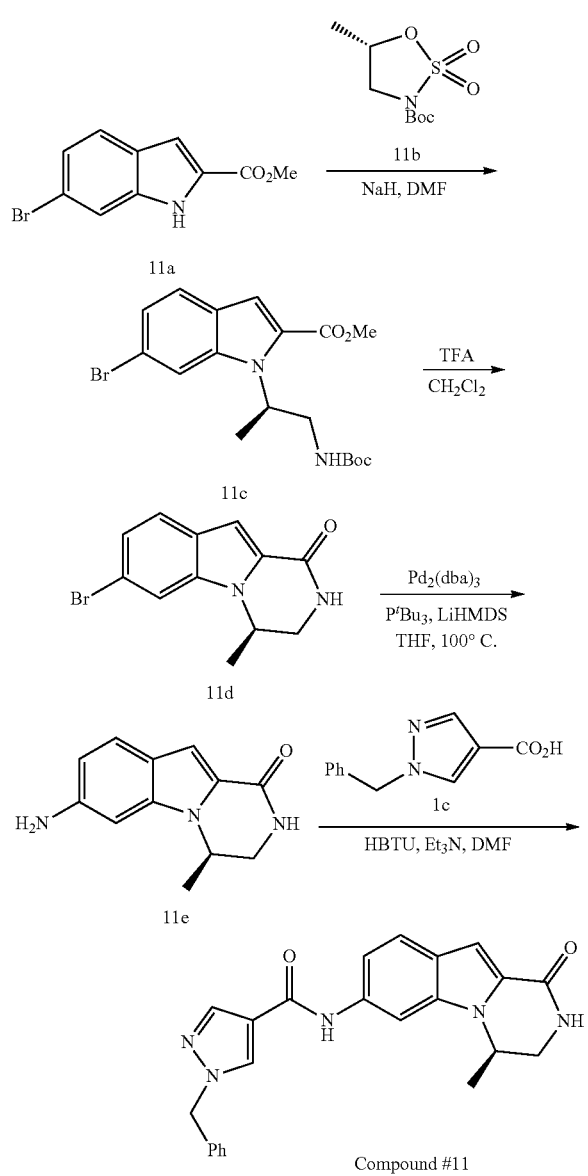

Compound #11

A. A solution of methyl 6-bromo-1H-indole-2-carboxylate (compound 11a, 2.0 g, 7.87 mmol) in dry DMF (10 mL) was treated with NaH (0.33 g, 8.65 mmol, 60% in mineral oil) at 0° C. and stirred at same temperature for 30 more min. The reaction was treated with a solution of tert-butyl (S)-5-methyl-1,2,3-oxathiazolidine-3-carboxylate 2,2-dioxide (compound 11b, 1.87 g, 7.87 mmol) in DMF (10 mL) drop-wise at same temperature. The reaction was brought to room temperature and stirred for 18 hours. The reaction was quenched with the addition of water (100 mL) and product was extracted into ethyl acetate (2×100 mL). The combined ethyl acetate layer was washed with water (2×50 mL), brine (2×50 mL) and dried ($Na_2SO_4$). Solvent was evaporated and crude was purified by column chromatography (EtOAc:Hexanes, 1:9) on silica gel to obtain methyl (R)-6-bromo-1-(1-((tert-butoxycarbonyl)amino)propan-2-yl)-1H-indole-2-carboxylate, compound 11c, (1.7 g, 51%) as an off-white solid.

B. A solution of methyl (R)-6-bromo-1-(1-((tert-butoxycarbonyl)amino)propan-2-yl)-1H-indole-2-carboxylate (compound 11c, 1.7 g, 4.133 mmol) in $CH_2Cl_2$ (15 mL) was treated with TFA (10 mL) at 0° C. The reaction was brought to room temperature and stirred for 3 hours. Solvent was evaporated and crude was basified with 1N NaOH solution (50 mL) and product was extracted into $CH_2Cl_2$ (3×50 mL). The combined $CH_2Cl_2$ layer was dried ($Na_2SO_4$), solvent was evaporated and crude was purified by column chromatography (2M $NH_3$ in MeOH:$CH_2Cl_2$, 2.5:97.5) on silica gel to obtain (R)-7-bromo-4-methyl-3,4-dihydropyrazino[1,2-a]indol-1(2H)-one, compound 11d, (0.65 g, 57%) as a pale yellow solid. $^1H$ NMR (DMSO-$d_6$) δ 1.29 (d, 3H, J=3.3 Hz), 3.35-3.38 (m, 1H), 3.82 (dd, 1H, J=2.4, 6.4 Hz), 4.88-4.90 (m, 1H), 7.03 (s, 1H), 7.22 (dd, 1H, J=0.9, 3.4 Hz), 7.62 (d, 1H, J=4.2 Hz), 7.89 (s, 1H), 8.11 (d, 1H, J=2.4 Hz).

C. A solution of $Pd_2(dba)_3$ (0.015 g, 0.026 mmol) in dry THF (5 mL) was treated with $P^tBu_3$ (0.32 mL, 0.107 mmol, 10% in hexanes) at room temperature. After stirring for 5 minutes, the reaction was treated with a solution of (R)-7-bromo-4-methyl-3,4-dihydropyrazino[1,2-a]indol-1(2H)-one (compound 11d, 0.15 g, 0.537 mmol) in dry THF (5 mL) followed by LiHMDS (1.1 mL, 1.074 mmol, 1M solution in THF). The resulting solution was heated at 100° C. in a sealed tube for 3 hours. The reaction was brought to room temperature, quenched with 2 N HCl solution (10 mL) and stirred for 10 minutes. The reaction was basified with 4N NaOH solution and product was extracted into ethyl acetate (2×50 mL). The combined ethyl acetate layer was washed with brine (25 mL) and dried ($Na_2SO_4$). Solvent was evaporated and crude was purified by column chromatography (2M $NH_3$ in MeOH:$CH_2Cl_2$, 2.5:97.5 to 5:95) on silica gel to obtain (R)-7-amino-4-methyl-3,4-dihydropyrazino[1,2-a]indol-1(2H)-one, compound 11e, (0.06 g, 52%) as a brown solid.

D. A solution of (R)-7-amino-4-methyl-3,4-dihydropyrazino[1,2-a]indol-1(2H)-one (compound 11e, 0.06 g, 0.278 mmol), 1-benzyl-1H-pyrazole-4-carboxylic acid (compound 1c, 0.062 g, 0.306 mmol) and $Et_3N$ (0.07 mL, 0.557 mmol) in dry DMF (5 mL) was treated with HBTU (0.105 g, 0.278 mmol) at room temperature and stirred for 16 hours. The reaction was diluted with 1N NaOH solution (50 mL), water (50 mL) and product was extracted into ethyl acetate (2×50 mL). The combined ethyl acetate layer was washed with brine (50 mL) and dried ($Na_2SO_4$). Solvent was evaporated and crude was purified by column chromatography (2M $NH_3$ in MeOH:$CH_2Cl_2$, 2:98 to 5:95) on silica gel to obtain (R)-1-benzyl-N-(4-methyl-1-oxo-1,2,3,4-tetrahydropyrazino[1,2-a]indol-7-yl)-1H-pyrazole-4-carboxamide, compound #11, (0.025 g, 23%) as a yellow solid. $^1H$ NMR (DMSO-$d_6$) δ 1.31 (d, 3H, J=3.3 Hz), 3.32-3.37 (m, 1H), 3.82-3.85 (m, 1H), 4.71-4.73 (m, 1H), 5.41 (s, 2H), 6.98 (s, 1H), 7.29-7.39 (m, 6H), 7.60 (d, 1H, J=4.5 Hz), 7.97 (d, 1H, J=2.4 Hz), 8.06 (d, 1H, J=1.8 Hz), 8.09 (s, 1H), 8.46 (s, 1H), 9.94 (s, 1H).

Synthetic Example 12

Synthesis of 1-benzyl-N-(1-oxo-1,2,3,4-tetrahydropyrazino[1,2-a]indol-7-yl)-1H-pyrazole-4-carboxamide, Compound #12

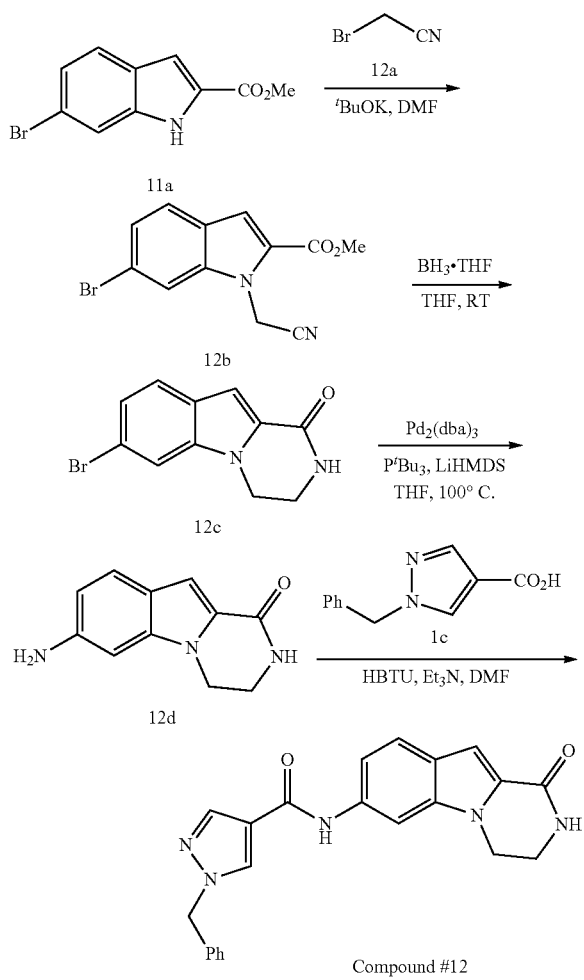

Compound #12

A. A solution of methyl 6-bromo-1H-indole-2-carboxylate (compound 11a, 0.865 g, 3.404 mmol) in dry DMF (10 mL) was treated with $^t$BuOK (0.57 g, 5.106 mmol) at room temperature and stirred for 15 minutes. The reaction was treated with 2-bromoacetonitrile (compound 12a, 0.47 mL, 6.808 mmol) drop-wise and was left to stir for 16 hours. The reaction was quenched with the addition of saturated NH$_4$Cl solution (20 mL) and diluted with water (100 mL). The brown solid was filtered off, washed with water (2×75 mL), hexanes (25 mL) and dried under vacuum to obtain methyl 6-bromo-1-(cyanomethyl)-1H-indole-2-carboxylate, compound 12b, (0.95 g, 95%).

B. A solution of methyl 6-bromo-1-(cyanomethyl)-1H-indole-2-carboxylate (compound 12b, 0.92 g, 3.138 mmol) in dry THF (15 mL) was treated with BH$_3$.THF (15.7 mL, 15.69 mmol, 1M solution in THF) drop-wise at 0° C. The reaction was brought to room temperature and stirred for 24 hours. The reaction was slowly quenched with methanol (10 mL) and then refluxed for 30 minutes. The reaction was brought to room temperature, solvent was evaporated and crude was purified by column chromatography (2M NH$_3$ in MeOH:CH$_2$Cl$_2$, 2.5:97.5) on silica gel to obtain 7-bromo-3,4-dihydropyrazino[1,2-a]indol-1(2H)-one, compound 12c, (0.27 g, 34%) as a pale yellow solid. $^1$H NMR (CDCl$_3$) δ 3.79-3.81 (m, 2H), 4.20-4.22 (m, 2H), 6.59 (brs, 1H), 7.24-7.27 (m, 2H), 7.49 (s, 1H), 7.57 (d, 1H, J=4.2 Hz).

C. A solution of Pd$_2$(dba)$_3$ (0.025 g, 0.043 mmol) in dry THF (5 mL) was treated with P$^t$Bu$_3$ (0.51 mL, 0.173 mmol, 10% in hexanes) at room temperature. After stirring for 5 minutes, the reaction was treated with a solution of 7-bromo-3,4-dihydropyrazino[1,2-a]indol-1(2H)-one (compound 12c, 0.23 g, 0.867 mmol) in dry THF (5 mL) followed by LiHMDS (1.74 mL, 1.735 mmol, 1M solution in THF). The resulting solution was heated at 100° C. in a sealed tube for 3 hours. The reaction was brought to room temperature, quenched with 2 N HCl solution (10 mL) and stirred for 10 minutes. The reaction was basified with 4N NaOH solution and product was extracted into ethyl acetate (2×50 mL). The combined ethyl acetate layer was washed with brine (25 mL) and dried (Na$_2$SO$_4$). Solvent was evaporated and crude was purified by column chromatography (2M NH$_3$ in MeOH:CH$_2$Cl$_2$, 2.5:97.5 to 5:95) on silica gel to obtain 7-amino-3,4-dihydropyrazino[1,2-a]indol-1(2H)-one, compound 12d, (0.09 g, 52%) as a brown solid.

D. A solution of 7-amino-3,4-dihydropyrazino[1,2-a]indol-1(2H)-one (compound 12d, 0.09 g, 0.447 mmol), 1-benzyl-1H-pyrazole-4-carboxylic acid (compound 1c, 0.1 g, 0.491 mmol) and Et$_3$N (0.12 mL, 0.894 mmol) in dry DMF (5 mL) was treated with HBTU (0.17 g, 0.447 mmol) at room temperature and stirred for 16 hours. The reaction was diluted with 1N NaOH solution (50 mL), water (50 mL) and product was extracted into ethyl acetate (2×50 mL). The combined ethyl acetate layer was washed with brine (50 mL) and dried (Na$_2$SO$_4$). Solvent was evaporated and crude was purified by column chromatography (2M NH$_3$ in MeOH:CH$_2$Cl$_2$, 2:98 to 5:95) on silica gel to obtain 1-benzyl-N-(1-oxo-1,2,3,4-tetrahydropyrazino[1,2-a]indol-7-yl)-1H-pyrazole-4-carboxamide, compound #12, (0.008 g, 5%) as a yellow solid. $^1$H NMR (DMSO-d$_6$) δ 3.62-3.64 (m, 2H), 4.18-4.20 (m, 2H), 5.40 (s, 2H), 6.98 (s, 1H), 7.29-7.39 (m, 6H), 7.60 (d, 1H, J=4.2 Hz), 8.05-8.08 (m, 3H), 8.46 (s, 1H), 9.93 (s, 1H).

Synthetic Example 13

Synthesis of 1-benzyl-N-(2-methyl-1,2,3,4-tetrahydrobenzofuro[3,2-c]pyridin-8-yl)-1H-pyrazole-4-carboxamide, Compound #13

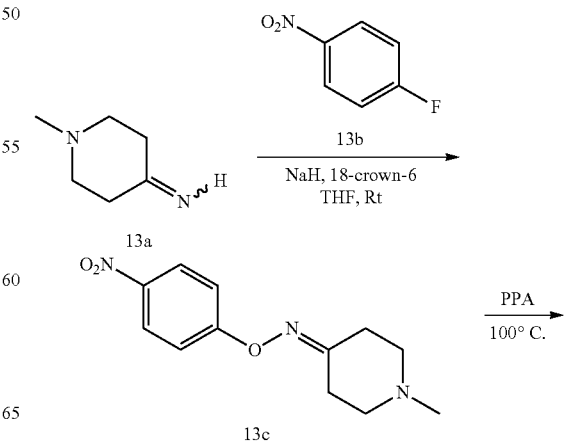

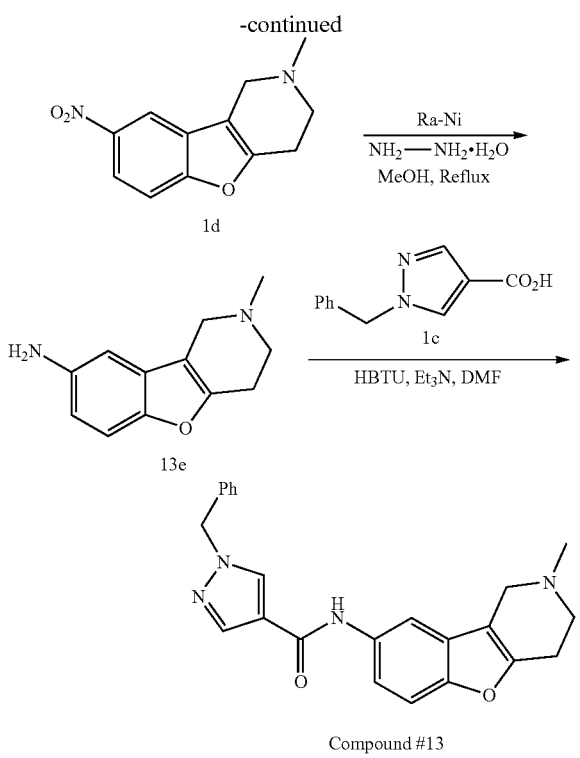

A. A suspension of NaH (0.5 g, 12.872 mmol, 60% in mineral oil) in dry THF (5 mL) was treated with 1-methylpiperidin-4-one oxime (compound 13a, prepared according to the methods disclosed in PCT Published Patent Application No. WO 2006/108965, 1.5 g, 11.702 mmol) in dry THF (20 mL) drop-wise at 0° C. The reaction was brought to room temperature and stirred for 30 minutes. 1-Fluoro-4-nitrobenzene (compound 13b, 1.36 mL, 12.872 mmol) followed by 18-crown-6 (0.12 g, 0.468 mmol) were added at 0° C. and the reaction was brought to room temperature and stirred for additional 4 hours. The reaction was quenched with water (50 mL) and product was extracted into ethyl acetate (2×50 mL). The combined ethyl acetate layer was washed with brine (25 mL) and dried ($Na_2SO_4$). Solvent was evaporated and crude was purified by column chromatography (MeOH:$CH_2Cl_2$, 2:98) on silica gel to obtain 1-methylpiperidin-4-one O-(4-nitrophenyl) oxime, compound 13c, (2.24 g, 77%) as a yellow solid.

B. Solid 1-methylpiperidin-4-one O-(4-nitrophenyl) oxime (compound 13c, 1.0 g, 4.011 mmol) was added to flask containing PPA (~50 mL) at 100° C. portion-wise and stirring was continued at same temperature for additional 3 hours. The reaction was brought to 80° C. and diluted with water (50 mL). The reaction was then brought to room temperature, basified with 4N NaOH solution and product was extracted into $CH_2Cl_2$ (3×50 mL). The combined $CH_2Cl_2$ layer was dried ($Na_2SO_4$), solvent was evaporated and crude was purified by column chromatography (2M $NH_3$ in MeOH:$CH_2Cl_2$, 2:98) on silica gel to obtain 2-methyl-8-nitro-1,2,3,4-tetrahydrobenzofuro[3,2-c]pyridine, compound 13d, (0.24 g, 26%) as a yellow solid.

C. A solution of 2-methyl-8-nitro-1,2,3,4-tetrahydrobenzofuro[3,2-c]pyridine (compound 13d, 0.2 g, 0.861 mmol) in MeOH (10 mL) was treated with Raney-Nickel (~50 mg) followed by hydrazine hydrate (0.41 mL, 8.611 mmol) at room temperature. The reaction was refluxed for 10-15 minutes in a pre-heated oil bath and then brought back to room temperature. The solution was filtered through a pad of celite and washed with methanol (2×15 mL). The combined methanol layer was evaporated and crude was purified by flash column chromatography (2M $NH_3$ in MeOH:$CH_2Cl_2$, 2:98 to 5:95) on silica gel to obtain 2-methyl-1,2,3,4-tetrahydrobenzofuro[3,2-c]pyridin-8-amine, compound 13e, (0.06 g, 35%) as a yellow solid.

D. A solution of 2-methyl-1,2,3,4-tetrahydrobenzofuro[3,2-c]pyridin-8-amine (compound 13e, 0.055 g, 0.271 mmol), 1-benzyl-1H-pyrazole-4-carboxylic acid (compound 1c, 0.06 g, 0.299 mmol) and $Et_3N$ (0.075 mL, 0.543 mmol) in dry DMF (5 mL) was treated with HBTU (0.10 g, 0.271 mmol) at room temperature and stirred for 16 hours. The reaction was diluted with 1N NaOH solution (50 mL), water (50 mL) and product was extracted into ethyl acetate (2×50 mL). The combined ethyl acetate layer was washed with brine (50 mL) and dried ($Na_2SO_4$). Solvent was evaporated and crude was purified by column chromatography (2M $NH_3$ in MeOH:$CH_2Cl_2$, 2:98 to 5:95) on silica gel to obtain 1-benzyl-N-(2-methyl-1,2,3,4-tetrahydrobenzofuro[3,2-c]pyridin-8-yl)-1H-pyrazole-4-carboxamide, compound #13, (0.06 g, 57%) as an off-white solid. $^1$H NMR (DMSO-$d_6$) δ 2.43 (s, 3H), 2.77-2.80 (m, 4H), 3.47 (s, 2H), 5.39 (s, 2H), 7.28-7.38 (m, 5H), 7.44-7.46 (m, 2H), 7.81 (s, 1H), 8.05 (s, 1H), 8.42 (s, 1H), 9.84 (s, 1H).

Synthetic Example 14

Synthesis of 1-benzyl-N-(2-methyl-2,3,4,5-tetrahydro-1H-pyrido[4,3-b]indol-8-yl)-1H-pyrazole-4-carboxamide, Compound #14

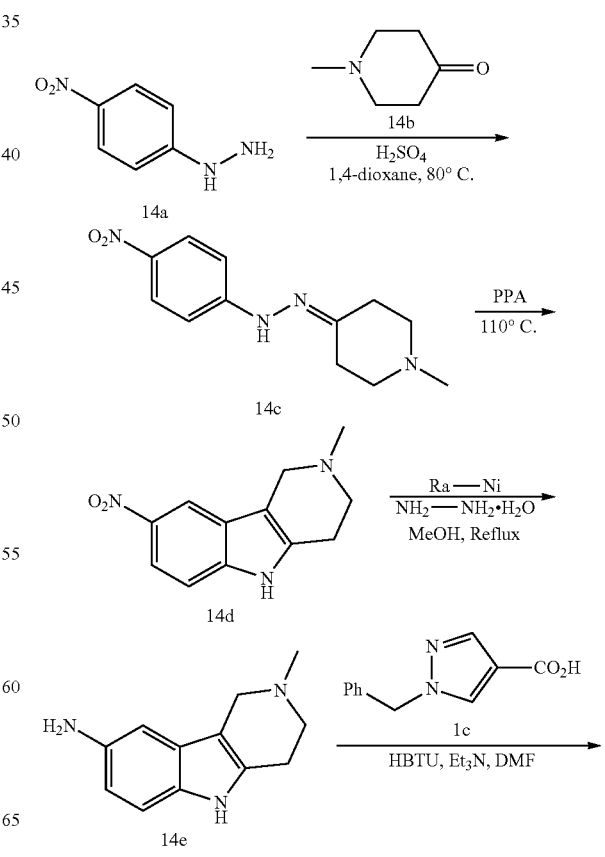

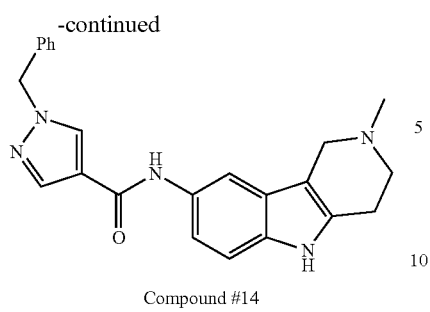

Compound #14

A. A solution of (4-nitrophenyl) hydrazine (compound 14a, 3.1 g, 20.24 mmol) in 1,4-dioxane (25 mL) was treated with $H_2SO_4$ (2 mL) followed by 1-methylpiperidin-4-one (compound 14b, 4.7 mL, 40.48 mmol) at room temperature and the resulting mixture was stirred at 80° C. for 30 min. The reaction was brought to room temperature, basified with 4N NaOH solution and product was extracted into ethyl acetate (2×50 mL). The combined ethyl acetate layer was washed with brine (25 mL) and dried ($Na_2SO_4$). Solvent was evaporated and dried under vacuum to obtain 1-methyl-4-(2-(4-nitrophenyl)hydrazono)piperidine, compound 14c, (4.5 g, 90%) as a yellow solid.

B. Solid 1-methyl-4-(2-(4-nitrophenyl)hydrazono)piperidine (compound 14c, 1.2 g, 4.83 mmol) was added to flask containing PPA (~50 mL) at 110° C. portion-wise and stirring was continued at same temperature for additional 3 hours. The reaction was brought to 80° C. and diluted with water (50 mL). The reaction was then brought to room temperature, basified with 4N NaOH solution and product was extracted into $CH_2Cl_2$ (3×50 mL). The combined $CH_2Cl_2$ layer was dried ($Na_2SO_4$), solvent was evaporated and crude was purified by column chromatography (2M $NH_3$ in MeOH:$CH_2Cl_2$, 2:98 to 3:97) on silica gel to obtain 2-methyl-8-nitro-2,3,4,5-tetrahydro-1H-pyrido[4,3-b]indole, compound 14d, (0.24 g, 22%) as a yellow solid.

C. A solution of 2-methyl-8-nitro-2,3,4,5-tetrahydro-1H-pyrido[4,3-b]indole (compound 14d, 0.15 g, 0.648 mmol) in MeOH (10 mL) was treated with Raney-Nickel (~50 mg) followed by hydrazine hydrate (0.31 mL, 6.486 mmol) at room temperature. The reaction was refluxed for 10-15 minutes in a pre-heated oil bath and then brought back to room temperature. The solution was filtered through a pad of celite and washed with methanol (2×15 mL). The combined methanol layer was evaporated and crude was purified by flash column chromatography (2M $NH_3$ in MeOH:$CH_2Cl_2$, 2:98 to 5:95) on silica gel to obtain 2-methyl-2,3,4,5-tetrahydro-1H-pyrido[4,3-b]indol-8-amine, compound 14e, (0.12 g, 92%) as a yellow solid.

D. A solution of 2-methyl-2,3,4,5-tetrahydro-1H-pyrido[4,3-b]indol-8-amine (compound 14e, 0.11 g, 0.546 mmol), 1-benzyl-1H-pyrazole-4-carboxylic acid (compound 1c, 0.12 g, 0.601 mmol) and $Et_3N$ (0.15 mL, 1.093 mmol) in dry DMF (5 mL) was treated with HBTU (0.20 g, 0.546 mmol) at room temperature and stirred for 16 hours. The reaction was diluted with 1N NaOH solution (50 mL), water (50 mL) and product was extracted into ethyl acetate (2×50 mL). The combined ethyl acetate layer was washed with brine (50 mL) and dried ($Na_2SO_4$). Solvent was evaporated and crude was purified by column chromatography (2M $NH_3$ in MeOH:$CH_2Cl_2$, 2:98 to 5:95) on silica gel to obtain 1-benzyl-N-(2-methyl-2,3,4,5-tetrahydro-1H-pyrido[4,3-b]indol-8-yl)-1H-pyrazole-4-carboxamide, compound #14, (0.14 g, 67%) as an off-white solid. $^1H$ NMR (DMSO-$d_6$) δ 2.42 (s, 3H), 2.71-2.77 (m, 4H), 3.48 (s, 2H), 5.38 (s, 2H), 7.18-7.38 (m, 7H), 7.63 (s, 1H), 8.04 (s, 1H), 8.39 (s, 1H), 9.64 (s, 1H), 10.70 (s, 1H).

Synthetic Example 15

Synthesis of (R)-1-benzyl-N-(9-methyl-6-oxo-6,7,8,9-tetrahydropyrido[3',2':4,5]pyrrolo[1,2-a]pyrazin-2-yl)-1H-pyrazole-4-carboxamide, Compound #15

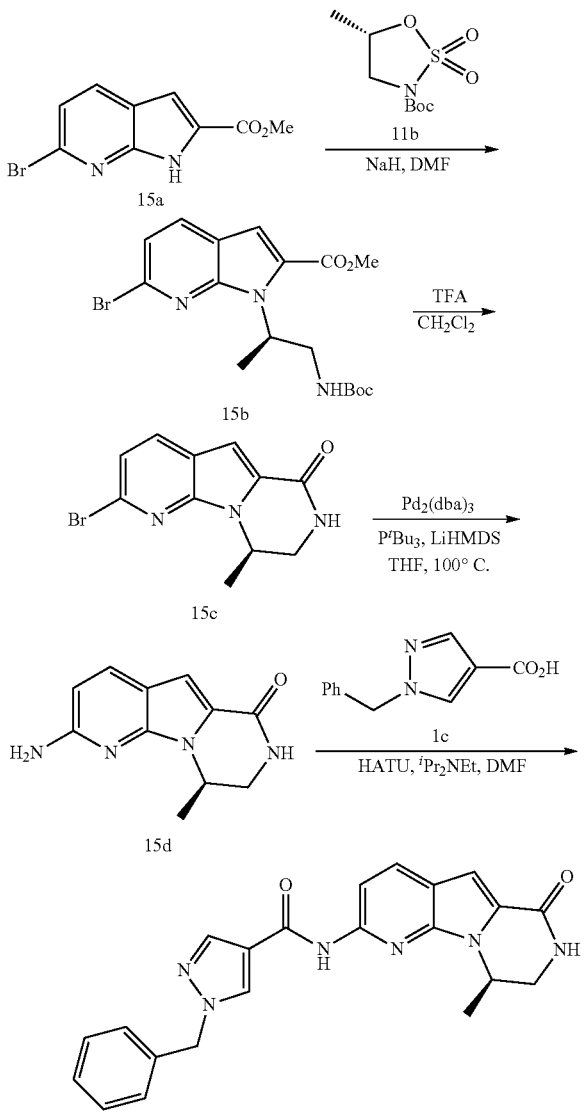

Compound #15

A. A solution of methyl 6-bromo-1H-pyrrolo[2,3-b]pyridine-2-carboxylate (compound 15a, 0.5 g, 1.96 mmol) in dry DMF (10 mL) was treated with NaH (0.087 g, 2.16 mmol, 60% in mineral oil) at 0° C. and stirred at same temperature for 30 additional minutes. The reaction was treated with a solution of tert-butyl (S)-5-methyl-1,2,3-oxathiazolidine-3-carboxylate 2,2-dioxide (compound 11b, 0.49 g, 2.06 mmol) in DMF (10 mL) drop-wise at same temperature. The reaction was brought to room temperature and stirred for 18 h. The reaction was quenched with the addition of water (50 mL) and product was extracted into ethyl acetate (2×25 mL). The combined ethyl acetate layer was washed with water (2×50 mL), brine (50 mL) and dried ($Na_2SO_4$). Solvent was evaporated and obtained crude product, methyl (R)-6-bromo-1-(1-((tert-butoxycarbonyl)amino)propan-2-yl)-1H-pyrrolo[2,3-b]pyridine-2-carboxylate, compound 15b, (0.75 g, 92%) as off-white solid, which was used directly in the next step.

B. A solution of methyl (R)-6-bromo-1-(1-((tert-butoxycarbonyl)amino)propan-2-yl)-1H-pyrrolo[2,3-b]pyridine-2-carboxylate (compound 15b, 0.75 g, 1.82 mmol) in $CH_2Cl_2$ (50 mL) was treated with TFA (5 mL) at 0° C. The reaction was brought to room temperature and stirred for 3 hours. Solvent was evaporated and crude was basified with saturated $NaHCO_3$ solution (50 mL) and product was extracted into $CH_2Cl_2$ (3×50 mL). The combined $CH_2Cl_2$ layer was dried ($Na_2SO_4$), solvent was evaporated and crude was purified by column chromatography (MeOH:$CH_2Cl_2$, 0:100 to 10:90) on silica gel to obtain (R)-2-bromo-9-methyl-8,9-dihydropyrido[3',2':4,5]pyrrolo[1,2-a]pyrazin-6(7H)-one, compound 15c, (0.185 g, 36%) as a pale yellow solid. $^1$H NMR (DMSO-$d_6$) δ 1.46 (d, 3H, J=3.0 Hz), 3.42-3.45 (m, 1H), 3.93 (dd, 1H, J=4.8, 12.6 Hz), 5.02-5.04 (m, 1H), 6.71 (s, 1H), 7.13 (s, 1H), 7.21 (d, 1H, J=8.8 Hz), 7.80 (d, 1H, J=8.4 Hz).

C. A solution of $Pd_2(dba)_3$ (0.024 g, 0.014 mmol) in dry THF (5 mL) was treated with P$^t$Bu$_3$ (0.5 mL, 0.167 mmol, 10% in hexanes) at room temperature. After stirring for 5 minutes, the reaction was treated with a solution of (R)-2-bromo-9-methyl-8,9-dihydropyrido[3',2':4,5]pyrrolo[1,2-a]pyrazin-6(7H)-one (compound 15c, 0.235 g, 0.839 mmol) in dry THF (10 mL) followed by LiHMDS (1.7 mL, 1.678 mmol, 1M solution in THF). The resulting solution was heated at 100° C. in a sealed tube for 3 hours. The reaction was brought to room temperature, quenched with 2 N HCl solution (10 mL) and stirred for 10 minutes. Reaction mixture extracted with ethyl acetate (2×25 mL) and recovered starting material (0.09 g, 38%). The aqueous layer was basified with 4N NaOH solution and product was extracted into chloroform (4×30 mL). The combined chloroform layer was washed with brine (25 mL) and dried ($Na_2SO_4$). Solvent was evaporated and crude was purified by column chromatography (2M $NH_3$ in MeOH:$CH_2Cl_2$, 2.5:97.5 to 10:90) on silica gel to obtain (R)-2-amino-9-methyl-8,9-dihydropyrido[3',2':4,5]pyrrolo[1,2-a]pyrazin-6(7H)-one, compound 15d, (0.09 g, 50%) as a brown solid. $^1$H NMR (DMSO-$d_6$) δ 1.28 (d, 3H, J=6.0 Hz), 3.28-3.32 (m, 1H), 3.73 (dd, 1H, J=4.8, 12.6 Hz), 4.70-4.80 (m, 1H), 6.20 (s, 1H), 6.35 (d, 1H, J=8.4 Hz), 6.76 (s, 1H), 7.74 (d, 1H, J=8.4 Hz).

D. A solution of (R)-2-amino-9-methyl-8,9-dihydropyrido[3',2':4,5]pyrrolo[1,2-a]pyrazin-6(7H)-one (compound 15d, 0.04 g, 0.185 mmol), 1-benzyl-1H-pyrazole-4-carboxylic acid (compound 1c, 0.038 g, 0.185 mmol) and diisopropyl ethylamine (0.043 g, 1.8 mmol) in dry DMF (3 mL) was treated with HATU (0.078 g, 0.2 mmol) at room temperature. After 30 minutes stirring at room temperature, the reaction mixture was heated at 50° C. for 72 h. The reaction was diluted with water (20 mL) and product was extracted into chloroform (3×25 mL). The combined chloroform layer was dried ($Na_2SO_4$). Solvent was evaporated and crude was purified by column chromatography (2M $NH_3$ in MeOH:$CH_2Cl_2$, 1:99 to 10:90) on silica gel to obtain (R)-1-benzyl-N-(9-methyl-6-oxo-6,7,8,9-tetrahydropyrido[3',2':4,5]pyrrolo[1,2-a]pyrazin-2-yl)-1H-pyrazole-4-carboxamide, compound #15, (0.015 g, 20%) as a off-white solid. $^1$H NMR (DMSO-$d_6$) δ 1.36 (d, 3H, J=6.6 Hz), 3.30-3.40 (m, 1H), 3.81-3.85 (m, 1H), 4.90-4.92 (m, 1H), 5.39 (s, 2H), 6.99 (s, 1H), 7.30-7.39 (m, 5H), 8.02-8.19 (m, 3H), 8.19 (s, 1H), 8.61 (s, 1H), 10.56 (s, 1H).

Synthetic Example 16

Synthesis of (R)—N-(1-(3-aminobenzyl)-1H-pyrazol-4-yl)-9-methyl-6-oxo-6,7,8,9-tetrahydropyrido[3',2':4,5]pyrrolo[1,2-a]pyrazine-2-carboxamide, Compound #16

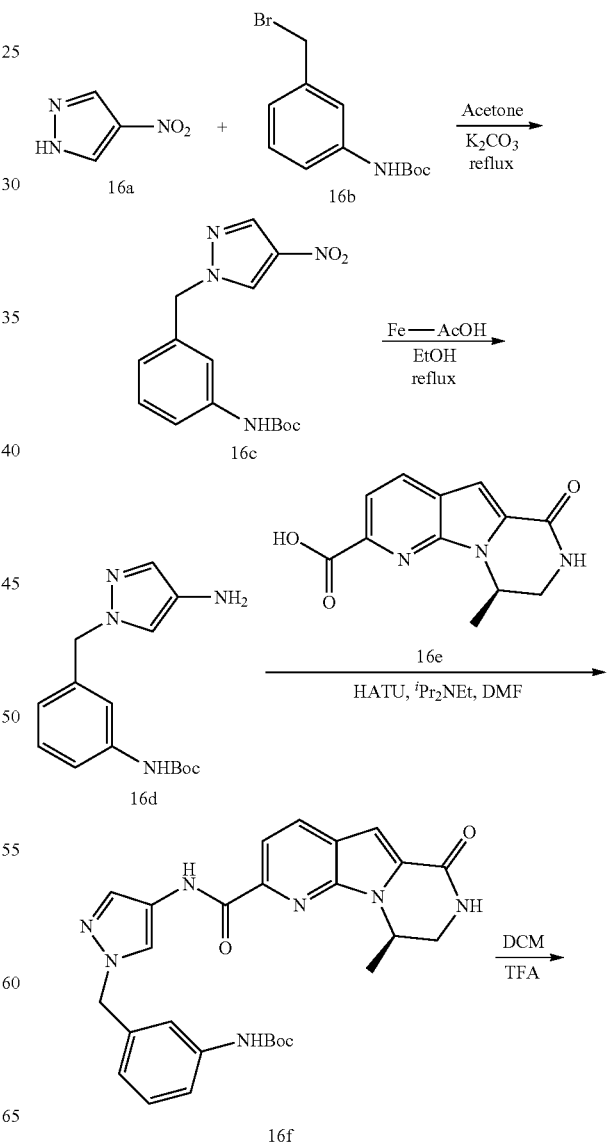

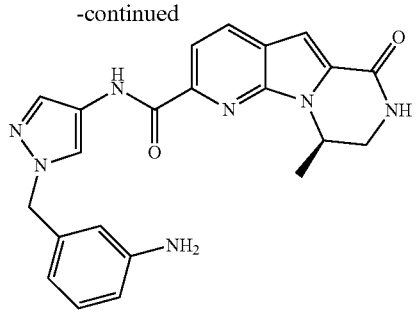

Compound #16

A. A solution of 4-nitropyrazole (compound 16a, 0.27 g, 2.45 mmol) and tert-butyl (3-(bromomethyl)phenyl)carbamate (compound 16b, 0.586 g, 2.04 mmol) in acetone (10 mL) was treated with potassium carbonate (0.563 g, 4.08 mmol) and heated to reflux temperature for 3 hours. The reaction was brought to room temperature and solvent was evaporated on rotavapor. The reaction was diluted with the addition of water (30 mL) and product was extracted into ethyl acetate (2×25 mL). The combined ethyl acetate layer was washed with water (2×25 mL) and dried ($Na_2SO_4$). Solvent was evaporated and crude product was purified through column using 10-30% ethyl acetate in hexanes and obtained tert-butyl (3-((4-nitro-1H-pyrazol-1-yl)methyl)phenyl)carbamate, compound 16c, (0.56 g, 95%) as off-white solid, which was used directly in the next step.

B. A solution of tert-butyl (34(4-nitro-1H-pyrazol-1-yl)methyl)phenyl)carbamate (compound 16c, 0.2 g, 0.69 mmol) in ethanol (2 mL) and water (1.5 mL) was treated with iron (0.115 g, 2.06 mmol) followed by acetic acid (0.042 g, 0.69 mmol). Reaction mixture was heated to reflux temperature for 2 hours. The reaction was brought to room temperature and solvent was evaporated on rotavapor. The reaction was diluted with the addition of water (10 mL) and pH was adjusted to pH 7-8 using saturated sodium bicarbonate solution. The product was extracted into dichloromethane (2×10 mL). The combined dichloromethane layer was washed with brine (10 mL) and dried ($Na_2SO_4$). Solvent was evaporated and the crude product, tert-butyl (3-((4-amino-1H-pyrazol-1-yl)methyl)phenyl)carbamate, compound 16d, (0.105 g, 58.6%) was obtained as light brown solid, which was used directly in the next step.

C. A solution of (R)-9-methyl-6-oxo-6,7,8,9-tetrahydropyrido[3',2':4,5]pyrrolo[1,2-a]pyrazine-2-carboxylic acid (compound 16e, prepared according to the methods disclosed in PCT Published Patent Application No. WO 2011/071725, 0.09 g, 0.367 mmol), tert-butyl (3-((4-amino-1H-pyrazol-1-yl)methyl)phenyl)carbamate (compound 16d, 0.105 g, 0.404 mmol) and diisopropyl ethylamine (0.153 g, 0.404 mmol) in dry DMF (5 mL) was treated with HATU (0.085 g, 0.66 mmol) at room temperature. After stirring at room temperature overnight, the reaction was diluted with water (20 mL) and product was extracted into ethyl acetate (2×20 mL). The combined ethyl acetate layer was dried ($Na_2SO_4$). Solvent was evaporated and crude was purified by column chromatography (2M $NH_3$ in MeOH:$CH_2Cl_2$, 1:99 to 10:90) on silica gel to obtain tert-butyl (R)-(3-((4-(9-methyl-6-oxo-6,7,8,9-tetrahydropyrido[3',2':4,5]pyrrolo[1,2-a]pyrazine-2-carboxamido)-1H-pyrazol-1-yl)methyl)phenyl)carbamate, compound 16f, (0.105 g, 55%) as a off-white solid.

D. A solution of tert-butyl (R)-(3-((4-(9-methyl-6-oxo-6,7,8,9-tetrahydropyrido[3',2':4,5]pyrrolo[1,2-a]pyrazine-2-carboxamido)-1H-pyrazol-1-yl)methyl)phenyl)carbamate (compound 16f 0.1 g, 0.194 mmol) in $CH_2Cl_2$ (10 mL) was treated with TFA (1 mL) at room temperature and stirred for additional 2 hours. Solvent was evaporated and crude was basified with 2N NaOH solution and product was extracted into dichloromethane (2×15 mL). The combined dichloromethane layer was washed with brine (10 mL) and dried ($Na_2SO_4$). Solvent was evaporated and crude was purified by column chromatography (2M $NH_3$ in MeOH:$CH_2Cl_2$, 1:99 to 10:90) on silica gel to obtain (R)—N-(1-(3-aminobenzyl)-1H-pyrazol-4-yl)-9-methyl-6-oxo-6,7,8,9-tetrahydropyrido[3',2':4,5]pyrrolo[1,2-a]pyrazine-2-carboxamide, compound #16 (0.065 g, 80.7%) as a off-white solid. $^1$H NMR (DMSO-$d_6$) δ 1.42 (d, 3H, J=6.6 Hz), 3.46-3.49 (m, 1H), 3.89-3.92 (m, 1H), 5.26 (s, 2H), 5.26-5.28 (m, 1H), 6.72 (s, 1H), 6.77-6.79 (m, 2H), 7.13 (s, 1H), 7.17 (d, 1H, J=7.8 Hz), 7.80 (s, 1H), 7.91 (d, 1H, J=8.4 Hz), 8.21 (s, 1H), 8.30 (d, 1H, J=8.4 Hz), 8.35 (d, 1H, J=4.8 Hz), 10.67 (s, 1H).

Synthetic Example 17

Synthesis of (R)—N-(1-(2-aminobenzyl)-1H-pyrazol-4-yl)-9-methyl-6-oxo-6,7,8,9-tetrahydropyrido[3',2':4,5]pyrrolo[1,2-a]pyrazine-2-carboxamide, Compound #17

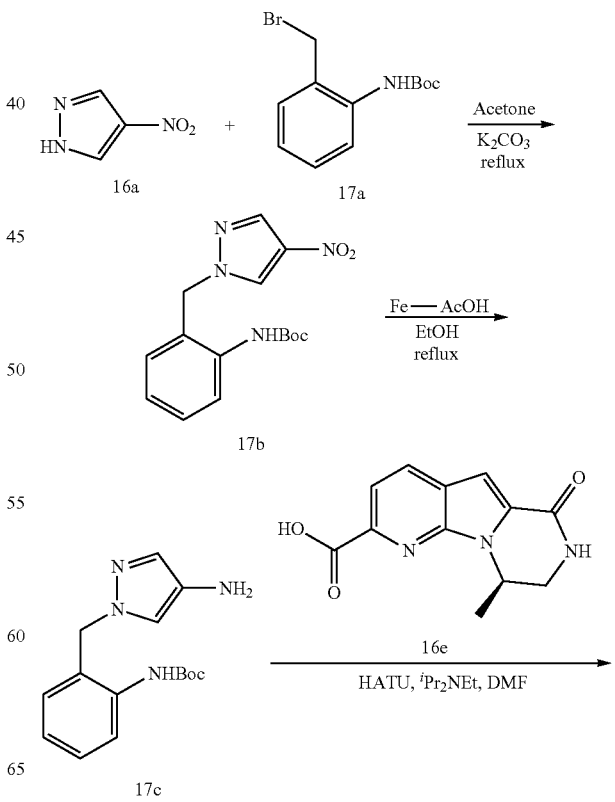

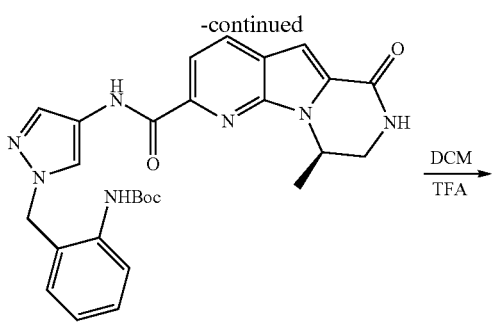

17d

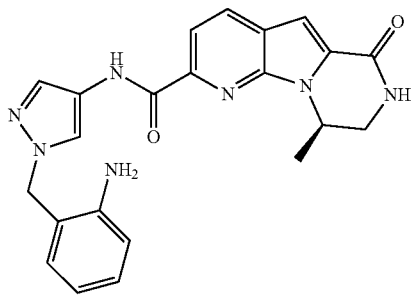

Compound #17

A. A solution of 4-nitropyrazole (compound 16a, 0.236 g, 2.09 mmol) and tert-butyl (2-(bromomethyl)phenyl)carbamate (compound 17a, 0.5 g, 1.74 mmol) in acetone (10 mL) was treated with potassium carbonate (0.48 g, 3.48 mmol) and heated to reflux temperature for 3 hours. The reaction was brought to room temperature and solvent was evaporated on rotavapor. The reaction was diluted with the addition of water (30 mL) and product was extracted into ethyl acetate (2×25 mL). The combined ethyl acetate layer was washed with water (2×25 mL) and dried ($Na_2SO_4$). Solvent was evaporated and crude product was purified through column using 10-30% ethyl acetate in hexanes and obtained tert-butyl (2-((4-nitro-1H-pyrazol-1-yl)methyl)phenyl)carbamate, compound 17b, (0.48 g, 95%) as off-white solid, which was used directly in the next step.

B. A solution of tert-butyl (2-((4-nitro-1H-pyrazol-1-yl)methyl)phenyl)carbamate (compound 17b, 0.2 g, 0.69 mmol) in ethanol (7 mL) and water (4 mL) was treated with iron (0.115 g, 2.06 mmol) followed by acetic acid (0.042 g, 0.69 mmol). Reaction mixture was heated to reflux temperature for 2 hours. The reaction was brought to room temperature and solvent was evaporated on rotavapor. The reaction was diluted with the addition of water (10 mL) and pH was adjusted to pH 7-8 using saturated sodium bicarbonate solution. Product was extracted into dichloromethane (2×10 mL). The combined dichloromethane layer was washed with brine (10 mL) and dried ($Na_2SO_4$). Solvent was evaporated and crude tert-butyl (2-((4-amino-1H-pyrazol-1-yl)methyl)phenyl)carbamate, compound 17c, (0.17 g, 94%) was obtained as orange solid, which was used directly in the next step.

C. A solution of (R)-9-methyl-6-oxo-6,7,8,9-tetrahydropyrido[3',2':4,5]pyrrolo[1,2-a]pyrazine-2-carboxylic acid (compound 16e, 0.09 g, 0.367 mmol), tert-butyl (2-((4-amino-1H-pyrazol-1-yl)methyl)phenyl)carbamate (compound 17c, 0.105 g, 0.404 mmol) and diisopropyl ethylamine (0.153 g, 0.404 mmol) in dry DMF (5 mL) was treated with HATU (0.085 g, 0.66 mmol) at room temperature. After stirring at room temperature overnight, the reaction was diluted with water (20 mL) and product was extracted into ethyl acetate (2×20 mL). The combined ethyl acetate layer was dried ($Na_2SO_4$). Solvent was evaporated and crude was purified by column chromatography (2M $NH_3$ in MeOH: $CH_2Cl_2$, 1:99 to 6:94) on silica gel to obtain tert-butyl (R)-(2-((4-(9-methyl-6-oxo-6,7,8,9-tetrahydropyrido[3',2': 4,5]pyrrolo[1,2-a]pyrazine-2-carboxamido)-1H-pyrazol-1-yl)methyl)phenyl)carbamate, compound 17d, (0.16 g, 84.6%) as a light brown solid.

D. A solution of tert-butyl (R)-(2-((4-(9-methyl-6-oxo-6, 7,8,9-tetrahydropyrido[3',2':4,5]pyrrolo[1,2-a]pyrazine-2-carboxamido)-1H-pyrazol-1-yl)methyl)phenyl)carbamate (compound 17d, 0.16 g, 0.31 mmol) in $CH_2Cl_2$ (10 mL) was treated with TFA (1 mL) at room temperature and stirred for additional 2 hours. Solvent was evaporated and crude was basified with 2N NaOH solution and product was extracted into dichloromethane (2×15 mL). The combined dichloromethane layer was washed with brine (10 mL) and dried ($Na_2SO_4$). Solvent was evaporated and crude was purified by column chromatography (2M $NH_3$ in MeOH:$CH_2Cl_2$, 1:99 to 8:92) on silica gel to obtain (R)—N-(1-(2-aminobenzyl)-1H-pyrazol-4-yl)-9-methyl-6-oxo-6,7,8,9-tetrahydropyrido[3',2':4,5]pyrrolo[1,2-a]pyrazine-2-carboxamide, compound #17, (0.08 g, 62%) as a pale yellow solid. $^1$H NMR (DMSO-$d_6$) δ 1.41 (d, 3H, J=6.6 Hz), 3.45-3.48 (m, 1H), 3.88-3.91 (m, 1H), 5.19 (s, 2H), 5.22-5.28 (m, 1H), 6.53-6.55 (m, 1H), 6.67-6.68 (m, 1H), 6.97-7.03 (m, 2H), 7.12 (s, 1H), 7.79 (s, 1H), 7.90 (d, 1H, J=8.4 Hz), 8.16 (s, 1H), 8.29 (d, 1H, J=8.4 Hz), 8.34 (d, 1H, J=4.8 Hz), 10.64 (s, 1H).

Synthetic Example 18

Synthesis of (R)—N-(1-(4-aminobenzyl)-1H-pyrazol-4-yl)-9-methyl-6-oxo-6,7,8,9-tetrahydropyrido [3',2':4,5]pyrrolo[1,2-a]pyrazine-2-carboxamide, Compound #18

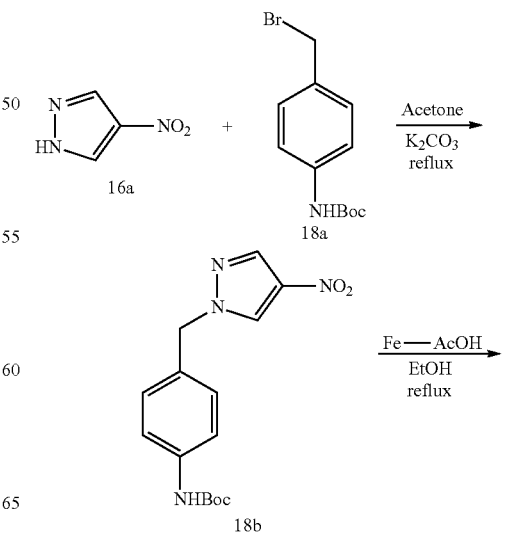

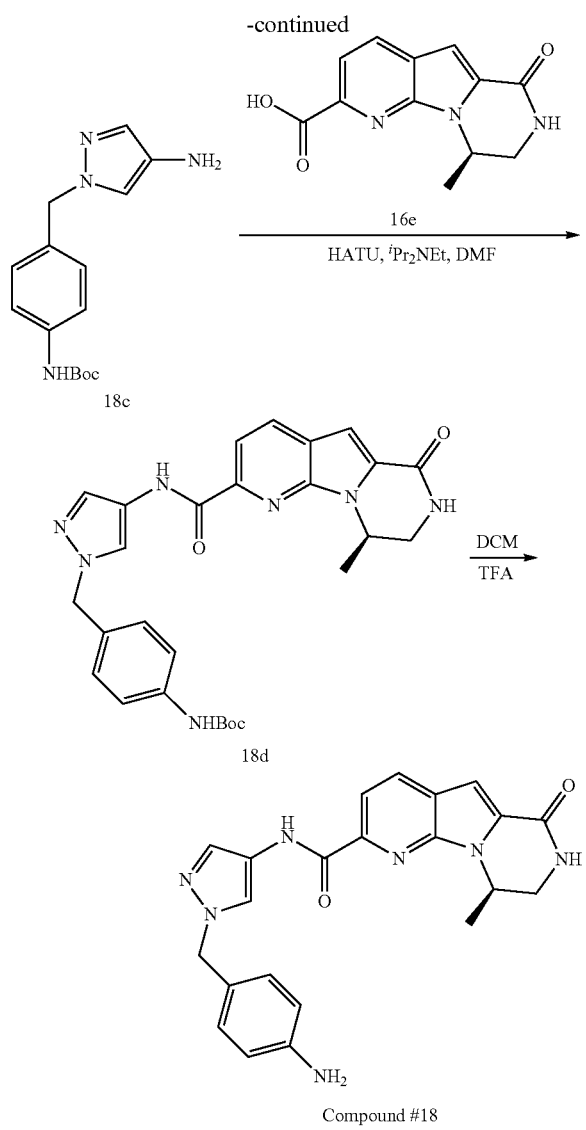

A. A solution of 4-nitropyrazole (compound 16a, 0.236 g, 2.09 mmol) and tert-butyl (4-(bromomethyl)phenyl)carbamate (compound 18a, 0.5 g, 1.74 mmol) in acetone (10 mL) was treated with potassium carbonate (0.48 g, 3.48 mmol) and heated to reflux temperature for 3 hours. The reaction was brought to room temperature and solvent was evaporated on rotavapor. The reaction was diluted with the addition of water (30 mL) and product was extracted into ethyl acetate (2×25 mL). The combined ethyl acetate layer was washed with water (2×25 mL) and dried (Na₂SO₄). Solvent was evaporated and crude product was purified through column using 10-30% ethyl acetate in hexanes and obtained tert-butyl (4-((4-nitro-1H-pyrazol-1-yl)methyl)phenyl)carbamate, compound 18b, (0.46 g, 91%) as pale yellow thick liquid, which was used directly in the next step.

B. A solution of tert-butyl (4-((4-nitro-1H-pyrazol-1-yl)methyl)phenyl)carbamate (compound 18b, 0.2 g, 0.69 mmol) in ethanol (5 mL) and water (2 mL) was treated with iron (0.115 g, 2.06 mmol) followed by acetic acid (0.042 g, 0.69 mmol). Reaction mixture was heated to reflux temperature for 2 hours. The reaction was brought to room temperature and solvent was evaporated on rotavapor. The reaction was diluted with the addition of water (10 mL) and pH was adjusted to pH 7-8 using saturated sodium bicarbonate solution. Product was extracted into dichloromethane (2×10 mL). The combined dichloromethane layer was washed with brine (10 mL) and dried (Na₂SO₄). Solvent was evaporated and crude tert-butyl (4-((4-amino-1H-pyrazol-1-yl)methyl)phenyl)carbamate, compound 18c, (0.17 g, 94%) was obtained as orange solid, which was used directly in the next step.

C. A solution of (R)-9-methyl-6-oxo-6,7,8,9-tetrahydropyrido[3',2':4,5]pyrrolo[1,2-a]pyrazine-2-carboxylic acid (compound 16e, 0.09 g, 0.367 mmol), tert-butyl (4-((4-amino-1H-pyrazol-1-yl)methyl)phenyl)carbamate (compound 18c, 0.105 g, 0.404 mmol) and diisopropyl ethylamine (0.153 g, 0.404 mmol) in dry DMF (5 mL) was treated with HATU (0.085 g, 0.66 mmol) at room temperature. After stirring at room temperature overnight, the reaction was diluted with water (20 mL) and product was extracted into ethyl acetate (2×20 mL). The combined ethyl acetate layer was dried (Na₂SO₄). Solvent was evaporated and crude was purified by column chromatography (2M NH₃ in MeOH:CH₂Cl₂, 1:99 to 6:94) on silica gel to obtain tert-butyl (R)-(4-((4-(9-methyl-6-oxo-6,7,8,9-tetrahydropyrido[3',2':4,5]pyrrolo[1,2-a]pyrazine-2-carboxamido)-1H-pyrazol-1-yl)methyl)phenyl)carbamate, compound 18d, (0.167 g, 88.8%) as a off-white solid.

D. A solution of tert-butyl (R)-(4-((4-(9-methyl-6-oxo-6,7,8,9-tetrahydropyrido[3',2':4,5]pyrrolo[1,2-a]pyrazine-2-carboxamido)-1H-pyrazol-1-yl)methyl)phenyl)carbamate (compound 18d, 0.158 g, 0.306 mmol) in CH₂Cl₂ (10 mL) was treated with TFA (1 mL) at room temperature and stirred for additional 2 hours. Solvent was evaporated and crude was basified with 2N NaOH solution and product was extracted into dichloromethane (2×15 mL). The combined dichloromethane layer was washed with brine (10 mL) and dried (Na₂SO₄). Solvent was evaporated and crude was purified by column chromatography (2M NH₃ in MeOH:CH₂Cl₂, 1:99 to 8:92) on silica gel to obtain (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide, compound #18, (0.065 g, 80.7%) as a off-white solid. $^1$H NMR (DMSO-$d_6$) δ 1.42 (d, 3H, J=6.6 Hz), 3.45-3.48 (m, 1H), 3.89-3.92 (m, 1H), 5.09 (s, 2H), 5.27-5.29 (m, 1H), 6.52-6.54 (m, 2H), 6.77-6.79 (m, 2H), 7.0-7.02 (m, 2H), 7.12 (s, 1H), 7.74 (s, 1H), 7.90 (d, 1H, J=7.8 Hz), 8.07 (s, 1H), 8.29 (d, 1H, J=7.8 Hz), 8.34 (d, 1H, J=4.8 Hz), 10.61 (s, 1H).

Synthetic Example 19

Synthesis of (R)-1-(3-aminobenzyl)-N-(9-methyl-6-oxo-6,7,8,9-tetrahydropyrido[3',2':4,5]pyrrolo[1,2-a]pyrazin-2-yl)-1H-pyrazole-4-carboxamide, Compound #19

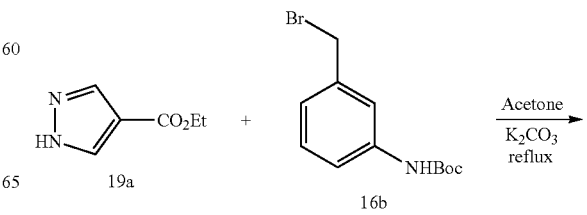

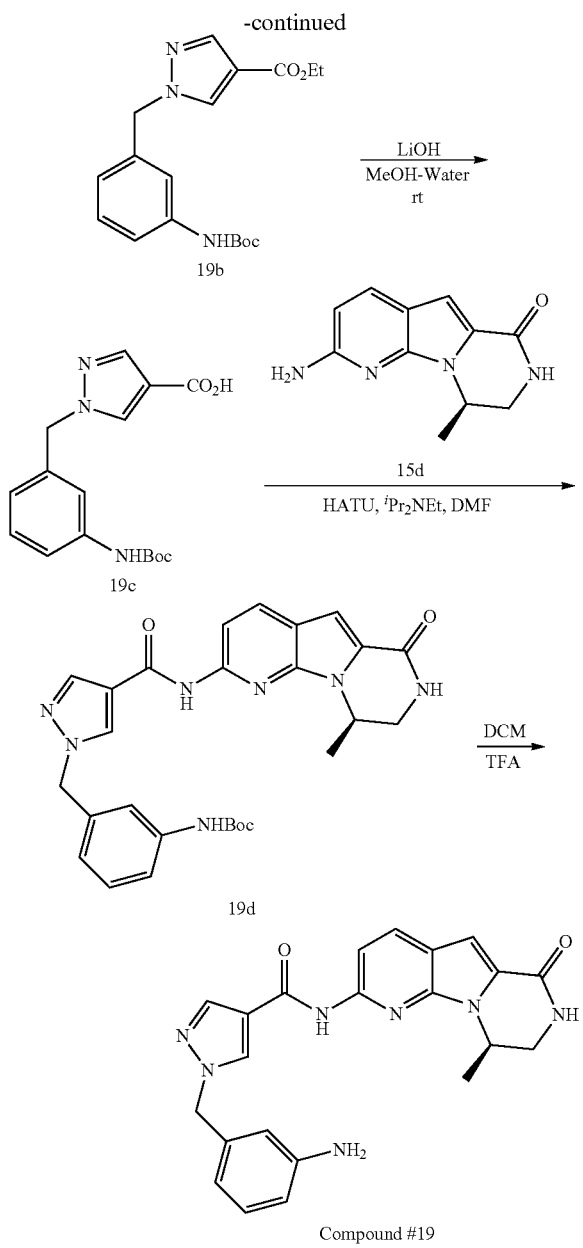

Compound #19

A. A solution of ethyl 1H-pyrazole-4-carboxylate (compound 19a, 0.25 g, 1.78 mmol) and tert-butyl (3-(bromomethyl)phenyl)carbamate (compound 16b, 0.51 g, 1.78 mmol) in acetone (10 mL) was treated with potassium carbonate (0.48 g, 3.48 mmol) and heated to reflux temperature for 3 hours. The reaction was brought to room temperature and solvent was evaporated on rotavapor. The reaction was diluted with the addition of water (30 mL) and product was extracted into ethyl acetate (2×25 mL). The combined ethyl acetate layer was washed with water (2×25 mL) and dried ($Na_2SO_4$). Solvent was evaporated and crude product was purified through column using 10-30% ethyl acetate in hexanes and obtained ethyl 1-(3-((tert-butoxycarbonyl)amino)benzyl)-1H-pyrazole-4-carboxylate, compound 19b, (0.635 g, 100%) as off-white solid, which was used directly in the next step.

B. A solution of ethyl 1-(3-((tert-butoxycarbonyl)amino)benzyl)-1H-pyrazole-4-carboxylate (compound 19b, 0.635 g, 1.78 mmol) in methanol (20 mL) and water (10 mL) was treated with $LiOH.H_2O$ (0.15 g, 3.55 mmol). Reaction mixture was stirred at room temperature for 24 hours. Solvent was evaporated on rotavapor. The reaction was diluted with the addition of water (10 mL) and pH was adjusted to pH 5 using acetic acid. Product was extracted into dichloromethane (2×10 mL). The combined dichloromethane layer was washed with brine (10 mL) and dried ($Na_2SO_4$). Solvent was evaporated and crude 1-(3-((tert-butoxycarbonyl)amino)benzyl)-1H-pyrazole-4-carboxylic acid, compound 19c, (0.525 g, 90%) was obtained as white solid, which was used directly in the next step.

C. A solution of (R)-2-amino-9-methyl-8,9-dihydropyrido[3',2':4,5]pyrrolo[1,2-a]pyrazin-6(7H)-one (compound 15d, 0.08 g, 0.24 mmol), 1-(3-((tert-butoxycarbonyl)amino)benzyl)-1H-pyrazole-4-carboxylic acid (compound 19c, 0.53 g, 0.24 mmol) and diisopropyl ethylamine (0.075 g, 0.57 mmol) in dry DMF (5 mL) was treated with BOP (0.212 g, 0.48 mmol) at room temperature. After stirring at 50° C. temperature for 7 days, the reaction was diluted with water (20 mL) and product was extracted into ethyl acetate (2×20 mL). The combined ethyl acetate layer was dried ($Na_2SO_4$). Solvent was evaporated and crude was purified by column chromatography (2M $NH_3$ in $MeOH:CH_2Cl_2$, 1:99 to 5:95) on silica gel to obtain tert-butyl (R)-(3-((4-((9-methyl-6-oxo-6,7,8,9-tetrahydropyrido[3',2':4,5]pyrrolo[1,2-a]pyrazin-2-yl)carbamoyl)-1H-pyrazol-1-yl)methyl)phenyl)carbamate, compound 19d, (0.008 g, 6.4%) as a light brown solid.

D. A solution of tert-butyl (R)-(3-((4-((9-methyl-6-oxo-6,7,8,9-tetrahydropyrido[3',2':4,5]pyrrolo[1,2-a]pyrazin-2-yl)carbamoyl)-1H-pyrazol-1-yl)methyl)phenyl)carbamate (compound 19d, 0.008 g, 0.0155 mmol) in $CH_2Cl_2$ (10 mL) was treated with TFA (0.5 mL) at room temperature and stirred for additional 2 hours. Solvent was evaporated and crude was basified with 2N NaOH solution and product was extracted into dichloromethane (2×10 mL). The combined dichloromethane layer was washed with brine (5 mL) and dried ($Na_2SO_4$). Solvent was evaporated and crude was purified by column chromatography (2M $NH_3$ in $MeOH:CH_2Cl_2$, 1:99 to 6:94) on silica gel to obtain (R)-1-(3-aminobenzyl)-N-(9-methyl-6-oxo-6,7,8,9-tetrahydropyrido[3',2':4,5]pyrrolo[1,2-a]pyrazin-2-yl)-1H-pyrazole-4-carboxamide, compound #19, (0.003 g, 46%) as a light brown solid. $^1H$ NMR ($CDCl_3$) δ 1.43 (d, 3H, J=6.4 Hz), 3.39-3.42 (m, 1H), 3.92-3.96 (m, 1H), 4.85-4.90 (m, 1H), 5.18 (s, 2H), 5.94 (s, 1H), 6.50 (d, 1H, J=2 Hz), 6.58-6.61 (m, 2H), 7.07-7.13 (m, 2H), 7.91-7.98 (m, 3H), 8.13 (d, 1H, J=8.8 Hz).

Synthetic Example 20

Synthesis of (R)-9-methyl-N-(1-((1-methylpiperidin-4-yl)methyl)-1H-pyrazol-4-yl)-6-oxo-6,7,8,9-tetrahydropyrido[3',2':4,5]pyrrolo[1,2-a]pyrazine-2-carboxamide, Compound #20

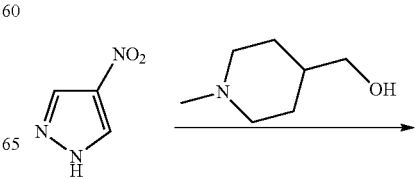

-continued

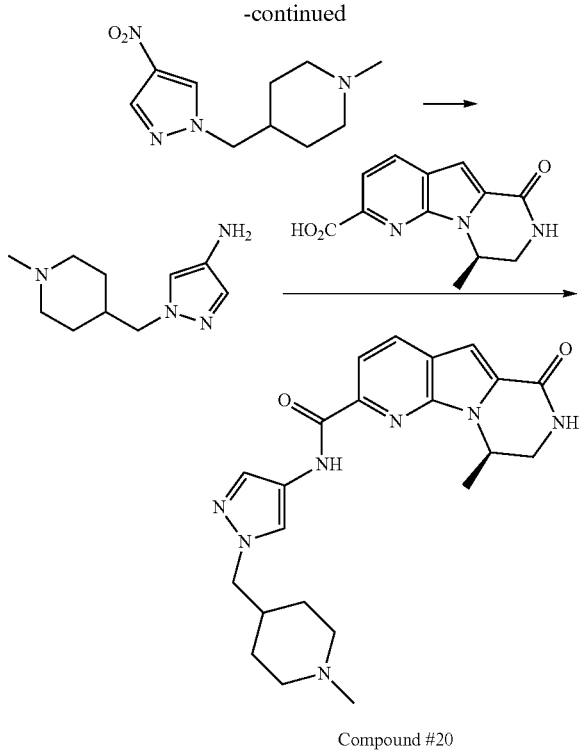

Compound #20

A. A solution of 4-nitro-1H-pyrazole (0.5 g, 4.421 mmol), (1-methylpiperidin-4-yl)methanol (0.57 g, 4.421 mmol) and triphenylphosphine (1.27 g, 4.863 mmol) in dry THF (20 mL) was treated with DTAD (1.22 g, 5.305 mmol) at room temperature and was stirred for additional 4 h. Solvent was evaporated and crude was purified by column chromatography (dichloromethane to MeOH: Dichloromethane, 1:99 to 5:95 to 2M $NH_3$ in MeOH: dichloromethane, 5:95 to 1:9) on silica gel to obtain the title compound (0.34 g, 34%) as an off-white solid.

B. A solution of 1-methyl-4-((4-nitro-1H-pyrazol-1-yl)methyl)piperidine (0.33 g, 1.471 mmol) in methanol (5 mL) was treated with palladium on carbon (0.05 g) and purged with hydrogen gas. The flask was evacuated and filled with hydrogen gas (three times) and stirred under hydrogen atm. (balloon pressure) for additional 3 h. The reaction was filtered through a pad of celite and washed with methanol (3×20 mL). The combined methanol layer was evaporated to obtain the title compound (0.27 g, 95%) as a light brown solid. $^1$H NMR ($CDCl_3$) δ 1.24-1.28 (m, 2H), 1.51-1.55 (m, 2H), 1.81-1.87 (m, 3H), 2.21 (s, 3H), 2.78-2.84 (m, 4H), 3.82 (d, 2H, J=5.4 Hz), 6.95 (s, 1H), 7.12 (s, 1H).

C. A solution of (R)-9-methyl-6-oxo-6,7,8,9-tetrahydropyrido[3',2':4,5]pyrrolo[1,2-a]pyrazine-2-carboxylic acid (0.05 g, 0.203 mmol), 1-((1-methylpiperidin-4-yl)methyl)-1H-pyrazol-4-amine (0.04 g, 0.203 mmol) and DIPEA (0.06 mL, 0.366 mmol) in dry DMF (5 mL) was treated with HATU (0.09 g, 0.234 mmol) at room temperature and stirred for additional 24 h. The reaction was diluted with water (50 mL), basified with 2 N NaOH solution (20 mL) and product was extracted into ethyl acetate (3×50 mL). The combined ethyl acetate layer was washed with water (2×25 mL), brine (50 mL) and dried ($Na_2SO_4$). Solvent was evaporated and crude was purified by column chromatography (2 M $NH_3$ in MeOH: Dichloromethane, 5:95 to 1:9) on silica gel to obtain the title compound (0.06 g, 71%) as a pale yellow solid. $^1$H NMR (DMSO-$d_6$) δ 1.34-1.43 (m, 2H), 1.43 (d, 3H, J=3.3 Hz), 1.61 (d, 2H, J=6.0 Hz), 1.95 (brs, 1H), 2.55 (s, 3H), 3.13-3.50 (m, 5H), 3.91 (dd, 1H, J=2.1, 6.4 Hz), 4.06 (d, 2H, J=3.6 Hz), 5.27-5.29 (m, 1H), 7.13 (s, 1H), 7.76 (d, 1H, J=0.3 Hz), 7.92 (d, 1H, J=3.9 Hz), 8.18 (s, 1H), 8.30 (d, 1H, J=4.2 Hz), 8.34 (d, 1H, J=2.7 Hz), 10.62 (s, 1H).

Synthetic Example 21

Synthesis of (R)—N-(2-carbamoylphenyl)-9-methyl-6-oxo-6,7,8,9-tetrahydropyrido[3',2':4,5]pyrrolo[1,2-a]pyrazine-2-carboxamide, Compound #21

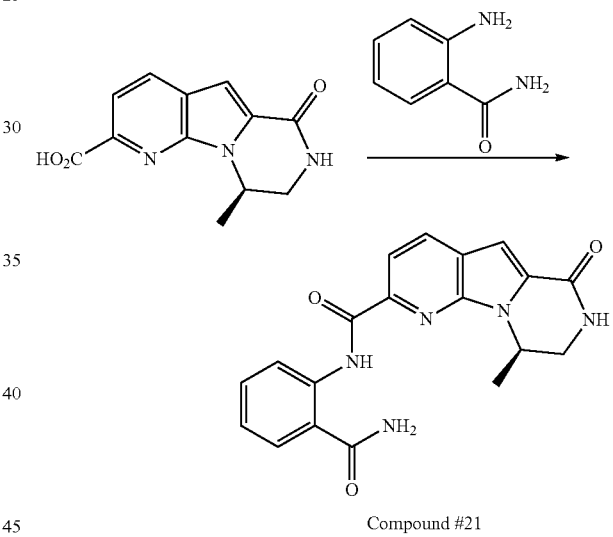

Compound #21

A solution of (R)-9-methyl-6-oxo-6,7,8,9-tetrahydropyrido[3',2':4,5]pyrrolo[1,2-a]pyrazine-2-carboxylic acid (0.05 g, 0.203 mmol), 2-aminobenzamide (0.027 g, 0.203 mmol) and DIPEA (0.06 mL, 0.366 mmol) in dry DMF (5 mL) was treated with HATU (0.09 g, 0.234 mmol) at room temperature and stirred for additional 24 h. The reaction was diluted with water (50 mL), basified with 2 N NaOH solution (20 mL) and product was extracted into ethyl acetate (3×50 mL). The combined ethyl acetate layer was washed with water (2×25 mL), brine (50 mL) and dried ($Na_2SO_4$). Solvent was evaporated and crude was purified by column chromatography (2 M $NH_3$ in MeOH: Dichloromethane, 5:95 to 1:9) on silica gel to obtain the title compound (19 mg, 26%) as a pale yellow solid. $^1$H NMR (DMSO-$d_6$) δ 1.51 (d, 3H, J=3.3 Hz), 3.47-3.50 (m, 1H), 3.95-3.98 (m, 1H), 5.19-5.21 (m, 1H), 7.17-7.20 (m, 2H), 7.56-7.59 (m, 1H), 7.73 (s, 1H), 7.86 (dd, 1H, J=0.6, 3.9 Hz), 8.00 (d, 1H, J=4.2 Hz), 8.26 (brs, 1H), 8.35 (d, 1H, J=4.2 Hz), 8.40 (d, 1H, J=2.4 Hz), 8.78 (dd, 1H, J=0.3, 4.2 Hz), 13.48 (s, 1H).

Synthetic Example 22

Synthesis of (R)-9-methyl-6-oxo-N-(1-(4-(trifluoromethyl)benzyl)-1H-pyrazol-4-yl)-6,7,8,9-tetrahydropyrido[3',2':4,5]pyrrolo[1,2-a]pyrazine-2-carboxamide, Compound #22

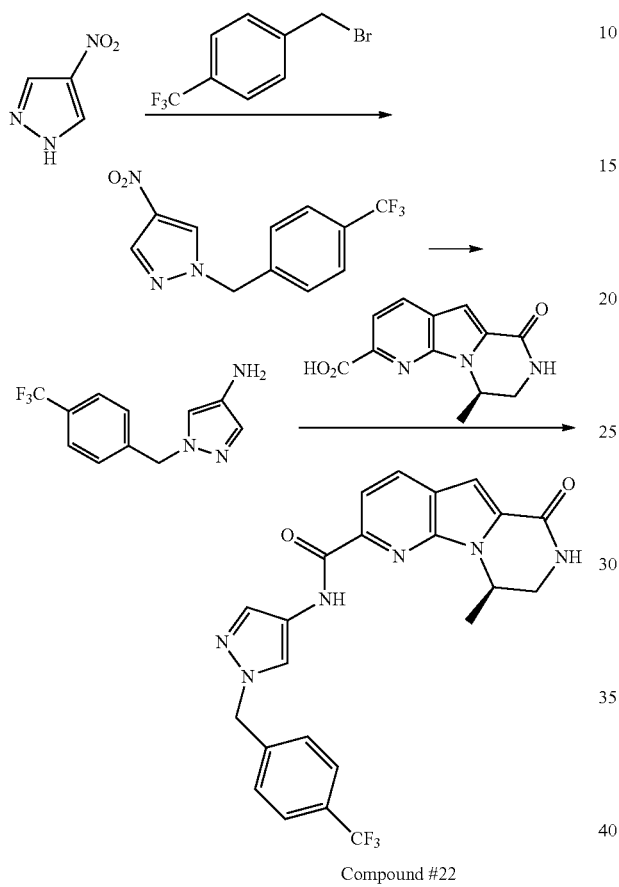

Compound #22

A. A solution of 4-nitro-1H-pyrazole (5.0 g, 44.216 mmol) and 1-(bromomethyl)-4-(trifluoromethyl)benzene (11.09 g, 46.427 mmol) in acetone (100 mL) was treated with potassium carbonate (30.5 g, 221.082 mmol) and heated at reflux temperature for 2 h. The reaction was brought to room temperature; solid was filtered off and washed with dichloromethane (3×35 mL). Combined organic layer was evaporated and the crude product was washed with hexanes to obtain the title compound (12.0 g, quantitative) as a white solid.

B. A solution of 4-nitro-1-(4-(trifluoromethyl)benzyl)-1H-pyrazole (2.1 g, 7.743 mmol) in ethanol (30 mL) and water (25 mL) was treated with iron (1.29 g, 23.229 mmol) followed by acetic acid (0.44 mL, 7.743 mmol) and the reaction was heated at reflux temperature for 2 h. The reaction was brought to room temperature and solvent was evaporated. The reaction was basified with 1 N NaOH solution and product was extracted into dichloromethane (3×50 mL). The combined dichloromethane layer was washed with brine (10 mL) and dried ($Na_2SO_4$). Solvent was evaporated and crude was purified by column chromatography (2 M $NH_3$ in MeOH: Dichloromethane, 5:95) on silica gel to obtain the title compound (1.75 g, 94%) as an orange-red solid.

C. A solution of (R)-9-methyl-6-oxo-6,7,8,9-tetrahydropyrido[3',2':4,5]pyrrolo[1,2-a]pyrazine-2-carboxylic acid (0.05 g, 0.203 mmol), 1-(4-(trifluoromethyl)benzyl)-1H-pyrazol-4-amine (0.049 g, 0.203 mmol) and DIPEA (0.06 mL, 0.366 mmol) in dry DMF (5 mL) was treated with HATU (0.09 g, 0.234 mmol) at room temperature and stirred for additional 24 h. The reaction was diluted with water (50 mL), basified with 2 N NaOH solution (20 mL) and product was extracted into ethyl acetate (3×50 mL). The combined ethyl acetate layer was washed with water (2×25 mL), brine (50 mL) and dried ($Na_2SO_4$). Solvent was evaporated and crude was purified by column chromatography (2 M $NH_3$ in MeOH: Dichloromethane, 5:95 to 1:9) on silica gel to obtain the title compound (65 mg, 68%) as a pale yellow solid. $^1$H NMR (DMSO-$d_6$) δ 1.44 (d, 3H, J=3.3 Hz), 3.47-3.50 (m, 1H), 3.90-3.93 (m, 1H), 5.28-5.30 (m, 1H), 5.48 (s, 2H), 7.14 (s, 1H), 7.45 (d, 2H, J=4.2 Hz), 7.73 (d, 2H, J=4.2 Hz), 7.85 (s, 1H), 7.94 (d, 1H, J=3.9 Hz), 8.29-8.37 (m, 3H), 10.70 (s, 1H).

Synthetic Example 23

Synthesis of (R)—N-(1-(2,4-difluorobenzyl)-1H-pyrazol-4-yl)-9-methyl-6-oxo-6,7,8,9-tetrahydropyrido[3',2':4,5]pyrrolo[1,2-a]pyrazine-2-carboxamide, Compound #23

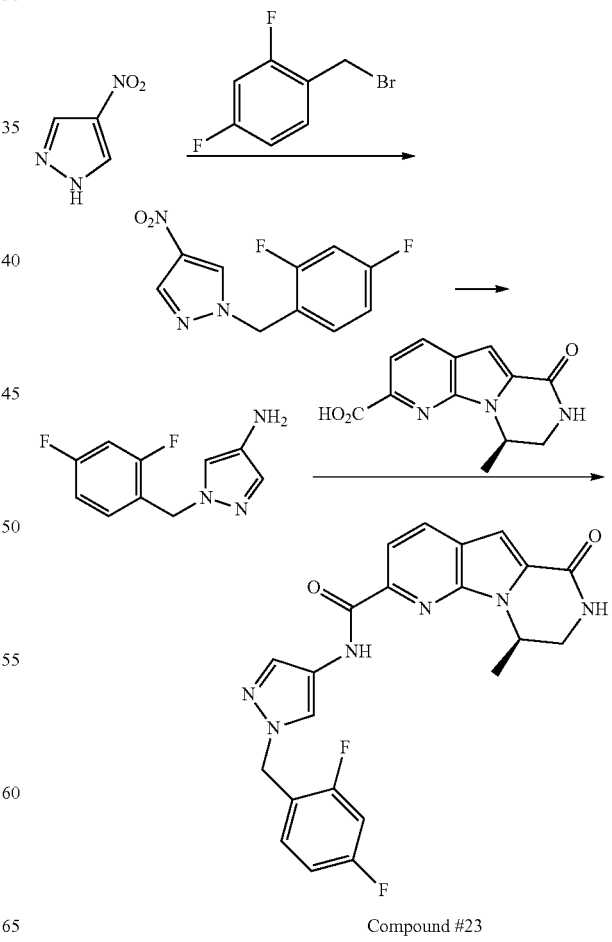

Compound #23

A. A solution of 4-nitro-1H-pyrazole (3.0 g, 26.529 mmol) and 1-(bromomethyl)-2,4-difluorobenzene (5.76 g, 27.856 mmol) in acetone (60 mL) was treated with potassium carbonate (18.33 g, 132.649 mmol) and heated at reflux temperature for 2 h. The reaction was brought to room temperature; solid was filtered off and washed with dichloromethane (3×25 mL). Combined organic layer was evaporated and the crude product was washed with hexanes to obtain the title compound (6.3 g, quantitative) as an off-white solid.

B. A solution of 1-(2,4-difluorobenzyl)-4-nitro-1H-pyrazole (2.1 g, 8.779 mmol) in ethanol (25 mL) and water (20 mL) was treated with iron (1.47 g, 26.339 mmol) followed by acetic acid (0.5 mL, 8.779 mmol) and the reaction was heated at reflux temperature for 2 h. The reaction was brought to room temperature and solvent was evaporated. The reaction was basified with 1 N NaOH solution and product was extracted into dichloromethane (3×50 mL). The combined dichloromethane layer was washed with brine (10 mL) and dried ($Na_2SO_4$). Solvent was evaporated and crude was purified by column chromatography (2 M $NH_3$ in MeOH: Dichloromethane, 5:95) on silica gel to obtain the title compound (1.42 g, 78%) as a dark red solid.

C. A solution of (R)-9-methyl-6-oxo-6,7,8,9-tetrahydropyrido[3',2':4,5]pyrrolo[1,2-a]pyrazine-2-carboxylic acid (0.05 g, 0.203 mmol), 1-(2,4-difluorobenzyl)-1H-pyrazol-4-amine (0.043 g, 0.203 mmol) and DIPEA (0.06 mL, 0.366 mmol) in dry DMF (5 mL) was treated with HATU (0.09 g, 0.234 mmol) at room temperature and stirred for additional 24 h. The reaction was diluted with water (50 mL), basified with 2 N NaOH solution (20 mL) and product was extracted into ethyl acetate (3×50 mL). The combined ethyl acetate layer was washed with water (2×25 mL), brine (50 mL) and dried ($Na_2SO_4$). Solvent was evaporated and crude was purified by column chromatography (2 M $NH_3$ in MeOH: Dichloromethane, 5:95 to 1:9) on silica gel to obtain the title compound (40 mg, 45%) as a pale yellow solid. $^1$H NMR (DMSO-$d_6$) δ 1.43 (d, 3H, J=3.3 Hz), 3.47-3.50 (m, 1H), 3.90-3.93 (m, 1H), 5.28-5.30 (m, 1H), 5.39 (s, 2H), 7.09-7.37 (m, 4H), 7.81 (s, 1H), 7.93 (d, 1H, J=4.2 Hz), 8.25-8.37 (m, 3H), 10.68 (s, 1H).

Synthetic Example 24

Synthesis of (R)—N-(1-benzyl-1H-pyrazol-4-yl)-5-chloro-9-methyl-6-oxo-6,7,8,9-tetrahydropyrido[3',2':4,5]pyrrolo[1,2-a]pyrazine-2-carboxamide, Compound #24

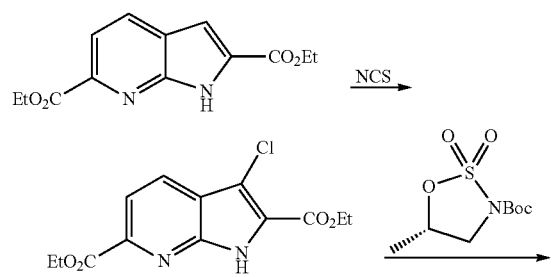

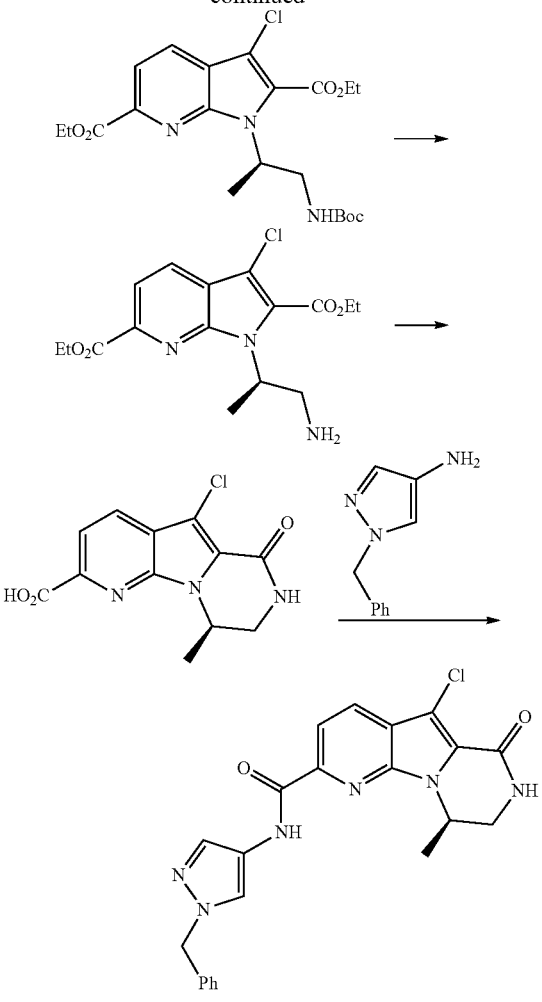

Compound #24

A. A suspension of diethyl 1H-pyrrolo[2,3-b]pyridine-2,6-dicarboxylate (0.102 g, 0.388 mmol) in acetonitrile (5 mL) was treated with N-chlorosuccinamide (0.062 g, 0.466 mmol) and the resulting solution was stirred at 60° C. for 24 h. The reaction was brought to room temperature, diluted with water (50 mL) and the product was extracted into ethyl acetate (2×25 mL). The combined ethyl acetate layer was washed with brine (20 mL) and dried ($Na_2SO_4$). Solvent was evaporated and crude was purified by flash column chromatography (EtOAc:Hexanes, 1:9 to 1:4) on silica gel to obtain the title compound (0.1 g, 87%) as a colorless oil.

B. A solution of diethyl 3-chloro-1H-pyrrolo[2,3-b]pyridine-2,6-dicarboxylate (0.1 g, 0.337 mmol) in dry DMF (3 mL) was treated with sodium hydride (14.2 mg, 0.370 mmol, 60% in mineral oil) at 0° C. The reaction was brought to room temperature and stirred for 30 min. A solution of tert-butyl (S)-5-methyl-1,2,3-oxathiazolidine-3-carboxylate 2,2-dioxide (83 mg, 0.353 mmol) in dry DMF (2 mL) was added and the reaction was stirred at room temperature for 18 h. The reaction was diluted with water (30 mL), acidified with 0.5 M citric acid (20 mL) and the product was extracted into diethyl ether (2×25 mL). The combined diethyl ether layer was washed with water (25 mL), brine (20 mL) and dried ($Na_2SO_4$). Diethyl ether was evaporated to obtain the title compound (0.12 g, 79%) as an oil.

C. A solution of diethyl (R)-1-(1-((tert-butoxycarbonyl)amino)propan-2-yl-3-chloro-1H-pyrrolo[2,3-b]pyridine-2,6-dicarboxylate (0.12 g, 0.264 mmol) in methanol (5 mL) was treated with 4 M HCl in 1,4-dioxane (0.33 mL, 1.321 mmol) at room temperature and stirred for additional 16 h. Solvent was evaporated, crude was taken in dichloromethane (50 mL) and washed with sat. NaHCO₃ solution (20 mL). The aqueous layer was further extracted with dichloromethane (2×20 mL). The combined dichloromethane layer was dried (Na₂SO₄) and solvent was evaporated to obtain the crude title compound (76 mg, 82%) as a pale yellow solid.

D. A solution of diethyl (R)-1-(1-aminopropan-2-yl)-3-chloro-1H-pyrrolo[2,3-b]pyridine-2,6-dicarboxylate (76 mg, 0.214 mmol) in ethanol (3 mL) was treated with potassium carbonate (89 mg, 0.644 mmol) and the resulting mixture was heated at 60° C. for additional 16 h. The reaction was brought to room temperature and solvent was evaporated. The crude was diluted with water (15 mL), acidified with citric acid and product was extracted into dichloromethane (3×20 mL). The combined dichloromethane layer was dried (Na₂SO₄) and solvent was evaporated to obtain the title compound (50 mg, 83%) as an off-white solid.

E. A solution of (R)-5-chloro-9-methyl-6-oxo-6,7,8,9-tetrahydropyrido[3',2':4,5]pyrrolo[1,2-a]pyrazine-2-carboxylic acid (0.05 g, 0.178 mmol), 1-benzyl-1H-pyrazol-4-amine (0.03 g, 0.178 mmol) and DIPEA (0.056 mL, 0.321 mmol) in DMF (5 mL) was treated with HATU (0.078 g, 0.205 mmol) at room temperature and stirred for additional 24 h. The reaction was diluted with water (50 mL), basified with 2 N NaOH solution (20 mL) and product was extracted into ethyl acetate (3×50 mL). The combined ethyl acetate layer was washed with water (2×25 mL), brine (50 mL) and dried (Na₂SO₄). Solvent was evaporated and crude was purified by column chromatography (2 M NH₃ in MeOH: Dichloromethane, 5:95 to 1:9) on silica gel to obtain the title compound (40 mg, 45%) as a tan solid. ¹H NMR (DMSO-d₆) δ 1.44 (d, 3H, J=3.3 Hz), 3.45-3.47 (m, 1H), 3.90-3.93 (m, 1H), 5.32-5.36 (m, 3H), 7.27-7.37 (m, 5H), 7.80 (s, 1H), 7.99 (d, 1H, J=3.9 Hz), 8.24-8.28 (m, 2H), 8.45 (d, 1H, J=2.7 Hz), 10.73 (s, 1H).

Synthetic Example 25

Synthesis of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride salt, Compound #25

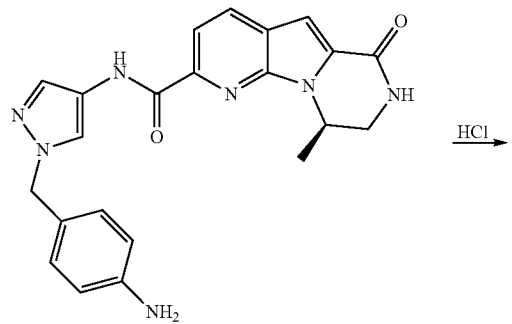

Compound #18

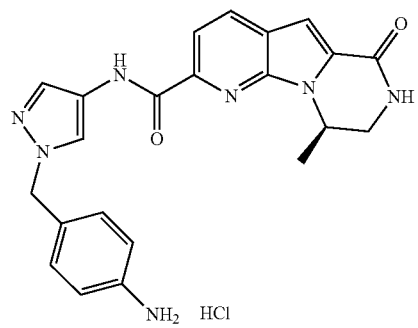

Compound #25

A. A solution of the Compound 18 (1.0 equivalent) in MeOH was treated with HCl in ether (1M solution, 1.5 equivalent) at room temperature and stirred for 30 min. The solvent was evaporated and dried under vacuum to obtain Compound 25.

Synthetic Example 26

Synthesis of (R)—N-(1-(4-(aminomethyl)benzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride salt, Compound #26

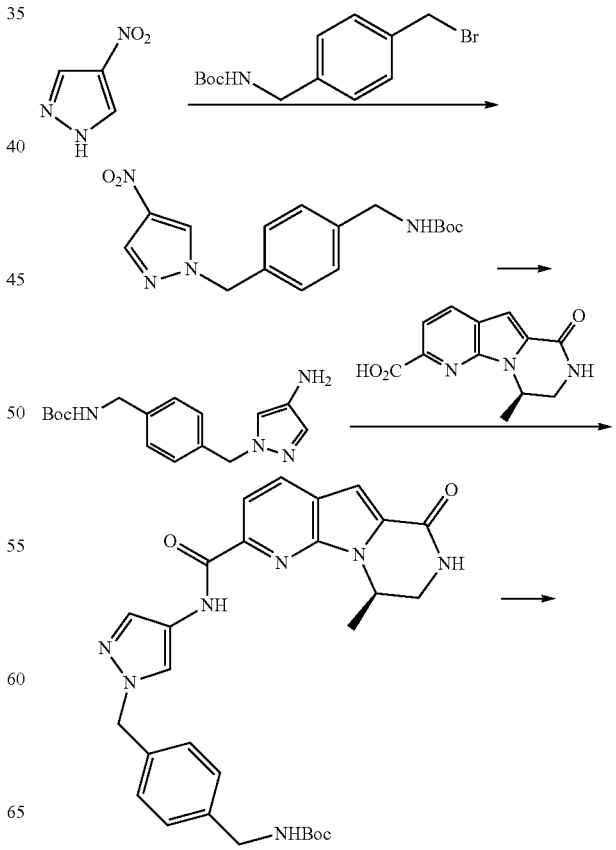

-continued

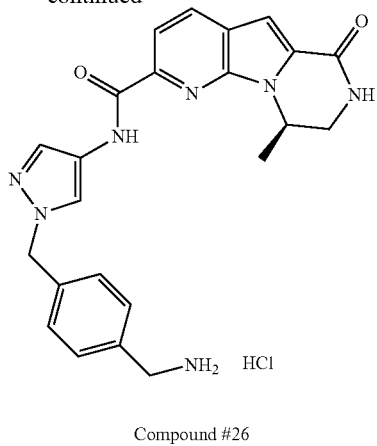

Compound #26

A. A solution of 4-nitro-1H-pyrazole (0.23 g, 2.048 mmol) and tert-butyl (4-(bromomethyl)benzyl)carbamate (0.615 g, 2.048 mmol) in acetone (10 mL) was treated with potassium carbonate (0.85 g, 6.145 mmol) and heated at reflux temperature for 2 h. The reaction was brought to room temperature; solid was filtered off and washed with dichloromethane (3×25 mL). Combined organic layer was evaporated and the crude product was washed with hexanes to obtain the title compound (0.68 g, quantitative) as an off-white solid.

B. A solution of tert-butyl (44(4-nitro-1H-pyrazol-1-yl) methyl)benzyl)carbamate (0.68 g, 2.045 mmol) in ethanol (10 mL) and water (7 mL) was treated with iron (0.34 g, 6.137 mmol) followed by acetic acid (0.12 mL, 2.045 mmol) and the reaction was heated at reflux temperature for 2 h. The reaction was brought to room temperature and solvent was evaporated. The reaction was basified with 1 N NaOH solution and product was extracted into dichloromethane (3×50 mL). The combined dichloromethane layer was washed with brine (10 mL) and dried (Na$_2$SO$_4$). Solvent was evaporated and crude was purified by column chromatography (2 M NH$_3$ in MeOH: Dichloromethane, 5:95) on silica gel to obtain the title compound (0.45 g, 73%) as a brown solid.

C. A solution of (R)-9-methyl-6-oxo-6,7,8,9-tetrahydropyrido[3',2':4,5]pyrrolo[1,2-a]pyrazine-2-carboxylic acid (0.11 g, 0.448 mmol), tert-butyl (4-((4-amino-1H-pyrazol-1-yl)methyl)benzyl)carbamate (0.135 g, 0.448 mmol) and DIPEA (0.14 mL, 0.807 mmol) in dry DMF (5 mL) was treated with HATU (0.196 g, 0.515 mmol) at room temperature and stirred for additional 24 h. The reaction was diluted with water (50 mL), basified with 2 N NaOH solution (20 mL) and product was extracted into ethyl acetate (3×50 mL). The combined ethyl acetate layer was washed with water (2×25 mL), brine (50 mL) and dried (Na$_2$SO$_4$). Solvent was evaporated and crude was purified by column chromatography (2 M NH$_3$ in MeOH: Dichloromethane, 1:99 to 5:95) on silica gel to obtain the title compound (170 mg, 72%) as a light brown solid.

D. A solution of tert-butyl (R)-(4-((4-(9-methyl-6-oxo-6,7,8,9-tetrahydropyrido[3',2':4,5]pyrrolo[1,2-a]pyrazine-2-carboxamido)-1H-pyrazol-1-yl)methyl)benzyl)carbamate (0.17 g, 0.32 mmol) in CH$_2$Cl$_2$ (6 mL) was treated with TFA (4 mL) at room temperature and stirred for additional 2 h. Solvent was evaporated and crude was basified with 2N NaOH solution and product was extracted into dichloromethane (2×15 mL). The combined dichloromethane layer was washed with brine (10 mL) and dried (Na$_2$SO$_4$). Solvent was evaporated and crude was purified by column chromatography (2M NH$_3$ in MeOH:CH$_2$Cl$_2$, 1:99 to 1:9) on silica gel to obtain (R)—N-(1-(4-(aminomethyl)benzyl)-1H-pyrazol-4-yl)-9-methyl-6-oxo-6,7,8,9-tetrahydropyrido[3',2':4,5]pyrrolo[1,2-a]pyrazine-2-carboxamide (0.13 g, 95%) which was converted to the mono-hydrochloride salt, Compound 26, by the procedure described in Example 25. $^1$H NMR spectrum for Compound 26 (DMSO-d$_6$) δ 1.42 (d, 3H, J=5.1 Hz), 3.45-3.50 (m, 1H), 3.88-4.01 (m, 3H), 5.27-5.35 (m, 3H), 7.13 (s, 1H), 7.31 (d, 2H, J=6.0 Hz), 7.47 (d, 2H, J=6.0 Hz), 7.78 (s, 1H), 7.90 (d, 1H, J=6.3 Hz), 8.24-8.41 (m, 6H), 10.68 (s, 1H).

In a similar manner as described above in Synthetic Examples 1-26, but using the appropriately substituted starting materials, the following compounds are prepared:

(R)—N-(1-benzyl-1H-pyrazol-4-yl)-5-fluoro-9-methyl-6-oxo-6,7,8,9-tetrahydropyrido[3',2':4,5]pyrrolo[1,2-a]pyrazine-2-carboxamide;

(R)—N-(1-benzyl-1H-pyrazol-4-yl)-9-isopropyl-6-oxo-6,7,8,9-tetrahydropyrido[3',2':4,5]pyrrolo[1,2-a]pyrazine-2-carboxamide;

(S)—N-(1-benzyl-1H-pyrazol-4-yl)-9-trifluoromethyl-6-oxo-6,7,8,9-tetrahydropyrido[3',2':4,5]pyrrolo[1,2-a]pyrazine-2-carboxamide;

N-(1-benzyl-1H-pyrazol-4-yl)-6'-oxo-7',8'-dihydro-6'H-spiro[cyclopropane-1,9'-pyrido[3',2':4,5]pyrrolo[1,2-a]pyrazine]-2'-carboxamide;

(R)—N-(1-(4-methylpiperazinyl)-1H-pyrazol-4-yl)-9-methyl-6-oxo-6,7,8,9-tetrahydropyrido[3',2':4,5]pyrrolo[1,2-a]pyrazine-2-carboxamide;

(S)—N-(1-benzyl-1H-pyrazol-4-yl)-9-isopropyl-6-oxo-6,7,8,9-tetrahydropyrido[3',2':4,5]pyrrolo[1,2-a]pyrazine-2-carboxamide;

(R)—N-(1-benzyl-1H-pyrazol-4-yl)-9-trifluoromethyl-6-oxo-6,7,8,9-tetrahydropyrido[3',2':4,5]pyrrolo[1,2-a]pyrazine-2-carboxamide;

N-(1-benzyl-1H-pyrazol-4-yl)-9,9-dimethyl-6-oxo-6,7,8,9-tetrahydropyrido[3',2':4,5]pyrrolo[1,2-a]pyrazine-2-carboxamide;

(S)—N-(1-benzyl-1H-pyrazol-4-yl)-6-methyl-9-oxo-6,7,8,9-tetrahydropyrido[2',3':4,5]pyrrolo[1,2-a]pyrazine-3-carboxamide;

(S)—N-(1-benzyl-1H-pyrazol-4-yl)-6-methyl-9-oxo-6,7,8,9-tetrahydropyrido[2',3':4,5]pyrrolo[1,2-a]pyrazine-2-carboxamide;

(S)-1-benzyl-N-(6-methyl-9-oxo-6,7,8,9-tetrahydropyrido[2',3':4,5]pyrrolo[1,2-a]pyrazin-3-yl)-1H-pyrazole-4-carboxamide;

(S)-1-benzyl-N-(6-methyl-9-oxo-6,7,8,9-tetrahydropyrido[2',3':4,5]pyrrolo[1,2-a]pyrazin-2-yl)-1H-pyrazole-4-carboxamide;

(R)-5-fluoro-9-methyl-N-(1-((4-methylpiperazin-1-yl)methyl)-1H-pyrazol-4-yl)-6-oxo-6,7,8,9-tetrahydropyrido[3',2':4,5]pyrrolo[1,2-a]pyrazine-2-carboxamide;

(R)-5-fluoro-9-methyl-N-(1-((1-methylpiperidin-4-yl)methyl)-1H-pyrazol-4-yl)-6-oxo-6,7,8,9-tetrahydropyrido[3',2':4,5]pyrrolo[1,2-a]pyrazine-2-carboxamide;

(R)—N-(1-benzyl-1H-pyrazol-4-yl)-6-methyl-9-oxo-6,7,8,9-tetrahydropyrrolo[1,5-a:2,3-b']dipyrazine-3-carboxamide;

(R)-1-(1-benzyl-1H-pyrazol-4-yl)-3-(9-methyl-6-oxo-6,7,8,9-tetrahydropyrido[3',2':4,5]pyrrolo[1,2-a]pyrazin-2-yl)urea; and (R)-1-(1-benzyl-1H-pyrazol-4-yl)-3-(9-methyl-6-oxo-6,7,8,9-tetrahydropyrido[3',2':4,5]pyrrolo[1,2-a]pyrazin-2-yl)guanidine.

General Synthetic Procedure

General Procedure for Converting Compounds in Free Base Form to Mono- or Di-Hydrochloride Salts A solution of a compound described herein as a free base (1.0 equivalent) in MeOH or a mixture of MeOH:$CH_2Cl_2$ (3:2) was treated with HCl in ether (1M solution, 1.5 equivalent for mono-hydrochloride salt and 3.0 equivalent for di-hydrochloride salt) at room temperature and stirred for additional 30 minutes at same temperature. Solvent was evaporated and dried under vacuum to obtain the required mono- or di-hydrochloride salt of the corresponding free base.

BIOLOGICAL EXAMPLES

Various techniques are known in the art for testing the activity of the compounds described herein in various in vitro and in vivo assays. In order that the invention described herein may be more fully understood, the following Biological Examples are set forth. It should be understood that these examples are for illustrative purposes only and are not to be construed as limiting this invention in any manner.

Biological Example 1

Kinase Assays to Determine the Structure Activity Relationship (SAR) of RSK Inhibitors The assay conditions for the RSK2 kinase target were optimized to yield acceptable enzymatic activity. In addition, the assays were optimized to give high signal-to-noise ratio.

Radioisotope assays (SignalChem) were performed for the evaluation of the kinase target profiling and all assays were performed in a designated radioactive working area. The kinase targets were RSK1, RSK2, RSK3, RSK4 and MK2. The kinase assays (in duplicate) were performed at 30° C. for 15 minutes in a final volume of 25 μL according to the following assay reaction recipe:

Component 1: 5 μL of diluted active kinase target (100 ng per reaction)
Component 2: 5 μL of peptide substrate (0.5 μg per reaction) (for RSK1, RSK2, RSK3 and RSK4, RSK S6K substrate was used; for MK2, HSP27tide was used)
Component 3: 5 μL of kinase assay buffer
Component 4: 5 μL of compound described herein (various concentrations: 0, 0.1, 1, 10, 100 or 1000 nM or 1, 3, 10, 30, 100, 300 nM)
Component 5: 5 μL of $^{33}$P-ATP (5 μM stock solution, 0.8 μCi; 20 μM final concentration)

The assay was initiated by the addition of $^{33}$P-ATP and the reaction mixture incubated at 30° C. for 15 minutes. After the incubation period, the assay was terminated by spotting 10 μL of the reaction mixture onto Multiscreen phosphocellulose P81 plate. The Multiscreen phosphocellulose P81 plate was washed 3 times for approximately 15 minutes each in a 1% phosphoric acid solution. The radioactivity on the P81 plate was counted in the presence of scintillation fluid in a Trilux scintillation counter.

Blank controls were set up for each target kinase which included all the assay components except the addition of the appropriate substrate (which was replaced with equal volume of assay dilution buffer). The corrected activity for each target kinase was determined by removing the blank control value.

Compounds described herein, when tested in the above-described radioistope assay, demonstrated the ability to inhibit RSK2 as shown below in Table 2:

TABLE 2

| Compound # | RSK2 $IC_{50}$ |
|---|---|
| 1 | >10 μM |
| 2 | >10 μM |
| 3 | >10 μM |
| 4 | >10 μM |
| 5 | >10 μM |
| 6 | >10 μM |
| 7 | >10 μM |
| 8 | >10 μM |
| 9 | >10 μM |
| 10 | >1 μM |
| 11 | 1377 nM |
| 12 | >1 μM |
| 13 | >1 μM |
| 14 | >1 μM |
| 15 | 94 nM |
| 16 | 23 nM |
| 17 | 14 nM |
| 18 | 12 nM |
| 19 | 123 nM |
| 20 | 124 nM |
| 25 | 18 nM |

There are four RSK isoforms; RSK1, RSK2, RSK3 and RSK4. In some embodiments, the compounds described herein are active against all RSK isoforms. In some embodiments, the compounds described herein are active against RSK1, RSK3 and RSK4 isoforms (Tables 3 and 4).

TABLE 3

| RSK Isoform | $IC_{50}$ of Compound #18 |
|---|---|
| RSK1 | 2.0 nM |
| RSK2 | 20 nM |
| RSK3 | 1.7 nM |
| RSK4 | 0.3 nM |

TABLE 4

| RSK Isoform | $IC_{50}$ of Compound #15 |
|---|---|
| RSK1 | 23.6 nM |
| RSK3 | 6.0 nM |
| RSK4 | 8.0 nM |

Biological Example 2

Solubility Assessments

Solubility is an important property for therapeutic drug candidates. Poor solubility can lead to low bioavailability resulting in suboptimal drug delivery. It can also prevent the evaluation of test agents in animals because the concentration(s) needed to achieve the desired effect cannot be achieved to to poor solubility. For solubility assessments, small molecules targeting RSK were compared. For these assessments, 100 mM solutions of the compounds dissolved in DMSO were diluted in DMEM growth media (Life Technologies) supplemented with fetal bovine serum (FBS, Life Technologies) and 100 units/ml penicillin and 100 units/ml streptomycin (Life Technologies) to make 20 mg/ml solutions. Once diluted, the solutions were vortexed and examined for the formation of precipitates. For compounds that remained in solution, the pH was determined using pH test strips (BDH Analytical Chemicals). For Compound 26, a 100 mM solution of the compound dissolved in DMSO was diluted in phosphate buffered saline (Life Technologies) to make a 20 mg/ml solution. The stock of 20 mg/kg was chosen because this is the upper end of what would be required to dose mice for a range of studies including MTD, PK, PD and efficacy. The pH of this solution was determined to be 2, as previously described. Subsequently, 4M NaOH was added and the compound remained in solution at a pH equal to 9. At high concentrations some RSK inhibitors were highly soluble while others were not. Compound 0 is (R)—N-(1-benzyl-1H-pyrazol-4-yl)-9-methyl-6-oxo-6,7,8,9-tetrahydropyrido[3',2':4,5]pyrrolo[1,2-a]pyrazine-2-carboxamide. Compound 0 was not soluble, whereas Compounds 18, 20, 21, 25 and 26 were soluble under the same conditions (Table 5).

TABLE 5

| Compound | Dissolving Compound | Diluting Solution | 20 mg/ml Solubility | pH |
|---|---|---|---|---|
| 0 | DMSO | DMEM | Precipitate | N/A |
| 18 | DMSO | DMEM | Soluble | 9 |
| 20 | DMSO | DMEM | Soluble | 8 |
| 21 | DMSO | DMEM | Soluble | 9 |
| 22 | DMSO | DMEM | Precipitate | N/A |
| 23 | DMSO | DMEM | Precipitate | N/A |
| 24 | DMSO | DMEM | Precipitate | N/A |
| 25 | DMSO | DMEM | Soluble | 2 |
| 26 | DMSO | PBS | Soluble | 2-9 |

Biological Example 3

Monolayer Growth Inhibition Assay

For cytotoxicity profiling of small molecule RSK2 kinase inhibitors against breast cancer cell lines, compounds of the invention or vehicle control (DMSO, Life Technologies) were diluted in media in 96 well plates (Grenier Bio-One) in triplicate at final concentrations of 0.1953125, 0.390625, 0.78125, 1.5625, 3.125, 6.25, 12.5, 25 and 50 μM. $1 \times 10^3$ cells per well were seeded for a final volume of 200 μl per well and plates were incubated for 5 days at 37° C. in a humidified incubator with 5% $CO_2$. Following the incubation period, cell survival was quantified by Alamar blue assay (Life Technologies). Briefly, media from each well was replaced with 100 μl of phosphate buffer saline (PBS, Life Technologies) and cells were incubated with 5% Alamar blue, which incorporates a propriety redox indicator that changes colour in response to metabolic activity, for up to 2 hours. During this period of incubation, the absorbance at 570 nm and 600 nm was measured at various time points, depending on the cell line or sample. Percent survival was calculated by comparing the absorbance ratio of the test well to the control well multiplied by 100%, as indicated in the following formula:

$$\% \text{ Survival} = \frac{(\text{Absorbance 570 nm} - 600 \text{ nm}(\text{Test Well})}{(\text{Absorbance 570 nm} - 600 \text{ nm}(\text{Control Well})} \times 100\%$$

Following, plates were prepared for crystal violet staining. To begin, 100 μl of an 8% formaldehyde (Alfa Aesar) solution diluted in PBS was added to each well and plates were stored at 4° C. overnight. Next, the formaldehyde solution was discarded and the wells were washed with 200 μl ultrapure water per well three times. Following, 50 μl of a 0.5% crystal violet solution (0.5% w/v crystal violet (Alfa Aesar), 25% methanol (VWR)) was added to each well and incubated at room temperature for 20 minutes. The crystal violet solution was discarded and wells were washed with 200 μl ultrapure water per well three times. Next, 50 μl of a 5% sodium dodecyl sulphate (SDS) (Alfa Aesar) was added to each well and the absorbance at 590 nm was measured. Similar to the Alamar blue assay, the percent survival was calculated by comparing the absorbance ratio of the test well to the control well multiplied by 100%.

A. Alamar Blue Assay Results:

Representative compounds described herein were tested in the Alamar blue assay against MDA-MB-231, MDA-MB-468, SUM149, SUM149-PTXR, MDA-MB-435, HCC1143, 4T1 and T47D breast cancer cell lines. The $IC_{50}$ values of the compounds when tested for 5-days are provided below in Tables 6A and 6B. In all instances a single dose was given on day 1 of the experiment. The cytotoxic ability of representative compounds against breast cancer cell lines MDA-MB-231, MDA-MB-468, SUM149, and 4T1 are shown in FIGS. 1, 2, 3, and 4, respectively.

TABLE 6A

| | | IC50 Values (μM) - Alamar Blue (5 Days) | | | | | |
|---|---|---|---|---|---|---|---|
| Type | Cell Line | 11 | 15 | 16 | 17 | 18 | 19 |
| TNBC | MDA-MB-231 | >50 | 21.3 ± 5.4 | 8.7 ± 1.8 | 10.3 ± 0.7 | 6.3 ± 1.1 | 25.6 ± 1.5 |
| | MDA-MB-468 | >50 | 13.3 ± 4.1 | 2.7 ± 0.5 | 2.1 ± 1.1 | 4.1 ± 2.5 | 14.7 ± 4.1 |
| | SUM149[+] | 36.0 ± 12.8 | 11.7 ± 2.8 | 3.4 ± 1.8 | 8.3 ± 4.9 | 3.3 ± 1.9 | 15.8 ± 6.4 |
| | SUM149-PTXR[+] | 36.4 ± 11.9 | 9.2 ± 3.0 | 2.5 ± 0.4 | 4.2 ± 1.5 | 2.1 ± 0.3 | 14.1 ± 4.3 |
| | HCC1143 | >50 | 3.6 ± 2.7 | 7.0 ± 3.0 | 5.0 ± 1.7 | 4.2 ± 2.5 | 11.5 ± 3.6 |
| | HCC1937[+] | >50 | 9.7 ± 3.9 | 17.4 ± 3.0 | 6.8 ± 1.3 | 9.2 ± 1.1 | 16.6 ± 11.5 |
| | 4T1 | 48.5 ± 2.6 | 8.8 ± 2.1 | 5.4 ± 0.9 | 3.8 ± 1.7 | 5.3 ± 2.5 | 20.6 ± 2.5 |
| ER/PR | T47D | 48.1 ± 3.3 | 7.8 ± 3.7 | 4.7 ± 1.7 | 5.7 ± 2.1 | 3.6 ± 1.7 | 13.5 ± 4.6 |
| HER2 | JIMT-1 | >50 | 8.3 ± 1.8 | 16.3 ± 1.0 | 12.6 ± 5.9 | 13.1 ± 6.4 | 37.3 ± 9.0 |
| Melanoma | MDA-MB-435 | 24.6 ± 10.3 | 13.7 ± 3.4 | 0.9 ± 0.5 | 1.2 ± 1.0 | 0.7 ± 0.5 | 10.5 ± 2.2 |
| Prostate | PC3 | 44.9 ± 8.8 | 11.5 ± 3.4 | 6.6 ± 2.3 | 6.0 ± 3.2 | 5.5 ± 0.5 | 17.1 ± 8.7 |
| All | Range | 24.6->50 | 3.6-21.3 | 0.9-17.4 | 1.2-12.6 | 0.7-13.1 | 10.5-37.3 |

[+] = BRCA Mutant

TABLE 6B

| | | IC50 Values (μM) - Alamar Blue (5 Days) | | | | | |
|---|---|---|---|---|---|---|---|
| Type | Cell Line | 21 | 22 | 23 | 24 | 25 | 26 |
| TNBC | MDA-MB-231 | 14.7 ± 4.3 | 13.9 ± 3.5 | 7.8 ± 2.0 | 9.8 ± 3.1 | 3.9 ± 0.1 | 7.4 ± 1.7 |
| | MDA-MB-468 | 6.5 ± 4.5 | 7.5 ± 2.1 | 9.7 ± 1.8 | 4.5 ± 2.3 | 3.0 ± 0.6 | 2.5 ± 0.7 |
| | SUM149[+] | 2.7 ± 1.3 | 7.7 ± 4.6 | 3.0 ± 2.4 | 1.1 ± 0.9 | 10.4 ± 3.5 | 9.8 ± 5.7 |
| | SUM149-PTXR[+] | 1.5 ± 0.8 | 7.8 ± 4.6 | 5.1 ± 4.0 | 3.4 ± 2.1 | 5.2 ± 4.2 | 8.8 ± 2.5 |
| | HCC1143 | 5.4 ± 3.7 | 9.9 ± 1.0 | 9.7 ± 1.3 | 4.4 ± 1.9 | 5.1 ± 0.3 | 9.6 ± 6.1 |
| | HCC1937[+] | 8.3 ± 2.4 | 12.6 ± 3.5 | 10.5 ± 1.0 | 9.2 ± 3.2 | 13.7 ± 3.8 | 5.6 ± 0.4 |
| | 4T1 | 1.2 ± 0.3 | 4.5 ± 1.0 | 2.5 ± 0.8 | 0.5 ± 0.3 | 4.2 ± 1.2 | 6.2 ± 2.5 |
| ER/PR | T47D | 8.0 ± 3.8 | 4.8 ± 0.9 | 6.0 ± 4.9 | 4.5 ± 4.1 | 8.9 ± 0.8 | X |
| HER2 | JIMT-1 | 12.6 ± 6.4 | 17.1 ± 2.4 | 19.8 ± 7.1 | 12.3 ± 5.9 | 19.9 ± 6.5 | 15.5 ± 6.6 |
| Melanoma | MDA-MB-435 | 8.3 ± 5.3 | 6.8 ± 6.4 | 1.1 ± 0.7 | 5.6 ± 0.1 | 0.9 ± 0.1 | 3.9 ± 1.3 |
| Prostate | PC3 | 7.1 ± 0.9 | 9.2 ± 1.5 | 10.7 ± 1.1 | 12.0 ± 4.5 | 8.5 ± 0.8 | 1.9 ± 0.8 |
| All | Range | 1.2-14.7 | 4.5-17.1 | 1.1-19.8 | 0.5-12.3 | 0.9-19.9 | 1.9-15.5 |

[+] = BRCA Mutant

B. Crystal Violet Assay Results:

Representative compounds described herein were tested in the crystal violet assay against MDA-MB-231, MDA-MB-468, SUM149, SUM149-PTXR, MDA-MB-435, HCC1143, 4T1 and T47D breast cancer cell lines. The $IC_{50}$ values of the compounds when tested for 5-days are provided below in Tables 7A and 7B. In all instances a single dose was given on day 1 of the experiment. The cytotoxic ability of representative compounds against breast cancer cell lines MDA-MB-231, MDA-MB-468, SUM149, and 4T1 are shown in FIGS. 5, 6, 7, and 8, respectively. Complete (100%) growth suppression was achievable with several of the compounds in multiple different cell lines. This indicated that resistance to the RSK inhibitors was not observed.

TABLE 7A

| | | IC50 Values (μM) - Crystal Violet (5 Days) | | | | | |
|---|---|---|---|---|---|---|---|
| Type | Cell Line | 11 | 15 | 16 | 17 | 18 | 19 |
| TNBC | MDA-MB-231 | 45.0 ± 8.7 | 21.0 ± 7.5 | 2.7 ± 1.3 | 5.1 ± 2.0 | 4.4 ± 2.0 | 17.2 ± 1.9 |
| | MDA-MB-468 | 37.3 ± 2.3 | 11.3 ± 0.7 | 1.9 ± 0.3 | 1.6 ± 0.7 | 2.3 ± 0.9 | 7.4 ± 1.0 |
| | SUM149[+] | 33.6 ± 14.5 | 9.9 ± 3.1 | 2.8 ± 0.9 | 5.3 ± 2.2 | 2.4 ± 0.7 | 11.1 ± 3.9 |
| | SUM149-PTXR[+] | 44.6 ± 3.9 | 8.8 ± 2.2 | 3.5 ± 1.2 | 5.2 ± 0.6 | 3.8 ± 0.7 | 13.0 ± 1.3 |
| | HCC1143 | >50 | 12.6 ± 3.4 | 5.0 ± 1.1 | 8.9 ± 3.2 | 2.4 ± 0.8 | 13.8 ± 4.3 |
| | HCC1937[+] | >50 | 12.0 ± 0.2 | 12.0 ± 5.3 | 7.3 ± 3.2 | 7.7 ± 3.5 | 19.9 ± 8.7 |
| | 4T1 | 39.5 ± 9.4 | 6.9 ± 3.0 | 4.5 ± 0.8 | 2.0 ± 0.6 | 5.3 ± 1.1 | 15.8 ± 4.8 |
| ER/PR | T47D | 30.1 ± 3.3 | 8.5 ± 0.7 | 3.8 ± 0.7 | 6.7 ± 1.6 | 2.2 ± 0.8 | 7.7 ± 1.5 |
| HER2 | JIMT-1 | >50 | 11.2 ± 0.2 | 13.3 ± 2.4 | 7.4 ± 2.5 | 11.1 ± 0.5 | 34.0 ± 12.8 |
| Melanoma | MDA-MB-435 | 17.9 ± 7.3 | 8.2 ± 2.5 | 1.2 ± 0.6 | 1.0 ± 0.3 | 0.5 ± 0.2 | 10.3 ± 3.5 |
| Prostate | PC3 | 45.6 ± 4.8 | 5.9 ± 1.4 | 3.7 ± 1.3 | 2.7 ± 1.2 | 2.9 ± 0.4 | 14.9 ± 6.6 |
| All | Range | 17.9->50 | 5.9-21.0 | 1.2-13.3 | 1.0-8.9 | 0.5-11.1 | 7.4-34.0 |

[+] = BRCA Mutant

TABLE 7B

| | | IC50 Values (μM) - Crystal Violet (5 Days) | | | | | |
|---|---|---|---|---|---|---|---|
| Type | Cell Line | 21 | 22 | 23 | 24 | 25 | 26 |
| TNBC | MDA-MB-231 | 9.1 ± 0.8 | 6.6 ± 2.1 | 3.6 ± 0.8 | 9.1 ± 1.3 | 4.2 ± 0.3 | 3.7 ± 1.8 |
| | MDA-MB-468 | 4.6 ± 1.4 | 6.6 ± 2.3 | 7.2 ± 1.5 | 3.3 ± 1.3 | 2.0 ± 0.4 | 1.7 ± 0.2 |
| | SUM149[+] | 2.4 ± 1.3 | 6.2 ± 4.8 | 2.1 ± 1.6 | 0.9 ± 0.3 | 4.1 ± 1.5 | 6.5 ± 4.4 |
| | SUM149-PTXR[+] | 2.0 ± 0.2 | 8.0 ± 1.3 | 5.0 ± 2.4 | 4.5 ± 1.4 | 4.2 ± 0.6 | 6.5 ± 2.1 |
| | HCC1143 | 9.5 ± 5.6 | 6.6 ± 3.1 | 7.3 ± 3.4 | 5.8 ± 2.6 | 4.4 ± 2.7 | 7.3 ± 2.7 |
| | HCC1937[+] | 11.0 ± 1.0 | 9.9 ± 3.0 | 8.6 ± 3.0 | 5.8 ± 0.4 | 8.4 ± 1.9 | 6.6 ± 1.6 |
| | 4T1 | 1.1 ± 0.7 | 2.6 ± 1.5 | 1.8 ± 0.8 | 0.3 ± 0.1 | 2.9 ± 0.3 | 4.9 ± 1.1 |

TABLE 7B-continued

| | | IC50 Values (μM) - Crystal Violet (5 Days) | | | | | |
|---|---|---|---|---|---|---|---|
| Type | Cell Line | 21 | 22 | 23 | 24 | 25 | 26 |
| ER/PR | T47D | 3.7 ± 2.7 | 4.3 ± 2.1 | 4.7 ± 4.9 | 2.7 ± 2.1 | 3.1 ± 0.1 | X |
| HER2 | JIMT-1 | 11.3 ± 4.1 | 14.2 ± 5.1 | 15.0 ± 6.1 | 7.5 ± 2.2 | 15.2 ± 2.6 | 12.3 ± 3.2 |
| Melanoma | MDA-MB-435 | 4.8 ± 2.1 | 3.2 ± 1.3 | 1.1 ± 0.8 | 5.0 ± 3.6 | 0.5 ± 0.3 | 1.6 ± 0.3 |
| Prostate | PC3 | 4.3 ± 0.5 | 6.8 ± 1.8 | 6.8 ± 1.8 | 6.5 ± 2.8 | 3.8 ± 0.4 | 1.5 ± 0.5 |
| All | Range | 1.1-11.3 | 2.6-14.2 | 1.1-15.0 | 0.3-9.1 | 0.5-15.2 | 1.5-12.3 |

+ = BRCA Mutant

Biological Example 4

Soft Agar Growth Inhibition Assay

Two agar (Alfa Aesar) solutions (0.8% w/v and 0.4% w/v) were prepared in ultrapure water. The 0.8% agar solution was mixed in equal volumes with 2× media previously prepared from powder (Life Technologies) following the manufacturer's instructions and filter sterilized. The 0.8% agar and media solution was added to 24 well plates (Mandel Scientific) at 500 μl per well. The plates were placed in a humidified incubator at 37° C. with 5% $CO_2$. Next, the 0.4% agar solution was mixed in equal volumes with 2× media. Breast cancer cell lines were added to this solution to achieve a final concentration of $2\times10^4$ cells per well and 500 μl was added to each well on top of the bottom agar and media layer. Following, a volume of 20 μl of compound or vehicle control (DMSO) was added to designated wells in triplicate at the following final concentrations: 0.078125, 0.15625, 0.3125, 0.625, 1.25, 2.5, 5, 10, and 20 μM. The plates were returned to the incubator for 10-32 days, with a re-dosing of compounds or DMSO every 7 days. After 10-32 days, colonies were counted in 3 different fields of view for each well. The counts for each treatment were averaged and the percent survival was calculated by comparing the number of colonies in the test wells to the control wells multiplied by 100%.

Figure 9A:
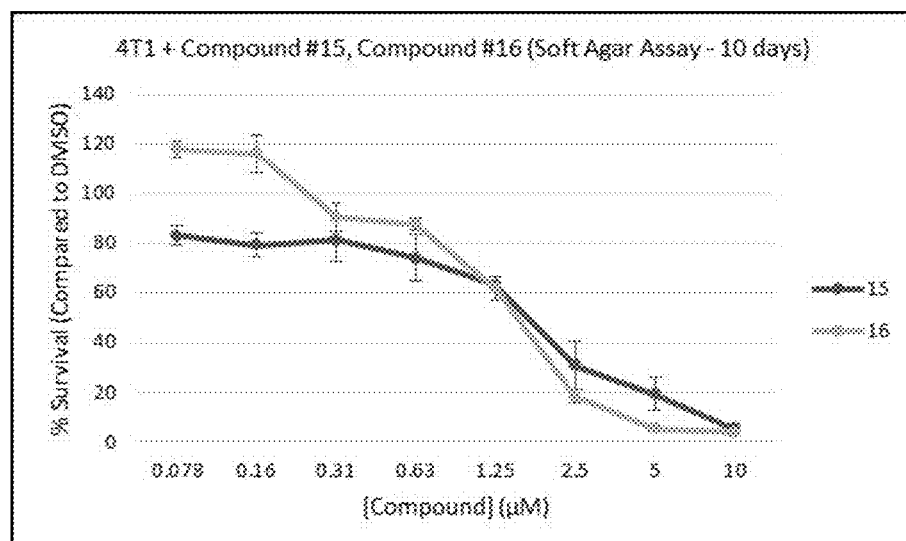
FIG. 9A depicts the percent survival of 4T1 breast cancer cells in the soft agar growth inhibition assay when treated with varying concentrations of either Compound 15 or Compound 16.
Figure 9B:
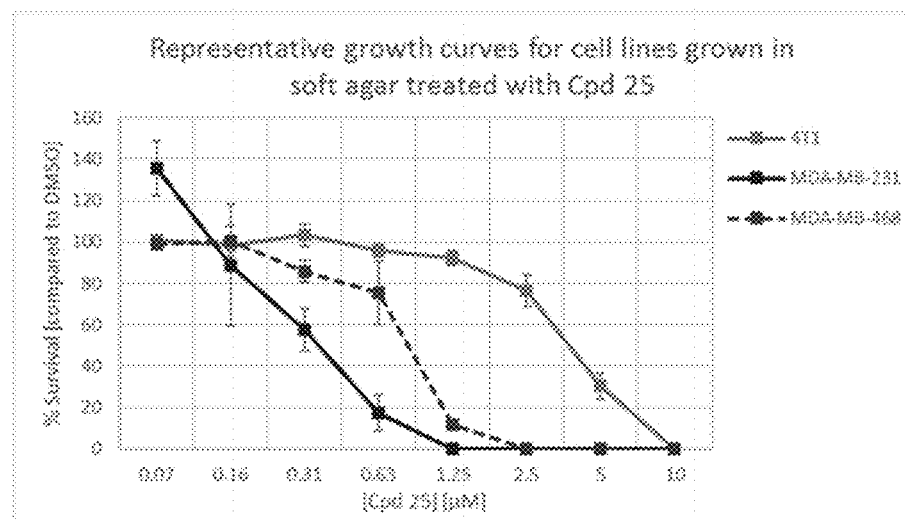
FIG. 9B depicts the percent survival of MDA-MB-231, MDA-MB-468 or 4T1 cells grown in soft agar when the cells were treated with varying concentrations of Compound 25.

Results:

Representative compounds described herein were tested in the soft agar growth inhibition assay against the 4T1 breast cancer cell line. The $IC_{50}$ values of the compounds when tested for 10 days are provided below in Table 8A and when tested for 14-22 days are provided below in Table 8B. The ability of representative compounds against the 4T1 breast cancer cell line to grow in soft agar is shown in FIG. 9A. Complete growth suppression was achievable with 10 μM. The ability of Compound 25 to similarly block growth in soft agar is shown in FIG. 9B using MDA-MB-231, MDA-MB-468 or 4T1 cell lines. Complete growth suppression was achieved between 1.25-10 μM depending on the cell line.

TABLE 8A

| 4T1 + Compound #15, Compound #16 | |
|---|---|
| $IC_{50}$ Values (μM), 10 Days, Soft Agar | |
| Inhibitor | $IC_{50}$ (μM) |
| Compound #15 | 3.8 |
| Compound #16 | 3.3 |

TABLE 8B

| | | IC50 Values (μM) - Soft Agar (14-22 Days) | | | | | | | |
|---|---|---|---|---|---|---|---|---|---|
| Type | Cell Line | Cpd 16 | Cpd 18 | Cpd 21 | Cpd 22 | Cpd 23 | Cpd 24 | Cpd 25 | Cpd 26 |
| TNBC | MDA-MB-231 | 0.2 ± 0.1 | 0.1 ± 0.0 | 2.0 ± 1.0 | 0.2 ± 0.1 | 0.3 ± 0.2 | 0.4 ± 0.2 | 0.2 ± 0.1 | 0.2 ± 0.1 |
| | MDA-MB-468 | 1.1 ± 0.3 | 0.3 ± 0.1 | 0.4 ± 0.1 | 6.9 ± 1.7 | 4.0 ± 0.8 | 2.5 ± 2.0 | 0.7 ± 0.2 | 2.0 ± 0.2 |
| | 4T1 | 3.5 ± 0.3 | 2.5 ± 1.5 | 3.1 ± 0.6 | 3.8 ± 1.9 | 2.4 ± 0.6 | 0.7 ± 0.3 | 4.1 ± 0.2 | 5.3 ± 1.3 |
| All | Range | 0.2-3.5 | 0.1-2.5 | 0.4-3.1 | 0.2-6.9 | 0.3-4.0 | 0.4-2.5 | 0.2-4.1 | 0.2-5.3 |

Biological Example 5

RSK Inhibitors Suppress Cell Signalling Through the Inhibition of Phosphorylated Y-Box Binding Protein-1 (P—YB-1)

Immunoblotting Assessment of Cell Signaling Changes and the Induction of Cell Death Generation of Cellular Extracts:

Following desired experimental conditions, breast cancer cell lines grown and treated in 6 well plates or 100 mm culture dishes (Grenier Bio-One) were placed on ice and the supernatant from each well was removed and the cells were washed in cold PBS. Following removal of PBS, cells were exposed to radioimmunoprecipitation assay (RIPA) buffer (50 mM Tris-HCl (pH 8), 150 mM NaCl, 1% NP-40, 0.5% sodium deoxycholate, 0.1% SDS; Fisher Scientific) supplemented with 1% phosphatase inhibitor (Fisher Scientific) and 1% protease inhibitor (Fisher Scientific) for 10 minutes. Samples were transferred to eppendorf tubes, vortexed and then centrifuged at 14 000 rpm for 10 minutes. Supernatants were collected as whole cell lysates. For mouse tumour tissues, each sample was place in a 35 mm culture dish with complete RIPA lysis buffer. The samples were diced in the buffer on ice with a sterile scalpel (VWR) and the buffer and tissue were transferred to an eppendorf tube. The samples were left on ice for 10 minutes with periodic vortexing every 2 to 3 minutes. The samples were then transferred to a Qiashredder (Qiagen) and centrifuged at 14 000 rpm for 2 minutes. The flow through was transferred to a new eppendorf tube and the samples were centrifuged again at 14 000 rpm for 5 minutes. Supernatants were collected as whole cell lysates.

Figure 10A:
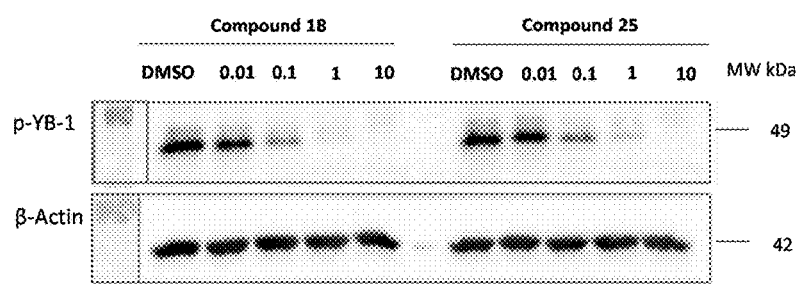
FIGS. 10A and 10B depict cell signaling inhibiton in MDA-MB-231 cells treated with compounds 18 and 25 wherein loss of signaling is measured by the reduction in the intensity of P—YB-1.
Figure 10B:
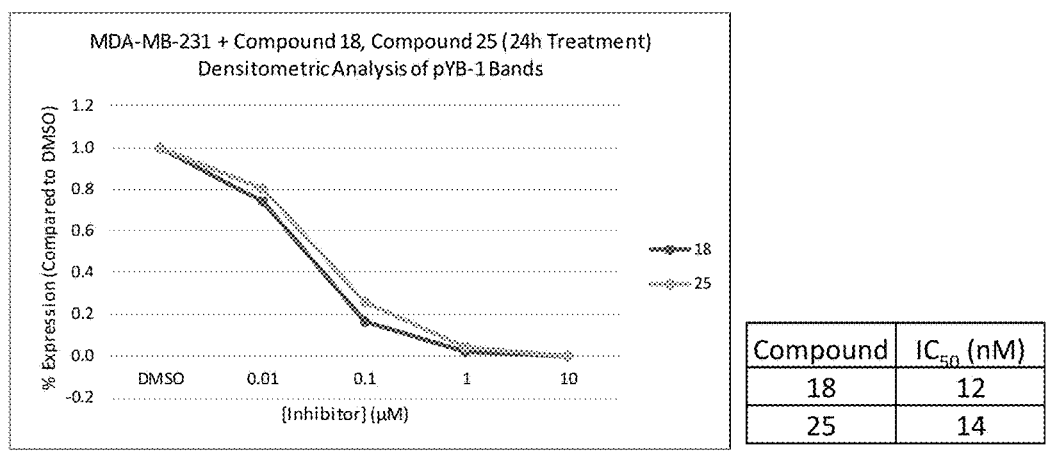
Figure 11A:
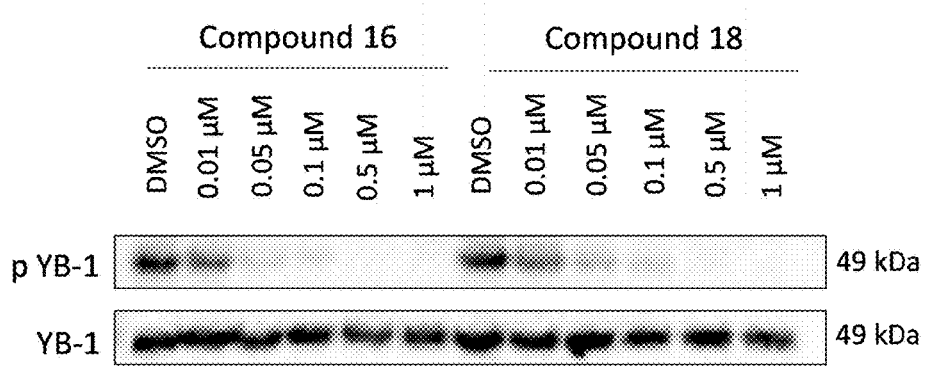
FIGS. 11A and 11B depict cell signaling inhibiton in MDA-MB-231 cells treated with compounds 16 and 18 wherein loss of signaling is measured by the reduction in the intensity of P—YB-1.
Figure 11B:
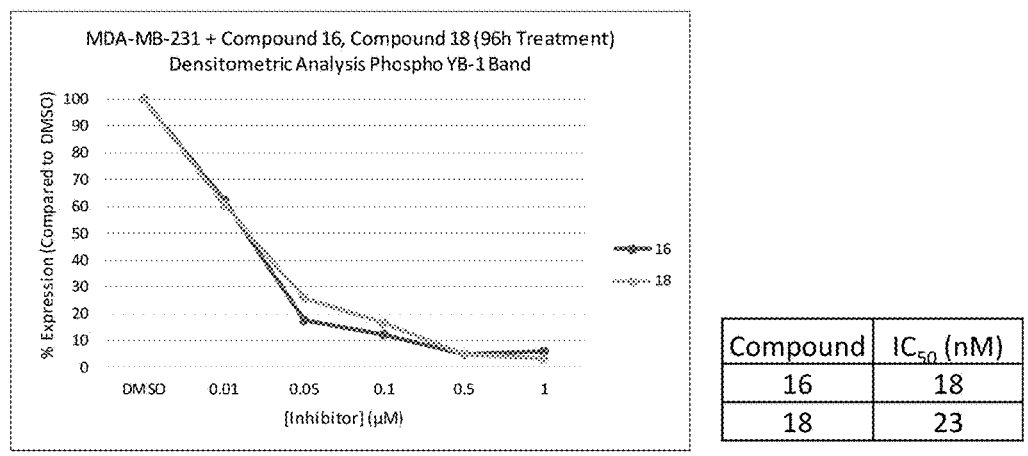

Immunoblotting:

To begin, the protein content of the lysates was measured using the Bicinchoninic Acid (BCA) Protein Assay Kit (Pierce), which included a protein standard curve generated with bovine serum albumin Appropriate volumes of samples and loading buffer (50 mM Tris-HCl (pH 6.8), 2% SDS, 10% glycerol, 1% β-mercaptoethanol, 12.5 mM EDTA, 0.02% bromophenol blue) were mixed, ensuring that equal amounts of protein were loaded. For the majority of experiments in this study, 30 μg of protein per well was loaded. Samples were then resolved on SDS-PAGE (polyacrylamide gel electrophoresis) using various percentages of acrylamide gels (8%-12%), depending on the proteins of interest. SDS-PAGE was run in SDS running buffer (25 mM Tris, 192 mM glycine, 0.1% SDS) and then transferred to nitrocellulose membranes (Bio-Rad) in transfer buffer (48 mM Tris, 39 mM glycine, 20% (v/v) methanol) at 100 volts for 90 minutes at room temperature. Immunoblots were then blocked in 5% skim milk in tris-buffered saline with 0.1% Tween-20 (TBS-T; 50 mM Tris-HCl, pH 7.5, 150 mM NaCl, 0.1% (v/v) Tween-20 (Fisher Scientific)) for 1 to 2 hours Immunoblots were then incubated with selected primary antibodies diluted in TBS-T with 0.1% gelatin (Bio-Rad) and 0.05% sodium azide (Alfa Aesar) overnight. Following washes with TBT-T 4 times for 8 to 10 minutes, immunoblots were incubated with appropriate secondary antibodies conjugated to horseradish peroxidise (Cell Signalling Technology) diluted in TBS-T plus 5% skim milk at a ratio of 1:5000 for 2 hours at room temperature. After an additional round of washes in TBS-T, immunoblots were exposed to combined enhanced chemiluminescence (ECL) reagents (Fisher Scientific) for 1 minute and developed using Chemi-Doc MP Imaging System (Bio-Rad). For certain immunoblots, bands of proteins of interest were scanned and band intensity ratios were determined by densitometric analysis (ImageJ). Inhibitory or inactivation activity of the compounds of the invention was assessed by monitoring loss of phosphorylated Y-box binding protein-1 (YB-1) at serine 102 (P—YB-1S102) (1:1000 Cell Signalling Technologies (CST) (FIGS. 10A, 10B, 11A, and 11B). Treating MDA-MB-231 cells with a range (0.01, 0.1, 1, or 10 uM) of Compound 18 or 25 led to a dose dependent loss of P—YB-1 after 24 hrs (FIG. 10A-B). B-actin was used as a loading control (1:5000 CST). The bands were quantified using densitometry. Likewise, dosing MDA-MB-231 cells with 0.01-1 uM of either Compound 16 or 18 for 96 hrs led to a dose dependent loss of P—YB-1 (FIG. 11A-B). Using this methodology, the $IC_{50}$ values for P—YB-1 for Compounds 22, 23, 24, 25 and 26 were determined to be 24, 33, 16, 41 and 47 nM respectively. Total YB-1 was used as a loading control (1:5000 Abcam). This was a direct measure of RSK inactivation as YB-1 binds directly to the N-terminal kinase domain (NTKD) of RSK. To assess whether cells are actively undergoing cell death, the activity of poly ADP ribose polymerase (PARP) (1:1000 CST) was also measured using the immunoblotting method.

Biological Example 6

RSK Inhibitors Induce Cell Death

Figure 12:
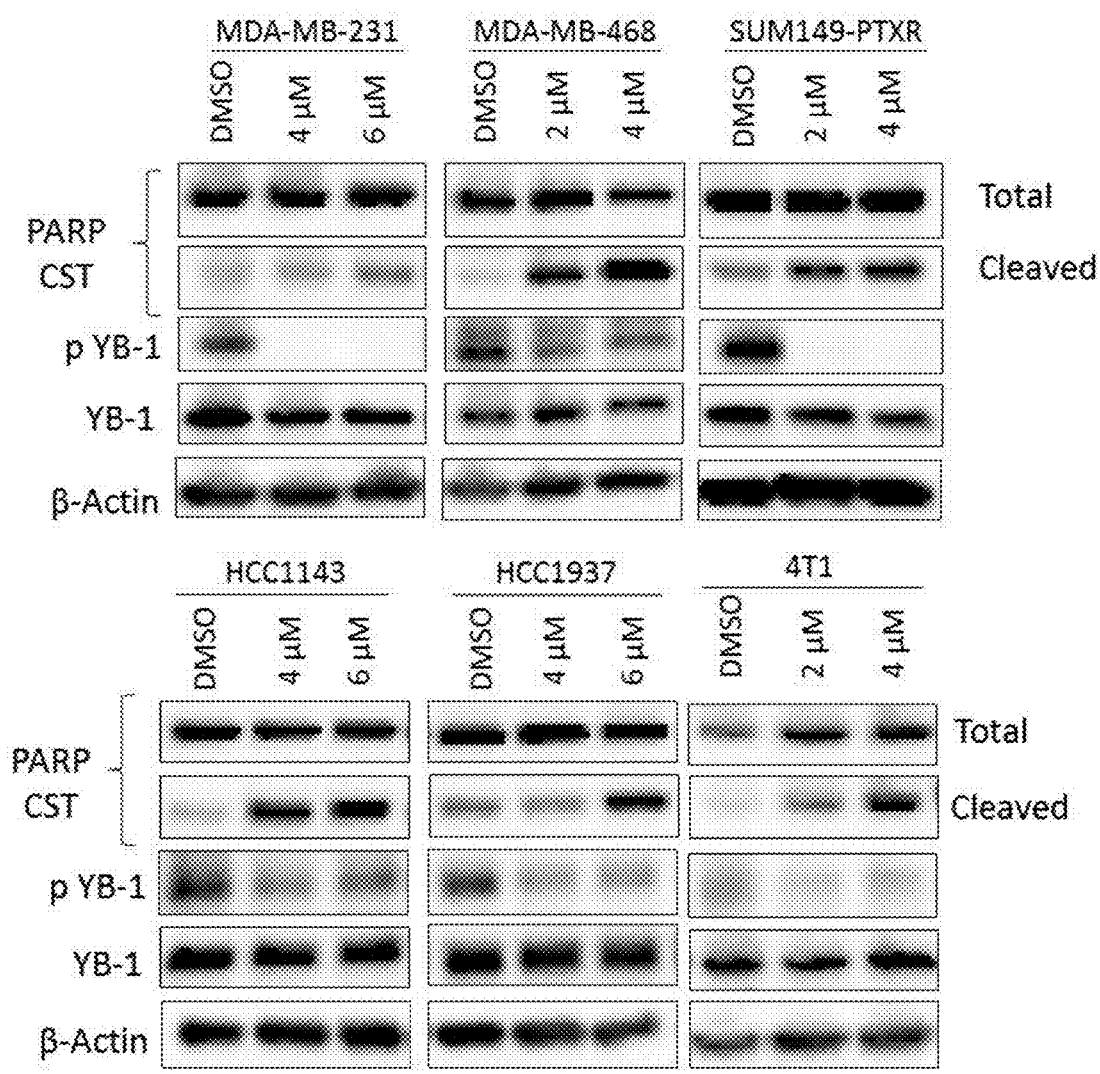
FIG. 12 depicts PARP cleavage induced by compound 25 (5 days of treatment, single dose) in TNBC models.

The method for detecting PARP, P—YB-1, YB-1 and β-actin are described above (FIG. 12). MDA-MB-231, MDA-MB-468, SUM-149-PTX, HCC1143, HCC1937 or 4T1 cells were treated with Compound 25 for 120 hrs at concentrations of 2, 4 or 6 uM. The cells were harvested by scraping to collect all cells including those that had undergone apoptosis. Cells shown to have undergone apoptosis based on PARP cleavage relative to the DMSO control. Further P—YB-1 was consistently reduced in all cell lines following treatment with Compound 25 relative to the DMSO controls. YB-1 and B-actin were included as loading controls. Total levels of PARP were not affected at this timepoint.

Biological Example 7

Figure 13:
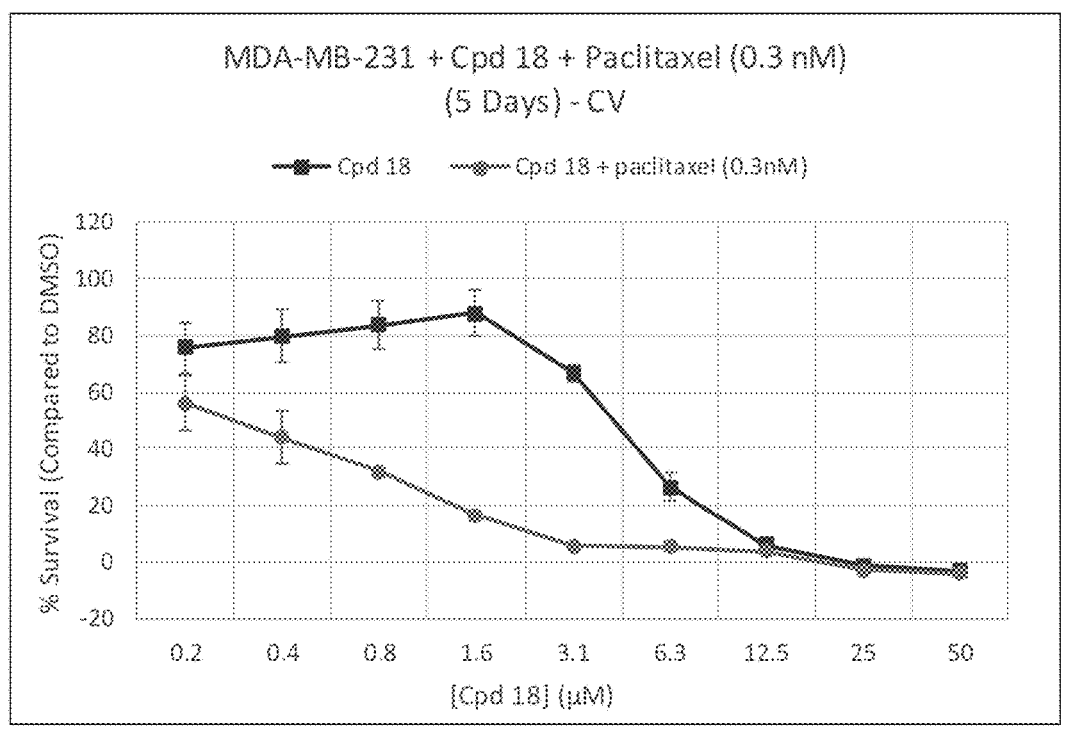
FIG. 13 depicts the effect of combination treatment with compound 18 and paclitaxel on monolayer growth in MDA-MB-231 cells.

RSK Inhibitors Combined with Standard of Care Chemotherapy have a Synergistic Effect on Suppressing Tumor Cell Growth For cytotoxicity profiling of combinations with compound of the invention and the microtubule stabilizing agent paclitaxel against breast cancer cell lines, refer to Biological Example 2: Monolayer Growth Inhibition Assay, with the following modifications. Dose response studies with paclitaxel as a single agent were carried out as described with paclitaxel at final concentrations of 0.078125, 0.15625, 0.3125, 0.625, 1.25, 2.5, 5, 10, 20 μM in order to determine the suitable doses for further experiments. Combination treatments were performed by treating breast cancer cell lines with single compounds of the invention at final concentrations of 0.1953125, 0.390625, 0.78125, 1.5625, 3.125, 6.25, 12.5, 25 and 50 μM alongside combinations consisting of the same concentrations of the compounds and a single concentration of paclitaxel determined by the dose response studies (FIG. 13).

For RSK inhibitor Compound 18 represents an example of improved cell growth suppression when combined with a standard of care chemotherapy (eg. Paclitaxel). The IC50 of RSK inhibitors was lowered approximately 10-fold by the addition of a sublethal dose of paclitaxel (PTX) (Table 9). The combination index was calculated indicating there was synergy across a range of concentrations (Table 10).

The RSK inhibitor Cpd 18 represents an example of improved cell growth suppression when combined with a standard of care chemotherapy (eg. Paclitaxel). The IC50 of RSK inhibitors was lowered approximately 10-fold by the addition of a sublethal dose of paclitaxel (PTX) (Table 9). The combination index was calculated indicating there was synergy across a range of concentrations (Table 10).

TABLE 9

| Compound/Combination | Cell Growth (CV) $IC_{50}$ Values (μM) |
| --- | --- |
| Compound 18 | 4.3 ± 1.0 |
| Compound 18 + PTX (0.3 nM) | 0.3 ± 0.1 |

MDA-MB-231 cells exposed to compounds for 5 days
MDA-MB-231 cells + 0.3 nM PTX: % Survival = 47.7%

TABLE 10

| Compound 18 (μM) | Coefficient of Drug Interaction (CDI) |
| --- | --- |
| 0.2 | 1.6 |
| 0.4 | 1.2 |
| 0.8 | 0.8* |

TABLE 10-continued

| Compound 18 (μM) | Coefficient of Drug Interaction (CDI) |
| --- | --- |
| 1.6 | 0.4* |
| 3.1 | 0.2* |
| 6.3 | 0.4* |

*Combination with paclitaxel (0.3 nM) considered synergistic
MDA-MB-231 cells treated for 5 days Biological Example 8

Immuno-Oncology

Figure 14A:
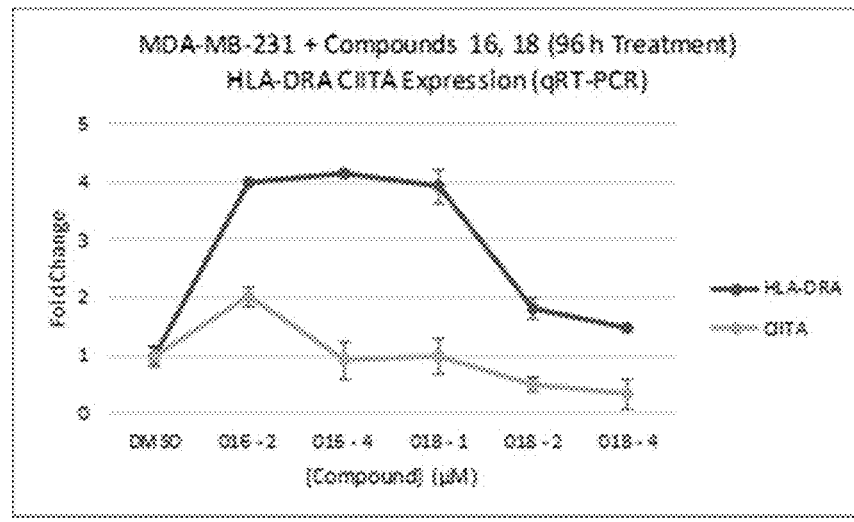
FIG. 14A depicts the effect of compounds 16 and 18 on immune recognition by inducing the MHC-II gene HLA-DRA in MDA-MB-231 cells.
Figure 14B:
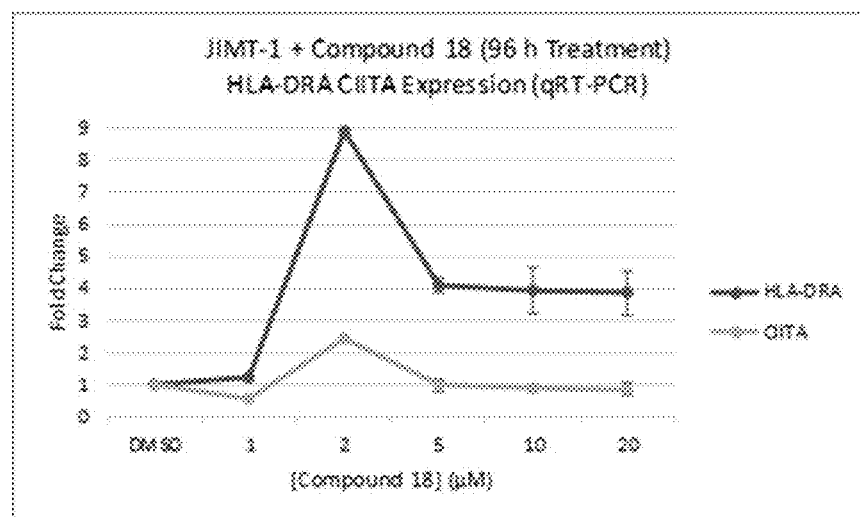
FIG. 14B depicts the effect of compound 18 on immune recognition by inducing the MHC-II gene HLA-DRA in JIMT-1 cells.
Figure 14C:
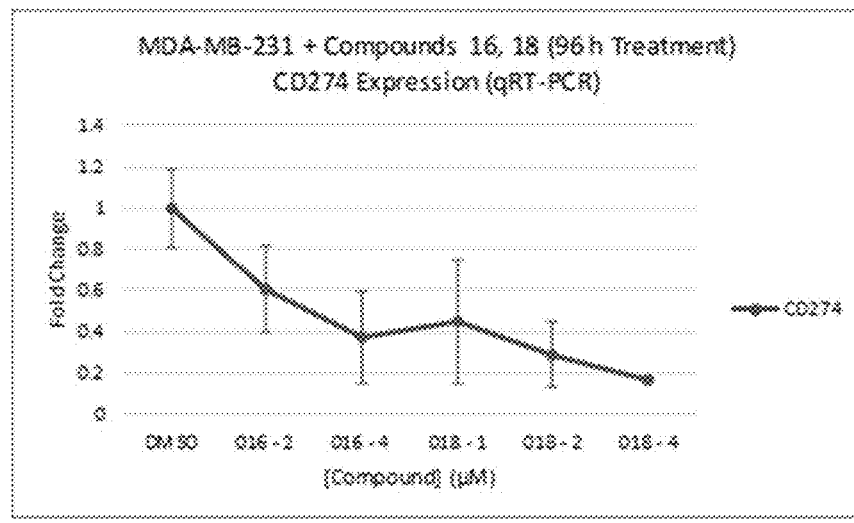
FIG. 14C depicts the effect of compound 16 and 18 on immune recognition by reducing CD274, the gene that encodes PDL-1 in MDA-MB-231 cells.
Figure 14D:
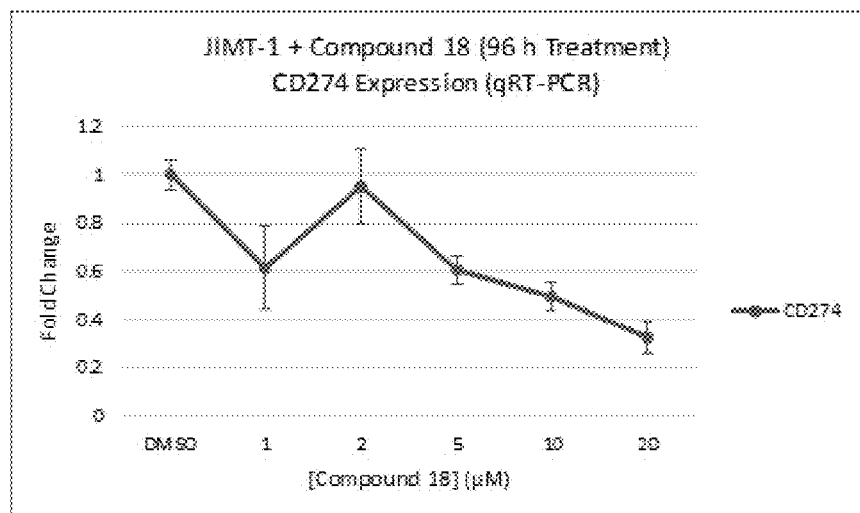
FIG. 14D depicts the effect of compound 18 on immune recognition by reducing CD274, the gene that encodes PDL-1 in JIMT-1 cells.

A key feature of cancer is low immunogenicity. This can occur by several mechanisms that allow the cells to escape immune recognition. Treating MDA-MB-231 and JIMT-1 cells with RSK inhibitors (ex. Compound 16 (2 or 4 uM), Compound 18 (1, 2, or 4 uM)) elevated levels of HLA-DRA mRNA, but had little effect on the mRNA expression of CIITA (FIGS. 14A, 14B). HLA-DRA is a member of MHC-II genes and CIITA is the master regulator of MHC II transcription. Thus it was surprising that CIITA, which would be expected to regulate MHC II gene expression, was not altered by RSK inhibition. Inhibiting RSK simultaneously inhibited CD274, the gene that encodes program death receptor ligand 1 (PD-L1) (FIG. 14C, 14D). Compound 16 (2 or 4 uM) or Compound 18 1, 2 or 4 uM) reduced levels of CD274 in MDA-MB-231 cells. Likewise, Compound 18 at varying concentrations (1-20 uM) also inhibited CD274 in JIMT-1 cells. HLA-DRA is important for immune recognition while PD-L1 is involved in immune checkpoints.

Biological Example 9

RSK Inhibitors have Favourable Pharmacodynamics Properties, Ex. Delivery to Tumors Due to its poor or nonexistent solubility, as discussed above at Biological Example 2, Compound 0 could not be evaluated for pharmacodynamics Conversely, Compound 25 had superior solubility for systemic delivery in mice (Table 5).

Figure 15:
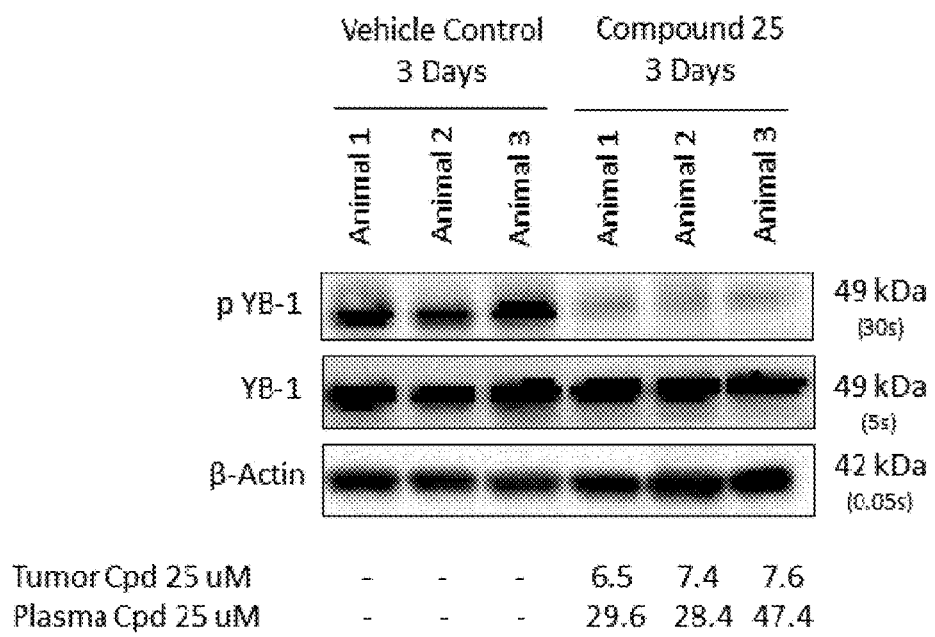
FIG. 15 depicts the effect of compound 25 on cell signaling in MDA-MB-231 xenografts after three days of treatment.
Figure 16A:
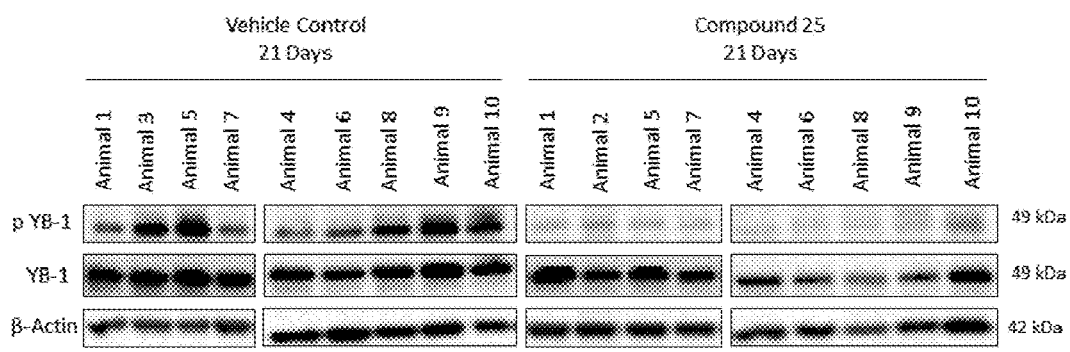
FIGS. 16A and 16B depict the effect as well as quantification of compound 25 on cell signaling in MDA-MB-231 xenografts after 21 days of treatment.
Figure 16B:
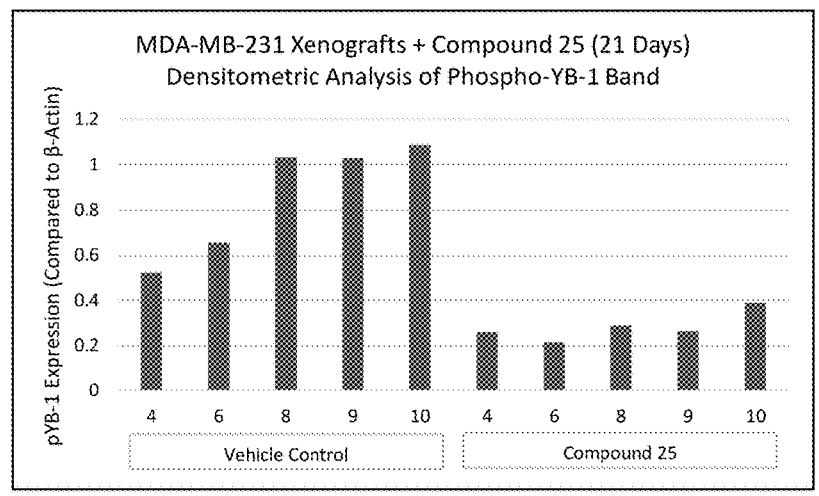

MDA-MB-231 cells were injected into the mammary fat pad of nu/nu mice and tumors were established. Once the tumors reached 50-100 mm$^3$ the mice were randomized into two groups, vehicle control or Compound 25 treated. The mice received Compound 25 100 mg/kg BID PO for three days. Cell signalling was evaluated by immunoblotting. The levels of Cpd 25 in the plasma and tumors was determined by LC/MS (FIG. 15). Compound 25 reduced cell signaling through loss of P—YB-1 in 3/3 tumors. YB-1 and B-Actin were included as loading controls. Tumor and plasma levels of Compound 25 were on average 7.1 and 35.1 uM respectively. The ratio between the tumor and plasma indicates excellent tumor uptake (20%). Similarly, tumors were also obtained from mice treated for 21 days with Compound 25 as described above and cell signalling was assessed by immunoblotting (FIG. 16A). Compound 25 consistently reduced P—YB-1 signaling in 9/9 tumors relative to the vehicle control treated tumors. YB-1 and B-actin were included as internal loading controls. The loss of P—YB-1 signaling was quantified using Image J for animals 4, 6, 8, 9, and 10 (FIG. 16B). Levels of Compound 25 were also quantified in the tumors taken from mice treated for 21 days, the average concentration in the tumors was 7.7 uM. The tumors from mice treated for either 3 or 21 days were harvested 30 minutes after the last oral dosing of Compound 25. In summary, Compound 25 exhibited excellent tumor uptake and reduced P—YB-1 signaling in 12/12 (n=3 (treated for 3 days), n=9 (treated for 21 days) tumors relative to the vehicle control treated tumors, whereas Compound 0 could not be dosed in vivo due to its poor solubility.

Biological Example 10

Colony Forming Unit Hematopoietic Stem Cell Assay

The hematopoietic colony forming cell assay was conducted based on a protocol outlined by StemCell Technologies. To begin, several concentrations of the compounds of the invention and DMSO (0.625, 1.25, 2.5, 5, 10, 20 μM) were added to separate tubes of MethoCult (StemCell Technologies), a methylcellulose matrix containing recombinant human cytokines stem cell factor (rh SCF), granulocyte macrophage colony-stimulating factor (rh GM-CSF), interleukin-3 (rh IL-3), granulocyte colony stimulating factor (rh G-CSF) and erythropoietin (rh EPO). Following the addition of CD34$^+$ cells isolated from human cord blood or peripheral blood (StemCell Technologies) at a final concentration of $5 \times 10^2$ cells per dish, the tubes were vortexed and allowed to stand for 5 minutes at room temperature. Next, the MethoCult mixtures were dispensed into 35 mm dishes (Corning Incorporated) through blunt end needles (StemCell Technologies) and 5 ml syringes (BD Biosciences) at a volume of 1.1 ml per dish. The medium was evenly distributed across the surface of each dish by gentle tilting and rotation. The dishes were then placed in a 100 mm culture dish (Grenier Bio-One) containing additional 35 mm dishes with sterile water to maintain humidity. The culture dish was then placed at 37° C. in a humidified incubator containing 5% $CO_2$ for 13 days. The number of myeloid and erythroid derived colonies in both the treated and control dishes were counted and compared.

RSK inhibitors do not inhibit the differentiation of normal human hematopoetic stem cell precursor cells as compared to cancer cells. By contrast, Compound #15 inhibited 50% of cancer cell growth with 3.8 uM, whereas 100% of the cells were viable in the HSC assay. A representative compound described herein, i.e., Compound #15, when tested in this assay, demonstrated the following IC$_{50}$, as shown in Table 11:

TABLE 11

| IC$_{50}$ Values (μM) - 14 days, CFU Assay | | |
| --- | --- | --- |
| Cells | Type | Compound #15 |
| CD34+ | HSC | 23.8 |

Figure 17:
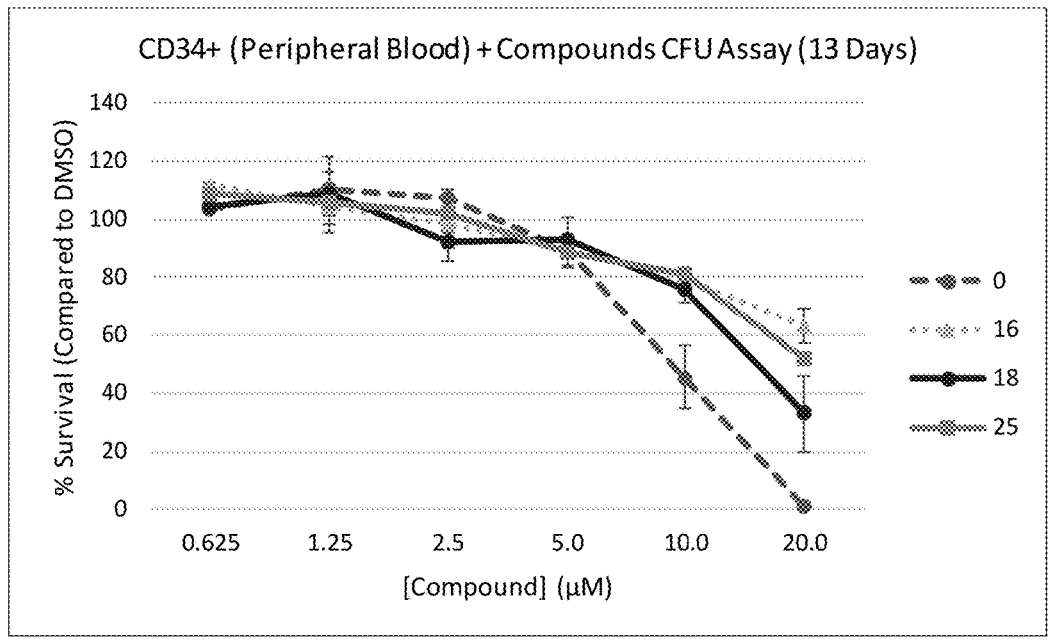
FIG. 17 depicts the percent survival of human CD34+ cells when treated with varying concentrations of compounds described herein.

A therapeutic window refers to the range of dosage of a drug or of its concentration in a bodily system that provides safe effective therapy. Hematopoietic stem cell differentiation from human primary bone marrow stems cells was used to assess therapeutic safety and to determine and compare safety windows of several compounds described herein, namely Compounds 0, 16, 18, and 25. Compared to Compound 0 and Taxol, Compounds 16, 18 and 25 have greater therapeutic windows, as indicated by the ratio IC$_{50}$ values of the compounds against CD34$^+$ cells and MDA-MB-231 cells (Table 12, FIG. 17). The values were compared to the concentration needed to block growth in soft agar (SA).

TABLE 12

| CD34+ (PB), MDA-MB-231 + Compounds, Taxol - IC$_{50}$ Values | | | |
|---|---|---|---|
| Compound | CD34+ (PB) | MDA-MB-231 | Therapeutic Window |
| 0 | 10.0 µM | 0.2 µM (SA) | 50X |
| 16 | >20.0 µM | 0.2 µM (SA) | >100X |
| 18 | 16.3 µM | 0.1 µM (SA) | 163X |
| 25 | >20.0 µM | 0.2 µM (SA) | >100X |
| Taxol | 9.7 nM | 1.4 nM (SA) | 6.9X |

All of the U.S. patents, U.S. patent application publications, U.S. patent applications, PCT published patent applications, foreign patents, foreign patent applications and non-patent publications referred to in this specification are incorporated herein by reference in their entirety.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (II):

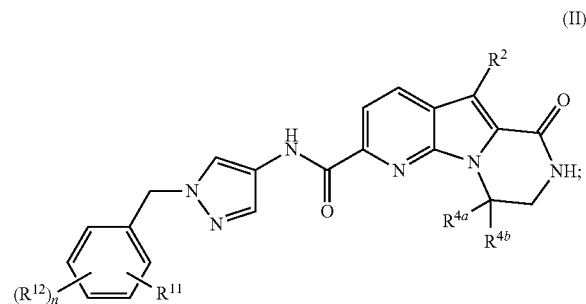

wherein:
R$^2$ is hydrogen, halo, C$_{1-6}$alkyl, or C$_{1-6}$haloalkyl;
R$^{4a}$ and R$^{4b}$ are each independently hydrogen, halo, C$_{1-6}$alkyl, or C$_{1-6}$haloalkyl;
each R$^6$ is independently hydrogen or C$_{1-6}$alkyl;
R$^{11}$ is halo, C$_{1-6}$haloalkyl, —N(R$^6$)$_2$, —C$_{1-6}$alkyl-N(R$^6$)$_2$, or —C(O)N(R$^6$)$_2$;
each R$^{12}$ is independently —OH, —CN, halo, C$_{1-6}$alkyl, C$_{1-6}$haloalkyl, C$_{1-6}$alkoxy, C$_{1-6}$haloalkoxy, —N(R$^6$)$_2$, —C$_{1-6}$alkyl-N(R$^6$)$_2$, —C(O)R$^6$, —C(O)OR$^6$, —C(O)N(R$^6$)$_2$, aryl, aralkyl, cycloalkyl, heterocyclyl, or heteroaryl; and n is 0, 1, 2, 3, or 4;
or a pharmaceutically acceptable salt, stereoisomer, or tautomer thereof.

2. The compound of claim 1, wherein R$^2$ is hydrogen.
3. The compound of claim 2, wherein R$^{4a}$ is C$_{1-6}$alkyl.
4. The compound of claim 3, wherein R$^{4a}$ is —CH$_3$.
5. The compound of claim 4, wherein R$^{4b}$ is hydrogen.
6. The compound of claim 5, wherein n is 0.
7. The compound of claim 6, wherein R$^{11}$ is —N(R$^6$)$_2$.
8. The compound of claim 6, wherein R$^{11}$ is —C$_{1-6}$alkyl-N(R$^6$)$_2$.
9. The compound of claim 7, wherein R$^{11}$ is —NH$_2$.
10. The compound of claim 8, wherein R$^{11}$ is —CH$_2$NH$_2$.
11. The compound of claim 1, wherein the compound is:
(R)—N-(1-(4-(aminomethyl)benzyl)-1H-pyrazol-4-yl)-9-methyl-6-oxo-6,7,8,9-tetrahydropyrido[3',2':4,5]pyrrolo[1,2-a]pyrazine-2-carboxamide;
or a pharmaceutically acceptable salt thereof.
12. The compound of claim 1, wherein the compound is:
(R)—N-(1-(4-(aminomethyl)benzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride salt.
13. The compound of claim 1, wherein the compound is:
(R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide;
or a pharmaceutically acceptable salt thereof.
14. The compound of claim 1, wherein the compound is:
(R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride salt.
15. A pharmaceutical composition comprising a pharmaceutically acceptable excipient and a compound of claim 1, or a pharmaceutically acceptable salt, stereoisomer, or tautomer thereof.
16. A method for inhibiting p90 ribosomal S6 kinase activity in a mammal, wherein the method comprises administering to the mammal a compound of claim 1, or a pharmaceutically acceptable salt, stereoisomer, or tautomer thereof.
17. The method of claim 16, wherein the mammal suffers from cancer.
18. The method of claim 17, wherein the cancer is breast cancer, prostate cancer, lung cancer, brain cancer, skin cancer, bone cancer, ovarian cancer, multiple myeloma or leukemia.
19. The method of claim 18, wherein the method further comprises administering a second therapeutic agent.
20. The method of claim 19, wherein the second therapeutic agent is a chemotherapeutic agent, hormonal therapeutic agent, or an immunotherapeutic agent.

* * * * *